(12) United States Patent
Devanaboyina

(10) Patent No.: US 11,071,678 B2
(45) Date of Patent: Jul. 27, 2021

(54) SYSTEMS AND METHODS FOR EXERTING FORCE ON BODIES

(71) Applicant: Udaya Sankar Devanaboyina, Fremont, CA (US)

(72) Inventor: Udaya Sankar Devanaboyina, Fremont, CA (US)

( * ) Notice: Subject to any disclaimer, the term of this patent is extended or adjusted under 35 U.S.C. 154(b) by 0 days.

(21) Appl. No.: 16/391,169

(22) Filed: Apr. 22, 2019

(65) Prior Publication Data
US 2019/0247269 A1 Aug. 15, 2019

Related U.S. Application Data

(63) Continuation of application No. 14/772,359, filed as application No. PCT/US2014/021448 on Mar. 6, 2014, now Pat. No. 10,265,237.
(Continued)

(51) Int. Cl.
*A61H 9/00* (2006.01)
*A47C 9/00* (2006.01)
(Continued)

(52) U.S. Cl.
CPC ........... *A61H 9/0078* (2013.01); *A47C 9/002* (2013.01); *A61H 1/001* (2013.01); *A61H 1/008* (2013.01);
(Continued)

(58) Field of Classification Search
CPC .......... A47C 9/002; A61H 1/00; A61H 1/001; A61H 1/006; A61H 1/008; A61H 1/0237; A61H 1/0274; A61H 2001/0233; A61H 7/00; A61H 7/007; A61H 9/00; A61H 9/0007; A61H 9/005; A61H 9/0078; A61H 9/0085; A61H 9/0092; A61H 11/00; A61H 2011/005; A61H 15/00; A61H 31/004; A61H 31/006; A61H 31/008; A61H 31/02; A61H 2201/0103; A61H 2201/0134; A61H 2201/0138; A61H 2201/0149;
(Continued)

(56) References Cited

U.S. PATENT DOCUMENTS

| | | | | |
|---|---|---|---|---|
| 2,142,689 A | * | 1/1939 | Emerson | A61H 9/005 601/9 |
| 2,270,313 A | * | 1/1942 | Kraft | 601/44 |

(Continued)

*Primary Examiner* — Gary D Urbiel Goldner
(74) *Attorney, Agent, or Firm* — Dave Law Group LLC; Raj S. Dave

(57) ABSTRACT

Systems and methods for exerting forces on a body, including a support structure defining a space and a plurality of surface contacting units that are configured to exert force upon the body, such that the weight is distributed away from the primary weight bearing regions to non-weight bearing regions of the body, or vice versa, without exerting significant shear or frictional forces on surfaces of the body. The systems and methods may be used to exert forces to cause fluid shift in different compartments of the body. Applications include treatment of various disease conditions including pressure ulcers, heart failure, high blood pressure, preeclampsia, osteoporosis, injuries of spine and to slow microgravity-induced bone and muscle loss. The systems and methods may be used to simulate gravity, weightlessness or buoyancy, in rehabilitation medicine. The system may include a chair, bed, a wearable suit or an exoskeleton.

11 Claims, 36 Drawing Sheets

Related U.S. Application Data

(60) Provisional application No. 61/773,154, filed on Mar. 6, 2013.

(51) Int. Cl.
| | | |
|---|---|---|
| *A61H 7/00* | (2006.01) | |
| *A61H 23/02* | (2006.01) | |
| *A61H 23/00* | (2006.01) | |
| *A63B 69/00* | (2006.01) | |
| *A63B 21/00* | (2006.01) | |
| *A61H 1/00* | (2006.01) | |
| *A61H 3/00* | (2006.01) | |
| *A61M 21/02* | (2006.01) | |
| *A63B 21/04* | (2006.01) | |
| *A63B 22/02* | (2006.01) | |
| *A61H 3/04* | (2006.01) | |
| *A61H 15/00* | (2006.01) | |
| *A61H 23/04* | (2006.01) | |
| *A61M 21/00* | (2006.01) | |

(52) U.S. Cl.
CPC ............... *A61H 3/00* (2013.01); *A61H 7/007* (2013.01); *A61H 23/006* (2013.01); *A61H 23/02* (2013.01); *A61M 21/02* (2013.01); *A63B 21/00181* (2013.01); *A63B 69/0064* (2013.01); *A61H 2003/043* (2013.01); *A61H 2015/0064* (2013.01); *A61H 2023/045* (2013.01); *A61H 2201/0103* (2013.01); *A61H 2201/0142* (2013.01); *A61H 2201/0149* (2013.01); *A61H 2201/0207* (2013.01); *A61H 2201/0214* (2013.01); *A61H 2201/1207* (2013.01); *A61H 2201/1215* (2013.01); *A61H 2201/1246* (2013.01); *A61H 2201/1253* (2013.01); *A61H 2201/164* (2013.01); *A61H 2201/165* (2013.01); *A61H 2201/168* (2013.01); *A61H 2201/1621* (2013.01); *A61H 2201/1635* (2013.01); *A61H 2201/1642* (2013.01); *A61H 2201/1645* (2013.01); *A61H 2201/1654* (2013.01); *A61H 2201/1695* (2013.01); *A61H 2201/1697* (2013.01); *A61H 2201/5007* (2013.01); *A61H 2201/5061* (2013.01); *A61H 2201/5064* (2013.01); *A61H 2201/5071* (2013.01); *A61H 2201/5082* (2013.01); *A61H 2201/5084* (2013.01); *A61H 2203/0406* (2013.01); *A61H 2203/0431* (2013.01); *A61H 2203/0456* (2013.01); *A61H 2205/12* (2013.01); *A61H 2209/00* (2013.01); *A61H 2230/045* (2013.01); *A61H 2230/105* (2013.01); *A61H 2230/405* (2013.01); *A61H 2230/805* (2013.01); *A61M 2021/0022* (2013.01); *A63B 21/0442* (2013.01); *A63B 21/4005* (2015.10); *A63B 21/4007* (2015.10); *A63B 22/02* (2013.01)

(58) Field of Classification Search
CPC ........ A61H 2201/0157; A61H 2201/12; A61H 2201/1207; A61H 2201/1238; A61H 2201/1236; A61H 2201/16; A61H 2201/1609; A61H 2201/1611; A61H 2201/1614; A61H 2201/1616; A61H 2201/1619; A61H 2201/1621; A61H 2201/1623; A61H 2201/1626; A61H 2201/1628; A61H 2201/163; A61H 2201/1633; A61H 2201/1635; A61H 2201/1638; A61H 2201/164; A61H 2201/1642; A61H 2201/1645; A61H 2201/1647; A61H 2201/165; A61H 2201/1652; A61H 2201/1654; A61H 2201/50; A61H 2201/5007; A61H 2201/5023; A61H 2201/5025; A61H 2201/5035; A61H 2201/5038; A61H 2201/5041; A61H 2201/5058; A61H 2201/5061; A61H 2201/5064; A61H 2201/5069; A61H 2201/5071; A61H 2201/5082; A61H 2201/5084; A61H 2209/00; A61H 2230/00; A61H 2230/04; A61H 2230/045; A61H 2230/06; A61H 2230/065; A61H 2230/08; A61H 2230/085; A61H 2230/10; A61H 2230/105; A61H 2230/30; A61H 2230/305; A61H 2230/40; A61H 2230/405; A61H 2230/50; A61H 2230/505; A61H 2230/85; A61H 2230/855; A63B 21/00058; A63B 21/00069; A63B 21/00076; A63B 21/00181; A63B 21/00185; A63B 21/00196; A63B 21/002; A63B 21/0023; A63B 21/04; A63B 21/0407; A63B 21/0414; A63B 21/0421; A63B 21/0428; A63B 21/0435; A63B 21/0442; A63B 21/065; A63B 21/068; A63B 21/08; A63B 21/4005; A63B 21/4007; A63B 21/4011; A63B 21/4013; A63B 21/4015; A63B 21/4023; A63B 21/4025; A63B 21/4027; A63B 21/4039; A63B 24/0087; A63B 69/0057; A63B 69/0059; A63B 69/0062; A63B 69/0064; A63B 71/0054; A63B 2071/0063; A63B 2071/0072; A63B 2071/0081; A63B 2071/009; A63B 2208/03; A63B 2208/05; A63B 2208/053; A63B 2208/056; A63B 2220/10; A63B 2220/13; A63B 2220/16; A63B 2220/40; A63B 2220/50; A63B 2220/51; A63B 2220/52; A63B 2220/56; A63B 2220/58; A63B 2220/70; A63B 2220/72; A63B 2220/75; A63B 2220/80; A63B 2220/801; A63B 2220/803; A63B 2220/805; A63B 2220/83; A63B 2220/833; A63B 2220/836; A63B 2225/09; A63B 2225/093; A63B 2225/096; A63B 2225/50; A63B 2225/60; A63B 2225/605; A63B 2225/62; A63B 2225/64; A63B 2225/66; A63B 2230/01; A63B 2230/015; A63B 2230/04; A63B 2230/045; A63B 2230/06; A63B 2230/062; A63B 2230/065; A63B 2230/067; A63B 2230/08; A63B 2230/085; A63B 2230/10; A63B 2230/105; A63B 2230/30; A63B 2230/305; A63B 2230/40; A63B 2230/405; A63B 2230/42; A63B 2230/425; A63B 2220/44

See application file for complete search history.

(56) References Cited

U.S. PATENT DOCUMENTS

| | | | | |
|---|---|---|---|---|
| 3,411,500 A | * | 11/1968 | Gatts | B64G 7/00 600/20 |
| 3,622,025 A | * | 11/1971 | Petersen | B63C 3/12 414/461 |
| 3,659,593 A | * | 5/1972 | Vail | A61H 9/0078 601/151 |

(56) References Cited

U.S. PATENT DOCUMENTS

| | | | | |
|---|---|---|---|---|
| 4,291,917 A * | 9/1981 | Hawks | A47D 1/00 | 297/452.56 |
| 4,925,133 A * | 5/1990 | Wurst | B64D 10/00 | 2/2.14 |
| 5,133,339 A * | 7/1992 | Whalen | A61H 9/005 | 128/202.12 |
| 5,489,259 A * | 2/1996 | Jacobs | A61F 5/012 | 128/882 |
| 5,520,402 A * | 5/1996 | Nestor | A61G 5/00 | 280/250 |
| 5,628,230 A * | 5/1997 | Flam | G01M 99/00 | 73/172 |
| 5,918,602 A * | 7/1999 | Shaw | A61F 5/0104 | 128/882 |
| 5,976,099 A * | 11/1999 | Kellogg | A61H 9/0078 | 128/877 |
| 5,987,705 A * | 11/1999 | Reynolds | A41D 19/01523 | 16/431 |
| 6,488,645 B1 * | 12/2002 | Reinhard | A61F 13/08 | 602/19 |
| 9,456,641 B1 * | 10/2016 | Mignone | A41D 31/185 | |
| 9,554,964 B1 * | 1/2017 | Johnson | A61H 3/00 | |
| 10,265,237 B2 * | 4/2019 | Devanaboyina | A61H 1/008 | |
| 2002/0032395 A1 * | 3/2002 | Klingler | A61H 15/0078 | 601/115 |
| 2002/0177793 A1 * | 11/2002 | Sherman | A61H 31/008 | 601/41 |
| 2003/0195445 A1 * | 10/2003 | Behan | A61F 5/012 | 602/19 |
| 2003/0212303 A1 * | 11/2003 | Kahn | A61B 5/0806 | 600/3 |
| 2003/0212352 A1 * | 11/2003 | Kahn | A61H 35/002 | 601/98 |
| 2004/0030411 A1 * | 2/2004 | Caspers | A61F 2/5046 | 623/37 |
| 2006/0070170 A1 * | 4/2006 | Copeland | A63B 71/10 | 2/411 |
| 2008/0249442 A1 * | 10/2008 | Brown | A61H 9/0078 | 601/152 |
| 2008/0294075 A1 * | 11/2008 | Nozzarella | A61H 31/00 | 601/44 |
| 2010/0144490 A1 * | 6/2010 | Purdy | A63B 21/154 | 482/1 |
| 2011/0043755 A1 * | 2/2011 | Gibson-Horn | A61F 5/026 | 351/203 |
| 2011/0098157 A1 * | 4/2011 | Whalen | A61H 9/00 | 482/52 |
| 2011/0120567 A1 * | 5/2011 | Kuehne | A63B 21/00181 | 137/14 |
| 2012/0059291 A1 * | 3/2012 | Nguyen | A61H 1/0288 | 601/40 |
| 2012/0234111 A1 * | 9/2012 | Molyneux | A43B 3/0031 | 73/862.541 |
| 2012/0238921 A1 * | 9/2012 | Kuehne | A63B 22/0235 | 601/5 |
| 2012/0316481 A1 * | 12/2012 | Purdy | A61H 9/0078 | 601/151 |
| 2013/0000021 A1 * | 1/2013 | Dolcetti | A41D 13/0015 | 2/455 |
| 2013/0013033 A1 * | 1/2013 | Lowe | A61F 7/02 | 607/104 |
| 2013/0041303 A1 * | 2/2013 | Hopman | A61B 17/135 | 602/23 |
| 2013/0085040 A1 * | 4/2013 | Bowers | A63B 21/0552 | 482/8 |
| 2013/0178764 A1 * | 7/2013 | Eckhouse | A61N 5/025 | 601/2 |
| 2013/0239976 A1 * | 9/2013 | Purdy | A61G 7/0755 | 128/845 |

* cited by examiner

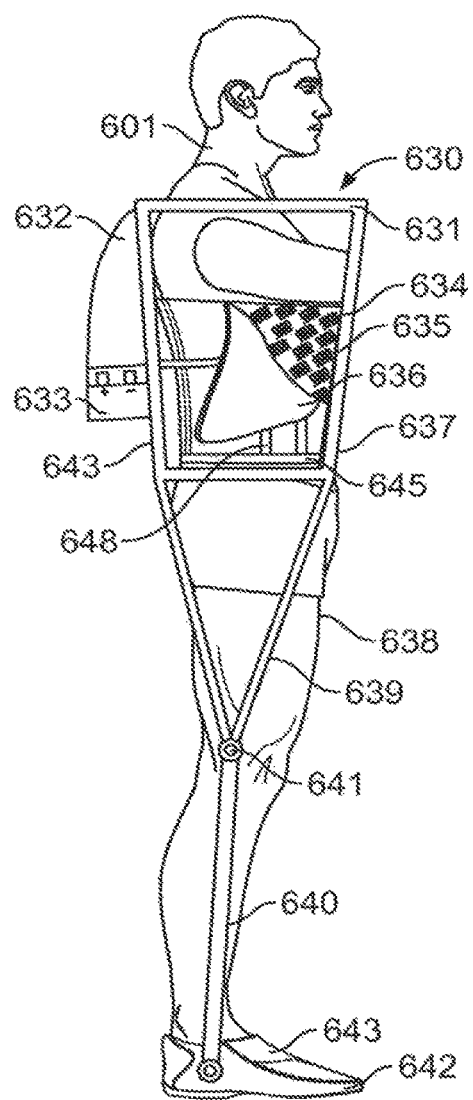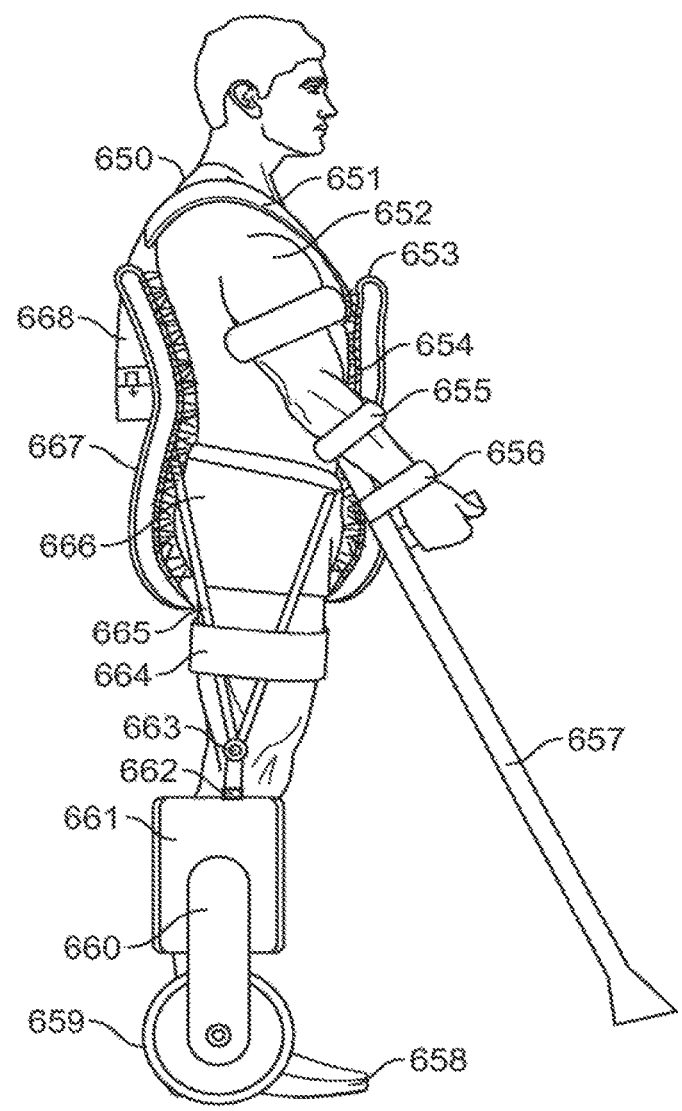
FIG. 6C
FIG. 6D

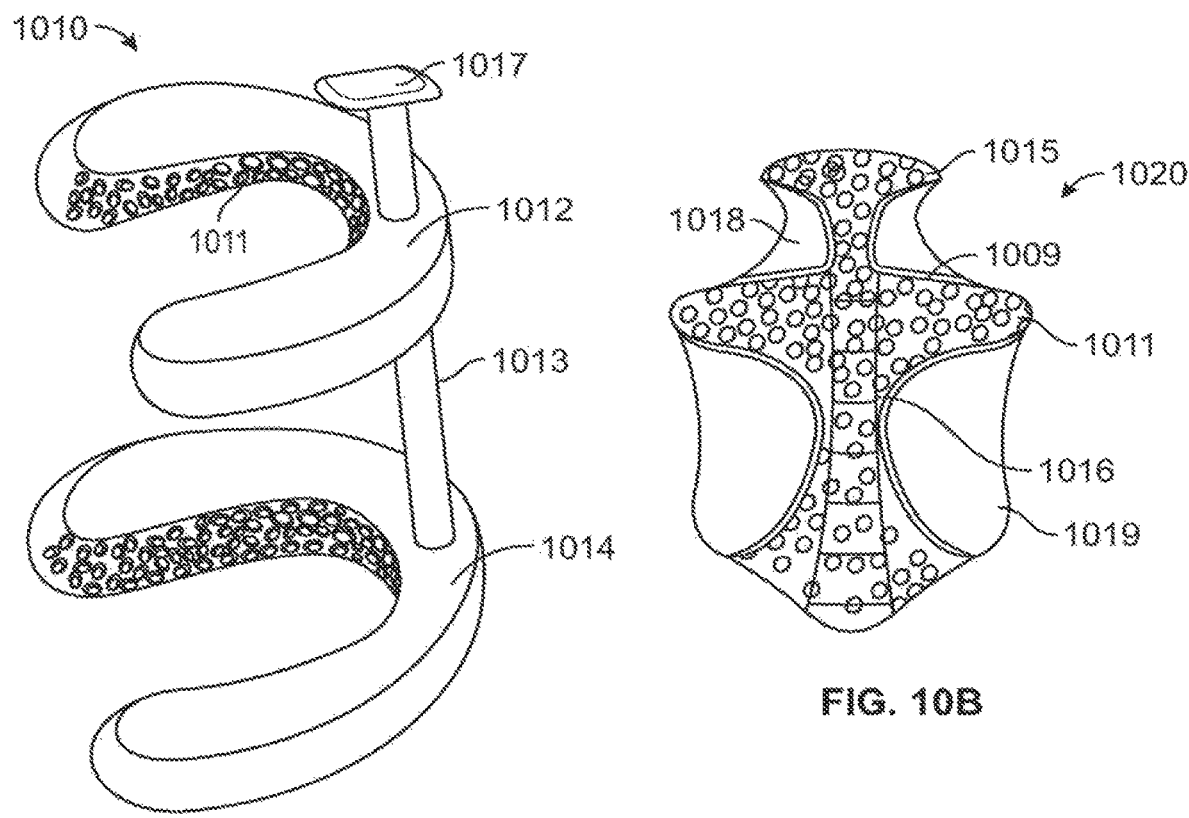
FIG. 10A
FIG. 10B
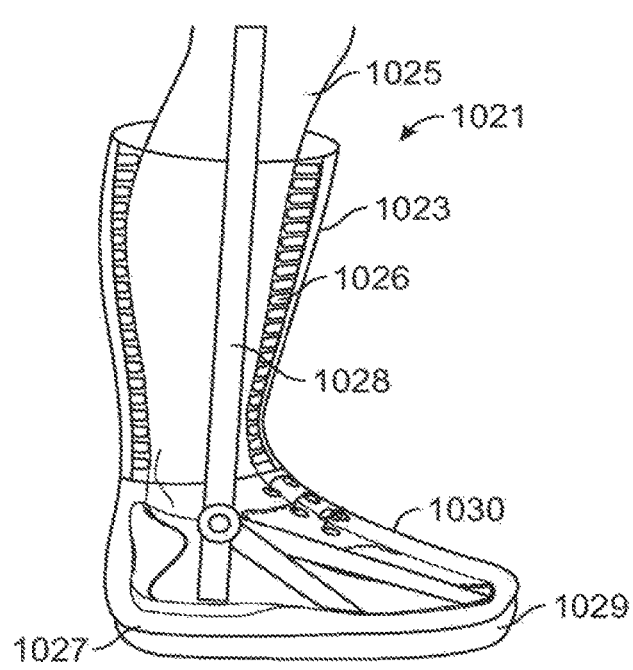
FIG. 10C
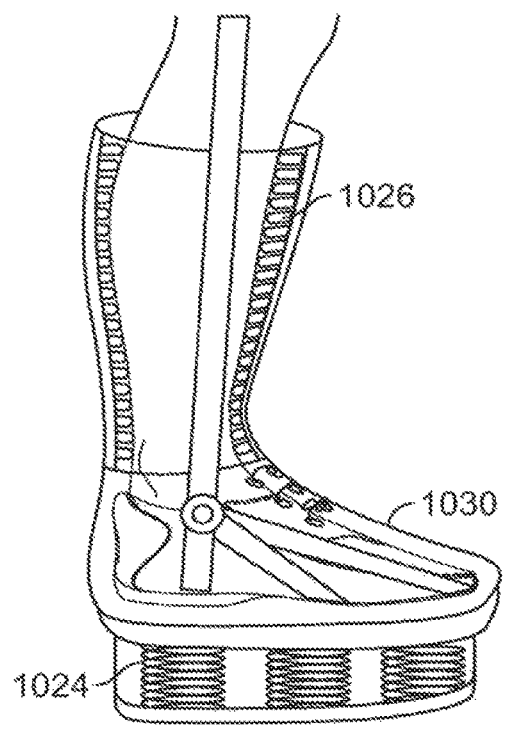
FIG. 10C-1

SYSTEMS AND METHODS FOR EXERTING FORCE ON BODIES

CROSS-REFERENCE TO RELATED APPLICATIONS

This application is a continuation of U.S. patent application Ser. No. 14/772,359 filed on Sep. 2, 2015, which is a U.S. National Stage of International Patent Application No.: PCT/US2014/021448, filed Mar. 6, 2014, which claims the benefit of priority of U.S. Provisional Patent Application No. 61/773,154, filed on Mar. 6, 2013, which are incorporated herein by reference in their entireties.

BACKGROUND OF THE INVENTION

Gravitational forces on humans play a fundamental role in biological development and physiological functioning of the body in both health and in several disease conditions. Systems and methods that counteract both physical as well as physiological stresses on the body are summarized in this application. Also described in this application are application of the same systems and methods to exert forces similar to gravitational forces on the body when such forces are desirable. Humans experience fatigue when they stay upright for extended periods, as compared to when sitting down on a chair or lying down on a bed, because various muscle groups have to work against gravitational force to maintain the upright body posture. The major weight-bearing regions of the body (e.g., the spine, the back and the buttocks, posterior region of thighs and feet) carry the load of significant portion of the body weight while a person is seated or in standing in an upright position. Prolonged periods of sitting in an office chair or in a car seat or even lying down on bed for long time (e.g., elderly in a long term care facility), often causes a significant pressure as well as shear forces on the weight-bearing regions. This often results in fatigue of the back muscles, stress and low productivity (e.g., in the office workers). Several conditions including chronic back pain due to poor posture, vertebral compression, sciatic pain due to pressed spinal nerves, pressure ulcers (e.g., as encountered in wheel chair-bound patients or in the elderly in long term care facilities) are some examples of consequences of the ailments that affect humans due to the gravitational forces acting on the weight-bearing regions of the body. Therefore, a significant need exists for innovative solutions to minimize the pressure on the weight-bearing regions of the body to increase comfort while seated or lying down and prevent the adverse effects on the weight-bearing regions of the body.

Patients with restricted ability to move, such as bed ridden patients, often loose bone density and muscle strength, as they do not exert forces against the body weight. Similar observations of loss of bone density, and muscle strength are noted in astronauts who spent prolonged time in the microgravity conditions. At present, there is no effective solution available to address these adverse effects on astronauts. Therefore, a significant need exists for preventing such adverse effects on people.

Gravitational forces also play a significant role in various disease conditions including hypertension, edema, gestational preeclampsia, diabetes, cardiovascular disorders, neurological conditions, motion sickness, various metabolic disorders associated with for example, increased body mass index, and the like. While effective therapeutic options are available for some of the conditions, the available treatment options for other conditions are either suboptimal or fraught with risks.

SUMMARY OF THE INVENTION

Disclosed herein are systems, devices and methods for distributing the body weight of a human from weight-bearing regions of the body to non-weight-bearing regions of the body while a person is in the upright position on the feet, in a seated position or when lying down. The invention also discloses methods and devices to reduce shear forces on the skin and underlying tissue to prevent development of or to treat pressure ulcers in people. To this extent, the invention discloses some new embodiments of chairs and beds. The invention also discloses methods, systems and devices for exerting loads on human body for possible use in a microgravity gravity environment, to prevent loss of bone, and muscles and cardiovascular function. Also disclosed are applications of methods, systems and devices described herein to several fields, including for prevention or treatment of hypertension, preeclampsia, some cardiovascular and metabolic disorders, orthopedic medicine, rehabilitation, sports, simulation of motion and tactile sensations.

BRIEF DESCRIPTION OF THE DRAWINGS

Various embodiments of the invention are described below by way of example only, without any limitation in the following figures and explained in the Detailed Description.

FIG. 4N illustrates an embodiment of a WDD integrated into portable cushion or stool for possible use for yoga, at ball games, at home and the like.

FIG. 6C illustrates an embodiment of a WDD integrated with an exoskeleton to support the body weight of a person in upright position or while carrying loads.

FIG. 6D illustrates side-view of an embodiment of a WDD integrated with an exoskeleton worn by a person with paraplegic condition to help with the walking.

FIG. 10A shows an embodiment of a WDD integrated with two adjustable back braces to support various parts of torso.

FIG. 10B illustrates an embodiment of WDD integrated with a brace to support neck and torso.

FIG. 10C illustrates an embodiment of WDD integrated with a shoe to minimize load on the sole of a person.

FIG. 10C-1 illustrates an embodiment of WDD integrated with a shoe containing springs in soles, to distribute pressure from soles to wider surface area of the body, while conserving energy.

DETAILED DESCRIPTION

Figure 1A:
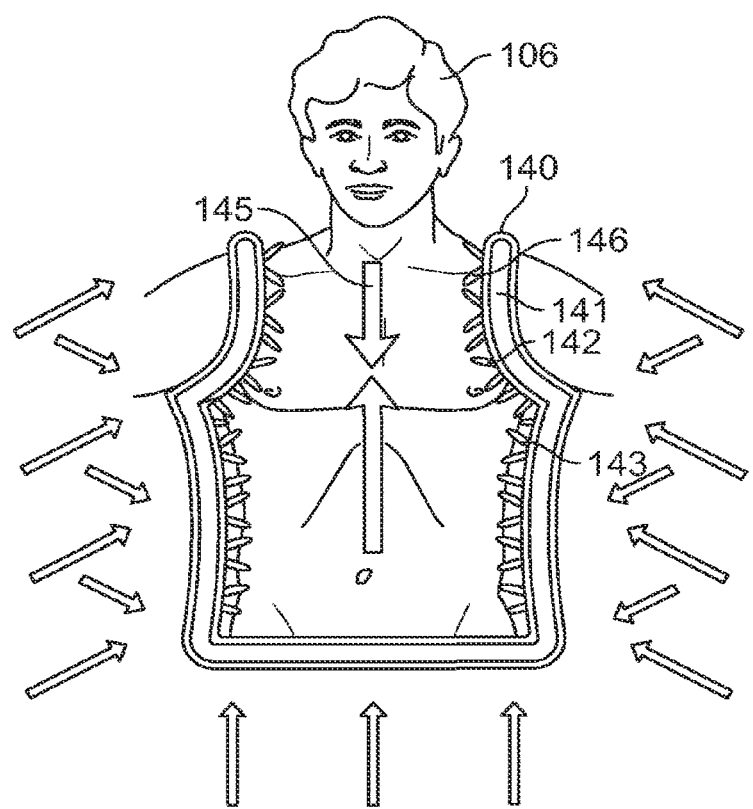
FIG. 1A illustrates an embodiment of WDD and shows direction of some of the forces acting on the torso of a person using the device.

The following is a brief background information on the effect of body weight on the weight-bearing regions of the body and the principles behind the disclosed innovative body weight-distribution device (WDD) and Load Concentration Device (LCD). Principles and operation of the device are explained using the WDD as an example hereinbelow, however, except for direction of forces these are also applicable to the LCD.

People spend less energy while sitting down, compared to when they stand up, as significant weight of the upper body is born by the seat of the chair and does not require to be balanced by legs. Therefore, a seated person exerts less pressure on the soles of the feet compared to a person who is standing. A seated person is in general more comfortable compared to a standing person, as the body weight of the seated person is distributed over a larger surface area, e.g., buttocks and the posterior part of the thighs, and therefore there is less pressure exerted on these weight-bearing portions of the body. In a similar manner, a person lying down on a bed, for example, feels even more relaxed compared to a seated person, as the body weight of the lying person is distributed on the entire side of the body that comes into contact with the bed, further decreasing the pressure on the body where it contacts the bed. Improvements in the design of various chairs, sofas, stools, bean bags, beds, etc that support the body weight of people over the years have significantly improved the user comfort. For example, chairs used in the office or at home, automobile seats or airplane seats are designed ergonomically and with leaning backrests, that can support the weight of a person by contacting larger surface of a body (e.g., back of torso). Various types of cushions including, for example, memory foams, are used which conform to the body curvatures have substantially improved user comfort, by increasing the area available for body weight distribution.

Nevertheless, these devices are not designed to completely relieve the weight of the upper parts of the body, (e.g., head, arms, shoulders, upper torso), exerted on the lower weight-bearing regions of the body (e.g., spine, coccyx, sacrum, buttocks, etc) in a seated person. This is because, in a seated person, often only one side or a limited area of the body touches the supporting surface. For example, the seat of a chair supports the posterior aspect (bottom side) of the thighs and buttocks. Similarly, the backrest, depending on the angle, may partially support posterior/dorsal aspect of the torso, when leaned back. As a result, the weight of a seated person is still concentrated on a limited number of regions of the body, often referred to as the "weight-bearing regions" of the body, e.g., buttocks, coccyx, trochanters, sacrum, vertebral column, underside of thighs etc. As a result, sitting on a chair for prolonged periods, subjects the weight-bearing regions to repeated stresses, and causes fatigue of these structures, and makes them prone to various disorders, e.g., chronic back pain due to stressed back muscles, compression of inter-vertebral discs, and the like. Likewise, prolonged standing in an upright position, or carrying loads, jumping or running may result in significant structures on other weight-bearing structures of the body, including spine, joints of the hips and knees, and on the soles, resulting in various disorders.

Disclosed herein are methods, systems and devices to distribute the body weight over larger area of the body, including on to the anterior (front), and lateral (left and right) sides of the torso and thighs of a seated person, in addition to the dorsal/posterior aspects of the torso and thighs, thereby minimizing the pressure on the weight-bearing regions. In other words, a seated person using the WDD as described herein, will feel pressure on the front, sides and back of the thighs and torso, instead of just on the weight-bearing regions, e.g., buttocks, underside of the thighs and back side of torso. A seated person is used as an example here; however, the principle of weight distribution applies to a person in any other positions (e.g., standing or lying down), or to a body part, and disclosed herein.

The principles of the disclosed invention may be best explained by using the analogy of buoyancy forces acting on the body of a person submerged either partially or completely in water (or any fluid medium). As an example, a person, or a body part of a person, submerged in a swimming pool will have pressure applied on all surfaces of the body that come into contact with the water. Based on Archimedes' principle, the total amount of force exerted on the immersed portion of the body is equivalent to the weight of the water displaced. Because, water exerts pressure on all sides of the body that come into contact with water, forces that act on opposite sides of the body cancel out, and therefore, the body does not move in a horizontal direction as a result of these forces. However, water also exerts a net upward buoyancy force on the person, because of the weight of the displaced water acting on the part of the body that is contact with the water, resulting in an upward movement of the body. As a result of the buoyancy forces on the body, due to weight of the surrounding water supporting the body weight of the person, using the entire surface of the body with which the water comes into contact, less weight is experienced on weight-bearing structures of the person, in this case, the spine, the joints, legs and soles of the feet. However, as water supports the weight of the person using a large surface area of the person, with whom it comes into contact, it exerts only a minimal pressure at each location on the skin. As an example, a person weighing 150 pounds, and with an assumed surface area of 50 square inches for both feet combined, experiences approximately 3 lbs/square inch of pressure on the soles. The same person when completely immersed in water experiences approximately 0.0544 lbs/square inch (2.813 mm Hg) that varies with depth, assuming a total body surface area of 1.78 m.sup.2 (2759 square inches). Therefore, the pressure on the soles of the feet drops from 3 lbs/square inch to approximately 0.0544 lbs/square inch in the pool, depending on the height and average specific gravity of the person and depth of the pool.

Unlike a solid surface, such as a seat of a chair, water however, does not cause significant friction or shear forces on the skin when supporting the body weight. Several factors contribute to this effect, including the ability of the water to slide over the layer of water that is in close contact with the body, decreased pressure exerted on the skin, exertion of force on opposite directions of the body, etc. As a result, the buoyancy forces on the body are able to lift a person upwards, without causing significant shear or stress on contacting surfaces or underlying tissue.

The methods and various embodiments of devices disclosed in this application, exert forces on the body of a person with or without using a fluid medium for reducing loads on weight-bearing structures of a body, or increasing loads weight-bearing structures of a body by exerting forces over a large body surface, in manner somewhat similar to how water exerts hydrostatic forces on the body. Disclosed also are methods and some embodiments to reduce or increase loads on weight-bearing structures of a body of a person, without significantly increasing shear forces on the skin and underlying tissues. Further, methods and embodiments are disclosed herein that are useful for either decreasing or increasing loads on soft tissues of a body, without increasing shear forces on the skin and underlying tissue of a person, to prevent or treat various disease conditions in humans.

The invention also involves use of either a passive or active force to distribute the weight of the person. The term "passive force" is defined as force exerted on the supporting structure or the body due to the body weight of a person, while the "active force" is the force exerted on the supporting structure or the body of the person using an external force.

Further examples of disclosures in this application are methods, systems and devices of a Load Concentration Device (LCD) for exerting forces on the body of a person on earth or an astronaut in a microgravity environment, such that, e.g., the astronaut feels a load on the weight-bearing parts of the body. The load is used to counteract weightlessness, which causes adverse physiological effects during prolonged stays in microgravity.

Further, various methods, systems and devices for applications of the WDD and LCD on earth and in space are disclosed in this application.

As the mechanism of the WDD and LCD are to some extent similar, except for the direction of the net force acting on the body, throughout the present disclosure WDD will primarily be described, it being understood that other embodiments, such as a LCD, are intended to be included within the scope of this invention and will be mentioned at other places when appropriate.

It is to be appreciated that certain aspects, modes, embodiments, variations and features of the invention are described below in various levels of detail in order to provide a substantial understanding of the present invention.

Definitions of certain terms as used in this specification are provided below. Unless defined otherwise, all technical and scientific terms used herein generally have the same meaning as commonly understood by one of ordinary skill in the art to which this invention belongs.

It is to be understood that this disclosure is not limited to specific method steps, as such can vary. It is also to be understood that the terminology used herein is for the purpose of describing particular embodiments only, and is not intended to be limiting. Methods recited herein can be carried out in any order of the recited events that is logically possible, as well as the recited order of events. Where a range of values is provided, it is understood that each intervening value, between the upper and lower limit of that range, and any other stated or intervening value in that stated range, is encompassed within the description. The upper and lower limits of these smaller ranges may independently be included in the smaller ranges, and are also encompassed, subject to any specifically excluded limit in the stated range. Where the stated range includes one or both of the limits, ranges excluding either or both of those included limits are also included in the present disclosure. Also, it is contemplated that any optional feature of the disclosed variations described can be set forth and claimed independently, or in combination with any one or more of the features described herein.

All literature and similar materials cited in this application, including but not limited to patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates, which may need to be independently confirmed.

As used in this specification and the appended claims, the singular forms "a", "an" and "the" include plural referents unless the content clearly dictates otherwise. For example, reference to "an element" includes a combination of two or more elements, and the like.

As used herein, "about" will be understood by persons of ordinary skill in the art and will vary to some extent depending upon the context in which it is used.

For purposes of simplifying the description of the disclosure, and not by way of limitation, a "body" will primarily be described herein, it being understood that essentially body may entail a whole body, a body part, an appendage, or an organ. While the present methods and systems will typically be used with human subjects, they may also be used with other vertebrates, primates, farm animals such as swine, cattle and poultry, sport animals such as horses, and pets including dogs, cats, and rodents.

In some embodiments, the instant invention attempts to provide a practical, safe, and effective device which exerts pressure over some or all of a body surface, in all directions including above, sides and underneath, thereby lowering significantly the pressure or weight on a given region.

In the application, the words "pressure", "weight", "force", "stress", "shear" and "load" are used to describe various forces acting on the body (e.g., gravitational force, buoyancy force, pressure exerted by the apparatus, weight exerted by the upper portions of the body on the lower portions of the body, hydrostatic force, mechanical force, reactionary force exerted by the surface with which the body comes in contact), or the body exerts on internal organs (e.g., capillary pressure, total peripheral resistance, tissue pressure, shear force, tissue deformation, load on the spine, tension on muscles, compression, expansion, stretch, contraction) or external objects with which it come in to contact (e.g., seat of a chair, bed).

It should be noted that pressure is generally defined as force per unit area and for example, can be expressed as pounds per square inch, mmHg, Pascals, etc. However, shear forces are defined as forces that act in opposing directions such that it deforms tissue in parallel planes. Shear stress occurs when there is sliding or the potential for relative motion between two surfaces. The units of shear force are pounds per square inch, mmHg, Pascals, etc. The skin and underlying tissue are subjected to shear forces when force is applied externally, potentially leading to discomfort to significant injury. In some embodiments described in this application, the systems and methods are configured to reduce the shear forces on the skin and underlying tissue. As such, the resulting shear can be in the range of 0 up to 100000 mm Hg, with ranges from 100000 to 10000 mm Hg, 10000 to 1000 mm Hg, 1000 to 100 mm Hg, 100 to 10 mm Hg and 10 to 0 mm Hg.

In some embodiments, provided herein is an apparatus that supports all or some of an individual's body or body portions that are weight-bearing. For example, the apparatus may be adapted to support the feet, legs, seating area (thighs, buttocks), abdomen and back of shoulder, and the like of an individual who is seated or lying down, in outer space or it may be adapted to support body regions or appendages such as the leg, torso, arm, chest, back, breast, belly, knee, ankle, pelvis, head, neck, thigh, calf, shin, hip, elbow, wrist, finger, toe, or any combination thereof. The apparatus can be adapted to accommodate a person in virtually any position, including, prone, seated, standing, kneeling, walking, running, flying, suspended freely, floating, submerged, hanging or supported by limbs, in space in microgravity conditions, on other planets or any one part or combination thereof. Various devices (e.g., chairs, seats, sofas, beds, mattresses, cushions, exoskeletons and the like) may be manufactured to include the principles of the apparatus, or the device may be a stand-alone unit designed to be worn by person while moving around (e.g. in the form of pants, jacket, backpack, undergarment, and the like), or made as an add-on device, that can be fitted to any existing devices in use (e.g., chairs and mattresses).

The main principles and the mechanism of the weight distribution (using WDD) and exerting load (using LCD) on the body are provided herein. When the mechanism of various embodiments described in sections are similar, the description of the WDD mechanism for individual embodiments is not repeated. As both WDD and LCD operate based on same broad mechanism, in terms of distributing load away from the body or exerting force on the body, the WDD is primarily used to describe the principles, design details and operation of various embodiments. Details on the design and operation of LCD are described in these sections as appropriate.

The principle of distribution of body weight on the weight-bearing structures of the body described in this invention is best explained using the analogy to a person standing in water in a swimming pool. The displaced weight of the water exerts hydrostatic forces on the body of the person in all directions, including from top, horizontally and upwards. The forces that act on the opposite directions on the body cancel out, leaving a net upward buoyancy force to act against net gravitational force that acts downwards. As the hydrostatic forces are exerted all over the surface of the body that comes into contact with the water, the body weight is borne by all surfaces of the body that come into contact with the water, instead of, as occurs on land, just the soles of the feet, leg joints and spine, thereby decreasing the amount of load experienced on the feet. It is to be noted that although water supports the weight of the person, the shear forces exerted by water on the skin and the underlying tissue are very minimal. In a similar manner, the WDD minimizes the shear forces on the body as explained hereinbelow.

To exert forces that are analogous to the hydrostatic forces, the WDD employs mechanical means referred to as Weight-Bearing Elements (WBEs), placed around the body to exert pressure on the body of the user. Similar to how the walls of a swimming pool holds water that supports a person in the water, the WBEs are supported by a frame which act like a wall, and contact the surface the person to bear the weight of the person. The WBEs exert pressure in all directions; however, they are designed to exert a net pressure that is directed either in an upward direction with WDDs resulting in decreased load on the weight-bearing structures of the body, or in a downward direction towards the feet when standing, and buttocks when seated resulting in an increased load on the weight-bearing structures of the body.

It is to be noted that "exertion of forces" is used to indicate various types of forces exerted on the body using the WDD or LCD. When body presses against WBEs or other parts of the WDDs/LCDs, the force exerted by the weight of the body on the WDDs/LCDs is also considered as exertion of forces on the user's body by these devices.

FIG. 1A illustrates an exemplified embodiment of a WDD that surrounds the torso of a person 106 on all sides. The WDD comprises WBEs (146, 143, and 142) that contact the surface of the body all around, and are supported by an inflatable bladder 141 that is contained in a frame 140. The WBEs may exert pressure against the body, e.g., in an upward (143), horizontal (142) or downward (146), or other direction, based on the direction of their alignment with the body and direction in which the pressure is exerted by the supporting surface. In the figure, the direction of forces exerted on the body by the WBE are indicated using various arrows, and the total force exerted by these WBEs on the whole body is designed appropriately to support the amount of desired body weight. The forces acting across the body may be similar in magnitude at all parts of the body (not shown in the figure) or variable, as shown in the figure. The length of an arrow reflects the approximate magnitude of force on the body, relative to other forces. In some embodiments, the WBEs exert a gradient of forces on the body, with higher forces at the lower portions of the torso, and lesser force while going upwards towards the head. As the forces that push the body on opposite directions cancel out, there is no physical movement of the body in any direction as a result of these forces. The gravitational force that acts on the body acts in a downward direction. This force is opposed by the various upward forces exerted by the WBEs, which result in a net upward force 144 that acts in the direction opposite of the gravitation force 145 that is directed downward. The net upward force 144 is similar to the buoyancy force that a person feels in the swimming pool, which is responsible for the reduced weight feeling and upper parts of the body on the spine, joints, feet and other weight-bearing structures of the body.

It should be noted, because the forces exerted by WBEs act in all directions against both the skin and the underlying tissue (upward, downward, horizontal, etc), although a net upward force is exerted on the body, such a force does not cause the skin to slide against the underlying tissue significantly, thereby reducing any shear forces on the underlying tissue. Further, as the WBEs are designed to move with the contact surface (skin, in this case), they do not increase shear forces on the skin. This is very significant, since skin and underlying tissue are often subjected to friction and shear forces, when they come into contact with the solid supporting surfaces such as seat of a chair or a bed. This characteristic of the WDD (or LCD) to decrease the shear forces on the skin, while distributing the body weight, or exerting additional load are discussed later in the application, with reference to pressure ulcers, motion simulation and for applications of LCD for preventing bone and muscle loss in astronauts, and for other applications on earth.

Figure 1B:
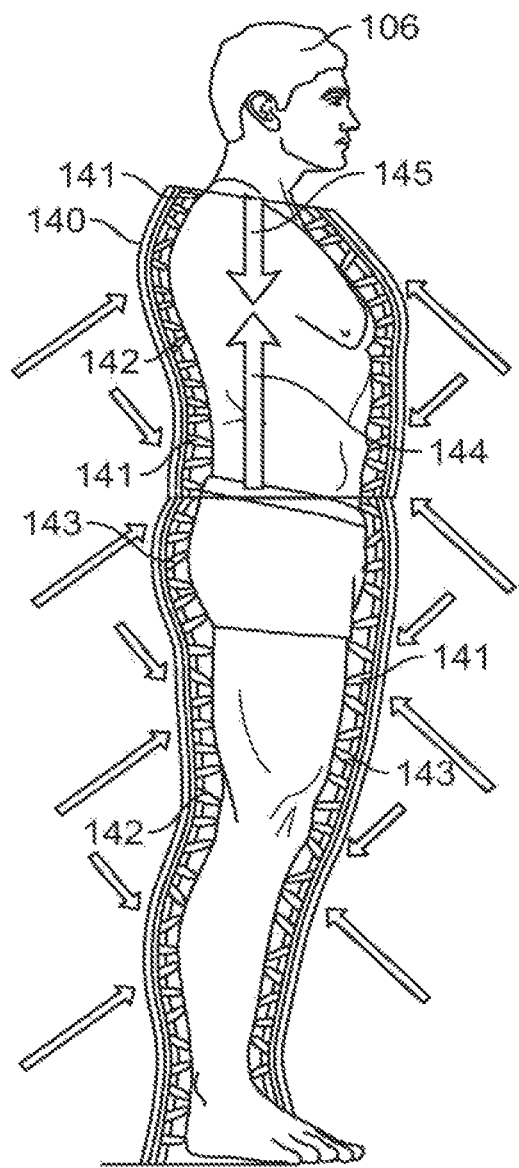
FIG. 1B illustrates an embodiment of WDD and shows direction of various forces acting on the person wearing the WDD while standing.

FIG. 1B shows some embodiments of WDD that covers the whole body of an individual 106, and various forces exerted by the WDD. As noted earlier in FIG. 1A, a net upward force 144 resulting from the upward push from WBEs, acting against the gravitational force 145 causes the person's weight to be shifted from the primary weight-bearing structures (e.g., soles of the feet, torso, joints of legs, spine) to all over the surface of the body, where the WBEs make a contact with the body. Direction and relative magnitude, which is not to be scale, of various forces that act on an individual standing in an upright position when using WDD, are shown in the figure as double arrows without numbers.

Figure 1C:
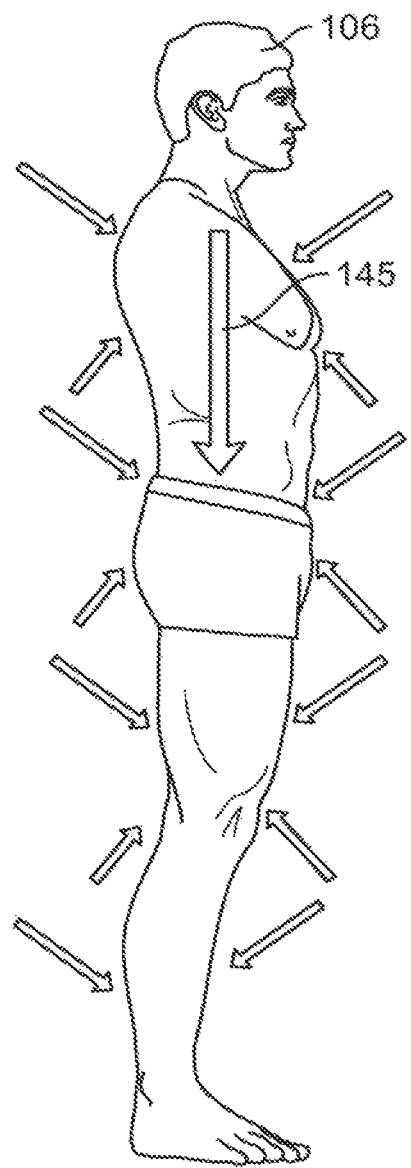
FIG. 1C illustrates direction of forces exerted on a person when standing, while wearing a Load Concentration Device (LCD) in microgravity conditions.
Figure 1D:
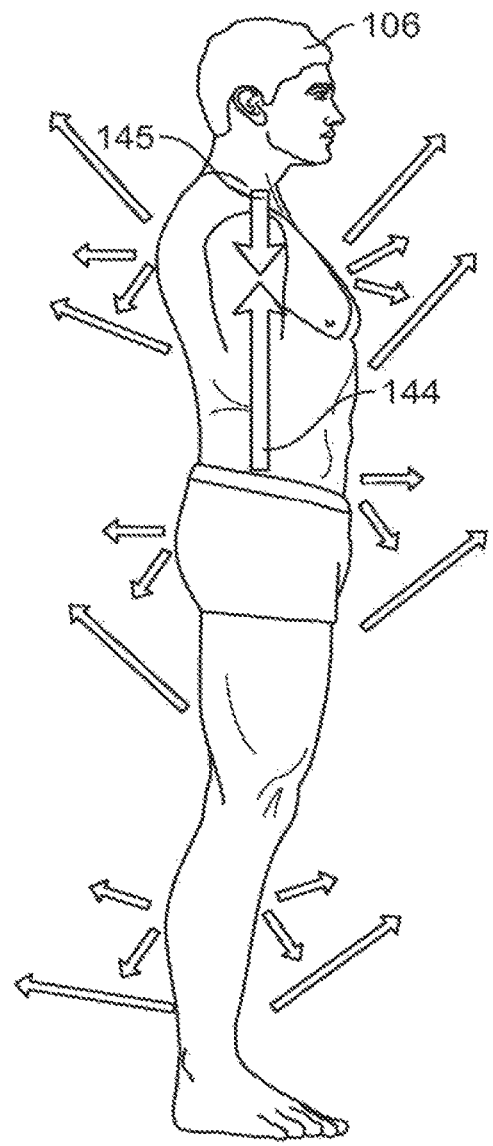
FIG. 1D illustrates direction of forces exerted on a person when pulling forces are exerted to distribute the weight of a person using WDD.

FIG. 1D shows some embodiments of WDDs and LCDs covering the whole body of a person standing in upright position, and various forces exerted by the WDD/LCD are shown.

Various embodiments of WDDs and LCDs may use different methods to exert forces on an individual. FIG. 1D shows how a WDD/LCD can distribute body weight or increase load on the body of a person, using pulling-type of forces. Some embodiments of WDDs/LCDs may employ fabric, bands, or straps and the like (with or without WBEs) that surround a person, and exert a pulling force in an opposite direction to achieve the desired effect. Similar to the WDD that uses push type WBEs, a net upward force is exerted by the bands that pull on the subject, resulting in decreased weight on the lower part of the torso or feet of the person.

In certain applications, it is advantageous to increase the weight or load on the weight-bearing regions of a body. For example, exerting forces that act in the same way as body weight under terrestrial gravitational conditions may be advantageous to prevent some of the adverse effects, such as bone and muscle loss, experienced during prolonged periods of stay in the space. However, exerting loads using traditional cords or harnesses, belts and waist bands cause discomfort to the astronaut's because they are unable to tolerate the increased local pressure. Therefore, some embodiments of methods and devices are described in this section useful for exerting forces on astronauts or on people on the earth, so as to exert force on the surface of the body, resulting in an increase in net load on weight-bearing regions of the body, but with minimal increase in friction or shear forces on the skin and underlying tissue.

FIG. 1C shows forces exerted by a Load Concentration Device (LCD) on the body. The LCD is mostly similar in design to the WDD shown in FIG. 1B, in that it covers the whole body of a person, except that the device exerts forces on the body of a person, such that the load on weight-bearing structures of the person is increased. The LCD surrounds the body of a person as shown in FIG. hB, however, note that no LCD is shown in the FIG. 1C. Instead, the figure only shows the direction and magnitude of various forces exerted by an embodiment of LCD that may be worn, e.g., by an astronaut. The LCD may appear similar to WDD shown in the FIG. 1B, except that additional force may be applied on the head, neck and shoulders, torso, waist, thighs and legs, etc of a person using LCD using rings in the frame at each joint or against a sole plate (not shown). The WBEs are designed to exert forces in all directions on the astronaut's body as shown by the arrows (upward, downward and horizontal, etc), with a net force directed towards the waist or feet, as indicated by large downward arrows. Note that no gravitational force is present in this situation, as the person 106 in the figure represents an astronaut in the space. Since the WBEs of the LCD, exerts force on all directions at the skin surface, minimal shear forces are anticipated at the skin surface or on underlying tissue. If the person 106 using the device shown in the figure were to be on earth or other gravitational fields, then the device increases the load on the person, as it acts in synergy with the gravitation force.

Some embodiments of methods and WDD and LCD devices disclosed herein reduce exert forces on a person, with minimal frictional forces on the skin and shear forces on the underlying tissue, so that the person is able to tolerate the exerted forced over longer periods. The principles behind the mechanism are described below in this section.

Briefly, a person standing on land, when lifted up into the air using straps or a harness usually feels high pressure (and may be discomfort or pain) at locations on the body where the straps come into contact with the body. Additionally, the skin at the contact location experiences friction, tends to move in the same direction in which the straps are pulled, and therefore, slides over the underlying tissue, thereby, exerting "shear forces" on the underlying tissue. Damage from shear forces occurs, when the subcutaneous structures including muscle and bone move in opposite direction of the force applied on the skin. Shear forces at the contact site cause discomfort and pain, sometime damage to the local tissue, and therefore, reduce the tolerability of supporting structures over prolonged periods. For example, a person wearing a cast to support an injured leg feels pressure and friction at the edges, where the cast contacts and exerts force on the skin and the underlying tissue. Similarly, a person sitting in a wheelchair is subjected to shear forces under the thighs that contact the seat of the chair, when the person moves, which over time may lead to formation of pressure ulcers.

Therefore, disclosed in this application are embodiments of methods and devices to minimize such shear forces; on the body. The WDDs/LCDS accomplish this by distributing the weight of the body over a larger surface, thereby lowering the pressure at the site of contact, and by applying forces on the body at the site of contact in several directions (upward, downward horizontally and at angles), thereby preventing the sliding of skin over the underlying tissue. Some of these forces (either a passive or an active force) are applied in opposite directions on the body. The phrase "passive force" is meant to indicate a force exerted by a fixed surface on the body, when the body is pushed against the fixed surface. As these forces act on both the skin and the underlying muscles in the opposite directions, they do not force the skin to slide significantly over the underlying subcutaneous tissue, and hence the shear forces are minimal. As such, unlike the belts, cords ropes, harnesses, casts, etc, which cause friction and shear forces on the skin and underlying tissue, when a person's body weight is supported by these devices or the loads is exerted (e.g., loads carried by a person using the straps) on a person using these devices, the WDD and LCDs essentially do not cause shear forces on the skin, and hence the devices are well tolerated. Further, as the weight is distributed over wider surface with the WDD and LCD, the pressure on skin is much less compared using the straps and other devices.

Various embodiments of the WDD systems also facilitate the body of a person to achieve a dynamic equilibrium between the body weight of the person and the forces exerted by the system on the body, such that exerted force on any location is quickly distributed on a larger surface area of the body, thereby minimizing significant increase in pressures at any location. The LCDs likewise, facilitate the body of an astronaut in microgravity condition to achieve a dynamic equilibrium between the forces exerted on the body and the reactionary force from the body against the forces.

A person's body weight may be distributed by WDDs that employ either inflatable or non-inflatable structures, or combinations thereof. LCDs may operate in a similar manner using either inflatable or non-inflatable structures, as described for WDDs. Various components of WDDs (e.g., frame, bladder, WBEs, sheet), and their mechanism of action without limitation on the number of parts, their design or function, are disclosed herein. A device integrated into a chair to support a seated person is used as an example to explain the mechanism of weight distribution. However, the method may be used for supporting a person in several other postures and doing various activities (e.g., standing upright or lying down). For the purposes of explanation, only a torso is shown to be covered by the device, however, it should be noted that the device can be used on the whole body or various individual parts of the body.

Briefly, the WDD comprises a frame that surrounds the body of an individual and supports the body weight of the individual. The frame encloses optional inflatable balloon-like structures between its layers, which in turn may support the weight-bearing elements (WBE) that exert forces similar to hydrostatic forces on the individual. Although WBEs exert forces in all directions, the WDD is designed to exert a net upward force that is similar to a buoyancy force exerted on the body, which acts in opposite direction of gravitational force on the body, resulting in a decreased overall body weight as experienced by a person wearing the WDD.

Figure 1E:
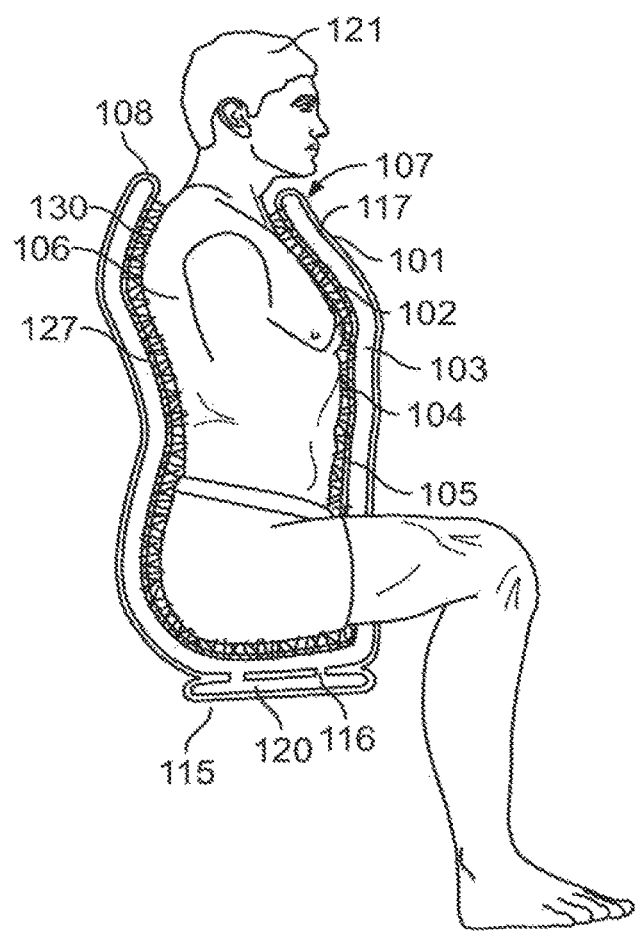
FIG. 1E is a view of generalized embodiments of a WDD/LCD weight distribution apparatus supporting the torso of the person.
Figure 1F:
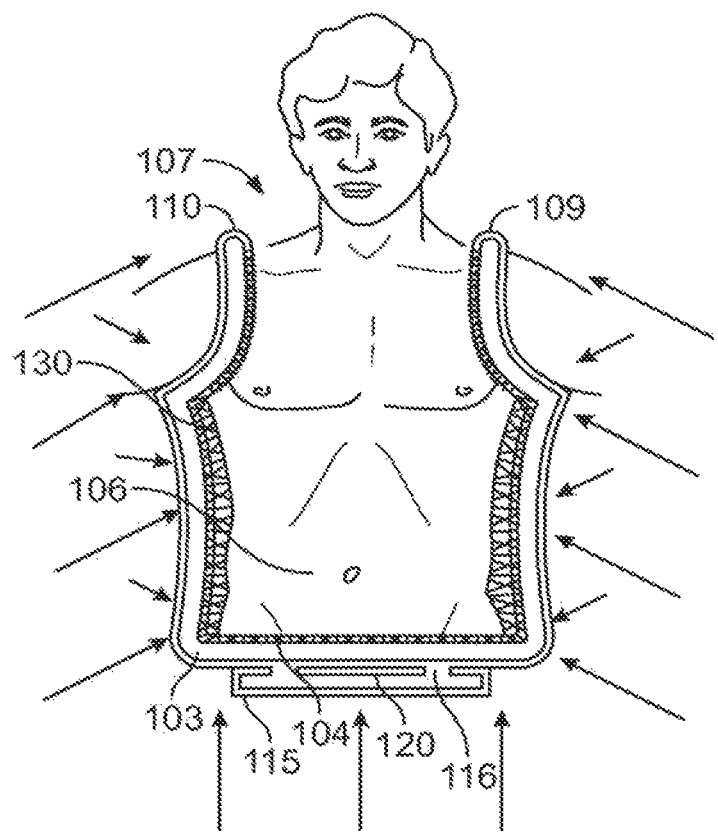
FIG. 1F is a front view of an embodiment of WDD/LCD supporting the torso of a person.
Figure 1G:
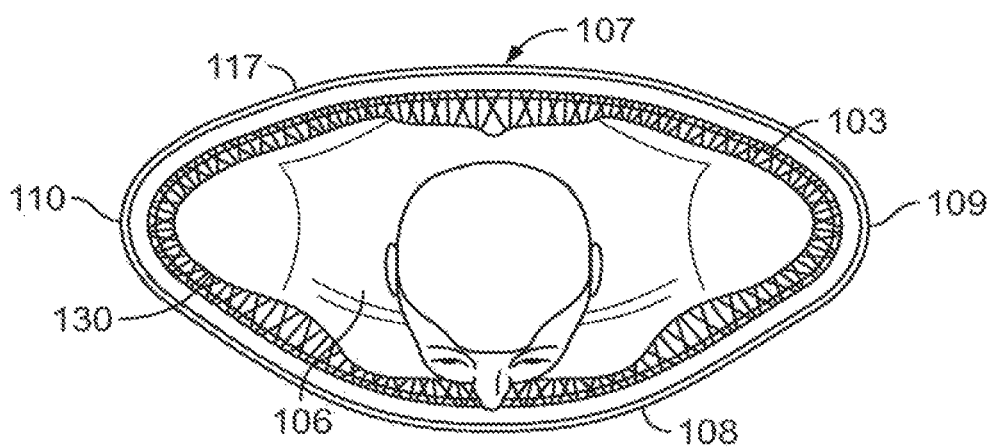
FIG. 1G is a cross-sectional view of an embodiment of WDD/LCD at the torso level, supporting the person.

The details of the individual components of WDD and LCD are provided in FIGS. 1E, 1F and 1G. Rather than describing the individual components of each figure, individual parts of the above figures are described in various embodiments, including: the frame, the inflatable structure, the WBEs and the sheet. Various forces exerted on a person using WDD and LCD shown in FIGS. 1E to 1G are described earlier (refer to FIGS. 1A to 1D). Operation of the embodiments shown in FIGS. 1E to 1G are explain herein below in this section, and together with the operation of device shown FIG. 2-A.

Referring to generalized sectional views of WDDs as depicted in FIGS. 1E, 1F and 1G, frame 107 that surrounds a person, comprises an outer surface 117 and an inner surface 127, designed to support at least a fraction of person's body weight or a part thereof. The frame, in some embodiments, may be supported within and/or elevated off a base surface, or may be integrated into a structure or surface, such as above a bed, chair, seat, car seat, recliner, sofa, tub, basin, chamber, shoe, dance shoe, ballet shoe, exoskeleton, sheet, clothing, cast, braces, pants, jacket, hat, helmet, various supporting structures, or the like. In some embodiments, frames of external devices such as chairs, seats, couches and the like may act as frame. The torso and thighs are used in the figures to explain the mechanism, however, it should be noted that the description of the methods and the device are applicable to other parts of the body, without limitation.

The frame along with the optional bladder and the WBEs surrounds at least one side of the body in some embodiments, as shown FIGS. 1F and 1G. FIG. 1F shows a front view of the apparatus with 107 showing the right side 110 and left side 109 of the frame. FIG. 1G shows a cross-sectional view of the WDD at the mid torso level. The frame may be made up of at least one layer or multiple layers, or may be comprised of sheets, mesh, tubes, rods, plates, fibers, threads, fabric, and the like to support the body weight. The frame may be supported from all sides, including from within or outside, as well as using structures that are not integral part of the device, e.g., walls, roof, furniture frame, interior of vehicles, and the like (not shown in the figure). The frame may be a single piece covering the part of the body of interest, or can be more than one unit, which can be overlapping and capable of sliding over each other. In some embodiments, the frame may be able to slide up and down over supporting structures to facilitate shifting of body weight on to the frame. In some embodiments, the frame may be a mesh of wire or a sheet supported by surrounding structures, which can keep the mesh stretched to provide tensile strength. In some embodiments, the mesh may be able to conform to the body contours and come into contact with the body directly (without the need for WBE) to support and distribute the body weight of an individual.

The frame may define an interior space which may generally extend the complete length and circumference of the body 106, or may just cover either the front, back or sides or a part thereof of the body, although one or more portions 121 (head and shoulders) of the body may extend beyond the interior space of the apparatus. In some embodiments, the interior space of the frame may contain at least one expandable and contractible structure (e.g. inflatable bladder or tubes containing any type of fluid, a gas or a liquid or a combination thereof) containing an outer layer 103 and an inner layer 102. The inflatable bladder may be a single unit or may comprise several smaller bladders, or tubes without any limitation to their size. In some embodiments the bladder may have an additional reservoir, as shown in one embodiment in FIG. 1E, in which reservoir portion of the bladder 120 is located in the base 115 and connected to the space between the inner and outer layers of the frame through opening 116 (or tubes). In some embodiments, the frame may extend above or beyond the seated person, and extend out in all directions, to be attached to various supporting structures. There are no limitations on the position of various structures supported by the frame (e.g. bladder, the WBEs). For example, the frame may accommodate the bladder or the fluid reservoir below the seated person under the seat, or overhead above the level of the seated person, or at other locations. In some embodiments, when the frame holds a reservoir of fluid at a level higher than the head of a seated person, the bladder or the reservoir may be configured to hold fluid displaced from the bladder by the weight of the person, the displace fluid in turn may exert force similar to hydrostatic forces on the seated person, thereby providing a means to distribute the body weight of a person, using one own weight.

The frame may also be configured to cover just the regions of interest on the body (e.g., an injured region of the body, such as leg or torso). The frame may be rigid, semi-rigid, resilient, flexible or soft and allow for predetermined flexibility (e.g., for stretching, relaxation, leaning forward and backward, or sideways, or movement generally, of the legs or arms through the entire range of motion), to permit natural movement of the body (e.g., be able to expand to accommodate expansion of the chest and abdomen during respiration, bending or extension of body to perform various activities). The frame may be conformed to the size and shape of the individual's body or body parts as supported therein. The frame can be a single unit or made up of several independent pieces without limitation on the size and shape. The apparatus may be used to support a whole body and/or body regions or appendages, including the neck, head, leg, arm, trunk, torso, chest, abdomen, hip, hand, foot, finger, shoulder, elbow, wrist, joint, limb, head, or a combination thereof. FIG. 1F shows front view of the same WDD shown in FIG. 1A, covering the lateral surfaces of the torso, with the right side 110 and left side 109 of the frame.

In some embodiments, there is no limitation on the size, weight, shape and number of layers of the frame. The frame without limitation may be shaped in the form of a body cast, shirt, pant, or a suite, or a jacket, an inner or outer garment, or in the form of a seat, chair, bed, mattress, cushion, a harness, and the like. The frame may be incorporated into other devices such as a driver's seat, or as an integral component of the cockpit, a walker of an elderly person, or a massage chair, a brace, a shoe and the like to support the complete body or a part thereof.

In some embodiments, some or the entire frame is fixed and stationary. In some embodiments, the frame, or portions thereof, are movable and/or flexible. The frame may be in contact with the body of the person, or without directly touching a person (for example, when magnetic forces are used to support body of a person). In some embodiments, a frame can be rigid, semi rigid, soft, expandable, collapsible, stretchable and/or resilient. In some embodiments, a frame can include various structures including, but not limited to, sections, panels, plates, beam, belt, sling, strings, rods, fabric, sheet, strings, hammock, rings, struts, hollow or solid structure, slings, belts, strap, flap, slat, rod, tubes, vertical member, horizontal member, members at an angle, mesh, cage, net screen, web, springs, fine brushes, inflatable or telescoping structures, casts, tiles, pads, cushions, securing means, attachment means, hinges, rivets, screws, belts, magnets, snaps, buttons, velcro, fasteners and combinations thereof. The frame can be made of any suitable material, non-limiting examples of which include: metal, alloy, plastic, polymer, wood, leather, magnetic materials, ceramic, stone, clay, plaster, plant or animal products, fabric, or combinations thereof. In some embodiments, the frame may cover the entire body or parts thereof.

Figure 5:
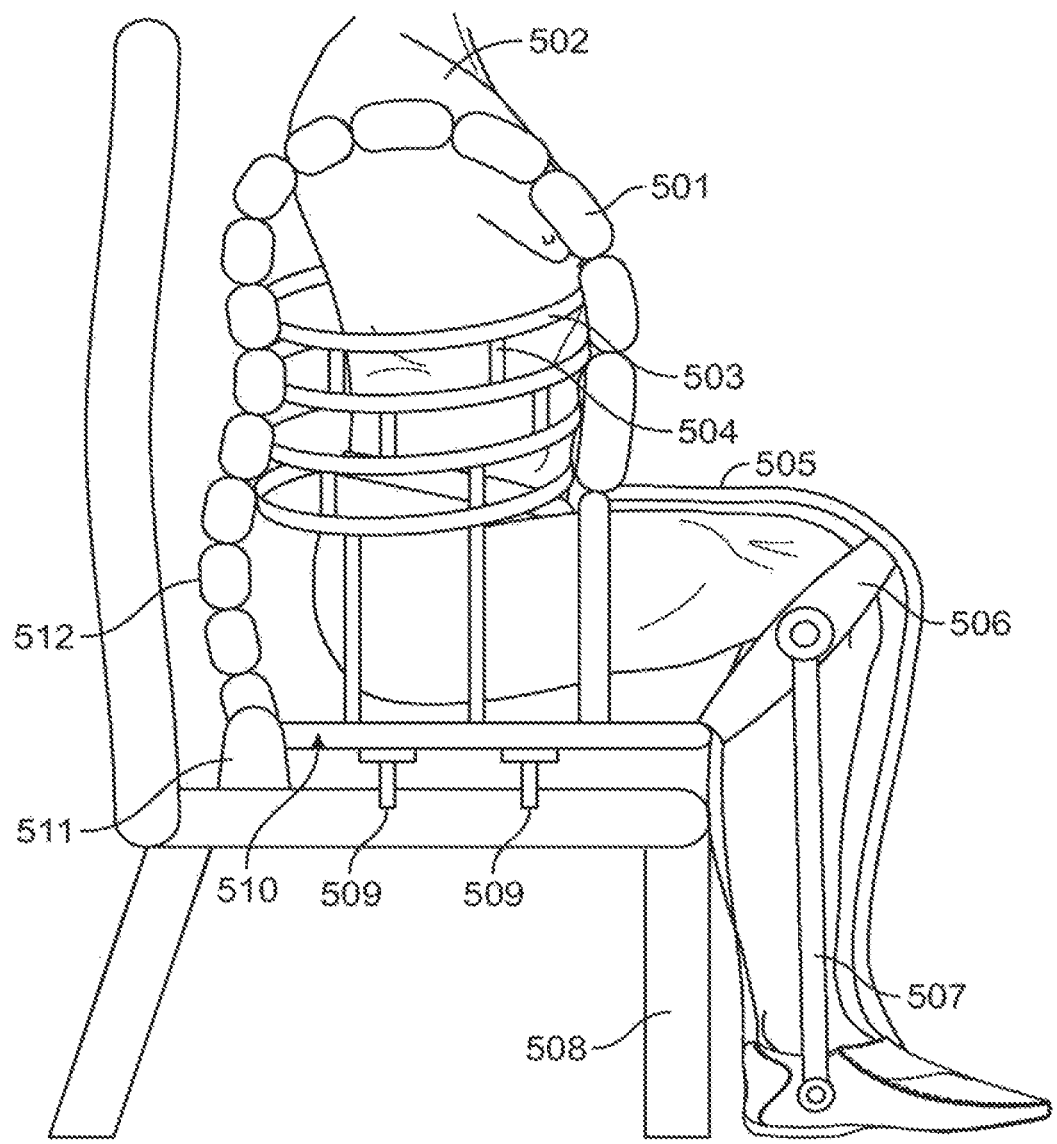
FIG. 5 illustrates an embodiment of a WDD/LCD, containing a flexible frame and supporting structures covering the torso and the legs that support the WBEs in accordance with the present invention.

FIG. 5 shows an additional embodiment of the frame, as an example, without limitations, for use in an apparatus of the present invention. Frames may be rigid, semi-flexible or flexible to accommodate free movement of the body, without compromising the strength required to support the body weight. Frame may be provided with sensors (not shown in the figure) that measure pressure exerted on each segment of the frame, which may be used to determine the amount of force to be applied on the body, either for the purpose of distributing the body weight from weight-bearing regions (as in WDDs) or to concentrate loads on the body (LCD). The frame in FIG. 5, comprises, members 512 that may possess flexibility and rigidity that is somewhat similar to that of the spine and back (vertebral column plus back muscles) of a person. Individual parts of the frame may be made to contain joints that have limited flexibility. The frame includes vertical members 504 and horizontal members 503. The frame members support various planks, flaps, and inflatable structures like bladders or other members that support the WBEs (not shown in the figure). The WBEs (not shown), which contact the body 502 of the user, off-load the weight of the person onto a frame, as described hereinbelow.

The frame members 501 covering the front or the top portions of the torso may be designed to facilitate expansion or contraction and have adequate flexibility in all directions to facilitate the user to perform various activities while seated. The weight of the frame covering the torso may be supported by a base of the frame 511 that rests on the seat of the chair 508. The frame may contain additional members 510 that may used to raise the frame using connecting members 509. The connecting members 509 may be connected to an external power source or to manual levers, to raise the frame. When the frame is raised after the user secures the frame to the body while seated, it results in pressure applied to the body through WBEs, facilitating off-loading of the weight of the person on to frame. The frame may cover the entire body including portion 505 that covers the thighs. The frame may have joints 506 at various locations to allow flexibility. The frame may contain longitudinal members 507 to connect the frame to the floor or shoes of the person. The frame shown in FIG. 5 may be integrated into furniture like chair, or used in portable WDDs to distribute weight of a person in various postures.

Figure 6A:
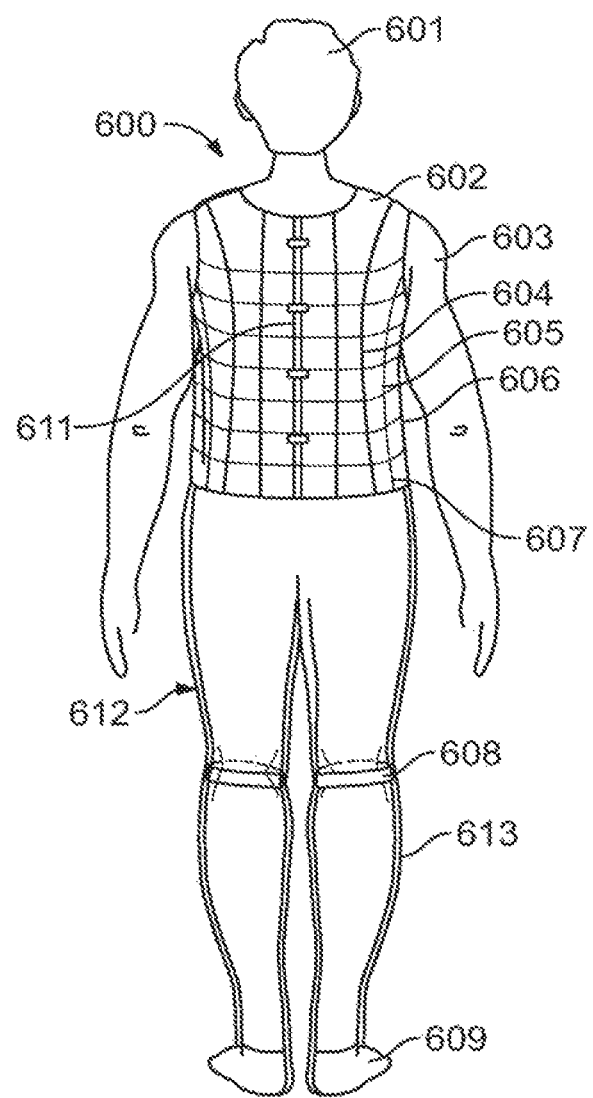
FIG. 6A illustrates an exemplary view of a WDD/LCD, worn by a person, while in an upright position, with the frame to reduce or increase load on the torso legs in accordance with embodiments of the present invention.

The individual sections of the frames that cover various parts of the body, supporting the WBEs, may facilitate staged unloading of weight of various parts of the body on to the frame. For example, in a sitting person (as in FIG. 5), individual segments of the frame covering the upper torso increase pressure on the WBEs, causing the weight of the torso to be unloaded on to the torso frame, which is passed down and ultimately unloaded onto the seat of the chair. However, in a standing person (as shown in FIG. 6A), weight of the torso is unloaded onto a frame that supports the thighs, and which in turn is unloaded on to leg frame, supported by the floor, in a staged manner.

Referring to a generalized sectional views of a WDD as depicted in FIGS. 1E, 1F and 1G, bladder frame 107 that surrounds a person, comprises an outer surface of the frame 117 and an inner surface of the frame 127, designed In some embodiments of the WDD or LCD devices, contained within or outside the frame is at least one inflatable structure, such as a bladder. The term "bladder" is used interchangeably with "inflatable structures" herein, although the inflatable structure can be a tube, balloon, expandable gel, polymer, or a mechanical expandable system (e.g., supported by expandable stent or mesh like structures that can be opened). In some embodiments, the bladder can be continuous, or can be divided into different compartments, or is comprised of small independent bladders. In a seated person the bladder may cover front, back, sides and above, or may cover at least one side of the body including lateral, front, back, top, below or a combination thereof. In some embodiments, the bladder covers all sides of the body for maximum effect. In some embodiments, only a fluid filled bladder is used, without WBEs. In some embodiments, various combinations of a fluid-filled bladder and protruding WBEs that rest on the bladder or are connected continuously to the bladder are used. In some embodiments, fluid-filled tubes are used instead of the bladder to exert the pressure on the WBEs or the body (not shown in the figure). The bladder can be in sections which can have any suitable size, which can range from, e.g., nano-size dimensions, to dimension of a body region, appendage or organ, to the dimension of the whole body.

Bladders may be filled with various types of fluids. The term fluid is meant to include gas, liquid, vapors, solution, suspension, gel, foam, solid material in the form of powder, small particles, or solid semisolid or foam type material in the shape of balls and the like that exhibit some fluid-like properties. In some embodiments, different fluid/fluid mixtures may be used, for example but not limited to, pure water, water with salt or other kind of solution, oil, gel, slurry, gas, air, helium, argon, gel, colloid, balls, powder or foam when appropriate may be used to provide different buoyancy/pressure properties.

In some embodiments, the individual bladders may support each WBE, while in additional embodiments, there may be single or multiple bladder like structures at the end of each WBE. In still additional embodiments, there may be more than one bladder, without limitation to the size and number, which may be independent or interconnected and which can be inflated or deflated either manually or using automated controls that are connected to external pumps and power sources. Each bladder may be provided with sensors (see FIG. 2-A) to collect data on various parameters including pressure, temperature, and humidity. The bladders may communicate with each other either through tubes, a network of interconnected openings, or through automated controls that are operated using a series of sensors and motors coupled with tubes and valves for increasing, decreasing or maintaining the pressure.

In still additional embodiments, the bladders may be rigid or may be inflatable structures, either connected directly to the WBEs (see FIG. 3B), or to support the WBEs, such that the WBEs are either pushed out or retracted back, in response to changes in the pressure of bladder. The WBEs and the bladder may cover all sides of the body including bottom and top, although only one or two sides may be shown in the figures herein. In some embodiments, the bladders may or may not be located at the bottom part buttocks and underside of the thighs, where the seat of the chair comes in contact with the body.

Bladders may be made of any suitable material which may be expandable or non-expandable, non-limiting examples of which include: metal, alloy, plastic, polymer, rubber, latex, wood, leather, ceramic, plaster, plant or animal products, fabric, or combinations thereof.

In some embodiments (not shown in the figure), the bladder may be inflated by fluid held in an over-head reservoir, placed at a level above the chair. The fluid may be displaced up into the reservoir, either by the weight of the person seated in the chair or using either manual or electrical controls. The fluid exerts its force on the bladder, which in turn exerts pressure on the WBEs and body, resulting in an upward net force on the body.

Figure 2A:
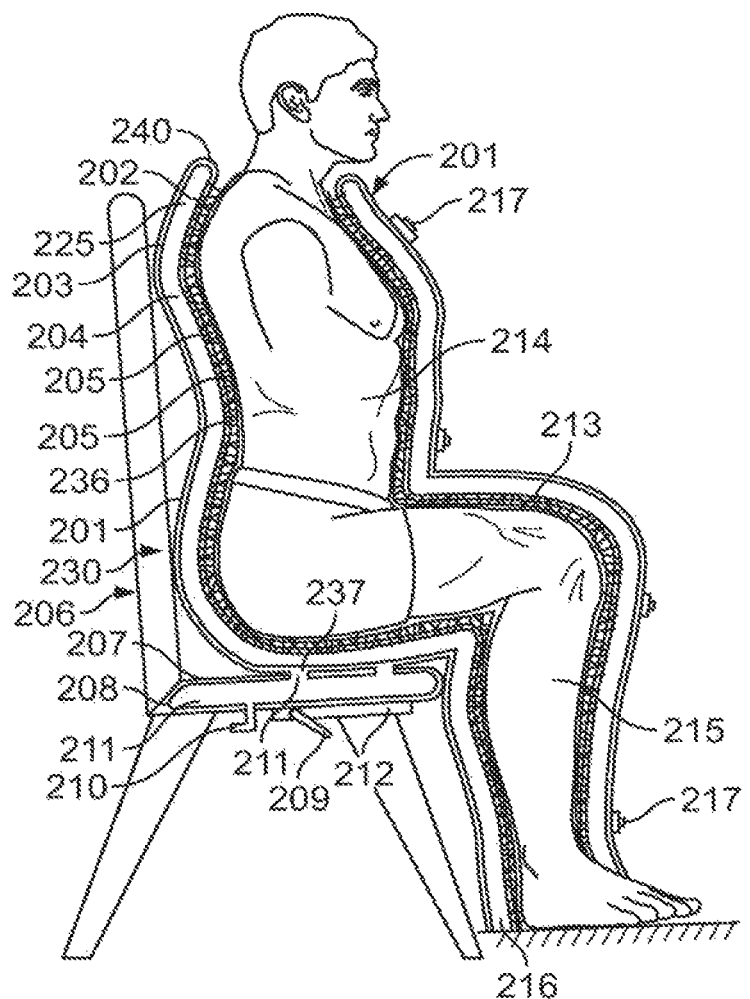
FIG. 2A illustrates a cross-sectional view of using WDD/LCD integrated into a chair, containing a bladder filled with fluid to support the body.
Figure 2B:
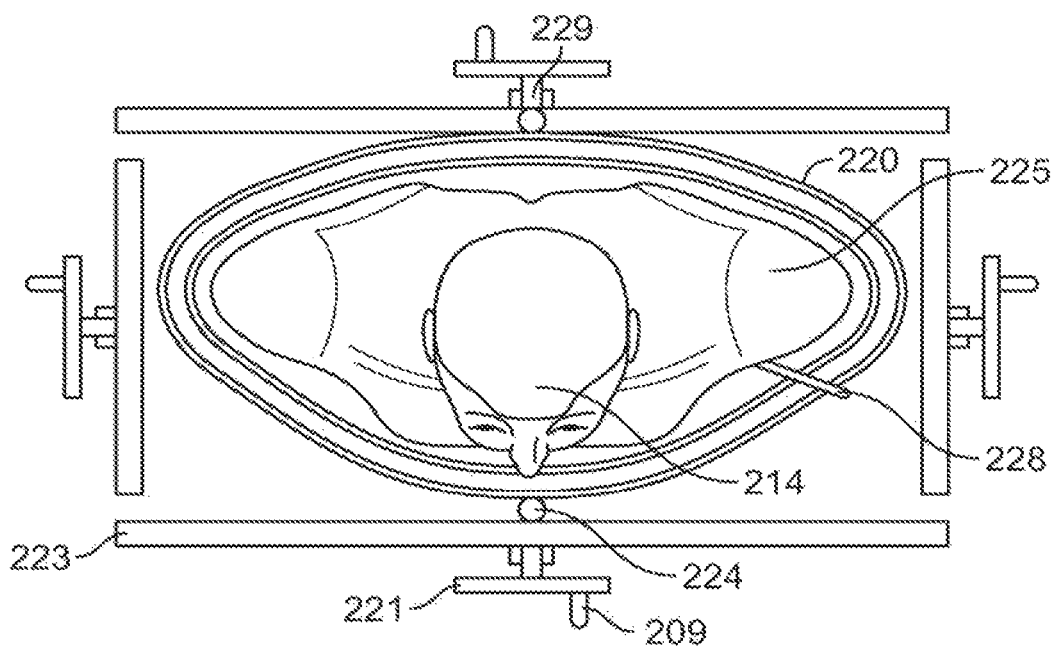
FIG. 2B illustrates a cross sectional view of an embodiment of WDD/LCD, with a frame, a bladder and panels to exert forces on a person.
Figure 2C:
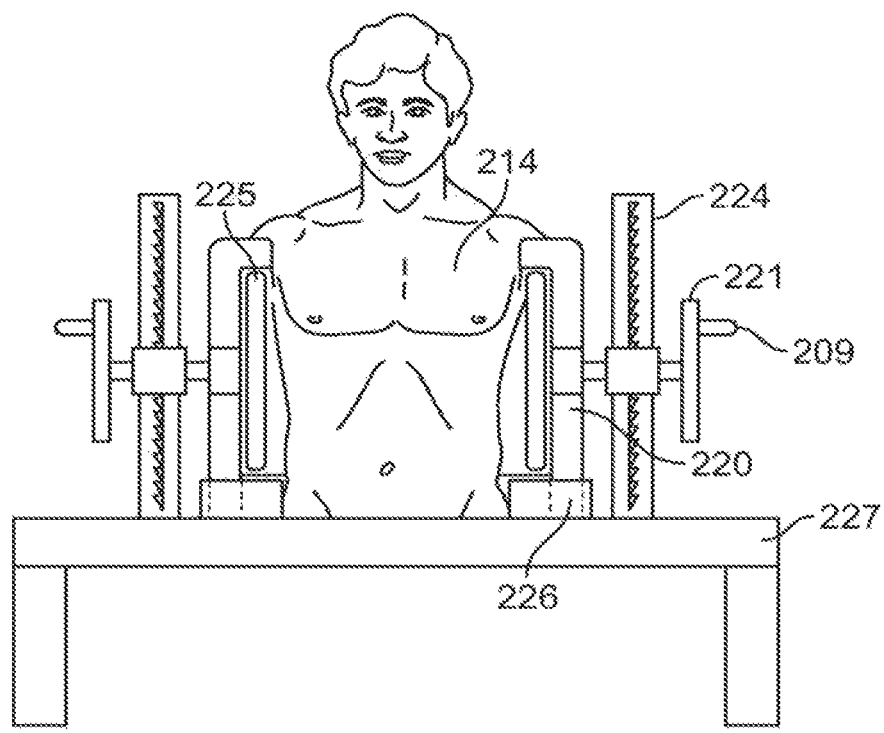
FIG. 2C illustrates a longitudinal section of an embodiment of a WDD/LCD containing a bladder on the sides, front and back, but no bladder on the seat, below the buttocks area of the person.
Figure 3A:
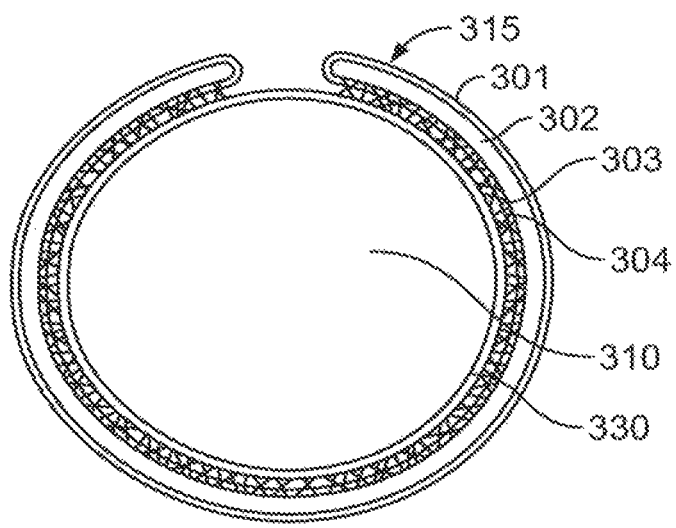
FIG. 3A illustrates a cross-sectional view of an embodiment of WDD/LCD around the leg of a person.
Figure 3B:
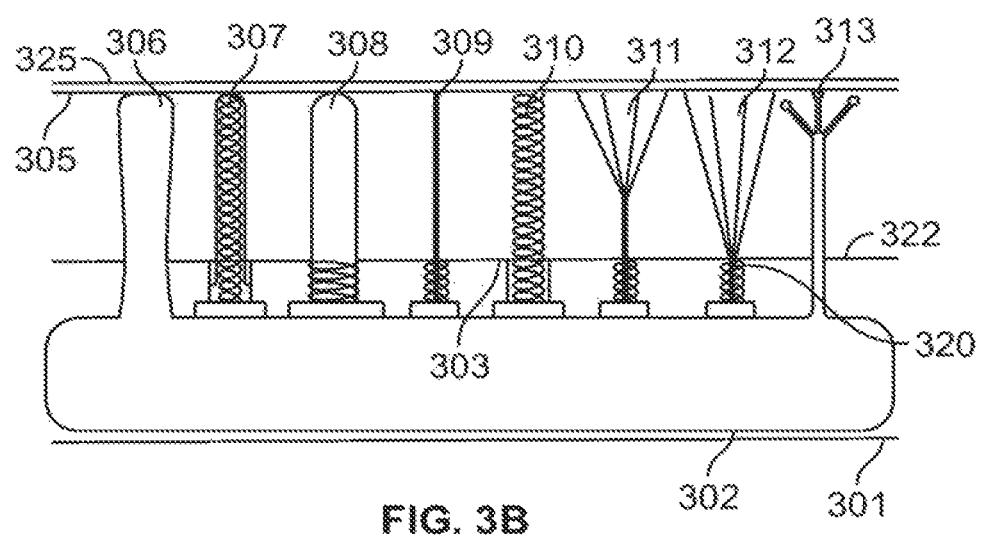
FIG. 3B shows some embodiments of weight-bearing elements (WBEs-body surface contacting units).
Figure 3C:
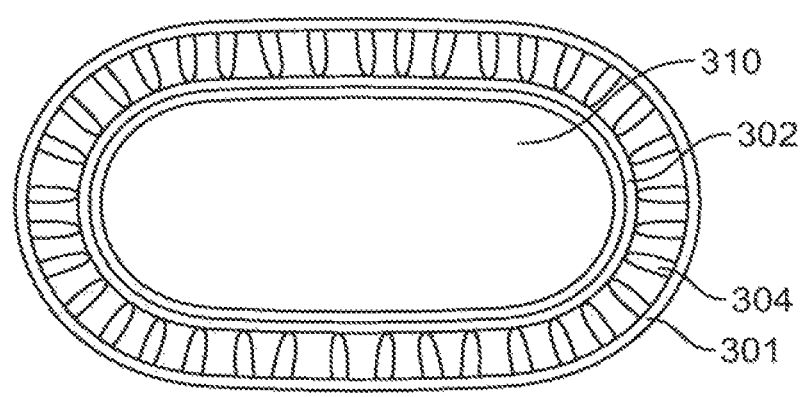
FIG. 3C illustrates a cross-sectional view of an embodiment of a WDD/LCD around the torso of a person with inflatable structures.

FIG. 3C shows an additional embodiment of a WDD, in which, the position of WBEs in relation to the body of the user is changed. In some embodiments of the WDD, it may be advantageous to surround the body 310 with bladder 302, first, followed by the WBEs 304 outside, and the frame 301. WBE exert pressure on the bladder when bladder is inflated or when the frame is compressed or raised. The mechanism operates in a similar to other WDDs as described in FIGS. 2-B and 2-C.

Some embodiments of WBEs are illustrated in FIGS. 3B, 4B, 4O, 4P-4Q. The weight-bearing elements are also referred to as "body surface contacting elements" in some sections and in the claims section of this disclosure.

Shown in FIG. 1E, located on the inner surface 127 of the frame, are a plurality of WBEs 104, which occupy the space 105 between the inner surface of the frame and the body 106. The WBEs are positioned to exert pressure on the body 106. In some embodiments, the WBEs may directly contact the body 106, and in some embodiments, there may be at least one layer of a fabric, such as a highly stretchable fabric or the clothing worn by the patient (not shown in the figure), in between the body 106 and the WBEs. In some embodiments, one or more layer of permeable material is provided between the user and the WBEs to absorb moisture and to provide passages for moisture and air flow. In some embodiments all of the body contacting portions can be protected by means of a cloth that can be washable, stretchable, permits air flow, remains warm or cool as needed for comfort, and may be disposable. The WBEs, in some embodiments, are expandable structures that traverse through the inner surface of the frame 127, and come into contact with the inner layer 102 of bladder or the fluid within the WBE may be in continuation with the bladder.

FIG. 3B represents several embodiments of WBEs, numbered from 306 to 313, connected to and/or resting on bladder 302 located in the space between the inner 322 and outer 301 layers of the frame around body of a person. For the sake of description, the FIG. 3B shows all WBEs as located on/connected to a single bladder, but it should be understood they may be separate from each other. The WBEs may come in direct contact with the skin 325 of the user or there may be a sheet 305 between the WBE and the body. The fabric is made of material that is highly stretchable and offers minimal resistance to the free movement of the WBEs.

For the purpose of description, in FIG. 3B, various types of WBEs are shown as resting on or connected to the same segment of bladder 302. But it is to be understood, that the various embodiments of WDD may have same or a different type of WBEs, as described herein. Some of the WBEs may be supported by individual inflatable structures. In some embodiments, the WBEs may be connected to the bladder and are in communication with the internal lumen of the bladder as shown in 306 and 313, which allows for these WBEs to expand when the pressure in the bladder increases. Additional types of WBEs shown in FIG. 3B, are not directly connected to the lumen of the bladder, but one of their end rests on the surface of the bladder wall, and are held in place by a spring 320 or a similar mechanism, to keep the WBEs in a retracted position, when the bladder is not inflated. The WBEs, however, may extend out and contact body when the bladder is inflated, and exert a force that is proportional to the pressure exerted on the bladder. The WBEs may have a telescopic end that elongates or shortens in and out of an outer shell as in 307, may be semi-flexible or rigid projections 308, a needle or bristle type 309, or a spring-type 310, and may contain multiple skin contacting structures at the tip as shown in 311, 312 and 313. In still other embodiments, the WBEs may be provided with magnets (not shown in FIG. 3B), with ends of the same polarity facing each other, which causes repulsive force, thereby exerting pressure on the body.

In some embodiments, the WBEs may directly come in contact with external supporting surfaces. There is no limitation on the diameter, length, size, shape, stiffness and number of WBEs for a given area. In some embodiments, the WBEs are free to move independently of each other while exerting pressure on the body. WBEs may resemble a pack of soda straws, bundle of small sticks, or may resemble hair or bristles on a brush, etc. In some embodiments, each WBE may rest on its own inflatable structure located between the outer and inner frame, that when inflated increase the pressure on the individual WBEs to push them against body. In some embodiments, the WBEs may be in communication with each other through a network of tubes.

A WBE can be provided with the ability to extend and/or retract, and expand or contract, and bend in any direction and can be operated by any suitable means, such as by a motor, piston, pump, valve, pressure regulator, air or fluid pump, control unit, pneumatic control, motorized control, gear, rocker arm, hinge, fluid drive, magnetic force, magnetic drive, thermal drive mechanism, or combination thereof. In some embodiments, the WBEs may be provided with limited flexibility in one direction, but not in other directions. In some embodiments, WBEs may be provided with either manual or automated systems to increase or decrease the force/pressure, and direction in which the pressure is exerted. In some embodiments, electrically powered or hydraulically driven pumps and valves, can be used to increase or decrease the force or pressure the WBEs exert on a region of interest on the body.

A WBE can include any structure and/or material capable of providing a suitable force/pressure against a body surface when included in an apparatus as described herein. A WBE can be, for example, soft, hard, rigid, resilient, bendable, telescoping, extendable, retractable, and/or twistable, non-limiting examples of which include: natural, synthetic or hybrid materials, metal, ceramic, wood, cotton, paper, plastic, polymer, or combinations thereof. Non-limiting examples of structures and materials include: needle, spike, rod, tube, stick, spring, bristle, sponge, knob, filament, fiber, wood, bubble, bladder, brush, nanostructure, nano-tube, nano-rod, hair, felt, natural material, synthetic material, polymer or combinations thereof. A WBE may be a combination of any of the above designs. For example, a meshwork of WBEs made of springs or rods may contact the body such that forces may be exerted on a body surface from all different directions. A WBE can be any suitable shape along its length or at its tip, non-limiting examples of which include: rod, cone, shaft, pin, nail, wedge, button, sphere, sharp, blunt, soft, resilient, hollow, solid or any combination thereof. A WBE can comprise a single rod or spike with a plurality of further elements, such as (e.g.) bristles, at the end. An element can comprise a spring mounted on a spike. A WBE can be capable of telescoping or twisting. A WBE can be composed of a material that is substantially safe and non-injurious, such as non-toxic, non-irritating, hypoallergenic, inert, disposable, washable, sterile or sterilizable, durable, and capable of withstanding damage from heat, cold, moisture, salt, liquids, including body fluids such as sweat, saliva, etc. A WBE can be coated or capped with any suitable material, such as, e.g., a protective coating, a soft coating, a sticky material, adhesive, magnetic, or an inert coating (e.g., Teflon).

In some embodiments, the WBEs may cover only a fraction of the body surface, while in some other embodiments may cover a significant portion of the body surface. The WBEs may come into contact with the body at any angle and exert force in any direction, including upward, downward, inward or outward.

The WBEs may be independent from each other or may be mounted in a mesh like interlocking manner. A WBE can have any suitable size and dimension, without any limitations. In some embodiments, the length can range from 0.01 nanometer to 100 cm, or more, and the diameter can range from 0.01 nanometer or less to 10 cm, or more. There may be a single stalk, from which multiple WBEs may be originate to contact with the body of the user. There is no limitation on the number, size or surface area of the WBEs. The number of WBEs per given area can be any suitable value, and can vary, depending on the dimensions of the element, from e.g., the number of WBEs in some embodiments can range from 1 to 1 million, or more per square centimeter. In some embodiments, the WBEs, contact the body of the person independently of each other, which allows for transfer of the pressure, with minimal shear force. The WBEs themselves may contain various sensors that measure pressure and direction of force.

WBEs may exert same amount of force at all parts of the body, or different types of forces on the body, which can be static or dynamic, and can include any pressure or pressure gradient or pattern, and can be modulated as desired. For example, in some embodiments, the forces/pressures can be adjusted to provide substantially any desired force including, but not limited to, massage, pulling, compression, an upward force, a net upward force, a downward force, a net downward force, bending, twisting, rolling, spinning, tumbling, bouncing, tickling, negative or positive acceleration, stretching, compression, massaging, undulating, kneading, rolfing, rubbing, squeezing, rippling, soothing, stimulating, and any combination thereof, and can be combined with other devices or treatments, such as, for example, cooling, heating, washing, rinsing, drying, deodorizing, or disinfecting means.

WBEs may exert either a passive force (a force exerted on the body due to the body weight of the person), or active force (force applied using an external energy source), or a combination thereof. The direction of the force exerted by WBEs on a person's body may be upward, downward, or at an angle to the surface of the body. A net upward force on the body may result in a force that is similar to a buoyancy force. A net downward force on the body, on the contrary, towards the spine, buttocks or feet, may result in an increased load on the body, which may be a desirable in certain applications.

Referring to the FIGS. 1A to 1D, in some embodiments, the amount of force each WBE exerts may be equal at all locations. In other embodiments, the WBEs may exert higher force on the lower portions of the body compared to pressure exerted on upper portions of the body. Such a pressure gradient with high pressure at the lower extremities and lesser pressure towards the torso and may be advantageous when the desired goal is to create a net upward buoyancy force on a body or a body part, with an objective to decrease the load on the weight-bearing structures of the body. In some embodiments, where an increased load on a body is the desired goal, higher pressure may be exerted on the top portions of the body (e.g., head, neck, shoulders, trunk) while lower pressure may be applied on the lower portions of the body, the feet, legs, buttock, etc.

There is no limitation of the direction of force exerted by the WBEs. In certain embodiments, without limitation, some WBEs are designed to exert force in an upward direction or perpendicular to the surface of the body or at less than or more than 90 degree angles to the surface of the body. The amount of force exerted in each different direction may be variable. The total amount of force against the body may be less than, more than or equal to support the total weight of the individual or individual body portions being supported. In certain embodiments, a variable amount of force may be exerted on WBEs at different regions of the body. For example, in some embodiments, higher pressure may be exerted on the WBEs located on the seat (below the buttocks) or at the lumbo-sacral region of a person compared to abdominal and chest regions. Similarly more pressure may be applied on the posterior aspect of thigh (bottom side of thigh, when the person is seated) and on left and right sides of the thigh compared to the front side of the thighs.

In some embodiments, the WBE is fitted with one or more individual sensors, such as, pressure and/or directional sensors. In some embodiments, a pressure distribution array can be used to monitor the pressure distribution on each WBE. Sensors can be incorporated into a WBE, or can be included within frame or a layer, such as between the body of the user and WBE. The data from the sensors may be used to by the electronic controls of the WDD to make desired changes.

In some embodiments, the pressure exerted on WBEs located at one region of the body may be communicated to the WBEs located at other regions of the body, and as a result either an increased or decreased pressure may be exerted by the WBEs at those regions. Sensors located within the WBEs or close to the WBEs may monitor the changes in the pressure, which is communicates with the central processor, which activates the motors that exert pressure on WBEs at other regions to increase the pressure.

In some embodiments described herein (see FIGS. 1D and 4L), bands, fabric, elastic material or threads, and the like may be used to exert pulling forces on a person, without the need for use of WBEs. However, the same may be used in combination with WBEs, to allow for uniform distribution of force.

In some embodiments, the WBEs may be attached to the outer surface of the sheet (opposite side of the sheet that contacts the skin), and enabled to move with the sheet, such that the WBEs are capable exerting shear forces on the skin. Embodiments of the WBEs attached to the sheet may be useful for example, in gripping the body of a person, to prevent one from sliding off a chair, or to allow a person to experience the sensation of being gripped or feel the skin and underlying tissue being stretched while simulating motion or tactile sensations, etc. Some embodiments of WDD may have WBEs attached to the sheet at some locations of the body, while at other locations the WBEs come into contact with the sheet, and slide over the sheet, thereby exerting only minimal shear forces.

In some embodiments, the WBEs may be attached to the frame either directly or indirectly, e.g., through a joint capable of pivoting, such that the direction force of the net force exerted by the WBE on the body is always same, irrespective of the position of the individual of part of the body or frame. For example, a person standing upright may have net force exerted by WBEs acting upward along the length of the femur and in the direction opposite of the gravitational force. If suppose, the same person is seated in a chair, then as the net force on the thigh still will be acting in an upward direction, opposite the direction of gravitation force, however, the WBEs will pivot around about 90 degrees from the vertical angle to do so. The same principle applies for embodiments of LCDs that act on an astronaut to increase the load and pressure on the body.

Figure 4A:
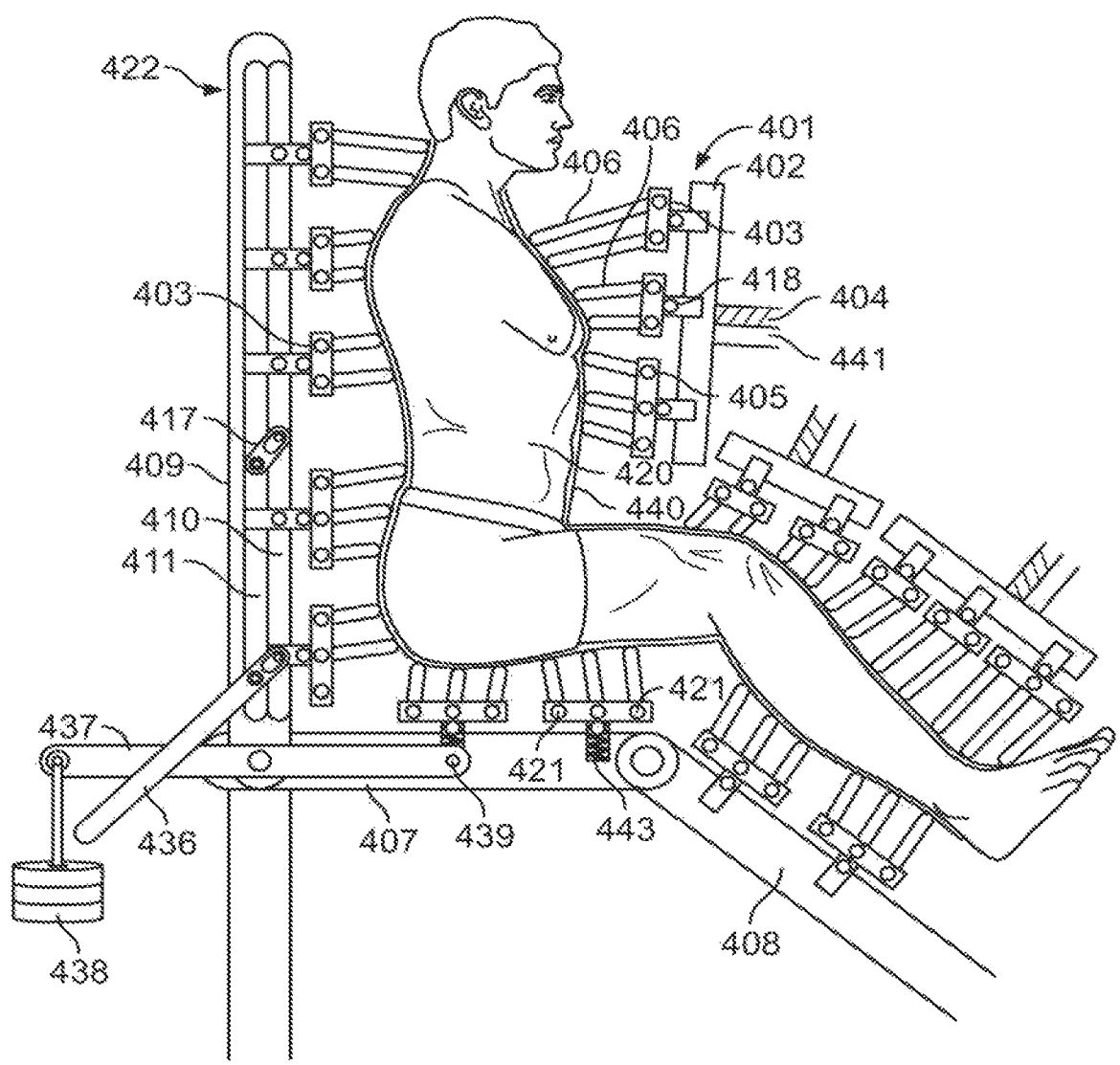
FIG. 4A is a vertical sectional view of one embodiment of WDD/LCD without inflatable structures integrated into a chair
Figure 4B:
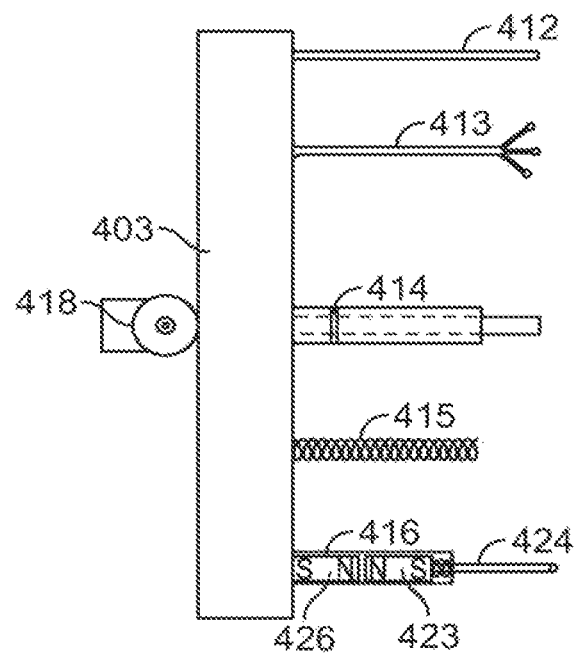
FIG. 4B illustrates exemplary embodiments of WBEs that may be used with WDD/LCD with or without inflatable structures.

FIG. 4B presents some embodiments of WBE that may be used with WDDs/LCDs that use either inflatable or non-inflatable structures.

Figure 4C:
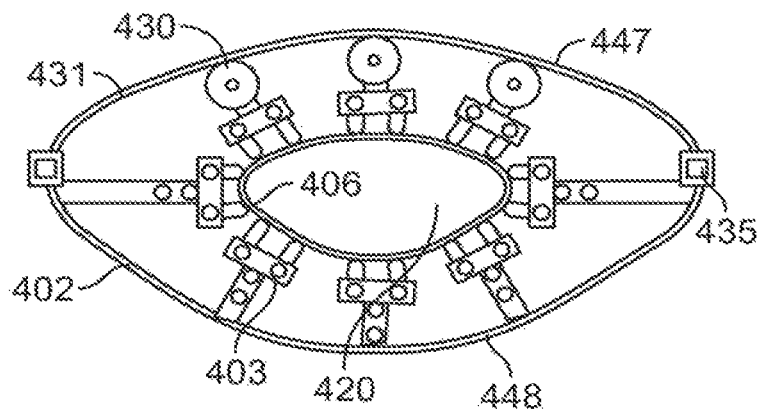
FIG. 4C illustrates a cross-sectional view of an embodiment of WDD/LCD showing WBEs located on the front side of torso pulled against the body using a fabric to the rods, and WBEs on the back and the sides supported by the movable plates and frame.
Figure 4D:
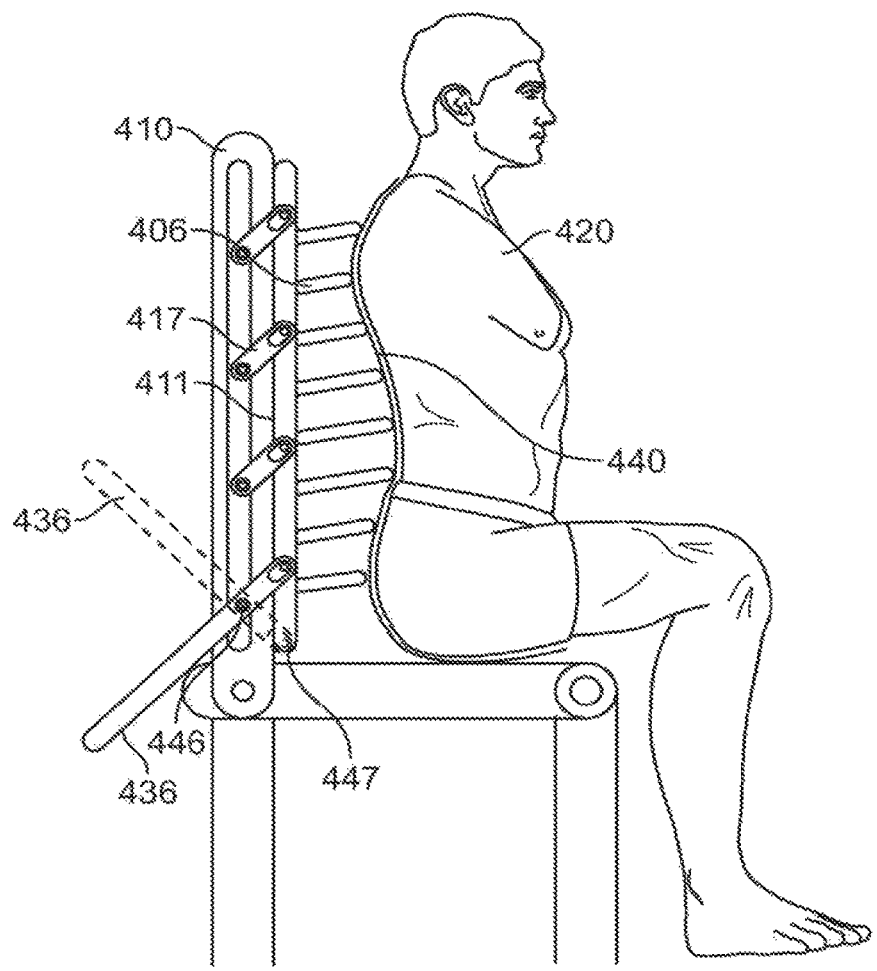
FIG. 4D depicts a detailed view of an embodiment of WDD/LCD showing WBEs and frame integrated into a chair that includes a mechanism to manually increase or decrease pressure exerted by WBEs on the body.
Figure 4E:
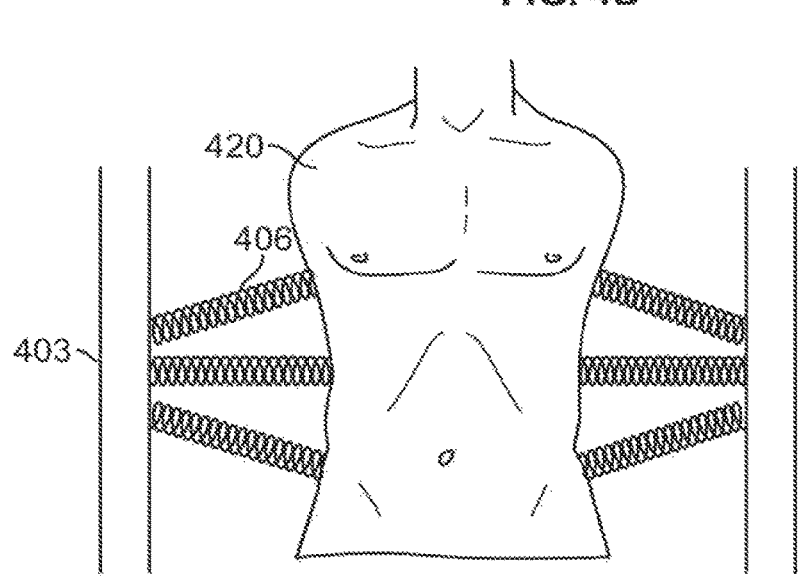
FIGS. 4E and 4F show a close up vertical-sectional view of embodiments of WDD/LCD with WBEs located on the frame to illustrate that WBEs may be designed to stay in close contact with the body of the user in various positions.
Figure 4F:
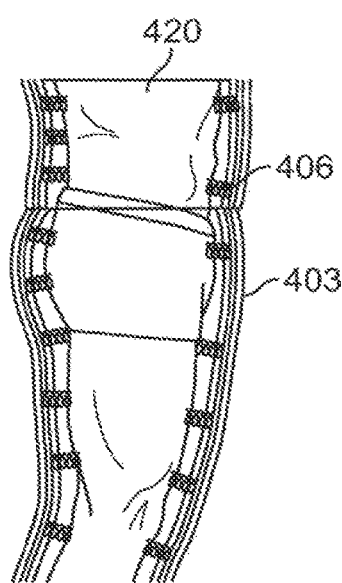
Figure 4G:
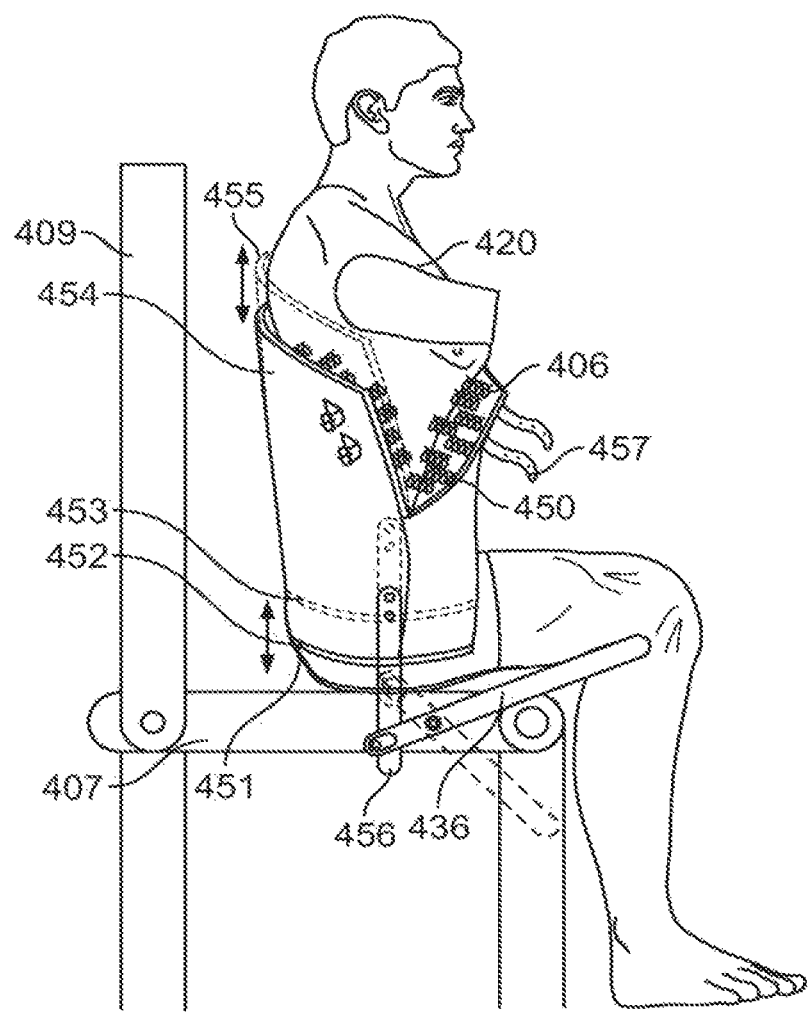
FIG. 4G shows a perspective view of an embodiment of WDD/LCD that can be used by person while sitting on a chair to support the torso.
Figure 4H:
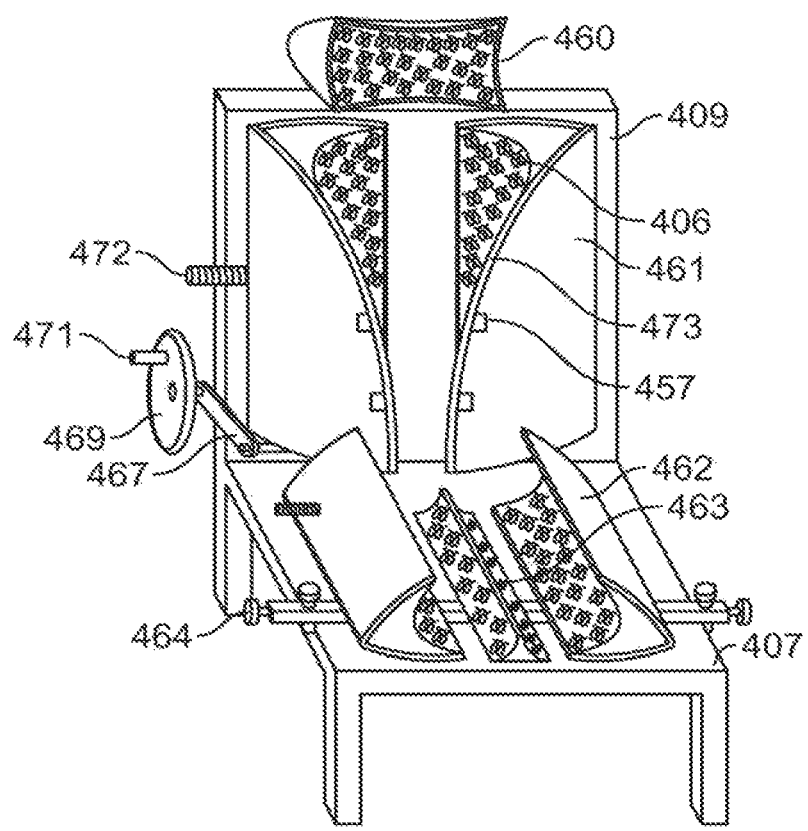
FIG. 4H shows a perspective view of a chair fitted with an embodiment of WDD/LCD supporting the head and neck, torso, buttocks and the thighs.
Figure 4I:
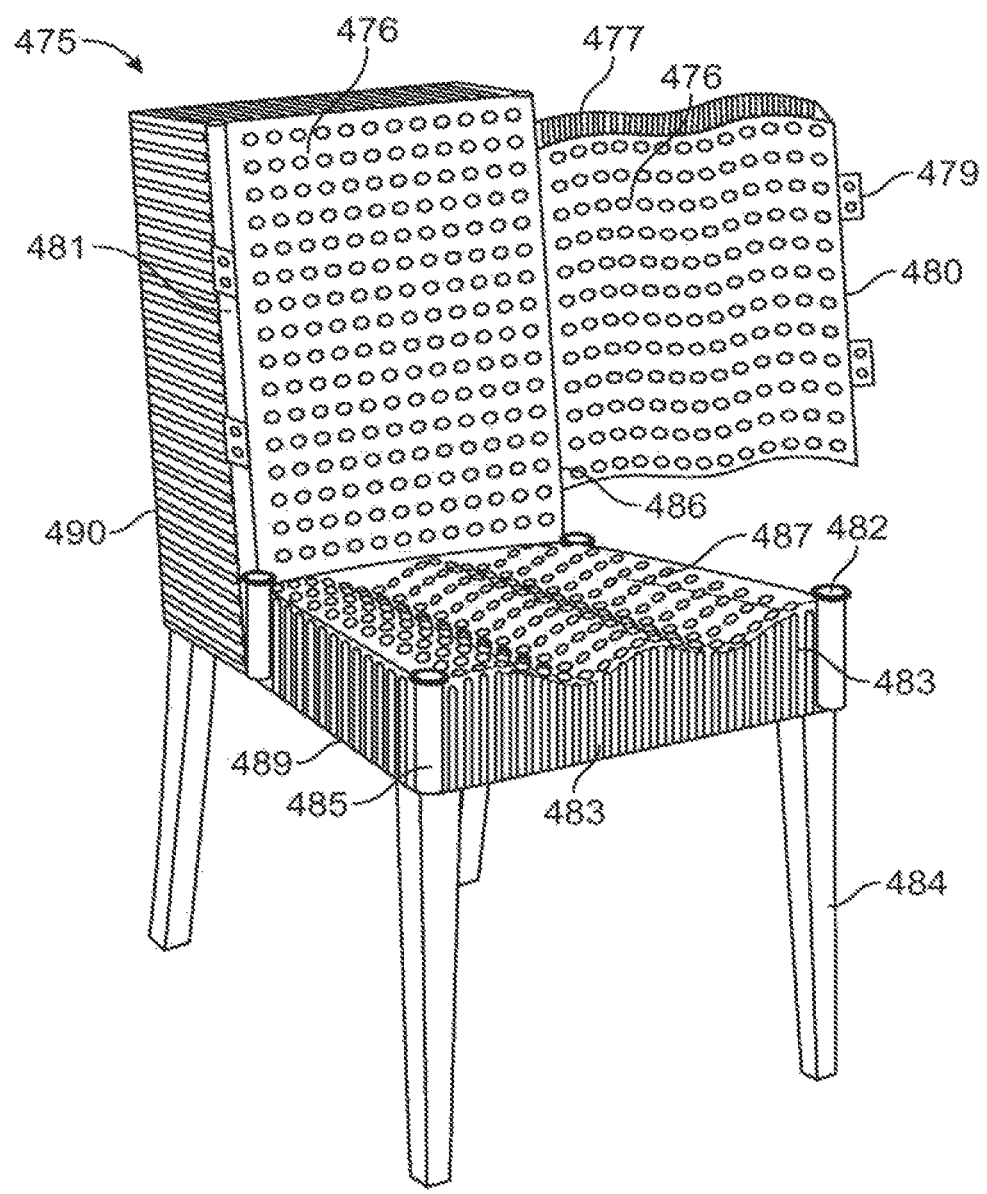
FIG. 4I is a perspective view of an embodiment of a chair with integrated WDD/LCD, showing a front flap, and WBEs in the frame, backrest and the front flap.
Figure 4J:
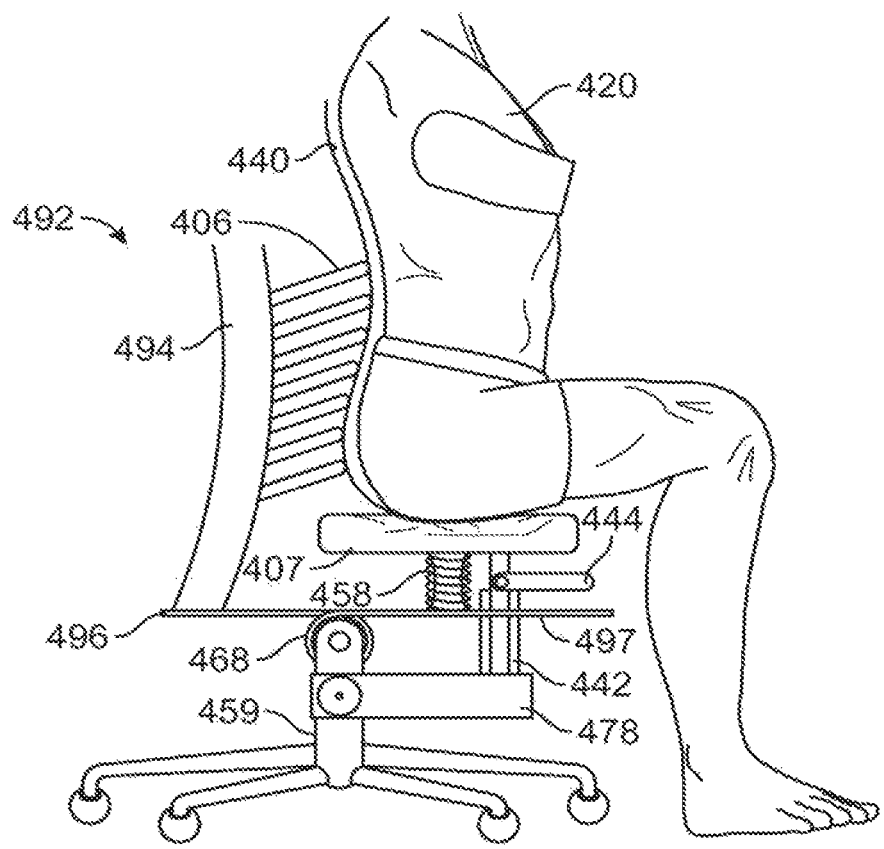
FIG. 4J illustrates an embodiment of a WDD integrated with a chair, with a torsion spring that uses the body weight of the person on the base of the chair to apply pressure on the body through WBEs to facilitate off-loading of the body weight onto the frame.
Figure 4K:
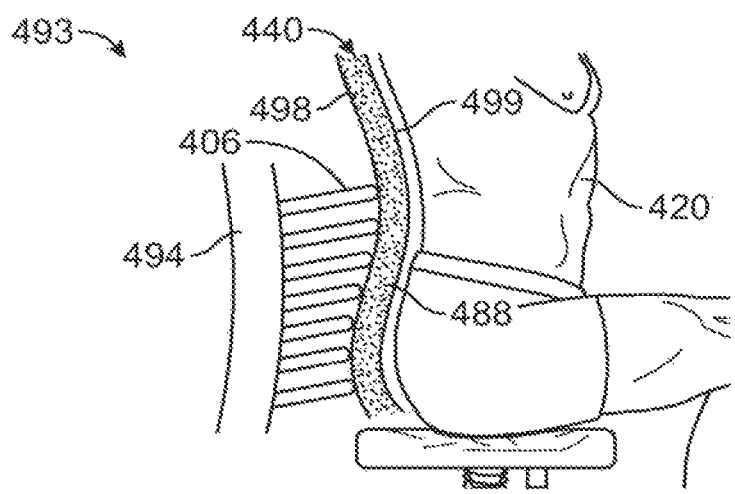
FIG. 4K illustrates an embodiment of a sheet positioned between the body and the WBE of the LCD/WDD, with two layers and a lubricating fluid in between the layers.
Figure 4L:
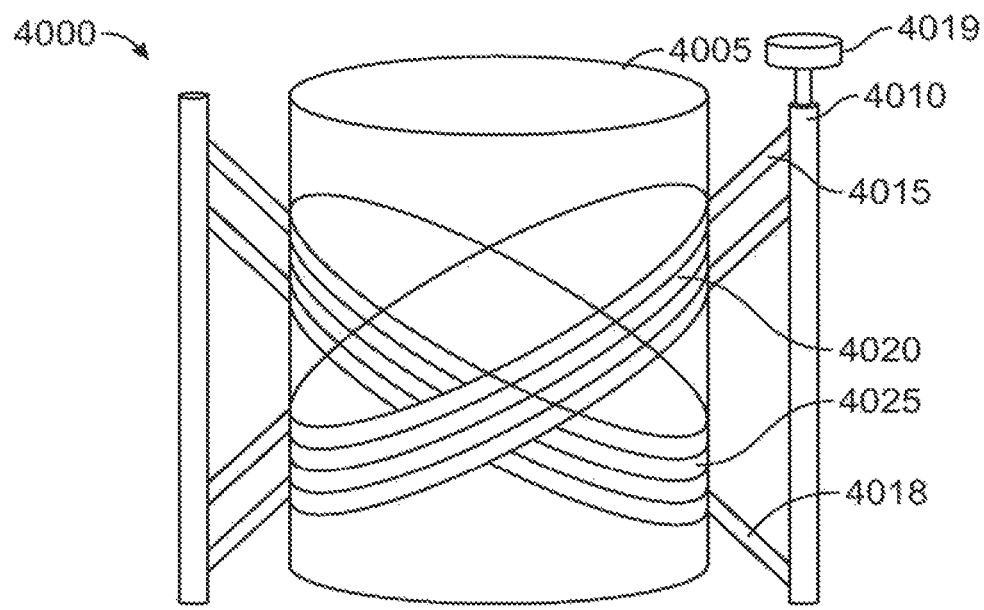
FIG. 4L illustrates an embodiment of a WDD/LCD showing front view of a portion of a torso covered by bands that exert pulling forces on the body at an angle to the vertical axis.
Figure 4M:
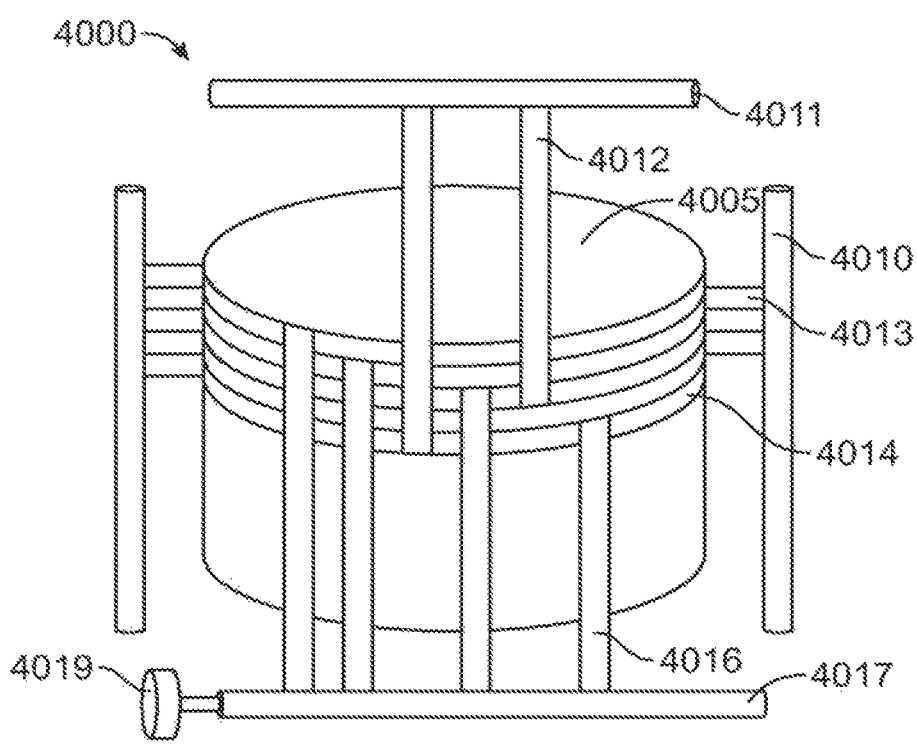
FIG. 4M illustrates an embodiment of a WDD/LCD showing front view of a portion of a torso covered by bands that exert pulling forces on the body in the horizontal and vertical directions.
Figure 4N:
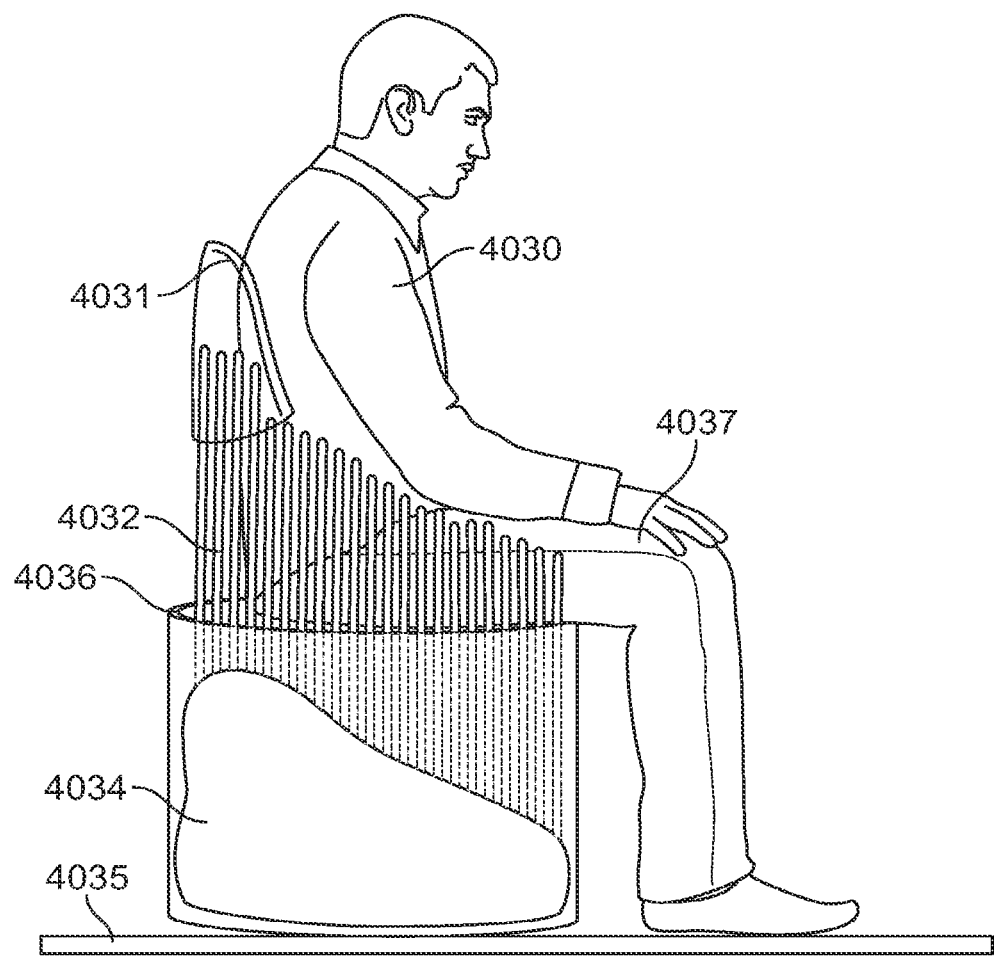
Figure 4O:
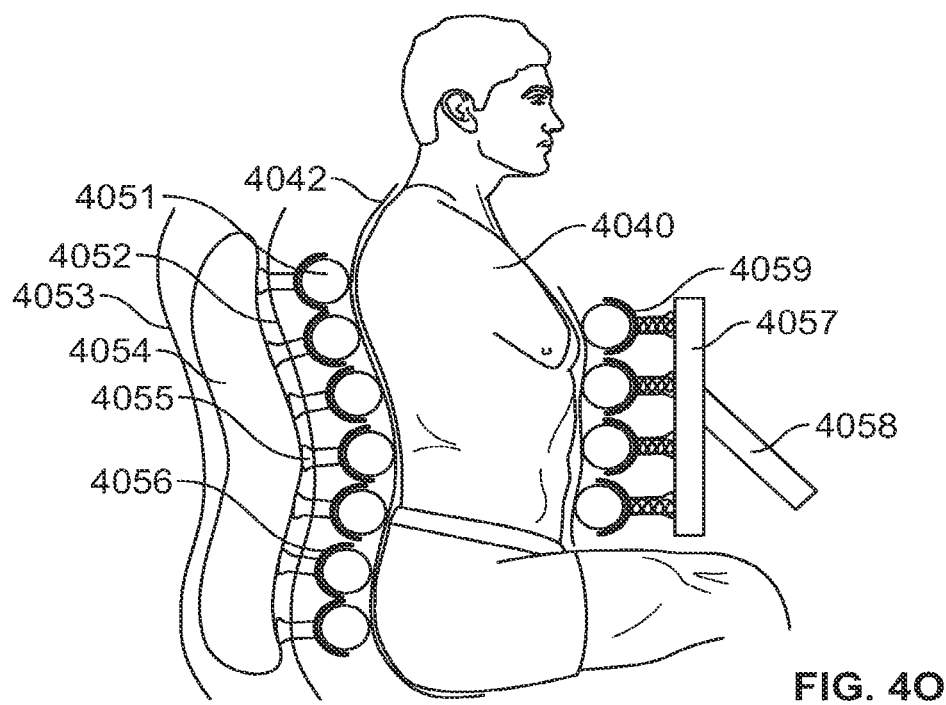
FIG. 4O illustrates a lateral view of an embodiment of WDD/LCD showing a frame and an inflatable structure supporting ball/roller-type WBEs for exerting forces on a human.
Figure 4P:
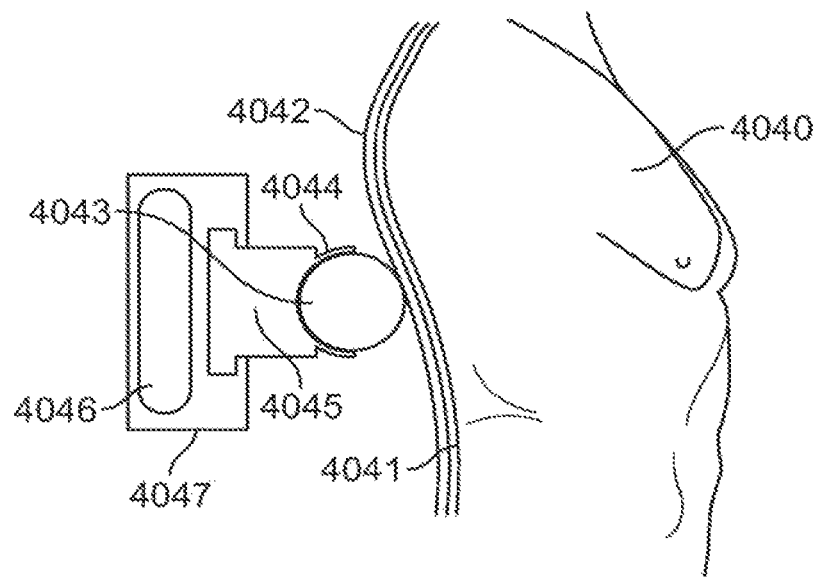
FIG. 4P shows an embodiment of a WBE with a ball/roller secured in a socket at the tip, useful for exerting pressure on the body with minimum friction on the skin.
Figure 4Q:
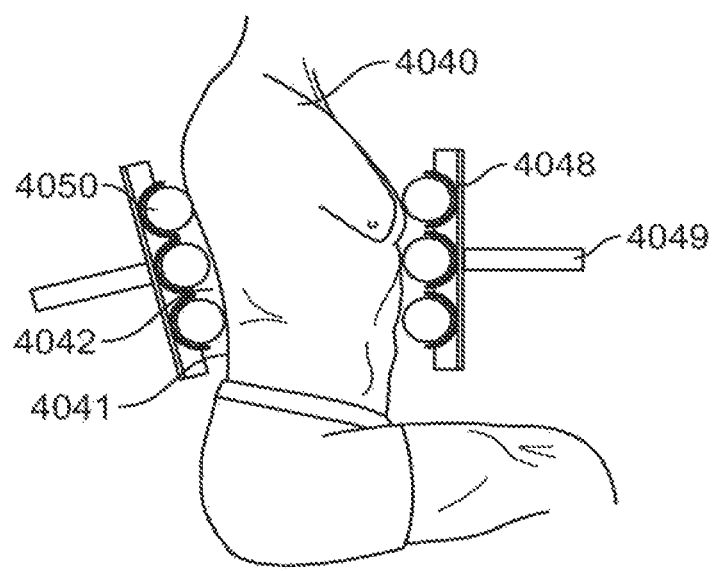
FIG. 4Q illustrates an embodiment of a ball/roller-type WBEs supported by non-inflatable structures (frame) for use in a WDD/LCD.

FIGS. 4O, 4P and 4Q illustrate some examples of WBEs that are in the form of balls or rollers, that are capable of rolling on the skin or a sheet covering the body of person, without exerting significant frictional forces at contact location.

In some embodiments, as shown in FIG. 1G, without any limitation, a separate sheet 130 (or cloth or garment) may be used for covering surfaces of the WBEs that come into contact with the surface of the body. The WBEs may also come into contact with clothing worn by the user. The sheet may be made of material that offers minimal friction and has significant ability to stretch when pressure is applied. The stretching ability of the sheet may be controlled by anchoring the sheet to the bed, frame, underlying seat or other structures either using sutures, hooks, buttons, zippers, Velcro, or other means, such that while it prevents uncontrolled sliding or slipping of the body of the person due to weight or movement, it allows the WBEs to push up or withdraw back freely, facilitating exertion of pressure against the body without modifying their direction significantly. The sheet may be made of any suitable material (e.g., cotton, silk, plastic, nylon, polyester, silk, latex, metal, non-metal, synthetic materials, and materials of plant or animal origin, a combination thereof, and the like), and may be shaped into a variety of shapes without limitation, including strips, net, mesh, sheets, pleats, overlapping sheets or formed into pleats, inflatable structures, and the like to impart the desired characteristics. Although, at several places in the application, it is mentioned herein that the WBEs contact the body, it should be understood, that the sheet may be present, in some embodiments, between the body and the WBEs. It is also to be understood that clothing of the user may be present between the WBEs and body, and therefore, direct contact includes either direct contact with the skin or the clothing of the individual.

Additional embodiments of the sheet are described in FIG. 4K. As noted in the figure, the free ends of the WBEs that contact the body of the person, may be covered by a sheet 440, or clothing of a person, or material that adds to the comfort of the user (e.g. foam or cushion, gel) that can be cleaned easily or disposed of. In a preferred embodiment, the sheet 440 is highly stretchable so as to offer little resistance to the movement of WBEs contacting the body in any direction, and especially to minimize shear forces. The sheet 440 can be made from a wide variety of materials, without any limitation, including cotton, foam, plastic, polymers, metals and nonmetals or a combination of the above. FIG. 4S illustrates an embodiment of a sheet with multiple layers to minimize frictional and shear forces on the body of a person.

A sheet may be present between the body and the WBEs in some embodiments. The sheet minimizes the frictional and shear forces on the body, by allowing the WBEs underneath the sheet to move freely with the skin, with each movement of the body, in any direction, in order to minimize frictional force exerted on the body of the user. Further, the ability of the sheet to stretch, allows the WBEs to exert force against the person's body without altering the intended direction, magnitude of the force, and area of body surface on which the forces are applied.

In some embodiments, an apparatus (WDD or LCD) provided herein may be provided with a plurality of sensors for sensing the direction and/or position of a body or body portion, or for sensing the force/pressure at a point or region (see FIG. 4A, sensor 421). Sensors may be used to provide manual or automated adjustment, or a combination of manual and automated adjustment, of the force/pressure. In some embodiments, the WBE is fitted with one or more individual pressure and directional sensors. In some embodiments, a pressure distribution array can be used to monitor the pressure distribution on each WBE. Sensors can be incorporated into a WBE, or can be included within frame or a layer, such as between the body of the user and WBE. When WDD/LCD are used for simulation, a wide variety of sensors may be located on the WBEs or separately that can measure the force, direction of force, tactile sensation, changes in the skin conductance or vital signs may be included. Software program may be included to integrate the data from the sensors and allow for appropriate changes to the pressure applied to the body of a person.

In some embodiments, inflatable structures may be used either in WDDs or LCDs to exert a net upward (against gravitational force) or a net downward force on the body of a person. FIG. 2-A describes a system in further detail, using one embodiment of person seated on a chair. In this embodiment, the frame 240 with outer surface 201 and inner surface 202, covers the trunk 214 and thighs 213 and leg 215 of the person, and encloses a space within the outer and inner layers to accommodate inflatable structure 225, with an outer lining 203 and an inner lining 204.

The frame may be held closely to the body using various securing means 217 that may include hooks, buttons, zippers, Velcro and the like. The inflatable bladder 225 surrounding the torso may be inflated manually or automatically using a hose 210 connected to a pump, or by exerting pressure on the bladder 208 located within the seat of the chair. The WBEs 205 may be supported by the inner lining 204 of the bladder, as well as by the inner surface of frame 202 and contact the body either directly or in some embodiments contact the sheet 236 that cover the body. The inner surface may either directly support the WBEs or may contain holes, openings or tubes (not shown in the figure), to allow the WBEs to pass through and come into contact with the body.

In one of the embodiments shown here, the outer layer 201 and inner layer 202 of the frame around the torso and the thighs of the person when seated may be supported at the base of the frame 207 by the seat 211 of the chair 206 containing back 230 and the frame around the legs may be supported by the floor 216, or by shoes or leg rest (not shown in the figure). In additional embodiments, there may be several frames around the individual parts of the body, and the frame that supports the torso may be configured to slide up and down to allow the torso (or the WBEs) to be pushed up and down when the pressure in the bladder contained within the outer and inner layers changes. In still additional embodiments, the outer frame may be flexible, and allow the stretching of the frame over the joints or other parts of the body that requires free movement. The flexibility of the frame allows it to keep the WBEs positioned against the skin closely, irrespective of the curvatures of the body or movement of individual parts of the body. It should also be noted that the frames may be made to fit the individual parts of the body (torso, thighs, legs below knee, arms and the like), and are joined with flexible material at the joints to allow for maximum flexibility.

An additional reservoir 208 containing fluid may be present in some embodiments, contained within the seat 211 of the chair, whose pressure can be changed by pulling lever 209, which exerts pressure on the plate 212 located below the chair that rests on the reservoir 208. Note that although bladder 225 and reservoir 208 hold the fluid, they are given separate part numbers and names for clarity. Although, referenced is made to a bladder as an inflatable structure, it should be noted that in some embodiments, just the pressure within the bladder may be changed, without changing the overall volume of the bladder. The pressure in the reservoir 208 and in turn in bladder 225 may also be modified using hose 210 that connects the reservoir with an external pump. The reservoir 208 may be in communication with the bladder 225 located in the frame or with the WBEs through holes or tubes 237 located in the seat and connect the bladder with the reservoir. Alternatively, in some embodiments, the weight of the person may be used to force the fluid from the reservoir into the bladder 225. The compartment holding the fluid may be expandable or contractible (not shown in the figure), such that it allows the bladder to expand, when displaced fluid enters the bladder (due to body weight of the person), but the resulting reactionary pressure from the bladder to exert force against the body till a dynamic equilibrium is reached.

In some embodiments, the increased pressure on the bladder 225, in turn exerts pressure on the WBEs, either via the direct communication of the pressure with the fluid located within the bladder through multiple openings in the inner layer 202 of the frame (not shown in the figure), or as the WBEs rest on the inner wall 204 of the bladder, but without directly communicating with the lumen of the bladder. In some embodiments, when the WBEs are in direct communication with the bladder, increased pressure in the bladder 208 results in the expansion of the WBEs, which in turn exert pressure on the body of the seated person. In still additional embodiments when the WBEs rest on inner layer of 204 of the bladder, increased pressure in the bladder causes the WBEs to be forced out of the frame and pushed against the body exerting increased pressure on all sides of the torso. As the frame is tightly secured to the body, and as the WBEs have only a predetermined limited space to expand, such an increase in pressure on the WBE results in the body 214 being pushed upwards from the frame.

The direction and magnitude of the force exerted by the bladder, and by individual WBEs on the body may be modified by providing predetermined tension WBEs, such that there may be higher pressure on the lower portions of the body of the user, which decreases towards the head of the seated person. Similarly, a graded pressure may be applied on the thighs of the seated person, to reduce weight on the underside of the thighs. For the thighs, which are in a horizontal direction and parallel to the seat of the chair, in the seated person, the pressure may be higher at the bottom (posterior aspect) and the sides (lateral aspects), compared to the top (anterior aspect) of the thighs. The net pressure (which is similar to a buoyancy force) on any part of the body or the whole body, may be towards an upward direction, which is opposite the direction of the gravitational force, and therefore, results in reduced pressure on the weight-bearing structures.

In some embodiments, where the frame can slide over another support, such a net upward force results in the frame to move in an upward direction along with the body. As the frame is designed to support the weight of the person, this action results in partial or complete unloading of the weight of the upper part of the body on the frame, and thereby, the weight on the vertebral column, especially at the lumbosacral region and on the buttocks will be reduced.

It is to be understood that upward force by WBEs or the bladder on the body does not necessarily require significant physical upward movement of the body. Instead, the upward pressure on the torso by the WBEs result in the WBEs pushed harder against the body surface, causing the body weight to be off-loaded on to WBEs. Also, only upward force is mentioned here, it is to be understood, the force exerted by WBEs can be in all directions, with the net force pointing upwards. In some embodiments, the WBEs may be arranged in horizontal circles on the frame around the torso such that the inward pressure of the WBEs located on the opposite sides of the each horizontal section of the torso, result in the weight of that section to be off-loaded onto the frame, thereby reducing weight on the lower parts of the torso (or vertebrae of the spine). The forces acting on the opposite directions of each horizontal section of the torso cancel or substantially cancel each other, leaving a net upward buoyancy force to push the body upward.

FIG. 3A, illustrates a cross-sectional view of an embodiment of the WDD 315 supporting the thigh 310 of a person. In some embodiments, the device can completely wrap around the leg, while in some embodiments, the device covers only a part of the body, for example the bottom and sides of the thigh of a seated person as shown in FIG. 3A. The outer layers 301 and inner 303 of the frame housing inflatable bladder 302 and WBEs 304 and sheet 330 are shown.

The WBEs on the inner surface of the frame that are in contact with the thigh push in all directions, with a net upward force (towards the anterior aspect of the thigh, when a person is seated). In some embodiments, the WBEs may exert same force on all parts of the body. In some embodiments, WBEs may exert a gradient of force with higher force exerted on the bottom and sides of the thigh, with progressively lesser force as one approaches the top of the thighs. When WBEs exert force against the sides, the weight of the thigh is off-loaded onto the frame, resulting in a decreased pressure on the underside of the thighs. In people who are wheel-chair bound, such an embodiment decreases the pressure between the seat and the underside of the thighs, preventing development of pressure ulcers. In a similar fashion, the weight of the leg below the knee is off-loaded onto the frame and to the floor 216.

In some embodiments of the LCD, the same principle as described herein in FIG. 3A may be used to exert force on an astronaut's body. The difference however, is that the orientation of the device with respect to the astronaut's body part (thigh, in this case) may have to be turned upside down. For example, when used in the astronaut seated in a chair, the opening depicted in the device in FIG. 3A, may be facing towards the seat of the chair or a bed, such that when pressure is exerted on the thigh from above, the underside of the thigh experiences body weight-like load as it is pressed against the chair.

The mechanism of action of LCD is not discussed in detail above. However, LCDs are somewhat similar to the WDDs in their design, except that the appropriate differences exist between the two types of devices in that LCDs are designed to exert a downward force on a person. The WBEs in LCD push against the frame secured to the body of the user, such that the counter force exerted by the body on the WBEs (and the frame) is experienced as a body weight by the person, although this is not a true body weight as one might experience on earth because of gravitational forces exerted on the body. LCDs in some embodiments may exert the same magnitude of force on all parts of the body, or may exert a gradient of forces against the body from top to bottom, with higher forces on the top decreasing as one move down.

The functioning of the WDD with inflatable structures as described in the figures (FIGS. 1E to 1G and 2A). The principles apply to all WDDs and LCDs that may operate with or without an inflatable structure. The operation of some embodiments of the device is described using the examples of WDD which depict a person seated on a chair, as illustrated in FIG. 2A. To operate the embodiment of the device shown FIG. 2A, the user 214 sits on the WDD located on the seat 211 of the chair, and secures the frame 240 to torso 214, thighs 213, and legs 215 using various fasteners 217. At the start, the body weight of used is borne by the WBEs located under the buttocks and underside of the thighs. The user may then increase the pressure in the bladder 225 using either external pumps connected to hose 210, or by increasing the pressure on the fluid reservoir 208 located below the based by pulling the lever 209, which causes the fluid in the reservoir to travel through the holes (or tubes) 237 and thereby increase the pressure in the bladder. As the bladder 225 has only a limited space to expand, the increased pressure in the bladder, in turn, causes the WBEs 205 to be pushed against the torso, thigh or the leg of the user.

In some embodiments, where there are more than one frame which can be raised from the base, or slide against each other in relation to the body of the user, the frames that support the bladder and the WBEs may be raised using either manual levers or using external power (not shown in the figure), which causes the WBEs to exert increased pressure on the body. Such a pressure on the body by the WBEs, in turn results in the body weight of the individual parts of the body, the torso, thighs or the legs of the user to be pushed against the WBEs, and the bladder, resulting in off-loading of some or all of the weight onto the frame.

There is no limitation on the methods to off-load the weight of the user on the WBEs, bladder and the frame. In some embodiments, the user's body weight may be used to increase the pressure in the bladder or on the WBEs, by for example securing the user first to the WDD, and then pulling a lever (not shown in the figure) to allow the body of the user to drop further, thereby exerting pressure on the WBEs and/or the bladder. In some embodiments, an over-head reservoir may be provided to hold the displaced fluid due to the user's body weight on the WDD (not shown in the figures). The weight of the displaced fluid will act on the bladder, which in turns pushes the WBEs to exert pressure on the body of the user. Therefore, in this situation, the displaced fluid acts like a counter-weight (or counter balance) to the body weight of the person, and supports the weight of the person by exerting pressure through WBEs, e.g., all over the surface of the body, in a manner very similar to how water in the swimming pools exerts buoyancy forces on the body.

To illustrate the potential usefulness of WDD to decrease the loads experienced on the weigh-bearing structures of the body, the following hypothetical example is used. For example, a person weighing 70 kg and measuring 6 feet height may have a body surface area of approximately 18,000 square centimeters. Assuming an approximate surface area of 162.5 square centimeters (.about.25 square inches) for each foot, the average pressure on the sole of the person is approximately 430 g/square centimeter, or 316 mm Hg. However, if 100% of the weight of the person is off-loaded onto the frame of the WDD and distributed over rest of body surface area (about 18,000 square centimeters), the pressure then becomes 3.8 g/square centimeters, or 2.86 mm Hg. The user may choose to cover only a part of the body and may choose to off-load only a part of the body weight, onto the frame, in which case, the pressure on the sole of the foot and rest of the body surface increases accordingly. Therefore, the disclosed WDD and LCD systems may be used to change pressure on a body surface of a person, e.g., from 0 to 32 mm Hg (below the capillary pressure to keep them from collapsing), from 32 to 100 mm Hg, or from 100 to 1000 mm Hg or from 1000 to 25,000 mm Hg or more.

The ratio of actual pressure (load or weight) experienced on the soles of the feet standing on dry land (actual pressure, A) is much higher than the pressure the person experiences when standing in a swimming pool (measured pressure, P). The same is true for other weight bearing regions of the body, including buttocks, joints, etc. The A:P ratio on the soles therefore can be equal to or higher than 1, for users of WDD and equal to or lesser than for users of LCDs, or span a whole range in the case of a hybrid device that uses both WDD and LCD methods. The A:P ratio for an individual, or a body part, may be increased or decreased, as needed for individual applications, by changing the magnitude and direction of the force applied by the WBEs. In some embodiments, the ratio A:P ratio may be 1 or is less than one, and can range, for example, from 0.999999 to 0.000001, or less. In some embodiments, A:P ratio is greater than one, and can range from 0.000001 to 10000 or more. In some embodiments, A:P ratio is greater than one, and can range from 1.000001 to 10000.

While fluid-inflatable devices may be effective in distributing body weight as described hereinabove, they may not be suitable for all applications. Therefore, alternative methods and embodiments of WDD devices are disclosed to distribute the body weight, which do not require fluid-filled bladders.

In FIGS. 4A to 4N, there are illustrated methods and various embodiments of an apparatus to distribute the pressure from major weight-bearing regions of the body such as vertebral column, buttocks and thighs while seated in a chair to other parts of the body without the use of fluid-filled bladders. Note that although, the description is focused on a person seated on a chair, the method and the device are applicable to various applications, whether person is standing, lying down or in various postures of the body and while performing various activities.

FIG. 4A illustrates an embodiment of a WDD integrated into a chair and its various components. A chair is used as an example in the figure and in the description below, but it is understood that there is no limitation for its use in other applications. The WDD 401 comprises WBEs 406 that are attached to a movable plank or tile 403, which in turn are supported by front flaps 402, seat 407, and leg supports 408 of the chair 422. Note that only the front flap 402 is shown, but flaps that support the sides of a person are not shown. The planks 403 supporting WBEs at the back of the person are supported by frame 410 anchored to the backrest 409 of the chair. In the embodiment shown in the FIG. 4A, a person is shown seated on the WBEs located on the bottom planks, supported by the seat of the chair. However, in some embodiments, WBEs may not be required on the WDD (on the seat of the chair) to support the bottom of a person, which means, the WBEs located on the front, back and both sides of a person may be adequate to distribute the body weight away from the weight-bearing regions of the person.

The WBEs in FIG. 4A, or the planks may be anchored to (or supported by) external locations that are not part of the apparatus, e.g., wall, roof, floor, etc (not shown in the figure). The flaps are made to withstand at least all or part of the body weight of a person, so as to allow the WBEs to transfer the weight onto the flaps so as to distribute the weight over wider body surface area. All the flaps are supported by various parts of the chair including back of the chair 409 or to the seat 407, a leg rest 408 and the like, through a rod 404 or similar means.

There is no limitation on the number or the size of planks 403 that support the WBEs. For example, a chair may contain only one plank 403 that is large and flexible enough to completely cover all sides of a person, allowing the person to come into contact with the WBEs in all directions. Or, the chair may contain one plank for each side of the particular portion of the body to support WBEs. In some embodiments, the planks 403 that support the WBEs may cover the whole body or a selected area of the body including torso and legs as shown in the FIG. 4A, when secured to the body by various means including belts, zipper, buttons, Velcro and the like (not shown in the picture). In some embodiments, the planks 403 may be very small and support only one or a small number of WBEs. The planks 403 can tilt or pivot at joint 418 that connect the planks to the flaps 402 to allow for change of the direction of the force exerted by WBEs on a person. For example tilting the plank 403 upward will result in upward pressure from WBEs at the torso. Similarly, when a seated person changes position from vertical position to either bending forward or sideways, the WBEs and the plank 403 on the same side and the opposite sides will pivot at the joint 418 to maintain the contact with the body surface to exert either higher or lower pressure on the body. The supporting flaps 402 or the planks 403 can be moved back and forward or up and down either manually, or connected to an external power source, through the connector 441 located on the flaps. Additionally, the position of the planks and flaps may be changed manually by pushing down the lever 436 or through use of counter weights 438, or a similar mechanism. The direction of the planks may be changed to allow the WBEs to come into contact with the surface of the person at any angle.

In case of torsion springs, when force is exerted on one free end of the spring, the force is transmitted to the other end of the spring, and depending on how both ends are positioned relative to each other, the direction of force can be changed as desired. In a similar fashion, for example, when a person exerts a load on a WBE, composed of a torsion-type spring, force exerted on one end of the spring can be transferred to another WBE, by connecting the second end of the torsion spring to another WBE, such that the second WBE may be pushed against the body of the person (not shown in the figure). Similarly, the base of a plank on which several WBEs are supported, may be connected to the base of another plank that supports several WBEs. A torsion spring type mechanism may be used for transmitting the force. Therefore, for example, when a person sits on a chair and secures the frame to the body, and then allows the body to drop onto the WBEs, the pressure exerted by the body weight on the WBEs at the base will be transmitted to the WBEs, which push against the upper body of the person. This is somewhat similar to the how a fluid such as water exerts hydrostatic forces.

The free ends of the WBEs that contact the body of the person, may be covered by a sheet 440, or clothing of a person, or material that adds to the comfort of the user (e.g., foam or cushion, gel) that can be cleaned easily or disposed of. In a some embodiments, the sheet 440 is highly stretchable so as to offer little resistance to the movement of WBEs contacting the body in any direction, and especially to minimize shear forces. The sheet 440 can be made from a wide variety of materials, without any limitation, including cotton, foam, plastic, polymers, metals and nonmetals or a combination of the above. The sheets may be pleated to increase the stretching properties, may have holes to allow WBEs to project out and retract in, concave structures to receive and support WBEs, may contain protrusions, alternating bumps and dips that can selectively stretch to allow WBEs to provide support at selected regions of the body, may contain additional reinforcing structures to support the WBEs to provide additional grip. The sheet may contain either mechanical, electrical or magnetic structures to allow for interaction with WBEs, may contain mechanical structures such as rollers, balls, and the like to apply massage to the body, may contain zippers, buttons, belts or other means to secure to the neighboring structures or the person. Additionally, the sheet may be incorporated into the cushion, base of the chair, backrest or other supporting structures as one of the layers to support a person. The sheet may be disposable and may have additional surface chemical properties, such as antibacterial, low friction coefficient and the like.

The device may further contain sensors 421 that can sense pressure, direction of the force exerted by the body and the WBEs, temperature, humidity, direction of the whole body or part relative to the ground, position, posture, body weight, conductivity and impedance of the skin surface, local tissue oxygenation and capillary pressure at the contact site, shear forces on the skin and underlying tissues at the point of contact, various physiological parameters such as electromyography, electrocardiography, respirations and the like. The sensors may be incorporated into the WBEs, on any part of the apparatus described, or on at any location on the chair, or the parameters monitored directly or remote from the person seated. Selected parameters may be used to modify position, direction, pressure and other aspects to increase the comfort level or the person to achieve the desired goal either manually or through electrical controls that are connected to the power source.

Pressure and direction of force by the WBEs can be exerted manually, as exemplified for the back region of the chair supporting an inner frame 410 and outer frame 411 that are held together by hinge 407 and can slide against each other when raised by pushing or pulling the lever 436 or using electrical controls. The frames 410 and 411 are anchored to the back 409 of the chair 422 fitted with the WDD. The frame 411 can be moved in any direction front, back, up or down or at an angle, which in turn can move the planks 403 and the WBEs located on the planks. In some embodiments, counter weights 438, or springs with known resistance (not shown in the figure) may be used to exert a predetermined force on the planks 403. Without limitation, in additional embodiments, planks may be comprised of mesh held under tension by a frame (similar to how a tennis rocket or trampoline holds the mesh under tension) may be used, to support the WBEs (not shown in the figure). The advantage with this type of frame/planks is that they are light weight and flex around the body contours easily. In some embodiments, the plank 403 may be designed to exert predetermined force on the WBEs by way of springs 443 mounted at the base of the plank, or through electrical controls that push the planks and the supported WBEs against the body of the user (not shown in the figure). All mechanisms described for the WBEs located on the back or on the seat may be used to exert force on WBEs that are located on the planks 402 on the front and side flaps and those covering the leg supports.

The operation of the embodiments of WDDs described in FIG. 4A is summarized below. To initiate the process of weight distribution, the user sits on the chair fitted with the apparatus, and secures the flaps 402 to the body with belts, zipper or other the like. This results in the WBEs (push spring type) mounted on the planks 403 to come in close contact with all sides of the surface of torso and legs. As the 402 is tightly secured, there is some pressure exerted by the WBEs on the body, but most of the person's body weight is supported by the seat of the chair or the leg rest. At this time, additional pressure is applied on the WBEs around the torso, by manually pushing lever 436 in a downward direction, which causes the frame 410 along with the mounted planks 403 to move forward and in an upward direction against the frame 411. Instead of the manual operation, such force may be applied using an external power source 441 connected to flap 402. As a result of the movement of the planks 403, the WBEs mounted on the planks exert pressure in an upward direction (at an angle), as well in the horizontal and downward directions on the torso of the seated person. The person sitting in the chair may also first sit in a very straight position by elongating the torso to the maximum extent possible in order to increase the vertebral column height, before securing oneself with the weight-bearing device.

Although not described in detail, the WBEs located all around the body of the person including the front and side flaps 402, act in a similar way as described for the WBEs on the back, thereby exerting an all-around pressure with a net upward force on the torso. The angle of the planks 403 and the WBEs that come into contact with the torso may be set such that, the amount of pressure applied in the upward direction is relatively higher than in other directions, in this embodiment. The same effect can also be achieved by adjusting the length or the strength of the springs (WBEs) that are facing upward direction, or employing similar other mechanisms. As pressure is exerted all around the torso by the WBEs at this stage, the forces that act in opposite direction cancel out, resulting in a net upward force on the body, in an analogous fashion to buoyancy forces experienced by a person in water in a swimming pool. As a result of such lifting forces, the weight of the head, arms and torso of the seated person is now shifted to the WBEs contacting the back, sides and front of the person, while the pressure on the WBEs supporting the buttocks located on the base of the chair decreases. Therefore, the weight of the person is now off-loaded onto the planks 403 and 402, which are attached to other supporting structures, relieving the weight on the vertebral column of the seated person. A similar mechanism works to elevate the thighs and legs (from foot to the knee) of the person, which reduces the pressure on the back part of the thigh that comes in contact with the chair or on the bottom of the feet that comes into contact with the floor. The WBEs located on the thighs also push upward (towards the anterior aspect of the thighs), thereby relieving pressure on the back portions of the thighs, which in turn, further reduces the load on the vertebral column, that is caused by the downward pulling force exerted by the weight of the legs.

In some embodiments the WDDs and LCDs may exert same pressure all over the body, or variable pressure on various regions of the body, depending on the application. A person standing or sitting in a swimming pool or diving experiences a gradient of pressure on the body, as the water pressure varies with the depth of water. For example for a person standing upright in a swimming pool immersed up to shoulder level, the pressure on the feet will be higher on the feet compared to shoulders, due to difference in the depth in water to which each part is exposed. Similarly, as an example, an individual seated on a chair integrated with WDD, may be subjected to higher pressure at the waist region and lower pressure at the shoulders. For example, to keep the pressures similar to experienced in a pool filled with fresh water at sea level, the WDD may exert approximately 67, 45, and 22 mm Hg pressure on a person's torso at the waist level close to the seat of the chair, at 2 feet and 3 feet height above the seat level, respectively, going upward from the seat of the chair towards the shoulders. When the atmospheric pressure is included, the pressure on a person's body seated in chair therefore, may be approximately 827, 805 and 782 mm Hg, at the base of the chair, 2 ft and 3 ft above the seat of the chair. Similarly, a downward gradient, with higher pressure on the shoulders and decreasing pressures as one moves down towards the waist may be applied, such as on an astronaut in a microgravity environment.

It is important to realize that the forces that act upward, horizontally and downwardly, although substantially cancelling out, they provide an important role in the functioning of the device, by minimizing the shear forces. The forces that act on opposite directions of the body against the skin and underlying tissue, thereby preventing the sliding of skin over the underlying tissue such as muscles and bones, thereby preventing shear forces. As the total upward force is higher than the downward force, the resulting force, which is in the upward direction opposite the direction of gravity (similar to a net buoyancy force acting against gravitational force on a person in the water), will act on the body to off-load the body weight on the frame, resulting in the reduced weight on the vertebral column. This is an important distinction for the WDDs and LCDs compared to other modes of exerting forces on the body.

Some embodiments of WDD, whether they are integrated into a chair-like device as shown in FIG. 4A, a bed-like device (FIG. 8A to 8C), or portable devices (FIGS. 6A, 6C), may be enabled to off-load only a fraction of the user's body weight or a part thereof, onto the WBEs and frame, ranging from 0 to 100%. Therefore, some embodiments may off load 5, 10, 20, 30, 50, 70, 90%, 99%, or essentially 100% of the user's body weight onto WBEs and frame.

FIG. 4B shows some embodiments of WBEs that may be used with the WDDs. There is no limitation on the size, shape or design of the WBEs, the type of force or the power the WBEs can exert on the body, the structures they can be attached to or the composition of the WBEs. A few types of WBEs, without any limitation, are exemplified by the embodiments presented in FIG. 4B identified as 412, 413, 414, 415 and 416. The WBE of the 412 may be similar to a bristle on a brush, a semi-flexible projection, an inflatable structure and the like. A large number of them can be present on a given surface area of the plank 403 that supports the WBEs. The WBE may have additional bristles at the end as in 413 that can contact more than one point on the body. Additional embodiments of WBEs include telescoping type 414 that has an inner shaft that contacts the body, which moves in and out of an outer shell that is attached to the plank 403. A spring attached to one end of the inner rod and located in the outer shell may be used to maintain the position of the inner rod.

Some embodiments may contain WBEs that comprise compression-type, extension-type, torsion-type or other types of springs. Such type of WBEs may exert either push or pull type of forces against the body. For example, when a person bends to the right side, the spring type WBEs 415 located on the right side of the body may exert more pushing force on the right side of the body, while the WBEs located on the left side may exert less pushing force on the body or may even exert pulling force depending on the structures to which they are anchored. In addition to the compressive forces exerted by the body on the WBEs, the weight may also exert deflective forces on the WBEs. Although the WBEs are shown to be mounted in a perpendicular direction to the surface of the body in various figures, it should be understood that the appropriate type of WBEs may be used to support against various types of forces (e.g., deflective, twisting, compressive, stretching forces) that the body may exert on the WBEs.

FIG. 4B also illustrates some embodiments of WBEs, exemplified by WBE 416, that use repulsive forces of magnets to exert force on the body of the person. As shown in the example, the WBE 416 may contain two magnets 426 and 423 contained in an outer tube, with magnetic poles of the similar polarity (both north poles in this case) positioned opposite to each other. A spring mounted pin 424 that rests on magnet, can move in and out of the outer tube, which can contact the body of a person to support the weight. When an adequate magnetic force is used, the pin 424 can support the body weight of the person, as the magnet 423 can theoretically float on the lower magnet 426. Similarly in other embodiments, magnetic beads or strips attached to the sheet 440 or other structures that come into contact with the body may be used bear the weight of a person (not shown in the figure).

In some embodiments, without any limitation, the WBEs may be located on inflatable devices that are deflated or inflated to decrease or increase the pressure on the body, may contain holes that can be used to circulate air or vent out air or moisture or body wastes or may contain sticky ends for attaching to various parts. The WBEs may be connected to controls and a power source that can be used to exert a massaging type action on the body parts of interest, or may provide a wave like pressure on the body for therapeutic or recreational purposes or to promote sleep or increase comfort.

Although WDDs are used to explain the mechanism, it should be noted that the same principles and mechanisms are applicable to LCDs to exert forces on a human body. FIG. 4D illustrates some embodiments of a WDD integrated into a chair supporting a person. One embodiment of the apparatus, showing levers used to manually move a frame that supports the WBEs, capable of applying an upward force on the backside (and around the torso) of a person seated in the chair, is illustrated in the figure. Although, in the figure, the WBEs acting only on the backside of the seated person are shown, the WBEs are present around the torso of the person, and exert forces all around the torso in a similar manner. The mechanism shown here is somewhat similar to the mechanism described earlier for the embodiment shown in FIG. 4A, with a few differences to make it easy to describe the operation of the device. Therefore, the details of the device described in earlier sections are not repeated hereinbelow.

The following is a brief description of embodiments of devices shown in FIG. 4D and their operation. To operate the device, a person seated in the chair, pushes the lever 436 down after securing the weight-distribution apparatus to the body 420. This action causes WBEs 406 to be pushed upwards and towards the body and to contact the body of the user either directly or through sheet 440. Note that in the embodiment shown in FIG. 4D, the WBEs are shown to be supported by the frame 411, while the planks 403 and flaps 402 shown in FIG. 4A are omitted here. Instead the WBEs are shown as being supported by the inner frame 411 that is attached to the lever 436 by a bolt 447, which allows the 411 to be raised and lowered. The inner frame is 411 is anchored to the outer frame 410 by hinges 417 and to the lever 436 by a bolt 446. In some embodiments, as shown in this figure, WBEs are only present around the torso and legs (which are not shown in the figure), but not under the buttocks of the person. In this embodiment, when the lever 436 is pushed down, the weight of the upper sections of the torso is transferred to the WBEs and then to the frame 411, thereby relieving the load on the spine, buttocks and thighs.

FIGS. 4E and 4F show a vertical sectional view of an embodiment of a WDD with the torso of a person, supported by WBEs 406 (push springs are used in this embodiment) on a frame 403 pressing on both sides of the body 420, and maintaining constant contact with both sides when the torso is in a vertical position. FIG. 4F shows the same longitudinal section of the body, when the person bends towards left side.

The objective of these two figures is to show that the WBEs will maintain their contact with the body during movement of the body. As a result, the pressure applied on the body by the WBEs at a particular location of the body may increase or decrease depending on the posture of the person, in relation to the frame, but overall, the body weight of the person will be distributed over a larger surface, resulting in less load on less load on weight-bearing structures.

As a result of the bending, as shown in the figures, the WBEs located on the left side of the body 420 are compressed, while the WBEs on the right side are more relaxed (shown elongated). As a result the WBEs on the left side of the person in this embodiment exert more pressure per unit area of the body surface, compared to the WBEs on the right side. Further, the outer frame 403 may be designed with different flexibility to resist significant bending movements away from the vertical position, thereby adding additional force to the WBEs. Although, not shown in this figure, the WBEs may be configured to exert force at an optimal direction (upward, horizontal or downward as appropriate) when the person changes posture. Together, these ensure to that the person feels less weight or pressure on the lower portions of the torso or legs when using the weight-distribution apparatus.

FIG. 4G shows a perspective view of embodiments of WDD supporting a person seated in a chair. In the figure, the torso 420 of a person seated in a chair, having a seat 407 and a backrest 409. To relieve the pressure on the lower portions of the body, a person, after sitting on the seat of the chair, secures frame 454 to the torso using straps 457 (or similar other securing means). The WDD may be a stand-alone device or integrated into the chair.

The frame 454 is made of at least one layer, and is made of flexible but strong material to support the body weight of the person seated. In some embodiments, the frame may be molded out of plastic and curved around the body contours to support the backside, lateral sides, the base and the front side (with e.g., a hinged front piece, which can be closed and secured after a person is seated) of the user. The circumference and the fitting of the frame may be changed by tightening various fasteners 457 or other means. The edges of the frame may overlap each other, and therefore may cause additional pressure on the WBEs when the overlapping edges slide against each other, thereby causing the circumference of the frame to decrease. The WBEs may be located on the inner surface of the molded frame (chair) and come into contact with the body of the person when the person when the device is secured to the torso. Although, only a torso is described here, it is to be understood that the device may be used to distribute weight of other parts of the body.

In some of the embodiments shown, the WBEs 406 (e.g., push springs) are located on an inner surface 450 (see peeled away surface) of the frame. The frame is composed of an outer frame 454 and an inner frame 451. The outer frame 454 is supported on the seat by the lower edge 452 of the outer frame and by the lower edge of the inner frame 451. The outer frame 454 may be able to slide up and down, when the lever 436 is pushed down or up, as lever 436 is attached to outer frame by another plate 456. The outer frame is also able to exert inward pressure on the WBEs mounted on the inner surface of the frame, when a vertical pressure is exerted on the frame. Therefore, an upward movement of the outer frame may result in WBEs exerting forces against body in all directions (upward, downward and horizontally). To initiate weight distribution, the user is seated in the chair, and the frame is secured tightly around the torso using the straps; such a securing of the frame results in the WBEs 406 on the inner surface 450 of the frame being pushed closely against the torso. At this stage, when the person pushes the lever 436 down, the outer frame will move from an initial position on the seat as indicated by solid 452 to a new higher dotted position 453 (and 455 at the top). As the WBEs are secured tightly to the body, such an upward movement of the frame is designed to cause the frame to narrow around the torso, or cause WBEs to extend out, or simply exert increased pressure on the body in several directions. The result is a net upward force on the torso, and as such causes the weight of the torso to be shifted to the WBEs, and then to the frame 454 and ultimately to base of the seat. As a result, a significant portion of the weight of the upper torso (including arms and head), which are usually borne by the spine, is now distributed on the outer surface of the torso and supported by the seat of the chair directly.

In some embodiments, the LCDs or WDDs operate by exerting forces on the body of the person, from at least on two opposite directions, to distribute the body weight of the person. For example, the WBEs that surround the body of a person exert such forces. Because the forces that have equal amount of magnitude that act in exactly opposite direction to each other cancel out. This may include exertion of force on one side of a body of a person, and causing the opposite side of the body to be pushed against another surface, thereby causing that surface to exert force in the opposite direction on the body. As an example, the WBEs may only act on the front portion of a person pushing the back of the person against the backrest of the chair. For example applying such a force on the abdomen and chest of a person sitting in a wheelchair using a WDD, and pushing the person against the backrest of the wheelchair, may relieve the pressure on the weight-bearing regions of the torso and the underside of thighs. In this case the force is exerted on two opposite directions of the torso, the front and the back.

The weight distribution apparatus as described herein, may be a stand-alone device or may be integrated into various articles including furniture (e.g., sofas, chairs, beds, cushions, mattresses, and the like), medical and non-medical devices (braces, casts, walkers, exoskeleton, shoes and the like), to provide the functionality described in this application. The weight-distribution apparatus does not have to be a suit-like structure that envelops the whole body. It can be used to support individual portions of the body such as the head, neck, arms, torso, legs, etc.

FIG. 4H shows an embodiment of the WDD, or the parts thereof illustrate that a WDD may be retrofitted onto existing furniture (a chair is used an example in this case), without any limitation, to enhance their utility. The figure shows a chair retro-fitted with WDD that comprises a head and a neck rest 460, and two wedges 461 to support the torso of a seated person. The WDD also comprises two outer leg support wedges 462 to support the outer sides of the thighs and an inner leg support wedge 463 to provide support to the inner side of the thighs. The outer surface of the wedges is the frame 473, made up of either rigid or semi-flexible material, which supports the WBEs and transfers the weight of the user from WBEs to the chair. Although only one center wedge is shown in the figure, separate independent inner wedges for each leg may be used. A front WDD support wedge that may be able to support the anterior portion of the torso, by pushing the WBEs against abdomen and chest is not shown in the FIG. 4H. Similarly, additional supports for the legs, knee below or arm supports (not shown in the figure) may be included, which may further enhance the functionality. Also not included in FIG. 4H are the portions of WDD that support the backside of a person, as well as the buttocks portion. Although these additional parts are not shown in the figure, it should be understood, that these may be included in additional embodiments.

The wedges contain WBEs 406 on the on the inner surfaces that come into contact with various parts of the body. The WBEs may comprise either mechanical types of devices, such as springs, or may have an inner inflatable bladder which can be inflated using optional hose 472 to increase or decrease the internal pressure in the bladder (bladder not shown in the figure). Note that although, this device is mentioned under the section that does not use inflatable bladders, for completeness sake, it is included here. Lever 467 is connected to torso supporting wedge 461, and may be operated by using wheel 469, which when turned with handle 471, will cause the torso supporting wedge 461 to move in an upward/downward direction. Several mechanisms may be used, without limitation, to raise and lower the torso supporting wedge 461, which include, a rack and pinion type device to raise or lower the frame using the wheel 469 (details not shown in the figure), a device driven by external power, and the like. The torso supporting wedge 461 may also be moved closer or away from the body in a horizontal direction and locked in place, by moving them using adjustable clamps 464 similar to those present on the seat of the chair. The leg support wedges may be raised or lowered from the seat or pressed close together to increase the pressure by WBEs on the legs using the adjustable clamp 464. Electrical controls and external power sources may be used to inflate the bladders, WBEs, or to move the torso and the leg support wedges (not shown).

To operate the device shown in FIG. 4H, the user sits down on the chair with torso leaning against the back-rest of the chair and positioned between the two left and right torso-supporting wedges 461, and with the each thigh positioned between thigh-inner wedge 463, and the thigh-outer wedge 462. The user then brings the both right and left torso-wedges of the torso supporting wedge 461 closer to the body and secures the body to the wedges using straps 457 or similar means. In some embodiments, in this position, it may not be required for the wedges to cover the front portion of the user, although a front flap together with a back flap (with WBEs in them, not included in the figure) will further increase user comfort and functionality of the device. Using chairs fitted with torso-supporting wedges 461 alone (without the front wedge—not shown) as shown here may be easy for the user to get into the seat and get out of the seat easily, without the need for elaborate preparation work, and therefore may increase the user acceptability of the device. In the embodiment presented in the figure, although torso-supporting-wedges 461 may be designed to easily move back and forth or to the sides to increase user comfort level and flexibility while using the device.

In some embodiments, the user may be able to slide the torso left and right torso-supporting wedges 461 inwards and outwards for the user to get in and get out of the chair easily. The sliding mechanism which may be located on the back of the seat is not shown in the figure. The user may also secure the thighs to the thigh wedges 462 using the lever 464, which can facilitate sliding inward and outward of the thigh wedges and for securing them in place. The lever 464 or a similar mechanism may also be raised using manual or electrical power to raise the wedges above the base of the seat, so as to shift the body weight on to the WBEs. Additional wedges that cover larger surface area of the seat including buttocks or middle of the backside of a person, may be used to increase user comfort (not shown in the FIG. 4H). Regarding the head and neck rest 460, although only showing the portion that supports the back of the head and neck, it should be understood that 460 can cover a significant portion of the sides and front of the neck, as well some part of the head as needed (without endangering the safety of the user) to provide maximum support to both head and neck.

The WBEs located in various wedges may be pressed against the body by moving the wedges upward so as to increase the pressure on the body. Alternatively, in some embodiments, the inflatable structures, located in the wedges may be inflated using motors to allow the weight of the person to be shifted to the WBEs. Note that although a bladder is mentioned for the ease of explanation, several other means such as springs, WBEs mounted on planks, etc., as described earlier in the FIG. 4A to 4C may be used in the wedges to exert pressure on the respective body parts. In some embodiments, a user may need only the WBEs supported by the bladder to transfer the weight of the torso to the supporting frame.

To operate the device, the user after securing her/himself between the torso and leg wedges, inflates the bladder(s) to press the WBEs against the body. Once the WBEs are pressed against the body, the user may raise the torso wedges 461 by rotating the wheel 469, which causes the WBEs to be further pushed against the user's torso, thereby resulting in transfer of some of the body weight on to the WBEs, and in turn onto the frame of the 461, thereby relieving the pressure on the spine. The leg wedges work similarly to reduce the pressure on the bottom side of the thighs, when seated. The advantage of the retro-fitted wedges described here is that they can be portable and can be fitted to furniture or devices already in use, thereby minimizing additional cost and space requirements.

FIG. 4I, illustrates a perspective view of some embodiments of WDDs integrated with a chair. The mechanism of the embodiment of WDD shown in this figure is somewhat similar to the embodiment presented in FIG. 4A, and therefore, only parts of the chair that are relevant to describe the mechanism of the WDD are shown in the FIG. 4I.

A chair is illustrated in some embodiments shown in FIG. 4I as an example. However, the WDD, device may be integrated with any other equipment, including an automobile seat, an airplane seat, wheel chairs, office chairs, home couches, and the like, so as to distribute the body weight from weight-bearing regions of a body to non-weight-bearing regions. The embodiment is particularly helpful for those that are required to sit for prolonged hours and those with back pain related issues. For the sake of clarity, only selected parts are included for demonstrating the functionality of the device.

In FIG. 4I, the chair integrated with WDD 475, comprises a backrest 490, seat 489 and a front flap 477 and supporting legs 484. The WBEs 483 may be supported by the frame of the chair, which may pass through holes 487 on the cover 476 that covers the seat, backrest and inside of the front flap of the chair. The cover 476 may contain holes to accommodate the WBEs that protrude out of them. The cover may be made of thick metal sheet, wood, plastic, leather, fabric or other suitable materials, can be raised or lowered manually or using electrical controls. The cover 476 may further be covered with an optional sheet (not shown in the figure), which contacts the body of the user on one side and the tips of the WBEs (when they protrude out of the frame of the chair), and the cover 476 on another side.

The WBEs comprise several types of mechanisms, but push springs are used as an example in this embodiment. WBEs may be located on the backrest of the chair to support back and sides, and on the seat to support bottom and the lateral sides of thighs. The WBEs may also be located on planks that are connected to levers or external power sources for better maneuverability of WBEs as discussed for earlier embodiments. Inflatable structures are not shown in the FIG. 4I, however, they may be used in certain embodiments to exert pressure on the WBEs. Although, the backrest and the seat of the chair are shown flat in the figure, they may be curved to suit the contours of the body, and to provide better support to the sides of the torso, and buttocks, and the lateral aspects of the thighs. The cover 476 may be thick and may be made of metal or plastic, foam, a mesh held under tension or other types of material and may be able to support at least the weight of a person.

The chair may include a front flap that when secured can support the front portion of the torso including the chest and abdomen, as well as some part of the sides. The front flap is connected to the chair with a hinge 486, and may have a contoured inner surface that will enable it to snugly fit the lateral and front parts of the torso. The front flap may be secured on its edge 480 to the backrest of the chair using fasteners 479 and 481. The backrest and front flap and the sides may be secured to the base of the chair through hinges so as to allow the user to move or bend forward or backward or onto either right or left sides easily.

A thigh flap (not shown in the figure), that covers the top and lateral aspects of the thighs may be connected to the seat of the chair, in a manner very similar to how the front flap 477 is connected to the backrest. The lower portions of the legs and the feet may also be covered by the similar flaps (not shown in the figure).

The cover 476 may be lowered into the frame of the backrest and the seat of the chair using the guides 482 and 485. Both the backrest and the seat of the chair may have elevated sides (not shown in the figure) to accommodate WBEs, to support the later side of the torso and the thighs, respectively. The portion of the seat between the thighs may be elevated (not shown in the figure) to accommodate WBEs, to support the inner sides of the thighs. The backrest, the front and the thigh flaps can be raised or lowered either manually or using electrical controls (not shown).

To operate the device, the user sits in the chair and pulls the front flap over to cover the anterior (front) and lateral portions of the chest and abdomen. The front flap covers the front portion and some of side portions of the user. The user tightens the front flap so that the flap is pressed against the body, which presses the user against the backrest. The user then causes the cover panel from the backrest and the front panel to retreat (using manual or electric controls—not shown in the figure) to the bottom of the backrest and the into the back of the front panel (sliding over the WBEs), respectively, such that the WBEs are now exposed and pressed against the body of the seated person (after contacting the overlying sheet), from all four directions, back, front and the sides. An alternative way to exert pressure on the body of the seated person is to push out the WBEs through the holes in the cover, using either manual or electrical/hydraulic force (not shown). Once the body of the user is secured to the WDD, the backrest and the front flap of the device may be raised using manual levers or electrical controls located on the chair (not shown in the figure). When the backrest and the front flap along with the WBEs are pushed against the body, the resulting net force in the upward direction causes the WBEs to be further pushed against the body of the person, resulting in the weight of the person shifted from weight-bearing regions (spine and buttocks) onto a larger surface area. In a similar manner using manual or electrical controls, the pressure on the WBEs supporting the thighs may be increased. As the thigh flap (not shown in the figure) is secured to the seat of the chair, the increased pressure of WBEs results in distribution of the pressure from the bottom side of the thighs and buttocks to other portions of the body. Therefore, as a result of combined action of the WBEs located on the front flap, backrest, the seat and the thighs flap (not shown), the load experienced by a seated person on the back (lumbo-sacral region), buttocks and underside of the thighs is reduced.

In addition to exerting pressure on the body either manually, e.g., using levers, or using external power sources, it is advantageous to have a system that uses the body weight of the person to distribute the weight from the weight-bearing regions to non-weight-bearing regions of the body, without using inflatable structures. Principles of such system and methods to distribute body weight is described in this section and some embodiments of the device are depicted in FIG. 4J. The rationale for methods and embodiments that employ the user's own body weight are summarized below. A person standing in water in a pool does not require additional external power sources to experience the decreased weight on the weight-beating regions the body. This is because the weight of the displaced water reaches a dynamic equilibrium with the body weight of the person (due to gravitational force on the body). In a similar manner, in the following embodiments, the WDD is configured exert a certain amount of load on the body of a person, when the act of sitting down by a person on the seat of a chair is designed to displace some volume of the fluid that exerts pressure on the body surface of the user. Similarly, the body weight of a person sitting in a chair may also be used to push against the body surface of the person, establishing a dynamic equilibrium between the body weight of the person and the WBEs that exert an upward force. The detailed mechanisms of some embodiments that work using this method are described below.

In FIG. 4J, a side view of some embodiments of WDD integrated with a chair are shown. The embodiments as shown use the same principles, method and various embodiments of WDDs described earlier. A chair is used here as an example, but without limitation, the method and the WDD mechanism may be applicable to distribute the body weight or exert pressure on the body in a wide variety of situations in various postures (e.g., automobile or airplane seats, wheel chairs, office chairs, sofas, stools, mattresses, hospital beds, orthosis, braces and assistive walkers and the like). Although, inflatable structures are not included in this embodiment, a combination of inflatable and non-inflatable structures may be used in this device. Because the mechanism of WDD has been described earlier, only a few parts are included in the figure to describe the operation of the device. Several supporting structures for the base of the chair, backrest, etc., are omitted from the figure and description below for the sake of clarity.

As shown in the figure, in some embodiments, the WDD 492 (chair integrated with WDD) supports a person 420 on the base 407 of the chair. A torsion spring 468 supported by the vertical shaft 459 of the chair, supports the frame 494 of the WDD, and the base 407 of the chair. A supporting member 458 that extends from the under-frame of the base of the chair rests on one arm 497 of the torsion spring, while the frame of the WDD rests on another arm 496 of the torsion spring. Torsion springs with two arms are illustrated here to refer in general to any supporting device that can allow use of the body weight of a person to exert pressure against other parts of the body, however, there is no limitation on the type of devices that can be used to support a person's weight, and how the frame, backrest or base of the chair are connected to each other.

In some embodiments, the base of the chair at rest is supported by telescoping rod 442, which rests on the horizontal support 478 anchored to the vertical shaft 459. The weight of a seated person may be shifted from the telescoping rod 442 to the supporting member 458, by pulling the lever 444. The frame 494 supports the WBEs 406, which contacts the sheet 440 that wraps around the body of the user. The WBEs are shown contacting the frame directly in this figure, but in some embodiments, several variations of this design may be implemented, for example, the WBEs may be supported by a backrest of the chair (not shown in the figure), or supported by an inflatable structure, or supported by planks and flaps that are similar to discussed earlier in FIG. 4A. The figure shows a frame and WBEs supporting the backside portion of the person only, however, it should be noted that the person's sides and the front portions and other parts of the body may be supported by the frame and the WBEs described herein.

The principle underlying the embodiment shown in FIG. 4J is, when force is applied on one end of a torsion spring, an applied force may be transmitted to another part of the spring, with minimum loss of energy. The force so transmitted may be used to push the WBEs against the body (preferably at the non-weight-bearing regions of the body), thereby causing the body weight to be shifted onto the frame, thereby reducing the pressure on the weight-bearing regions (buttock, sacrum, coccyx and underside of thighs).

To operate the device, the user sits on the seat of the chair and secures the frame with the WBEs to the torso (and other body parts as appropriate). At this stage, the weight of the torso and the thighs of the seated person may be borne by the base 407 of the chair, either partially or completely. The user's weight is supported by telescoping rod 442, which is supported by the main vertical shaft 459 that is connected to the legs of the chair. The user may shift the weight from the telescoping rod to supporting member 458, by pulling the lever 444. As a result, the body weight of the user is now born by one arm 497 of the torsion spring, which forces it down. Only one torsion spring is shown in the figure, however, there is no limitation of the type of springs or similar other devices, size and number of springs or their location on the WDD or the chair. The downward movement of the arm 497 due to force of the body of the torsion spring results in upward movement of the arm 496. As a result, the frame of the WDD that rests on the torsion spring arm is pushed upward and inward against the seated person's body. As the frame may be secured to all sides of the body, this results in the WBEs being pushed against the body of the person from all directions. In some embodiments, the force that causes the upward movement of the frame may be configured exert forces on all directions. The strength and the direction of force exerted by the lever may be configured to cause a net upward force on the body, which decreases the load on the load-bearing regions of the body.

Some embodiments of WDD may use a combination of both inflatable and non-inflatable structures to exert pressure on person's body. A separate figure for this embodiment is not included herein, however, a brief description of the embodiment and its operation are included here. In some embodiments, the hybrid devices are somewhat similar to the embodiment of WDD shown in FIG. 4J, except that instead of the torsion spring, an inflatable structure (e.g., a fluid filled-bladder) is provided below the base 407 of the chair. The pressure in the bladder increases when a user sits on the base of the chair and releases the lever 444, which causes the body weight of the user to exert pressure on the bladder. The bladder may be connected to structures (e.g. tubes, telescopic structures or springs) which are either compressed or pushed up and transmit the force to the frame 494. The frame and the WBEs may be either connected to the bladder directly or through various structures mentioned above. Due to the pressure, the frame and/or the WBEs will exert pressure against the torso or other parts of the body, resulting in the off-loading of the body weight onto the WBEs and the frame, as explained earlier. For the purpose of description of the device, a chair is used as an example, but without limitation this device and the method may be used in several applications. The advantage of such a system is that it may be easily integrated into various equipment such as a car or airplane seats, chairs or mattresses, without adding significant weight. An additional advantage is that the above system may be used as a standalone cushion connected to a frame and WBEs that can be placed on the top of, for example, a chair or a vehicle seat or a mattress and used immediately.

The same mechanism of distributing weight using the WDD using the torsion springs (or the similar devices and methods) may be applied to other embodiments and applications mentioned in this disclosure.

FIG. 4K illustrates a detailed view of some embodiments of an optional sheet that may be positioned between the body of an individual and the tips of the WBEs. In the figure, the WDD 493 comprises a frame 494 and WBEs 406 that are in contact with sheet 440, placed in between the WBEs and the user's body 420. The sheet may comprise at least one outer layer 498 that is in contact with the tips of the WBEs, and at least one inner layer 499 that may be in contact with the body of the user. The outer and inner layers may be able to slide freely against each other, or stitched or anchored to each other or to the underlying supporting layer (not shown in the figure), to provide a controlled amount of sliding movement against each other or the body of the user. Fluid 488 that may have lubricating properties may be present between the inner and outer layers of the sheet. The fluid may be gas, liquid, oil, powder, balls, gel, polymers and the like. The inner surfaces of the layers that face each other may be made of a material and surface structure which provide little friction in some embodiments, in which case a lubricating fluid may not be required. The sheets may be made of porous, mesh-like, foam type or similar material. There is no limitation on the number of layers and locations where the sheet can be anchored.

In some embodiments, the sheet may incorporate elastic type stretchable bands configured to stretch and exert a predetermined force on the skin of the user. The elastic bands may traverse the length of the sheet in different directions, longitudinal, horizontal, and at various angles to the edges of the sheet. The sheet may be anchored to the edges of the WDD, mattress, seat of the chair, or any structure that supports the person's body. The elasticity of the bands may be modified and therefore, some bands may have higher elastic strength versus others. The elastic bands from the edges of the sheets may terminate at different lengths of the sheet, such that when the sheet is pulled from underneath the body of the person, forces applied on the body are spread out over a wider body surface, rather than focused on a single location as happens with the standard fabric. Such an embodiment of a sheet allows for distributing the frictional forces applied on the body surface when the user's skin moves against the supporting structure.

The sheet serves several purposes in the operation of a WDD. The sheet shown in this embodiment may minimize friction between the WBEs and the body, such that the magnitude and direction of the forces are passed onto the user's body without any change. The user when covered by the said sheet may be able to maintain the targeted force and the direction on the body surface, even when the body moves in relation to the original contact position with WBEs. In some embodiments, a two layered sheet as shown in FIG. 4K with fluid between the layers may be used, which will minimize any friction between the WBEs that contact the outer sheet, and the body with contacts the inner sheet. With such a sheet inbetween the body and the WBEs, when pressure is exerted, the outer layer that is in contact with the WBEs simply slides over the inner layer, and therefore no shear or frictional forces are exerted on the skin or underlying tissue due to such movement. Such an embodiment allows a person wearing the WDD seated in a chair to move freely and perform various activities.

FIG. 4N shows some embodiments of WDDs, which may be used for supporting a person in a seated position. Depicted in FIG. 4N is a WDD mechanism which may be used as a portable cushion for use outdoors such as at ball games or indoors, as a yoga/meditation cushion and the like. The device comprises the body of the cushion 4036 surrounded by sturdy material, supported at the base by straps (not shown), bands or extendable arms 4035. The body of the cushion holds WBEs 4032, which contact the body of the user 4030 on one end, while supported on an inflatable bladder 4034, or torsion-type spring like mechanisms (not shown) to transfer the load from weight-bearing regions of the body (e.g., buttocks and thighs, in this case) to outer surfaces of the torso. The WBEs can extend and cover either part or a significantly larger portion of all sides. A back frame 4031 that may be used for additional support to the WBE is shown in the figure.

To operate the device, the user is seated on the top of the device and may optionally secure the frame 4031 that supports the WBE to the torso. At this stage the complete weight of the user's upper body is borne by the buttocks and thighs that come into contact with the cushion. The user then pulls a lever (not shown in the figure) that causes the body weight of the person to be shifted onto to the WBEs (or bladder) located in the base of the cushion or allows the seat of the cushion to drop below onto the bladder. This causes the WBEs located on the bladder located below the buttocks region to exert pressure on the portion of the bladder directly underneath those WBEs, but causes the part of the bladder at the rear to be pushed up, thereby causing the WBEs located in the rear to be pushed against the back side (dorsal side of the torso) of the person, thereby helping to off-load some weight of the torso onto the WBEs. As a result, the load on the spine and lower portions of torso or underside of the thighs is decreased, resulting in increased comfort to the user.

The embodiment of the WDD shown in FIG. 4N, may be used as a portable cushion or a small seat that people can take with them, as an example either for sitting on the hard ground or floor (e.g., for a yoga practice), to take it to the ball games (to sit on the benches), where no backrest is available. The device may comprise flaps on the sides and back, which may be foldable for easy carrying. The flaps may extend up to sacral, lumbar or thoracic region and may be secured to the user using straps, belts or other means. The device may have either inflatable bladder or mechanical means to exert pressure on the body, and both mechanisms are described below. The flaps may contain more than one layer and the outer and inner layer may hold a space within which inflatable structures may be included. The inner surface of the flaps may support the WBEs, which are either in communication with the bladder or rest on the bladder, and push against the body, when the bladder is inflated. The WBEs may be made up of telescoping springs, push springs, and the like. Instead of the flaps, the WBEs may directly rest on the bladder, and come into contact with torso and base of the person, in a manner very similar to how a bean bag will surround the seated person. In additional embodiments, the WBEs (for example made of push springs) may directly be supported by the frame of the cushion, and support the seated person on the free end. When the person is seated on the cushion, the free ends of the WBE, not only come into contact with the bottom portion of the buttocks and the thighs, but most preferably come into contact with the torso (back, sides and the front) and lateral sides of the thighs. The device may be secured to supporting structures (e.g. benches, bleachers, stools, etc) structures by means of straps. Alternatively, plates or rods from the frame may extend outwards, to provide additional support to the cushion when it is used on the ground, floor or carpet, to provide additional support to a person seated.

When the flaps are used, they may be made up of a strong material, to support the weight of the body or reinforced with a metal frame. The seat portion of the device may contain an inflated bladder or similar structures, and the bladder may be in communication with the tubes or the extendable structures located in the flaps. To use one embodiment of the cushion, the user sits on the cushion, and straps the side, back and front flaps. This results in high pressure on the bladder in the seat. Then when the person allows the fluid from the seat cushion to communicate with the inflatable structures located in the flaps, by pulling a lever, the increased pressure will cause the WBEs to be pushed out and cause the body weight of the person to be shifted to the WBEs and in turn to the frame of the cushion or floor or the bench, on which the cushion is placed. This results in the weight of the person to be shifted from the weight-bearing regions (e.g., buttocks and the underside of thighs) to sacral, lumbar, thoracic regions of the torso, on the back, front and the sides of a person's trunk depending on where the WBEs come into contact with the body. In some embodiments of the cushion, when compressible springs or other types with similar functionality are used as WBEs, which rest on the bladder, the weight of the seated person on the cushion will push the springs, against the torso or other portions of the body to distribute the weight. For the ease of explanation, inflatable WBEs are mentioned in this description, however, the WBEs may be comprise of sticks, needles, wires, bristles, springs and the like. The pressure may be exerted on the body using without using the inflatable bladders in the seat and the flaps. For example, a lever may be used to push the inner frame supporting the WBEs against the body, which causes the spring type WBEs to exert force against the body in all directions, with majority of the force being directed upwards. In addition to the torso, other regions of the body of the person may be supported. Although a frame is mentioned here and in other locations of the application, it should be noted that other embodiments of the frame may be possible. For example, the springs and the other WBEs may be long and contact the surface of the body directly on one end, and the floor or other supporting structure on other end, which obviates need for a frame.

In some embodiments, systems and methods that distribute the body weight of person by exerting pulling forces are disclosed herein. These embodiments of the WDD and LCDs may be used with or without WBEs. Unlike the other embodiments described, the WDDs are made of elastic or non-elastic bands that traverse the surface of the body in various directions. The bands may be integrated into a fabric that is in close contact with the skin. A semi-flexible or a rigid frame that is made up of several pieces may be placed around the body from above the head or above the shoulders to the waist and from waist to the feet, with appropriate joints to allow flexibility. A body suit may be made of fabric and elastic fibers that cover the torso and legs (and other parts of the body as appropriate), and are anchored to the frame. When the suit and the frame are secured and tightened, the user appears as if suspended in the frame by the suit, very similar to a person in a harness. There may be foot plates and shoulder plates, and waist rings to the frame that serve as anchor points to some parts of the suit, to allow the suit to exert a lifting force against the body.

Shown in FIGS. 4L and 4M, are some embodiments of WDD and LCD, that pull against the body, instead of pushing against the body to exert forces. The previous embodiments described hereinabove exert pushing forces (similar to hydrostatic forces) against the body, which result in a net upward force (similar to a buoyancy force) against the gravitational force on the body, or a net downward force in an astronaut using a LCD. It is however, advantageous for some applications, to have a WDD that exerts a pulling force against body, to exert forces on a person. The embodiment may use inflatable or non-inflatable structures and may use a combination of various methods and embodiments described earlier. Although, the present description mainly focuses on decreasing the load on the weight-bearing structures, the devices may also be used to increase load on weight-bearing structures of the body, in certain environments such as in microgravity, to prevent various adverse effects on the physiology of the body including muscles, bones and the cardiovascular system.

The principles of weight distribution and reduction of shear and frictional forces disclosed herein apply to the embodiments illustrated in FIGS. 4L and 4M and therefore are not repeated again. Only parts that are different from other embodiments or critical for describing the operation of the new WDD embodiment are shown in the figures. Although the description of the embodiments in the application includes a body or a portion of a body, it is generally meant as an example and applies to either a full body, or part of a body without any limitation. Similarly, when referring to some of the embodiments, the terms surrounding, encircling, extending and the like are used with the understanding that the body may be surrounded or encircled partially or completely without any limitation. When referring to the various forced acting on the body or parts positioned in vertical, horizontal, at an angle, upward or downward directions, it is meant to include the vertical and horizontal, as well in various directions at all angles (including a z-axis), in a three dimensional space, without any limitation.

FIGS. 4L and 4M show front views of an embodiment of a WDD 4000 supporting the torso 4005 of a person. In FIG. 4L, the torso is supported by a frame, represented by the vertical bars 4010 that bear the weight of the person. Attached to the frame are the anchoring members 4015 that exert slightly upward force at an angle and 4018 that apply downward force at an angle. The force on the bands may be in more than one direction. Both anchoring members are attached to bands that partially or completely circle the body, with some of the bands position at an angle to the vertical axis of the torso. The bands 4020 are positioned with lower side on the right and the upper side on the left side, while bands 4025 are positioned with lower side on the left side and the upper side on the right side. The bands are either pulled in an upward or downward direction or at an angle to the vertical axis of the body such that they exert a pulling force on the body. Pulling force is exerted on the body by turning the wheel 4019 located at the end of the supporting frame or various other manual or using external sources of power.

In FIG. 4L the same embodiment of WDD 4000 discussed in FIG. 4L is shown in a front view. Shown in the figure are additional parts of the frame including the top 4011 and bottom 4017 parts of the frame. Horizontal bands 4014 circle the torso either completely or partially, and are anchored to the vertical frame 4010 by anchoring member 4013, that exert a pulling force in the horizontal direction either towards right or left direction or both. Not shown in the figure are vertical bands that circle the body or individual parts of the body in a longitudinal direction, parallel to the vertical axis of the body. Although, only vertical and horizontal bands are shown, it is to be understood that these bands can be supported at an angle by the supporting members and the frame. The top frame supports the anchoring member 4012 that exerts an upward force, while the anchoring member 4016 exerts downward force on the horizontal members.

The bands without limitation may be composed of individual threads, belts, ropes, fabric, foam, inflatable or non-inflatable material, tubes that contain thread like structure inside, and the like. In some embodiments, the bands may be incorporated into at least one sheet and worn as a garment around the body of a person. The term "bands" refers to wide variety elements such as straps, ropes, wires, sheets, without limitation, that may be used to exert pulling forces on a person. The thickness and other characteristics of the sheet are such that while it holds the bands together, it does not interfere with the function of the bands or distort forces exerted by individual bands on the body. The frame may be semi-flexible or rigid and may be made up of several flexible joints. The bands may be anchored to the frame in several stages. For example, the bands surrounding the torso may be anchored to the part of the frame placed above the shoulders and to another part of frame approximately at the waist area (e.g., like a belt). The frame around the legs may include a sole plate (under the foot), a knee joint and an ankle joint. The bands from the waist piece of the frame may be connected to the frame that supports the legs such that a load on the torso and legs may be off-loaded separately, in a stepwise manner or together and/or in a graded fashion. The pulling force exerted on each band and on each direction may be modified, to uniformly distribute the pressure on the body.

In some embodiments, the frame that surrounds the body of the person is used to hoist the person upwards using a fabric integrated with bands/straps. The weight of the frame is supported by the foot plate on which the person stands. When seated, the weight of the frame above the waist level is borne by the ring that is at the waist level and rests on the base of the chair. In certain embodiments a plate below the buttocks and the thighs of the seated person may be more appropriate instead of a waist ring. It should be noted that pulling forces are applied on the body in various directions, including, upwards, horizontal and downward direction, and at an angle. In some embodiments, a graded pulling force may be applied on the body of the user from toes to the head using the straps. Higher pulling force may be applied at the lower regions of the body with progressively lesser force towards the head of the person. As a result, the pulling force exerted by the straps is distributed over a wider surface area of the body. As the suit is raised up (by the frame above the head or the shoulders), it results in off-loading of the weight of the body onto the elastic bands and suit, and in turn onto the frame which is supported by the foot plate on the ground or the waist ring on the base of the chair. When the user is lying flat on a mattress, the same principles may be used to take the load off the user's body. In this case, the frame that surrounds the body is supported by the bed. The person wearing the suit containing the elastic bands will have the highest pulling force exerted at the side that is on the bottom contacting the surface of the bed, and the amount of pulling force will be smaller on the sides and at top of the body, decreasing in a graded fashion. As the fabric stays in close contact with the user's body, the pulling force is distributed across all body surface areas that the fabric covers. As a result, the body weight of a person or individual segments of the body is off-loaded onto the frame, which in turn is supported by the bed or other structures.

Similar to the other embodiments that use WBEs to exert push type of force, on various segments of the body, the embodiments of WDD shown in FIGS. 4L and 4M may transfer the body weight onto a frame in several stages. For example, each segment of the frame that surrounds a part of the body that lies between two joints (e.g., thigh) may be connected to an upper (e.g., frame covering the torso) or to a lower (e.g., frame covering the leg between ankle and the knee) segments of the frame. Therefore the weight of the leg frame, thigh frame and torso frame each may be sequentially transferred on to the next frame and which finally borne by the top of the frame located above the shoulders of the person. The weight of the frame along with the person will finally be transferred onto the ground or other supporting structures.

Some embodiments of WDDs and LCDs shown in FIGS. 4L and 4M exert a net pulling force on the whole body or the individual parts thereof which may be directed against gravitational force to minimize the load on the body, or directed towards the feet or the weight-bearing structures of the body, to increase the load on the weight-bearing structures on the body, without exerting undue pressure on the locations of the skin or underlying tissue, where the pulling force is applied.

The device is operated by the user wearing the WDD, which is in the shape of garment, and after securing the garment to the body. The suit is tightened by increasing the tension on the anchoring members 4015, 4018, 4013, and 4016, using the wheel 4019, which results in the pulling force exerted by the bands on the body in several directions, resulting in off-loading of the body weight of the person onto the frame. The same forces all over the body, or a gradient of forces, may be exerted on the body, with higher force on the bottom, compared to the top. The amount of force that is exerted may be adjusted such that a net upward force is exerted on the body, thereby decreasing the pressure on the weight-bearing regions of the body.

The bands that surround the body of a person either partially or completely may be vertical, horizontal or at an angle to the vertical axis of the body. The bands may be in the form of inflatable tubes, or a separate set of inflatable tubes may be incorporated into the suit in some embodiments. Various bands that are positioned horizontally around the circumference of the body and those that are positioned at an angle from the vertical position of the body exert pulling forces against body in the respective directions. Further, these bands are pulled against the frame not only from bottom to the top, but also in all directions. Therefore, for example a horizontal band located at the mid-torso level, the left side of that band may be pulled upward and downward on the left side (by the vertical bands), pulled towards the right side and inwards against the body due to the elasticity, and at an angle to the vertical down and upwards towards the right side of the body. The suit, in addition to being anchored to the top, at the waist ring level and at the bottom, is also anchored to the frame on all sides of the body from top bottom. The pulling forces on various directions that are opposite to each other substantially cancel out each other, resulting in minimal shear forces on the body. However, as a significant force is applied in an upward direction, a net upward force is exerted on the body, which is similar to a buoyancy force that acts in the opposite direction of gravitational force on the body, thereby minimizing the load on the weight-bearing portions of the body. The amount of pulling force exerted per unit area (pressure) on the surface of the body is expected to be much smaller compared to when one uses traditional harness type or hammock type devices. This is because, in hammocks and harnesses, the forces are usually concentrated at the place where the straps or ropes come into contact with the body, while in the presently disclosed embodiments the weight is distributed on a larger surface of the body. Although arms, head and neck are not mentioned specifically, it is to be understood, these parts can be covered by the elastic bands and the fabric and supported by the frame to allow for exertion of a net upward pulling forces on these parts.

An embodiment of LCD that does not require WBEs to exert force on the body of is discussed later in the application.

An additional embodiment of WDD and a method, which is not included in FIGS. 4L and M, include a mechanism, whereby a person's body parts may be suspended using materials that may cling or stick to the skin of the person, and then pulled in several directions, such that a net upward or a downward force is exerted on the body of a person, without causing significant shear forces on the skin. Further, a combination of pushing elements, e.g., using spring-type or inflatable WBEs, pulling elements using elastic or regular bands, and pulling elements using sticky or cling-on structures may be used to exert a net upward or downward force on the body.

Disclosed herein are methods and some embodiments of WDD and LCDs to exert forces on the body of a person using some embodiments of ball/roller-type WBEs, bladders or sheets. Because the detailed mechanism of WDD and LCD have been explained earlier, including how the WBEs and frame may be used to exert forces on a person creating a net upward (WDD) or a downward (LCD) forces, either to increase or decrease pressure on load-bearing regions of the body, this information is not repeated below. The description below is focused on how some embodiments of ball/roller type WBEs, bladders or sheets operate to exert forces on the body, with only minimal friction and shear forces.

FIGS. 4O, 4P, 4Q, 4R and 4S show some embodiments of WBEs, inflatable structures (e.g., bladder) that can be used in some embodiments of the WDDs and LCDs. FIG. 4O shows an embodiment of WDD/LCD that comprises balls/roller-like WBEs 4051, mounted on a frame containing outer wall 4053 and an inner wall 4052. The ball/roller-like WBEs may be mounted on a socket 4056 that prevents the ball from coming loose out of the socket. Alternate embodiments of WBEs include rollers, with axial bearings mounted on the frame to exert pressure on the body. In some embodiments, the socket along with the ball may be supported on a stump 4055 that rests on the inner surface of the bladder 4054, which is located within the frame. The pressure on the bladder may be increased or decreased either by pressing on the frame or inflating the bladder. The stumps may comprise springs, rods, plates, connectors and inflatable or non-inflatable structures, and the like to transfer the force from bladder to the ball/roller type WBEs. In some embodiments, where non-inflatable structures are used, in those devices, as illustrated by the front-flap 4057 in the figure, which is pressed on to the abdomen or chest of the user, the stumps may comprise various types of springs 4059, rods or similar structures that support the ball. The front-flap may be supported by a supporting element 4058, which may be used to exert pressure on the ball/roller type WBEs.

In some embodiments, the WBEs, may contact the body of a person either directly or through a sheet 4042. When the WBEs are pushed against the body and exert pressure, the WBEs (balls/rollers) role over on the sheet without causing significant friction. There is no limitation on the type of rollers, shape of the balls, number of balls per square centimeter, materials used to manufacture the balls, direction in which the balls/rollers can move, and the like. For example, the balls may be of smooth surface, with depressions and bumps, may have hard or soft structures on the surface, may have spikes, rods, cups, tooth like structures, etc., on the surface of the balls/rollers. In some embodiments multiple wheels may be used as WBEs instead of ball/rollers. Although the term balls or rollers are used, the terms are used interchangeable herein. When rollers are used as WBEs, they may be supported by a supporting structure by means of axial bearings, rods, sockets, plastic, ceramic or metal structures that hold the rollers on at least one side, etc., to facilitate easy rolling.

In some embodiments, the ball/roller-type WBEs may be connected to a power source and enabled to rotate on an axis, such that they may be able to exert pressure on the body of the user while rotating. When the rollers/balls are provided with uneven surface, e.g., bumps, ridges or depressions on the surface or underneath the surface of the balls/rollers, the rotational force (or other types of motion) causes massage type of action in the desired direction. Such type of effect may be used to exert uniform pressure in upward, downward or other directions, and may be useful in encouraging fluid shift in desired locations of the body. In some embodiments the massaging action exerted by WBEs of the ball/roller-type may also be used to provide massage to the user for the purpose of relaxation or therapy. Therefore, in some embodiments, the WDDs and LCDs may be used as massaging devices.

FIG. 4P shows some embodiments of a WBE 4045, which at its tip holds a ball 4043 or a roller type structure in a socket 4044. The base of the WBE rests on a bladder 4046 located in a frame 4047, while the tip of the WBE containing the ball touches the sheet 4042, that is positioned in between the skin surface 4041 of the user 4040 and the WBE. When the user is secured to the WDD/LCD, the WBEs can roll along the surface of the sheet on skin of the person, thereby, minimizing any friction, as well as the shear forces. The ball type roller may be attached to any of the various types of WBEs disclosed herein above (e.g., FIGS. 3B and 4B), with or without inflatable structures to exert pressure on the body.

FIG. 4Q shows a close up view of some embodiments of WBEs that comprise balls, rollers and the like. Shown in the figure are two frames 4048 supporting the front and back side body of a person 4040. Ball/roller type WBEs 4050 accommodated in a socket-type holder in each frame come into contact with the sheet 4042 position between skin 4041 of the user and the WBEs. The WBEs exert force on the user when pressed against the body using supporting element 4040, which may be connected to springs, inflatable devices, or external power sources to exert force on the body. When pressed against the body, the WBEs that comprise balls/rollers roll over the sheet without exerting significant frictional forces.

Figure 4R:
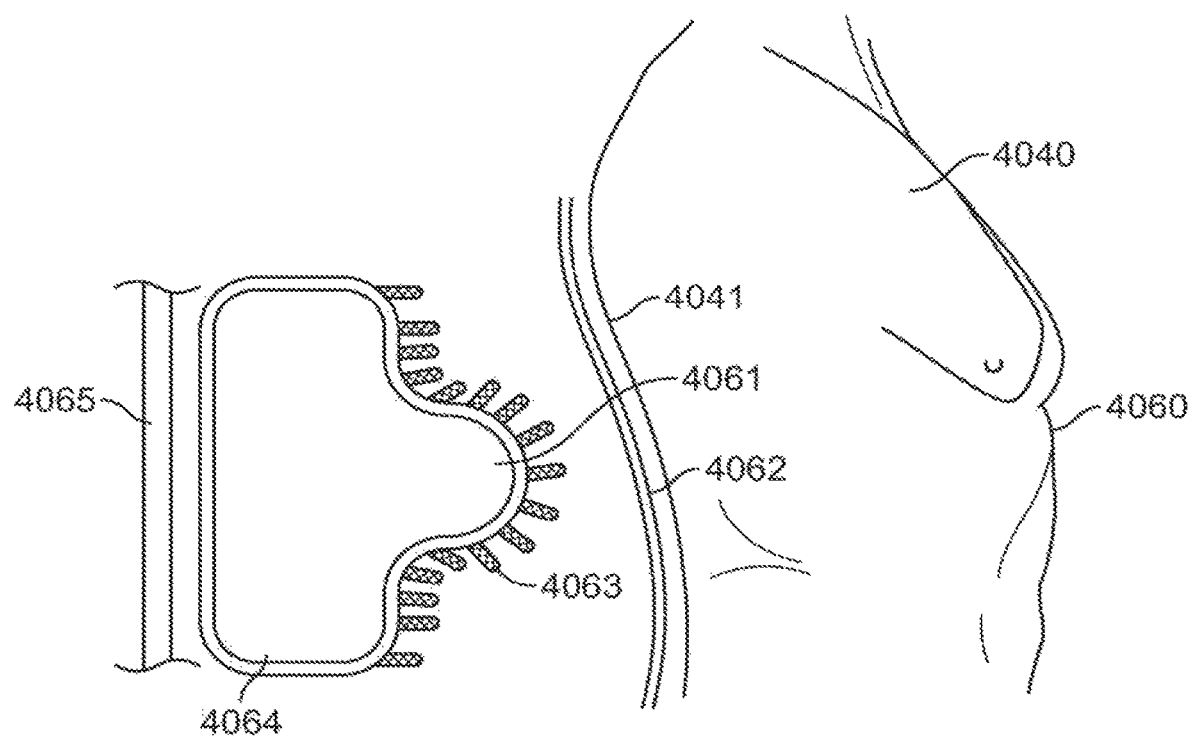
FIG. 4R shows an embodiment of a bladder without WBEs useful for exerting forces against a human body.
Figure 4S:
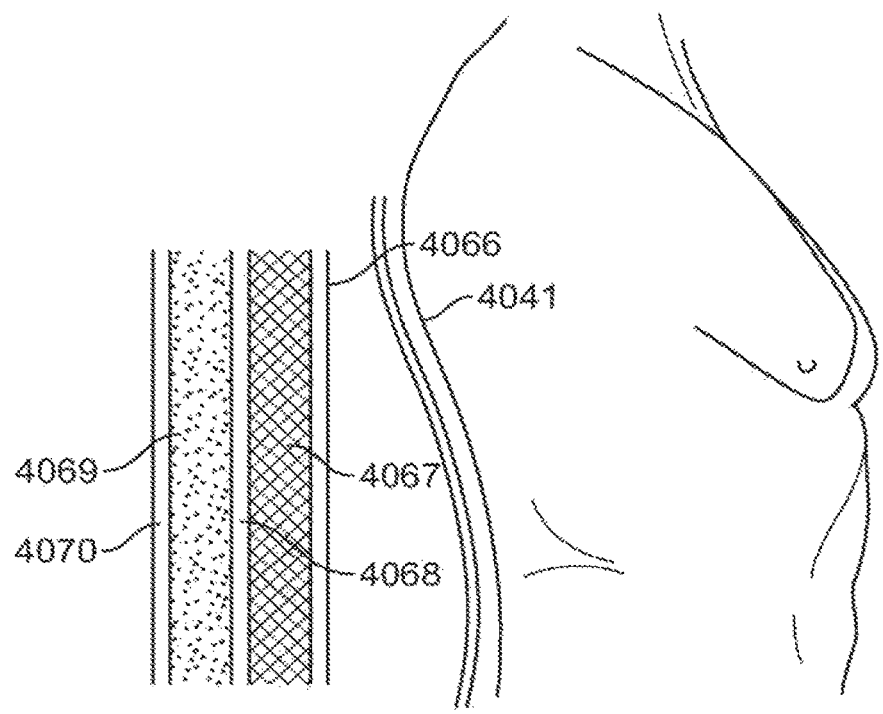
FIG. 4S illustrates an embodiment of a multilayered sheet useful for reducing friction and shear forces against skin and underlying tissue.

FIG. 4R shows some embodiments of inflatable structures (e.g., bladder) that may be used to exert force on the body of a user secured to a WDD/LCD. There may be a single bladder 4064, covering the whole body of a person using the WDD/LCD, or there may be several very small bladders. There is no limitation on the size (area, volume, width, height, etc) or the number of bladders; for example, in some embodiments, the number can be from 1 to 1,000,000 bladders/one square centimeter. The bladders may be supported directly by the frame 4065 to which the bladder attached to, or enclosed within the frame. The bladder may come into contact with the user directly, or through a sheet 4062, which is positioned between the user 4040 (with front portion 4060 and back 4041) and the bladder. The bladder may have bumps 4061, which in turn contain various protrusions 4063 which come into contact with the sheet. The bumps 4061 may be made of a hard or a soft material (e.g., soft plastic, silicone, foam) and may be stretchable. The bladder and the bumps may be made of any fluid or a viscous material such as a silicone or foam. When the bladder is pressed against the body of the user, by either exerting pressure on the frame, or by means of increasing pressure within the bladder, protrusions 4063 and bumps 4061 come into close contact with the sheet 4062, which is next to the skin. When the bladder is pushed upwards, downwards and towards the direction of the user using the frame or by inflation, the protrusions and the bumps will maintain contact with the sheet or the body of the user, but the remaining part of the bladder moves up or down against the body with only a minimal frictional or shear forces.

FIG. 4S shows a magnified view of a sheet that has multiple layers, to decrease the friction or shear forces on the skin. The sheet may be position between the WBE (not shown) and the skin 4041 of the user, and comprises an outer layer 4070, and an inner layer that may be composed of a layer 4069 of soft viscous material such as silicone which is highly stretchable. An additional layer 4068 of sheet may be attached to the inner layer of sheet 4066 through another layer composed of foam 4067 or elastic type material. Each layer may have different chemical or physical properties that allow them to stretch to different lengths. For example, the inner layer 4066 may stay attached to the skin 40141 of the user at all time. When pressure is applied on the skin by WBEs or the frame, the outer layers may slide over the inner layer, without exerting significant frictional or shear forces on the skin or underlying tissues.

Disclosed herein are several embodiments and variations of the WDDs and LCDs that may exert pressure on the body to distribute weight or exert forces, using mechanisms other than those described earlier. In some embodiments, WDD/LCDs may be used to exert forces on a person without WBEs in some applications. FIG. 2B shows a cross-sectional view of some embodiments of the WDD without the WBEs to distribute the weight of a person. The body 214 of a person is surrounded by at least one bladder 225 that can be inflated or deflated through a tube 228. The bladder may be a single unit or may be comprised of several tubes that are either in the horizontal, vertical or at an angle and which crisscross the length of the body, or may be composed of small peg or pin-like inflatable or deflatable structures, that can project at an angle to the body, when inflated. In one example, when the bladder is in the form of a circular inflatable tube(s) that encircles the torso, by inflating the tubes, pressure may be exerted on the torso, such that force is exerted on the body in all directions, resulting in a net upward pressure on the body. The bladder in some embodiments may be able to bear the weight of the person directly. Although, an inflatable bladder-like structure is mentioned here, the bladder may be replaced with other materials that do not require inflation, for example, without limitation, foam, rubber, gel, wool, fabric, leather, plastic and the like which may be used around the body to exert pressure.

An embodiment of a WDD that employs inflatable structures is shown in FIG. 2B and described in detail below. In the figure, the said bladder and the body may be surrounded by a frame 220, which is made of either rigid or flexible material, and may be able to support at least some weight of a person. The frame 220 can be a single unit or made of several panels and may be supported by the seat of a chair when a person is seated on a chair. The frame may be attached to rods 224, which may be supported on the base of the chair, and may be used to either raise or lower the frame 220. Panels 223 may enclose the frame 220 at least on one side, two sides, three sides and all sides in some embodiments as shown in the figure. Four panels covering front, back, and both sides are shown in the figure. The panels 223 may be connected to a wheel 221 by an axle 229, wherein, when the wheel may be turned using lever 209 that may be able to raise the attached frame in an upward or downward direction, traveling on the supporting rod 224.

FIG. 2C shows a vertical-sectional view of the same embodiment of the weight-distribution of apparatus described in FIG. 2B. Shown in the figure is a torso 224 of a person seated on chair 227, surrounded by bladder 225 and frame 220. Pressure may be applied against the body by inflated bladder or by exerting a net upward force using the frame and the panels. The embodiments of WDD shown in FIGS. 2B and 2C show that the method disclosed in some embodiments may be used to distribute weight of a person without use of WBEs, and with and without the bladders located below the bottom of the person. There is no limitation on the order in which the WBEs, bladder and frame are located with respect to the body of the person. In some embodiments of WDDs or LCDs as shown in FIG. 3C, the inflatable structures come into the contact with the body of the user first, followed by the WBEs on the outside, that push the body against the user. In any of the embodiments discussed in this application there is no limitation on the number of bladders, frames, or WBEs and the order in which they are arranged.

To operate some embodiments of WDD without the WBEs shown in the FIGS. 2B and 2C, the user is seated in the chair integrated with the WDD (without WBEs), and secures the frame 220 to the body using various fasteners. The bladder 225 may be inflated to help secure the device to the body of the user tightly. Similarly, when the body is covered with other material such as foam, rubber, fabric, etc., instead of the inflatable structure, then pressure may be applied on the material by the frame, by exerting force against the body at various locations that come in contact with the material.

Once the body is held tight by the inflated bladder, the frame 220 is raised from the seat of the chair slightly by rotating the wheel 221, using handle 209. As the frame is closely pressed against the bladder and the body, the elevated frame causes an upward movement of the body, due to the frictional force that holds the body to the bladder and the frame. Complete lifting of the person's torso off the seat of the chair may not be required to relieve the pressure on the spine using this method. Instead of the manual turning of the wheels, the same effect may be accomplished by electrical controls connected to a motor, which increases pressure (not shown). The pressure exerted by the bladder against the torso causes the body weight to be off-loaded onto the frame, thereby relieving the pressure off of the weight-bearing regions such as the buttocks and the underside of the thighs in a seated person. It should be noted that the turning wheel is mentioned here as an example to enable the device to operate, but several mechanisms may be used to apply pressure on the body.

FIG. 4C, illustrates a cross-sectional view of some embodiment of WDDs and LCDs that do not use the fluid-based bladders. The embodiment of WDD in shown in FIG. 4C differs from the other embodiments of WDDs shown earlier, e.g., as in FIG. 4A, with respect to the support to the WBEs located on the planks, which use a flexible sheet, instead of more rigid frame. The plans that support the WBEs in this case are pulled against the body of the user, instead of being pushed against the body (e.g., see FIG. 4A).

Shown in the figure is the body 420 of a person at the torso level with front (anterior) 447, lateral and back sides 448 of the person, surrounded by a flexible sheet to support the planks 403, the flaps 402 and the WBEs 406. As shown in the exemplary embodiment in FIG. 4C, the planks 403 may be pushed against the body 420, by a sheet 431 that is wrapped around and on the outside of the planks 403, and secured to a post 435 or other fixtures on the chair 422. The planks 403 may be supported by either rods or similar structures 430 to enable the sheet 431 to roll over them smoothly. The figure shows the planks 403 on the anterior side of the WDD as covered by the sheet 431, while the planks on the lateral and the backsides of the person are supported by the flaps 402, as described in FIG. 4A. Instead of fabric 431, other type of structures such as a straps, belts, rope, a net, a tape, a cast, sheet and the like, may be used to secure the planks 403 and the WBEs to the body. The advantage of using sheet 431 or similar structures is that it allows the WBEs and planks 402 and 403 to support body by pulling action. As an example, using the sheet (or fabric) 431, the front portion of a person sitting in the chair may be supported by anchoring the 431 to supporting structures 435 that may be located on the back or sides of the chair. A combination of rigid or semi-flexible frames pushing WBEs against the body on some sides, and frames composed of fabric/ropes pushing WBEs against the body (by pulling the fabric in the same direction around the body) may be used in certain embodiments to transfer the body weight on to the WBEs.

It should be noted that a person is suspended in a hammock or similar structures, will often experience significant pressure and shear forces on the locations of the skin where the ropes of the hammock come into contact with the skin. Such type of focal pressure and shear damage can be avoided by using the embodiment of the WDD disclosed in FIG. 4C.

In this section various portable embodiments of the WDD and methods that may be used for distributing the body weight of a person are described. In earlier sections, WDDs that are stand-alone or integrated into the various pieces of furniture like chairs were described. However, it is advantageous to have WDD systems that are portable, so that the user either can wear them or carry them along for use in various applications. Included in this section are embodiments of WDD that can be used by a person while standing, portable WDDs that can be used with exoskeleton type devices, a wearable jacket-type WDD that can worn by a person, and a cushion type WDD that is portable.

Figure 6B:
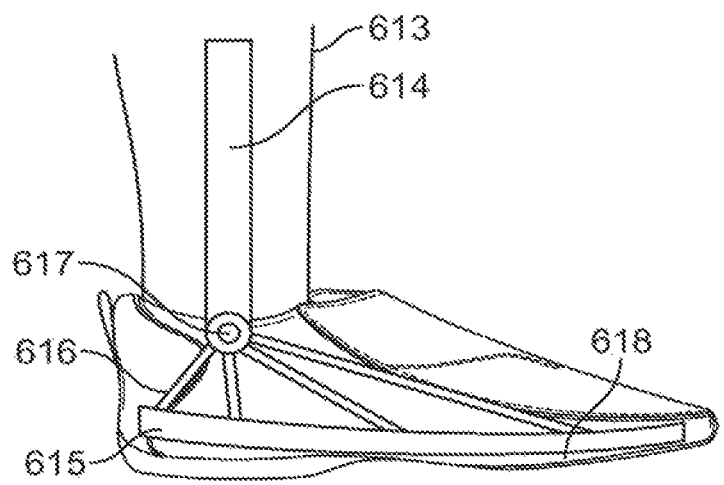
FIG. 6B illustrates an embodiment of a WDD/LCD device attached to sole plate to exert forces against the body either to reduce or increase load on the body.

In FIGS. 6A and 6B, the main features of some embodiments of a portable frame to support the WDD/LCD are shown. The WBEs and additional components such as bladders, planks, flaps, levers, etc are not shown in this figure. FIG. 6A illustrates some embodiments of a WDD that comprises two parts; a torso section and a leg section. The first piece, the torso-frame 600 supports the torso and the second piece, a thigh-frame 612 supports the thighs. Frames that support the arms, neck, and head are not included. Note that the whole body may be covered with the WDD, including head, arms, torso, and legs. In the FIG. 6A, however, only the trunk and the legs are shown to be covered. The frames can be used to cover independent portions of the body (e.g., torso, legs) or whole body as needed. The frame supporting the torso has openings for the neck 602 and arms 603, and is secured to the body with fasteners 611. The frame has vertical 604, and horizontal 605 elements, as well as elements that are positioned in several different angles (not shown) to provide support to the torso. The frame may be made as a single unit or comprise several pieces 606, joined together to provide more flexibility. The torso-frame may be supported by a waist-ring 607, located at the bottom of the torso-frame, which rests on seat of a chair when a person is seated. It is the waist-ring that ultimately bears the weight of the torso in a seated person, which in turn is transferred to the seat of the chair.

The waist-ring 607 connects the torso-frame 600 to the thigh-frame 612, which in turn is connected to leg frame 613 by a knee-ring 608. Such jointed frames allow for flexibility, while fully supporting the body weight of the person. There is no limitation on the number of joints a frame may have, but only the waist and knee joints are shown in the figure.

When a person wearing the WDD stands upright, the weight of the person is supported by various pieces of the frame in a staged manner. For example, weight of the torso is borne by frame 600, which in turn transfers the torso weight on to the thigh-frame 612, as they are joined together at the waist ring 607. The thigh frame 612 in turns transfers the weight of the upper body including the thighs on to leg frame 613, as it is connected to the thigh frame at knee ring 608. The leg frame ultimately transfers the whole weight of a person to the floor or onto shoes 609 of a person.

When WBEs located on the inner surface of the WDD exert forces on the body of the person, the weights of the successive segments of the body, for e.g., the torso, pelvic region, the thighs and the legs are off-loaded onto various respective pieces of frame supporting that part, and finally onto the floor. As such, the WDD helps to remove load of the upper sections of the body in a staged manner, while causing only minimal shear forces on the body. As the weight of the individual segments of the body is lifted off from the lower weight-bearing regions, a person feels less pressure on the lower torso or legs, which gives the feeling of reduced weight to the user of WDD. Because of this, the WDD creates feeling to the user, similar to when someone gets when standing in swimming pool. Similar to the water in a pool, the WDD also exerts minimal shear forces on the body.

Manual levers or power sources that may be required for tightening the frame, inflate or deflate the bladders, increase pressure on the WBEs, are not shown in the above embodiment, but were described earlier for the weight-distribution apparatus described for a person seated in the chair (e.g., see FIGS. 2A and 4A). Although, only torso and the legs are shown to be covered by the frame in FIG. 6A, it is to be noted that whole body or any of the individual body parts may be covered in some embodiments of the WDD. For example, orthosis, casts or braces integrated with WDD may be used to support independent parts of a body that may have been injured or need rehabilitation. The device may be coupled with several types of casts, or braces to provide support to individual parts of the body. The device may be integrated with shoes to lighten the pressure on the bottom of the feet or any injured portion of the feet.

The device described above may be used as an LCD, with appropriate modifications, to exert a net downward force on an astronaut, for example, in someone suffering from a backpain, due to microgravity.

FIG. 6B illustrates an embodiment of a leg support in more detail. The leg 613 is supported by at least one frame 613, which at the ankle level is attached to a joint 617, that in turn is attached to several plates 616 that terminate in the sole of the shoe 618. A rigid support 614 connects the joint 617 to the rest of the frame supporting the body, and helps off-load the weight of the person on to the sole of the shoe, thereby minimizing the load on the person's feet. An arrangement similar to this will ensure that the weight of the legs are always born by the shoe (or floor) when the person is standing or while walking because one of the plates 616, from either the left foot or the right foot will always stay in contact with the ground and bear the weight of the person when standing or walking.

In some embodiments, when the device shown in FIG. 6B is used with LCD, the soleplate is attached to the rest of the frame that covers the legs, thigh, torso, shoulders, neck and the head in a sequential/stage manner. Each of these parts is supported by individual frames that are joined together at joints, e.g., at knee joint, hip joint, etc. In some embodiments, the frame applies pressure against the WBEs, which in turn exert pressure on the body of, e.g, an astronaut. Although, pressure is applied in all directions, the net force is directed towards the feet supported by the sole plate. When push type pressure is exerted, such pressure may be exerted from head/shoulder plate down towards the sole plate. In some embodiments a pull type of force may be exerted by using frame that is pulled towards the sole plate, or suits using various types of bands/straps to exert a downward pressure on the body of the astronaut, without causing significant friction or pressure.

The operation of some embodiments of the WDDs shown in FIG. 6A to support a person standing in upright position is described herein. To operate the device, the user secures the device shown in FIG. 6A, to the body using fasteners, while in a standing position. When secured, the bottom portion of the frame of the device rests on the floor or may be supported by the shoes other structures on the body of the person. Initially, before activating the device, the body weight of the user is borne by his/her own weight-bearing structures (skeleton, muscles, joints, soles of the feet, spine, etc.). The user then shifts the body weight onto the WBEs by pressing WBEs against the body (using either inflatable or non-inflatable structures, or by exerting force using the frame, as described earlier), Pressure using the frame may be accomplished for example by, either manually pushing the frame inward and upward by using levers attached to the frame or by using external power sources and motors (not shown in the figure). As a result, the weight of the torso is transferred to the frame covering the thighs at the waist level. In turn this weight is transferred to the floor by the leg frame.

Note that each segment of the body may be supported by an independent section of frame that surrounds it, e.g., leg, thigh, waist and torso, etc. Each section of frame is joined to the adjacent sections in some embodiments such that weight of the individual parts of the body can be borne by the WBEs and transferred on the frame independently. Further, the weight of the person may be transferred onto frame in a staged manner. For example, when a person is standing after securing WDD, the weight of the torso may first be off-loaded onto the torso-frame. The torso frame weight (which includes the weight of torso and the upper body and the torso-frame) is then transferred onto thigh frame, which then is transferred onto the leg which is supported by the floor or sole plate. The WBEs may be attached to the frame using a pivoting support, that is designed to exert force in a predetermined direction, e.g., in upward or horizontal direction.

Some embodiments of the WDD and LCDs may either apply same pressure on the body surface all over the body, or they may apply different pressures at different locations of the body, or a gradient of pressure. The amount of pressure applied by the WBEs also may vary depending on the amount of body weight to be off-loaded onto the frame; higher pressure will off-load more amount of body weight onto to frame when using WDD.

In some embodiments, for example, following pressures may be exerted in a gradient manner by the WDD; for example from feet, buttocks or any other part and moving upwards. The starting pressure and the ending pressure can be of any pressure that is tolerated by the humans. For example the pressures can be 136, 113, 90, 67, 45 and 22 mm Hg, respectively at 1, 2, 3, 4, 5 and 6 feet height starting from the soles of the feet moving towards head.

When using LCD to apply pressure on body surface of an astronaut, either the same pressure or variable pressure may be applied. A pressure gradient which decreases from head towards feet may be used to create a reverse gradient of pressure.

Embodiments of LCD described hereinbelow likewise, exert pressure on individual segments of the body, in a graded fashion from head towards feet, in a staged manner as described above for WDD.

The frame that supports the torso and neck, may be made up of several segments of frames that are joined together to provide flexibility in a manner very similar to how the torso and the neck can bend and flex using the vertebrae as base.

In some embodiments the device shown in FIG. 6A may be modified in design slightly and used to increase the load on various parts of the body, including on the weight-bearing regions. Such a device is useful in some applications, for example to exert body weight-like loads on various weight-bearing regions as well as soft tissue of, e.g., astronauts living in altered gravity (<1 g-force or >1 g-force) conditions or to prevent bone and muscle loss in people that are taking bed rest.

Such an embodiment mainly differs from the WDD described in FIG. 6A (used for reducing load on the weight-bearing regions), in that the direction of the net force is reversed, and is directed top down from head towards feet. A pressure exerted by the WBEs in such an embodiment may be adjusted such that a gradient of pressure with higher pressure exerted on the head, shoulders, torso, waist, thighs and legs and lower pressure as one progresses towards the feet.

Therefore, the device that is used to increase the load on the body may be aptly called Load Concentration Device (LCD). The WBEs of the device applies force in various directions (upward, downward, horizontal and in various angles to the surface of the skin) on the body, with a net downward force towards the buttocks (when the person is in a seated position), or towards the feet, when standing upright. The forces acting on a person when using the LCD are shown in FIG. 1C. The application of some embodiments for use in microgravity environments is presented in detail hereinbelow.

Various embodiments of WDD and LCDs disclosed herein may be configured to be used with an exoskeleton (that supports the body weight of a person) or a powered assist device that can be worn by the user externally and are activated by movement of the user's body parts. Exoskeletons can be used, e.g., by soldiers, for carrying heavy weights over long distances, as prostheses for people that have lost limbs due to accidents, injured veterans, para- or quadriplegics, elderly, etc., to assist them with mobility. For example, the embodiment shown in FIGS. 6A and 6B may be fitted with external power sources (e.g., battery) and electrical controls such that the movements of the person may now be assisted by the power source.

Various embodiments of the devices described in FIGS. 1A to 6B, may be adapted to be used with an exoskeleton, such that the WBEs, transfer the weight of the user, to the exoskeleton, in a similar fashion as described hereinabove.

FIG. 6C presents an embodiment of a WDD disclosed herein configured to work with an exoskeleton. In the embodiment shown in the figure, the exoskeleton 630 is worn by the user 601 as shown from the shoulders, extending down to the feet. The exoskeleton may contain different parts, for example, a shoulder piece 631 to secure the exoskeleton to the person, as well as to help carry any additional load 632 and/or power supplies 633 on the back. The exoskeleton, which can be constructed of a wide variety of materials including metal, ceramic, plastic, wood and the like, may contain several pieces that support various parts of the body as shown here, e.g., a torso piece 634, waist piece, thigh piece 639, which is connected lower leg piece 640 through joint 641, and finally to a shoe piece 642. A weight-bearing device described in this application can be attached directly to the exoskeleton as shown in FIG. 6C. The WBEs 635 (see the peeled away portion 636 on the torso in FIG. 6C), may be supported by the horizontal 645 or vertical 648 supporting members (supporting members that traverse in other directions are not shown), and these in turn may be attached to the exoskeleton 630. When a user wears the weight-distribution apparatus and transfers the weight to the WBEs (either by inflating bladder or by a mechanical means, as described hereinabove), the weight is transferred to various parts of the exoskeleton, e.g., the "waist-piece" 637. The load transferred to the waist-piece 637, in turn is transferred to the "sole plate" 642 which supports the shoes 643 and the body weight of the user. As a result, the weight of the user is ultimately transferred to the floor, but supported by a larger surface of the body, instead of just the weight-bearing regions. It should be noted that, if the exoskeleton were to be used without the WDD, the primary weight-bearing structures of the body (e.g., the spine, the joints, and the legs) would have borne most of the body weight. As a result of integrating the exoskeleton with WDD, only a desired fraction of the body weight need to be carried by these weight-bearing structures, and therefore, much less energy is used by the person to while standing.

Some embodiments of the WDDs shown in FIG. 6C, which is integrated into an exoskeleton, may be operated in manner that is somewhat similar to the operation of the device shown in FIG. 6A. The user of the device wears the WDD integrated with an exoskeleton, and secures it to the body. Based on the amount of weight to be unloaded from the trunk, feet or other portions of the body, the user will apply appropriate pressure on the body using WBEs, which results in a net upward force against the gravitational force on the body. As a result of integrating with WDD, a user, for example a soldier, marching 20 miles in a day with a load on the back, will feel less exhausted, because the soldier is able to off-load some or all of the body weight onto the exoskeleton, thereby reducing the amount of energy spent, leading to an increasing the overall productivity.

Figure 6E:
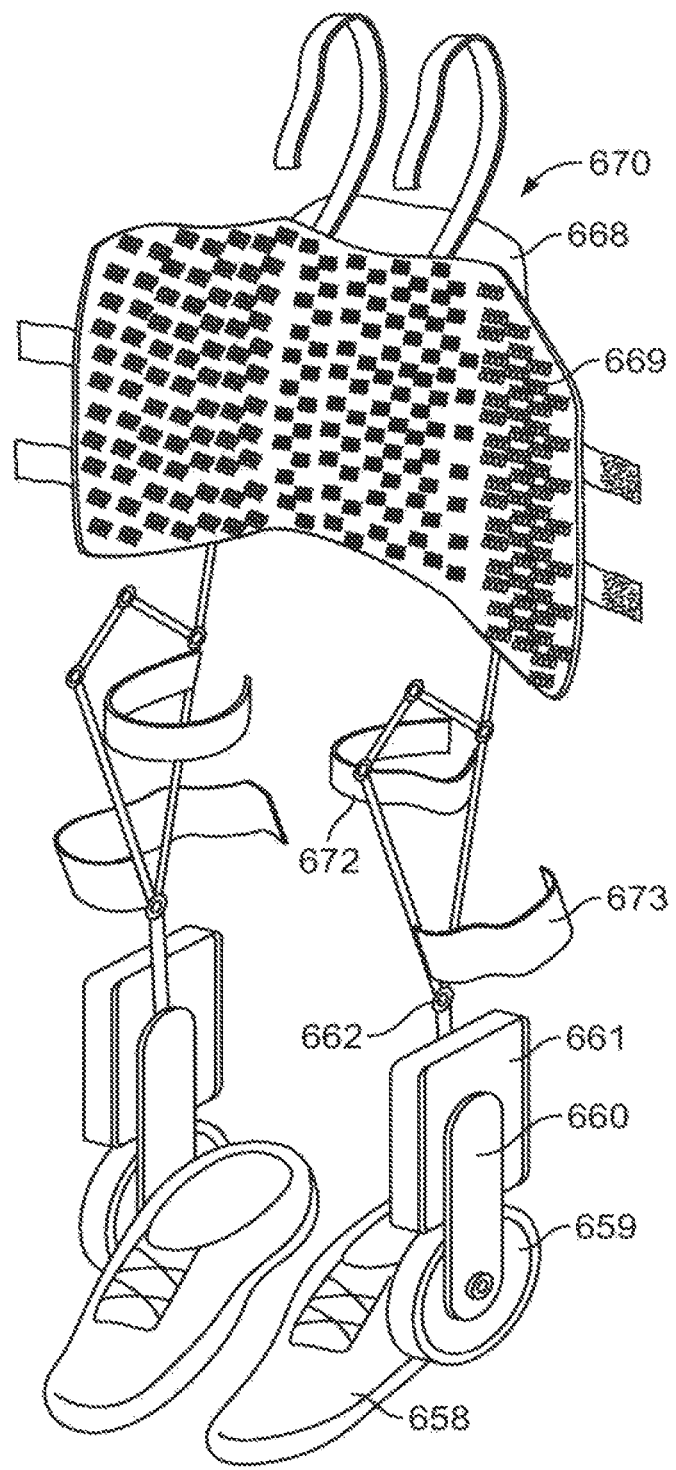
FIG. 6E illustrates front-view of an embodiment of a WDD integrated with an exoskeleton described in FIG. 6-D without a person, to clearly show various parts.

FIGS. 6D and 6E present additional embodiments of the WDD integrated into an exoskeleton that may be used to help paraplegics to stand upright or to move around.

Several advances in technology have allowed paraplegics to move freely unassisted, including wheel chairs, various crutches, exoskeletons with stimulators for muscles, personal mobility devices, etc. Some of the personal mobility devices like Segway®, Winglet®, etc., may be used to allow a person with paraplegia to travel while standing, if secured properly to the equipment. Walking assists like Exohiker®, Rewalk®, etc., help support a patient's body weight while standing and help them with walking. However, it is still challenging for a paraplegic to carry their own weight while standing, which limits their ability to move around freely. Therefore, methods and some embodiments of WDD devices are disclosed to assist the paralyzed, or people with limited mobility for various reasons, to ambulate while standing in an upright.

Although, the currently available personal mobility assist devices, such as "exoskeletons", support an individual to walk (for e.g., by stimulating leg muscles), the upper body weight of the person is still borne by the spinal column, in these devices, which require significant effort on the part of the user move around carrying his/her own body weight. Therefore, an embodiment of WDD shown in FIG. 6D is disclosed to off-load the weight of the upper body from lower weight-bearing regions such as the legs (which may not be functional in a quadriplegic person), buttocks, spine, etc.

The disclosure draws its inspiration from the observation that small animals such as dogs or cats, which are paraplegic, can move around easily, if their back portion and the paralyzed hind legs are supported on a set of wheels. However, it is challenging for humans to do the same, as the arms of humans did not evolve to carry body weight. Further, humans need to be in an upright posture to be comfortable and function with ease, due to the way their anatomy evolved. From a social behavioral standpoint of view, people prefer to communicate with other humans at the same eye level. Therefore, it is desirable to provide a mechanism, wherein people with paraplegia or elderly who can't support their own body weight well, can stay upright (instead of in wheel chairs), while standing or ambulating. However, the challenge is to support a paraplegic person's upper body weight on legs that do not respond to the brain commands. Therefore, disclosed herein are methods and devices to partially or completely relieve the legs or the torso of a person from the body weight-bearing function of the body. Some embodiments of the device comprise at least one frame that is supported by at least one wheel touching the floor at the feet, and use one of the balancing technologies (e.g., gyroscope), to keep a person in an upright position, thereby freeing the person's torso and arms from weight-bearing responsibility (e.g., when using crutches) to assist in movement, e.g., for pushing around or using crutches or cranks that can be rotated using hands, and connected to the wheel through a chain or other driving mechanisms. In some embodiments, a frame that extends out from the base of the WDD (at the feet) and supported by additional wheels may be used to provide additional support to a standing person, and to prevent from falling.

Briefly, the methods and some embodiments of the WDDs herein, therefore allow a person to transfer most of their body weight (including paralyzed limbs) using WDDs to the frame, which is supported on at least one wheel. To aid in keeping the balance of the person, additional weights may be added to the frame close to the ground, to lower the center of gravity of a person and support a person to balance in an upright position. Instead of wheel(s), the person may use any of the personal mobility devices (e.g., Segway, U3X®, Winglet®) that will allow a person to move around while standing. Because the user does not have to support his/her own body weight, the arms may now be used push the body around, even without using any of the about personal mobility devices.

In some embodiments, the device comprises an exoskeleton 650 with power pack 668 attached to the body with straps 651. The WDD 653 with frame 667 and WBEs 654 are secured to the body of the user 666. The upper body of the user and the WDD surrounding the torso may be supported by frame 665, which is connected to frame supporting the lower leg using joint 663. The lower leg frame ends in the piece of the frame that supports the feet or shoe of the user. The body of the user may further be supported by a crutch 657 that is attached to the arm by wrist band 656, elbow band 655 and/or arm band 652. A weight 661 is attached to the leg frame of the exoskeleton, which in turn is supported by plate 660 that rests on at least one wheel 659 which is located to close to the feet of the person.

The parts including the wheels, the weights, driving mechanism etc, may be attached to feet, shoes or other structures. The device may include at least one gyroscope or similar mechanism (not shown in the figure) to maintain an upright position of the person. The device may have at least one wheel to support the user's body weight, however there is no limitation on the number of wheels that may be used with the device and their position; the number of wheels may be one or more and they may be positioned between the legs, on the sides or front. There may be a single wheel, or more than one wheel, and the wheel may be of compound when type (e.g., omni wheel), which comprises multiple wheels or discs that allow for movement in several directions. The device may behave as unicycle, or dicyle (wheels next to each other like in a Segway), or as a bicycle, and the like. The wheels and the exoskeleton may operate on external power to assist in movement of the user. The above WDD system may also be integrated with various mobility assist devices (e.g., Segway, U3-X, Winglet, various wheel chairs, and similar devices) to allow a person to move while standing upright or seated. The person may be able to move around using the force from torso or the arms, with or without the use of a personal mobility device. The device shows two wheels positioned on either side of the legs, however, a central single wheel (not shown) may be used. To maintain the stability of the user, the frame may have optional additional extensions that rest on the floor with or without wheels (not shown) at a distance from the feet of the person to maintain balance. Additional details of the device are included in FIG. 6F and the respective description of the device hereinbelow.

Figure 6F:
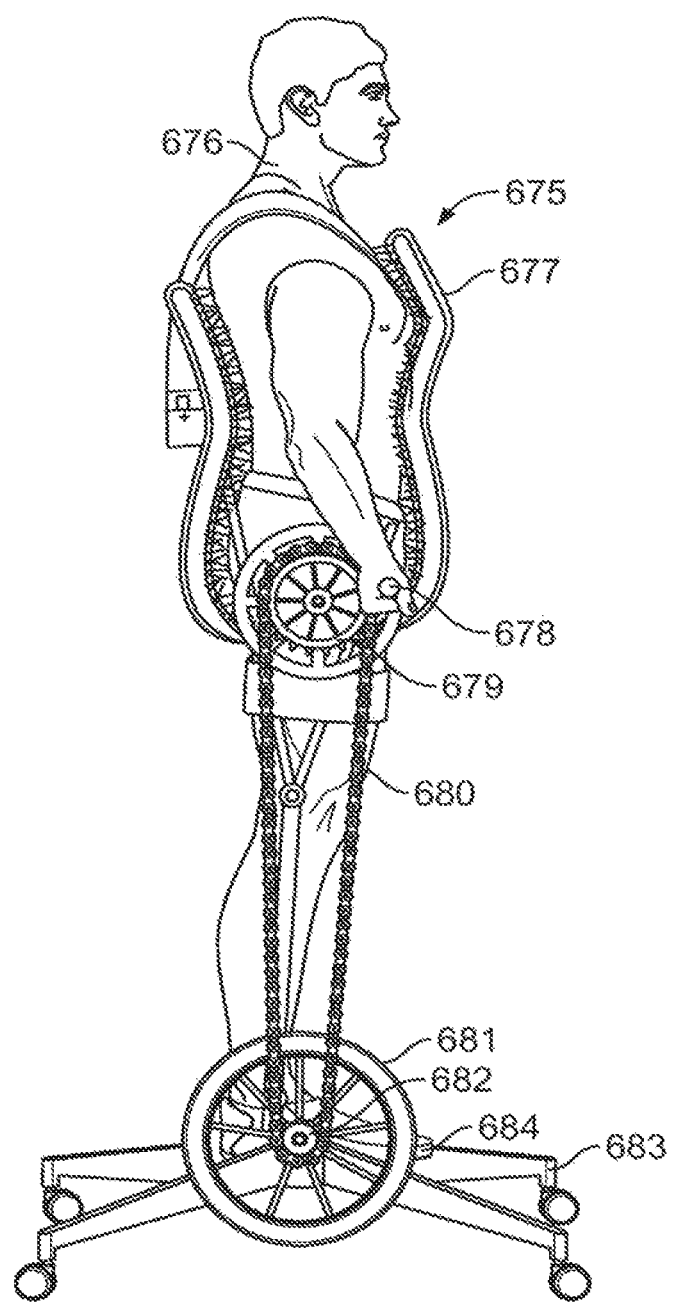
FIG. 6F illustrates side view of an embodiment of a WDD mounted on wheel(s) to serve as a personal mobility assistant for humans with paraplegia or other conditions

The device may also be provided with a crank and a chain that is connected to the wheel(s) on the ground, and provided with pedals (or handles) to rotate using the hands of the individual to move around (handles, crank, chain and the driving mechanism-see FIG. 6F). The advantage of the device is that it allows a paraplegic person to stand upright, on the feet, and frees up the person's hands to various activities, including assisting in moving around. The device to some extent acts like a traditional wheel chair, except that it allows a person to stand upright, and therefore, offers several advantages, such as preventing pressure ulcers, allows a better social interaction due to eye to eye contact, conserves energy of the person, allows for a better circulation to the lower parts of the body and improves overall health and wellbeing of the paraplegic person.

FIG. 6E shows an embodiment of an exoskeleton 670 without the user. The exoskeleton is fitted with weights 661 attached to the leg frame using a connector 662 and to the wheel 659 using connecting rod 660. The user and the WDD 669 are secured to the exoskeleton using the thigh bands, 672 and knee bands 673. In a person with paraplegia, maintaining balance is the most challenging task, and therefore, disclosed in FIG. 6E is an embodiment of WDD integrated with an exoskeleton type supporting device, which is to show the anchoring of the weights and the wheels to the leg frame in more detail.

FIG. 6F shows an embodiment of WDD, which may be used as a personal mobility assist device. Currently people who lost legs (e.g., veterans) or function of their legs (e.g., para- or quadriplegics), or elderly (who can't support their upper body weight on their legs) use wheel chairs and various other mobility devices. Most of these devices require a person to stay in a seated position, and move around using either manual or electrical power. Walking crutches can be used by people with leg functional leg stumps and have casts/orthosis. Moving with walking crutches, however, is very slow and is physically more demanding, as the arms have to lift a person's body against gravity while walking, and therefore are not entirely free to perform other tasks when the person is in an upright position. Recent advances in exoskeleton assistance-based, power assist walking devices have helped people to walk upright. However, even with these devices, the torso and the arms have to support the body weight of a person and to maintain the balance. But most of these devices are still in early development stage.

Therefore, some methods and embodiments of WDD are disclosed, which may be used as mobility assistance devices by various people, to allow people to be supported in an upright as well in a seated position, and ambulate around using manual or electrical power, but allows hands to be free to other tasks when needed.

One embodiment of the device 675 comprises a frame 677 that surrounds the body of the user 676, and supports WBEs. The WBEs are able to exert pressure on the user's body using either inflatable or non-inflatable structures (not shown) and transfer power on to the frame of the WDD. The WDD may be integrated with an exoskeleton (not shown), as described hereinabove (FIGS. 6D and 6E). The WDD is provided with a crank 679 and a chain 680, which can be operated by turning handle 678. In some embodiments, the crank may be located on either side of a user, in the back or front, between the legs, or any other position, without limitations. The chain is connected to another freewheel (toothed wheel) 683. At least, one wheel 682, containing a tire mounted on a rim or spokes located between the two feet or on either side of the user, or in other configurations is attached to the freewheel. The person secured to the WDD in FIG. 6F, therefore, will be able to move around by turning the handle 678, in the direction. The user's balance is maintained by either gyroscopic mechanism (not shown), or using frame extensions 683, that extend out from the bottom of the frame of WDD located close to the shoes 684.

The embodiments shown in FIGS. 6D, 6E and 6F are operated by securing the user's body to the exoskeleton/supporting structure. The user transfers the body weight to the frame, which is supported by the wheel(s) which rest on the floor, thereby relieving the arms from the responsibility of supporting the upper body weight. As WBEs exert pressure against the body, minimum shear force will be experienced by the user while using the device.

Extra weights may be used at the base of the frame, close to the feet to keep the user's center of gravity low to the floor, and help maintain the upright balance in some embodiments. The user may also balance the body to stay in the upright position either by using either crutches or a mechanism similar to the gyroscope. The user may ambulate around by pushing against the floor with the crutches, or using a battery driven power source to drive the wheel(s) attached to the frame/feet/shoes. Alternatively, the user may be able to use a hand crank set or a similar mechanism, mounted on the front or both sides of the body, to operate a drive train that is connected to the wheel(s) at the feet to move around. The user may also use the trunk, shoulders, and/or pelvic muscles to operate the drive train connected to the wheels for moving around.

An embodiment of WDD personal mobility device shown in FIG. 6F may be operated by securing the device to body using various fasteners, and transferring the user's body weight onto WBEs and the frame as described hereinabove using manual levers or other mechanisms. The weight of the user is ultimately transferred onto the wheel(s) at the bottom, and the user is able to ride around by rotating the handle of the crankshaft. User can maintain balance in the upright position, with the help of gyroscopes (not shown), or the base with castors as shown in the figure above, or using heavy weights at the base (not shown) to lower center of gravity. The WDD device may use either manual force, or motors powered by either electrical or gas, or a combination. The device may be used together with some of the available personal mobility assist devices, e.g., Segway, U3-X, and Winglet. In some embodiments, the user may be able to enter and exit the device, by using manual hoist mechanism embedded in the device or using the power controls (not shown). In some embodiments, the device may also be converted into a seat, by flexing at the knees and at thighs (not shown), thereby allowing the user to assume a seated position for the purpose of working at a desk or to use bathroom. A trip bar (not shown) or an extended base towards the back will maintain the balance of the user in the seated position. An important advantage of the said embodiment of the device shown in FIG. 6F is that the user can stay in an upright position, which is very beneficial for social interactions, allows them to be more independent at home and outside. Some of the embodiments of the WDD device may use a single use (unicycle), and therefore, the device may occupy a smaller foot print, and use less force, since the frictional forces can be lower when using a single wheel.

Figure 7:
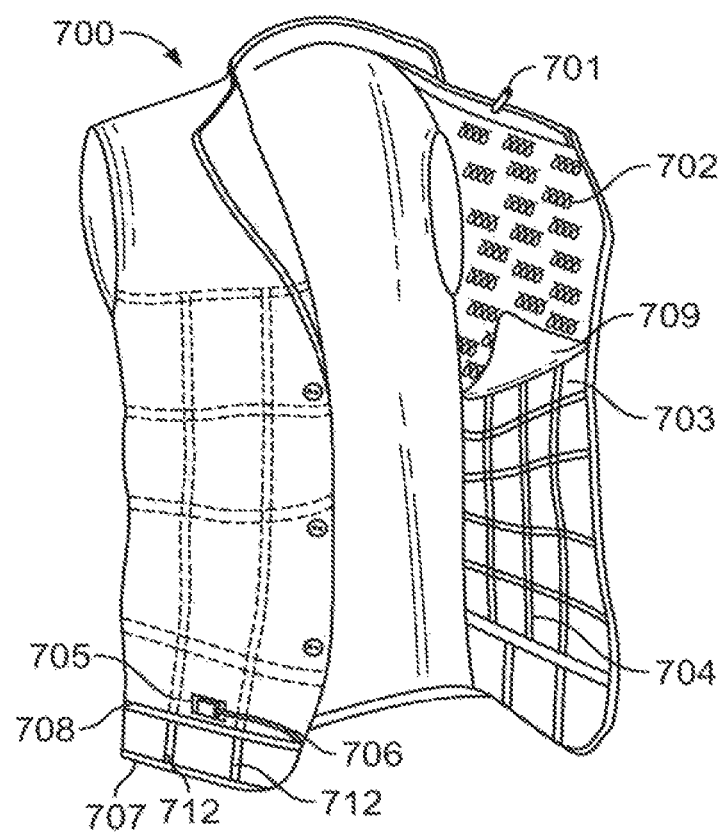
FIG. 7 illustrates an embodiment of a WDD integrated into a wearable jacket shape, in accordance with embodiments of the present invention.

FIG. 7 illustrates an embodiment of the present invention in the form of a wearable garment, a jacket, in this example. The jacket 700 can be secured to the user using zipper 701 or similar fastening means. The jacket may have several layers, and the inner layer 709 is peeled off partially to show the middle layer containing circular supporting members 703 and vertical supporting members 704 that rest on the base plate 708 located at the lower end of the jacket. The supporting members are similar to a frame described in earlier embodiments. Both 703 and 704 may comprise flexible or rigid rods or plates, capable of supporting weight of the torso of a person. The supporting members may have joints (not shown) for flexibility, and may have additional structures (not shown) to facilitate folding of the structures when not in use. On the interior face of the jacket are WBEs 702, that contact the body (not shown) either directly or through another sheet. The WBEs are attached to an expandable bladder (not shown) located between the WBEs and the layer containing the vertical and circular supporting members. The bladder may connect via a tube 706 to a pump 705 the user may carry, that can be operated by a battery. Pressure on the WBEs may be exerted in several ways, including manual levers, to exert force on the supporting members, for example to exert upward and inward force on the jacket using vertical members 712, that are supported by the base plate 707. Such an upward and inward pushing of the jacket 700 results in the WBEs to be pushed up against the body of the person, resulting in shifting of the weight to the WBEs that are supported by the jacket with the vertical and circular members. The mechanism is similar to the method described for other embodiments hereinabove. Instead of a battery-powered pump, manual levers (not shown), inflatable and/or non-inflatable structures may be used to apply pressure against the body.

Pressures ulcers are areas of local tissue necrosis that develop when soft tissues of the body (e.g., skin, muscle, connective tissue) are compressed, for long periods of time, between an external supporting structure such as a chair or a mattress and bony prominences of the patient. The prolonged pressure on the local tissue leads to microvascular vessel occlusion and the development of tissue ischemia, hypoxia, increased vascular permeability, and increased tissue edema, which leads to necrosis and development of a pressure ulcer. Bony prominences such as cervical vertebrae, scapula, elbow, ischeal tuberosities, trochanter, coccyx, heels, etc. are at the highest risk of developing pressure ulcers. Elderly people with limited mobility, those that are confined to wheel chairs or beds, people who are unable to change position voluntarily, and in those with diabetes or other general health issues are often prone to the development of pressure ulcers.

Several factors contribute to the development of pressure ulcers, including the magnitude of pressure, the duration of applied pressure, tissue tolerance, shear forces at the site, friction from the surface, humidity, temperature, health and nutritional status of the individual, age, and the like. Of various causes, two factors, the "pressure applied on the local tissue" and the "shear forces" that act on the local tissue play a significant role in the development of pressure ulcers.

Pressure applied on the local tissue is probably the single most important contributing factor in pressure ulcer development. Although pressure on the skin that is in contact with the supporting surface is important in the disease process, the pressure is often higher in the subcutaneous tissue including muscles and fat close to the bony prominences, than on the skin. Hence, the subcutaneous tissue close to the bony prominences often sustains more damage than the skin itself. Therefore, it is not an uncommon situation, to have a more subcutaneous muscle and tissue damage occurring prior to visible epidermal damage to skin at the bony prominences, which often delays the diagnosis of pressure ulcers. The blood pressure in the capillaries is approximately 32 mm Hg (a number that is widely used in the industry, however, the actual capillary pressure varies over a wider range based on several factors), is required to keep the capillaries open to maintain blood circulation in the tissue. When the local pressure exceeds the capillary pressure, collapse of the local circulation and the associated chain of events that eventually lead to the pressure ulcer development occur.

Several mattresses and chair cushions, as well a wide variety of accessories that incorporate air, other fluids, foam, gel, etc are effective in reducing the pressure on the skin to below 32 mg Hg. Some air loss mattresses and alternative pressure cushions cycle between various contact points to minimize the duration of high pressure. However, these are either too expensive or require significant maintenance and therefore, alternative alternatives methods and devices to prevent pressure ulcer development are needed.

While the pressure at the local site plays a major role, the second most important contributing factor to the development of pressure ulcers is 'shear force', which is an applied force on the body, that causes a sliding motion in a direction parallel to body's surface. Shearing may occur, for example, when a person for example, moves forward or backward on the seat of a wheel-chair, or when the head-section of the bed of patient is elevated which a results in the patient sliding towards the foot of the bed. In these cases, the skin tends to stay in the same place in contact with the surface of the chair or bed, while the underlying muscles and bones below the stationary skin move downwards, thereby stretching and collapsing the capillaries that provide blood supply to the skin and dermis, as well as diminishing the blood supply to the underlying tissue.

The major impact from shear force on the skin is due to the fact that when the shear occurs, significantly smaller amounts of pressure on the skin are required to occlude blood vessels, making the area more prone to develop pressure ulcer. Very few methods and devices, however, are available to minimize shear forces on the skin and the underlying tissue in people. Therefore, methods and some embodiments of devices to minimize pressure on the load bearing parts of the body, as well as to minimize shear forces on the body, to prevent development of or to treat the pressure ulcers are disclosed herein. The methods and devices may also be used to provide support to patients with burns, patients undergoing surgery (anesthetized) and the like. The methods and the systems disclosed in this application may be used as stand-alone devices or integrated into various devices (e.g., seat, wheel chair, mattress), or retrofitted onto existing devices, or added as an overlay on the top of existing devices.

Figure 8A:
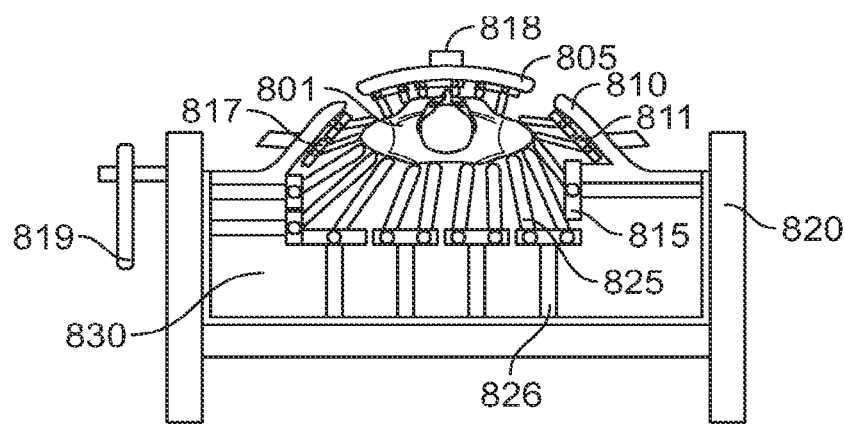
FIG. 8A illustrates cross-sectional view of an embodiment of a WDD integrated into a bed/mattress for prevention/treatment of bed sores.
Figure 8B:
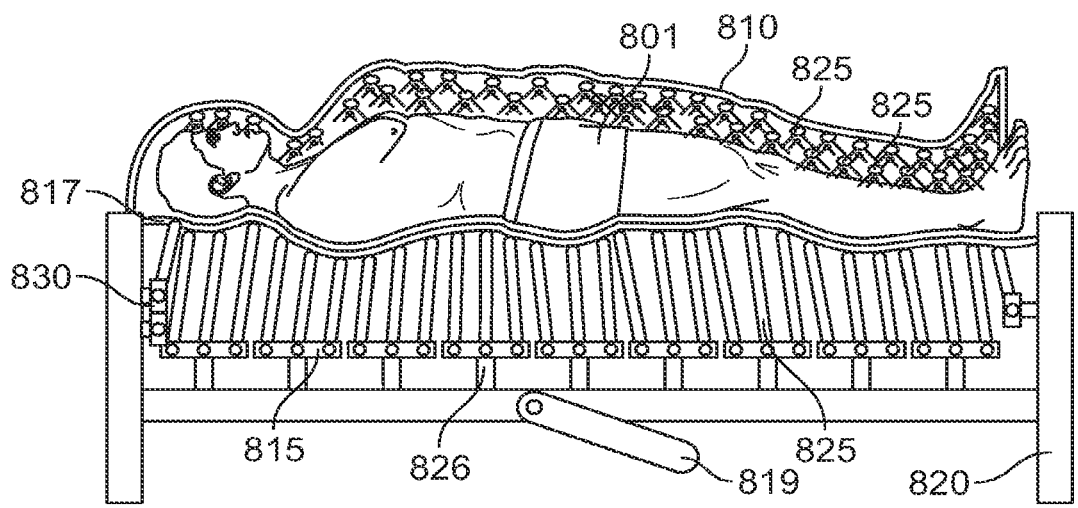
FIG. 8B illustrates a longitudinal-sectional view of an embodiment of a WDD integrated into a bed/mattress, for prevention and treatment of bed sores.
Figure 8C:
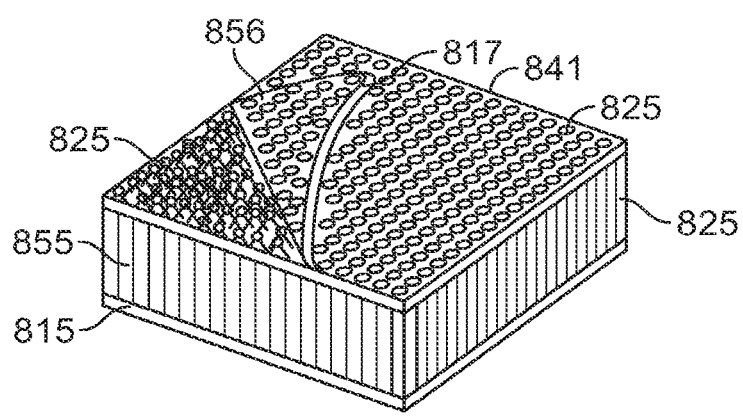
FIG. 8C illustrates a perspective view of an embodiment of mattress with top foam layer pulled back to partially expose the WBEs.

FIGS. 8A, 8B and 8C illustrate an embodiment of a WDD useful for reducing pressure on the body of a person, who is in a lying position. Although only a bed is shown in the figures, the device is applicable to various other situations such as a person sitting in a wheel chair or to support an anesthetized person on a surgical table, and the like. A detailed description of the embodiments shown provided below.

FIG. 8A shows a cross-sectional view of a person 801, covered by a sheet 817, lying on a bed 820. The person is supported by WBEs 825 that contact the person through the sheet 817, and the WBEs are supported by planks 815, which in turn are supported by the frame of the bed 830, by the supporting shafts 826. Side flaps 810, support the WBEs located on the left and right side of the person, while an optional front flap 805, supports the WBEs located on the top of the person. The front (top flap when lying down) and side (lateral) flaps are secured in place using support 818, which is anchored to the bed frame or an external support (not shown). The lever 819 is connected to the shafts 826 (connection not shown), and is used to increase the pressure on WBEs which push against the body.

FIG. 8B shows a longitudinal view of an embodiment of WDD with a person 801 lying on the bed 830 covered by sheet 817. The WBEs are supported by planks 830 and which in turn are supported by shafts 826 connected to the bed frame. The WBEs on the front flap (not shown) and the side flaps 810 (only the left side flap shown) support the body from the front and the sides.

The WBEs in FIGS. 8A, 8B and 8C may be supported by either inflatable or non-inflatable structures, to increase or decrease the pressure on the WBEs; however, these are not shown in the figures.

In some embodiments, the apparatus may be integrated into a bed, and may have elevated sides to support the body of the user on both sides. In some embodiments, the apparatus integrated into other furniture, for e.g., a bed, may look like a regular mattress with a depressed area that may be in the shape of a person, or a rectangle to accommodate the person including head, arms, torso, arms and legs.

A manual lever is shown in the figure, which may be used to increase pressure on the WBEs; however, the pressure on the person's body may be increased in several ways, without limitation, including external power sources, electrical controls, etc.

FIG. 8C shows a perspective view of a portion of the bed (or front and side flaps), with sheet 817 peeled back to show the top of the WBEs 825, contact point 856 of WBEs on the peeled back sheet, and a side view of the WBEs 855. The WBEs are supported on the plank 815.

In the embodiment shown in FIG. 8C, the WBEs may be supported by the frame of the bed or panels, which can exert pressure on the WBEs and used to change the direction and magnitude of the force. The person on the bed may be supported by a heavy cover that has holes for the WBEs to pass through. Overlaying on the top of the cover and the tips of the WBEs there may be a highly stretchable sheet whose ability to stretch may be controlled using various means (e.g., anchoring to the cover underneath, using elastic bands or using stitches). The WBEs bear the weight of the person that lies on the bed and there is no limitation on the size of each WBEs or number of WBEs per unit area. For example, there may be from 1 to 1,000,000 or more WBEs per square inch, which can be made of various types of material. Only a mechanical (e.g., compressible spring like) WBEs with panels are shown in the figures, however, various other embodiments including non-inflatable or inflatable structures (e.g., bladder), magnetic, soft brush like forms, etc., may be used as WBEs.

Figure 9:
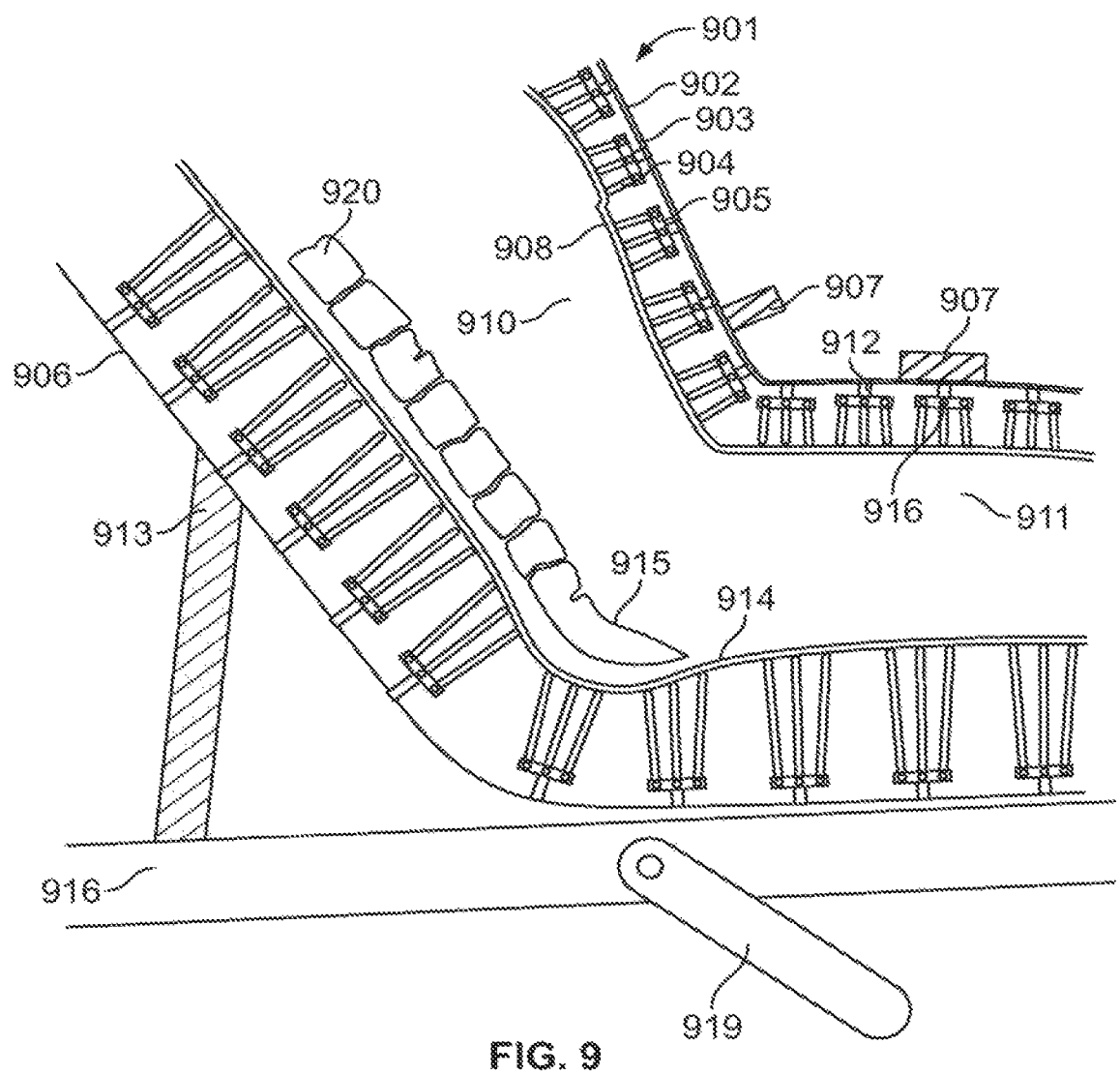
FIG. 9 illustrates an embodiment of a magnified view of WDD integrated into a mattress/bed to minimize shear forces on the skin and underlying tissues when the head and shoulders are raised.

FIG. 9 shows a magnified side view of an embodiment of a WDD 901 supporting a person lying on bed 906, with the torso 910 (and the head) of the person elevated compared to the legs 911, using a supporting rod 913 anchored to the bed frame 916. The outer surface of the frame of the front flap 902 and the side flap (not shown) are anchored to the bed frame by supporting structure 907, and on the inner surface 903 support shafts 912, which in turn support the planks 905, that can change direction at the joint 916. The bed is covered by sheet 914, and is supported by WBEs 904 that contact the sheet to bear the weight of the body. The vertebral column 920 at the lumbar region and the coccyx 915 are shown. The lever 919 is connected to the support shafts 912 (connection not shown) which allows the user increase the pressure on WBEs in the bottom, side and front flaps towards the user to facilitate shifting of the user's weight to the WBEs and frame of the weight distribution apparatus.

The principles and methods described earlier for various embodiments of the WDD are applicable to the operation of the mechanism shown in FIGS. 8 (A to C) and 9. To operate the device, the user lays flat on the bed equipped with the WDD. An optional top (front) flap that covers the anterior portion of the person may be provided to support the front portion of the person (not shown in the figure). The side flaps surround both inside and outside of each leg. The frame of the side and front flaps is strong enough to support the weight off-loaded on to them. When the apparatus is not in use, the side and the front flaps may be lowered or retracted into the mattress or onto the sides, which makes the device looks like a regular mattress.

For using the device, the user may lay flat on the bed in FIG. 8B, in a supine position (or other positions), and may secure the side (lateral) flaps and the top (anterior—not shown in the figure) flaps close to the body (as shown in FIG. 8A). At this time, the weight of the person is still borne by the weight-bearing regions like the back of the heel, the calf muscles, the back of thighs, buttocks, ischeal tuberocities, scapula, back, and back portion shoulders, head and neck, that contact the bed, but no pressure is exerted on the sides or on the front portions of the person. The user then off-loads the body weight from the weight-bearing regions of the body, as described above, to a larger surface area, including the left and right sides of the body, and to some extent onto the front side. This may be accomplished by pulling the lever 819 manually or using electrical controls (not shown in the figure), which results in the WBEs located on the underside of the person (in the bed frame or mattress), and the WBEs located in the side flaps and those on the top to be pushed against the body surface from the side and front side.

In order to exert pressure on the body, the WBEs may extend out of the frame, from the bottom and the side and front flaps, and push against the sheet and come into contact with surfaces of the body, including the weight-bearing as well as non-weight-bearing portions of the body. WBEs may apply pressure on the body of the user in various ways without limitation. The pressure exerted on individual areas of the body may be less than, equal to or higher than the weight of that particular portion of the body. The WBEs may exert pressure in all directions on the body; however, the net force is directed upward, such that it acts against the gravitational force exerted on the body. As a result, the weight of the body is now re-distributed over more extensive surfaces of the body with which the WBEs come into contact, thereby minimizing the overall pressure on the weight-bearing regions of the body.

For example, for a person weighing 200 lbs, with an approximate surface area of about 3000 square inches, the average pressure on the buttocks when the person is lying down on a standard bed may approximately from 50 to 70 mm Hg (and which may be as high as up to 300 mm Hg on the ischeal tuberocities when the same person is sitting on a chair). Pressures of this magnitude cause discomfort to the person within, e.g., a couple of hours. However, on a bed fitted with the WDD, as the surface area that bears the body weight increases, assuming that WBEs exert pressure on ⅔rds of the total body surface area available (underside plus side flaps), the pressure on the surface of the body, including weight-bearing regions of the becomes approximately 5.1 mm Hg. This is based on the 200 lbs of body weight distributed over 2000 square inches=0.1 lbs/1 sq. inch. This equals to .about.5.1 mm Hg. This pressure is considerably below the capillary pressure and therefore, should allow the person to maintain blood circulation at the weight-bearing surfaces of the body and prevent pressure ulcer development.

In some embodiments, the pressure on a weight-bearing surface of a body may be lowered (using WDD) or increased (using LCD) 1-fold, 2-fold, 5-fold, 10-fold, 20-fold, 50-fold, 100, 1000, 10,000, 100,000-fold or more, or in the range of, e.g., 1-fold to 100-fold, 1-fold to 100,000-fold. In case of weightless conditions, in space, where the pressure exerted on the body may be close to zero due to weightlessness, in some embodiments the pressure may be increased up to 1, 10, 100, 1000 or 10,000 or 100,000 mm Hg, or in the range of, e.g., 1 to 100 mm Hg, or 1 to 100,000 mm Hg.

For an elderly patient or a hospitalized patient lying on a standard mattress, when the head-board is raised, it may cause the patient to slightly slide forward, thereby increasing shear forces as well as pressure on the ischeal tuberosities, sacrum and on buttocks. However, when the same person were to be lying on a mattress integrated with WDD, as shown in FIG. 9, since the WBEs push against the sides, front and the back side of the torso with a net upward force, the shear forces and the pressure on the buttocks regions will be lower compared to a standard hospital bed.

As described hereinabove, when WBEs press against the body of a person, they are designed to exert forces in all directions of the body. However, the position and direction of the planks on which the WBEs are located may be adjusted such that a net force is directed upwards against the gravitational force (irrespective of the position of the body). In additional embodiments, a graded force may be exerted by WBEs with higher force at the bottom and lighter force on the top sides, or using WBEs of different strength and orientation may be used to modify the direction and strength of the net force. Therefore, although the WBEs push in all directions, forces that push in the horizontal and downward direction cancel out and leaving net upward force. The horizontal and downward forces however are important as they prevent the slippage of the muscles and bone underneath the skin there by preventing shear forces on the tissue.

Several different embodiments of the weight distribution apparatus for beds may be used including, a retrofitted version, similar to what was shown in FIG. 4H for a chair. Note that a separate figure describing a retrofitted version for a mattress or for supporting a patient during a surgery is not shown in the figures, however, such embodiments of the WDD may be operated in a fashion similar to the embodiment shown in FIG. 4H. Briefly, the retrofitted wedges containing the WBEs that support the torso, and legs are pressed against the person lying on the bed, and pressure is applied (mechanical means or by inflating) such that the WBEs, transfer the weight of the body to the frame, thereby relieving the load on the weight-bearing regions. The retrofitted types of WDD embodiments can be placed over or fitted to any existing suitable furniture for immediate use.

A significant portion of a person's life is spent on beds, mattresses or similar devices that distributed the body weight of a person over a wide body surface area, thereby providing comfort and relaxation. Several types of furniture are available to cater to a wide variety of applications, including, for e.g., benches or beds that have hard tops (made of wood, metal, plastic, etc), mattresses of various firmness ranging from soft to hard, sofas, lean back chairs, hammocks, etc. Mattress composed of memory foam, for example conform better to the contours of the body and therefore, reduce the amount of pressure on the at the contact surfaces. However, several people still feel back pain and feel uncomfortable with various types of beds or sleeping mattresses available currently. Although, latest designs, e.g., adjustable beds include reclinable sections can be raised or lowered to remove pressure from selected parts of the body. However, these are expensive and usually require a power source to operate. Therefore, a need exists for new type of devices to distribute weight while lying down.

The various embodiments of the WDD discussed in this application, for example, the ones with inflated bladders and without inflated bladders, the hybrid devices, and the ones with fabric, or containing bands etc., may be used as a stand-alone devices or integrated into beds or mattresses, etc. for distributing the weight of a person when lying. Referring to the embodiments described in FIGS. 8A-C and 9, and the one described in FIGS. 2A and 4H, 4J and 4L- and 4M, for example, the following is the procedure to increase the user comfort of a person when lying down. The embodiment (not shown in the figure), may resemble a regular mattress or pillows to support the respective body parts. The WBEs and the frame may be either retractable into the bed, or hidden below an upper foam layer or a cushion. The WBEs may extend out of the holes in the upper foam layer to support the weight of a person, as needed based on sensors that detect the position and location of a person's body. The WBEs from the WDD may be extended out and pushed against the body using either manual or electrical controls. The WBEs may contact bottom, as well as the sides or top of a person or a combination thereof. In certain embodiments, where a hybrid type of WDD is used, the mattress may have an inflatable top, under pressure. When a person lies down on the bed, the pressure and the outline of the location of various parts of the body may be sensed by the mattress, and cause the WBEs from the adjacent positions (that are close to the outline of the body on the bed) to be projected out of the bed and contact the sides and top of the body to take the load off the weight-bearing regions. Similarly, when a person lies down on the bed, the weight of the person on the bed may be transferred to, for example, a torsion spring which in turn may cause the WBEs from the adjacent portions of the body to project and decrease load on the weight-bearing parts of the body. In additional embodiments, the mattress may be retrofitted with removable WDD such that the WBEs will project from the sides of the mattress or frame of the bed. It is also possible to make thin overlay mattresses that incorporates the WDD and the method, such that these can be used either for sleeping or in hospitals or in operation theaters.

Snoring is a major social and health issue for a significant number of people in the world. Several factors contribute to snoring, including misalignment of the head, neck and torso while sleeping, relaxation of certain tissues in the pharyngeal region and the throat while sleeping, partial obstruction of the nasal passages, obesity, old age, etc. Sleep apnea is a condition characterized by abnormal pauses in breathing or low breathing, which lead to unsatisfactory rest in the night resulting fatigue in the day time as well as several long term effects on the health. One type of sleep apnea called "obstructive sleep apnea" results from physical blockage or collapse of air way.

Several treatment options including lifestyle changes, and various devices including, cervical pillows, chin straps, continuous positive airway pressure (CPAP) machines, mouth guards and surgical correction techniques are used to minimize or treat snoring or sleep apnea. Raising the head and shoulders of a person is another way of reducing the incidence of snoring. However, some of the devices are not well tolerated by all patients while they are sleeping. The surgical procedures are associated with some risks to the patients. Therefore, methods and some embodiments are disclosed herein, to prevent or mitigate snoring and/or sleep apnea using the principles of redistribution of weight and the WDD devices described.

Embodiments of WDDs that are either stand-alone devices or integrated into a mattress, pillow or cushion are disclosed in this application to address snoring and/or sleep apnea. Sleep apnea, as observed in people with excess body weight, may be due to the deformation of the soft tissue (soft palate, respiratory tract opening and tissue in the nasopharyngeal region and that is close to the opening of the respiratory tract at the back of the throat) in the throat region, exerting pressure or causing partial obstruction of the respiratory passages. Snoring likewise, occurs when flappy tissue located in the rear part of the nasal passages and the throat relaxes when a person is sleeping and vibrates. Embodiments of WDD disclosed herein to treat apnea or snoring act by shifting the weight from the weight-bearing regions of the head, neck, upper and lower torso (when a person is sleeping) to other parts of the body and therefore, the device minimizes the pressure of tissue on the respiratory passages located in head and neck and throat. Reduced pressure on the structures in and around the neck, head and shoulders thereby reduces the tissue deformity experienced by these tissues when the person sleeps. Certain devices available in the market some of which are called "snoring pillows" claim to mitigate snoring in people, for example by keeping the alignment of the neck, head and spine. However, such devices are not able to minimize the deformity of tissue beyond a certain point, as the pressure exerted by the weight of head, neck and shoulder regions on the tissue surrounding the throat and the pharyngeal cavity is not decreased.

Embodiments of the WDD devices similar to those presented in FIGS. 8A to 8C, and FIG. 9 (exemplified using bed or mattress as an example), or those various embodiments shown in FIGS. 2A, 4A, 4H (exemplified using chair as an example) may be used for mitigating snoring and/or sleep apnea. Only parts of the user's body, e.g., head, neck, shoulders and torso or whole body may be supported using the WDDs described. To use the device, for e.g., the person sleeps on a bed fitted with the WDD activates the WDD. As the device distributes the weight of the head, neck and shoulders away from these regions to larger surface area, the pressure experienced by the tissue surrounding the respiratory passages is minimized. In certain embodiments, additional pressure may be applied on certain locations of the head, neck or shoulders to facilitate patency of the respiratory tract while the patient is sleeping. The device in some embodiments may contain sensors that may detect snoring, as well as measure the pressure exerted by various body parts on the WDD, and either increases or decreases the local pressure using bladder that can inflated or deflated, or other mechanical means. The adjustment of the pressure exerted by the body corrects the deformity of the tissue that is causing the snoring. No figures are shown for the snoring application in this disclosure, but without limitation, various methods and embodiments described earlier with appropriate modifications are applicable to mitigate the snoring and/or sleep apnea.

Methods and WDD and LCD systems described in this application may be used in a wide range of applications including human and animal health and well being. Included in this section are several of such embodiments, which fall under a wide variety of categories. As such, they are all described together in this section. Individual components of WDDs and LCDs, their mechanism of action, were described in detail in earlier sections. Therefore, this information is not repeated in the following sections to avoid redundancy.

Chronic back pain affects millions of people worldwide. Both upper and lower portions of the back are affected.

Upper back pain is a common condition among people that work in offices, drivers, or others that sit in same position for long hours. It is also common in people that perform jobs that subject them to repetitive stress, that require them to use particular upper back or neck muscles. Additional causes of upper back pain are sudden trauma, maintaining poor posture for long time, and the like.

Lower back pain is another important medical condition. A significant number of people in the world are estimated to be affected with low back pain, at least once in their life time. Low back pain is characterized by a sudden, sharp, persistent or dull pain experienced at about the waist level or below and occasionally shooting down the leg, and which tends to get worse with spinal loading (e.g., staying in an upright position, sitting, walking standing, walking, lifting) but often relieved when one lies down, due to unloading of the spine. Several causes such as herniated or bulging discs, spinal nerve root afflictions such as stenosis and entrapment, degenerative diseases of the discs, and the like cause low back pain.

Cervical pain is another acute or a chronic disorder that affects a number of people, due to disorders of the spinal cord, nerves and vertebrae and the supporting structures located in the neck. The supporting structures and the nerves are often injured in people involved in car accidents, or those hurt in contact sports and often with devastating consequences. Several commercially available cervical, thoracic, lumbar and lumbo-sacral braces or a combination thereof, made of rigid, semi-flexible, flexible or inflatable material are used to stabilize, support, decompress, or align, the vertebral column. Various types of devices used are designed to relieve the weight of the upper portions of the body on the on the vertebral column. For example, harness-type devices are available to hold and suspend a person's upper body, and thereby relieving the pressure on the lower vertebral column. Various "inversion tables" are available to relieve back pain, which are operated by tilting a person secured to a table at an angle, with head down, and keeping them in that position for some time.

Sciatica is another symptom that refers to pain, weakness, numbness, or tingling in the legs, due to damage or pressure on the sciatic nerve. Sciatic nerves originate from the spinal cord at the level of the lower spine and innervate various parts of the legs. The condition also gets worse with activities that increase the spinal load in addition to other causes. Spinal decompression is one of the methods used to treat sciatica, which involves gently stretching of the spine, creating a vacuum effect, which can restore disc height and even reduce the severity of bulging disc condition. Various devices such as VAX-D®, DRX9000® and AccuSpina®, Antalgic-Trak® are available to decompress the vertebra.

None of these devices off-load pressure from the vertebral column effectively, and therefore, better solutions are required to manage, treat or prevent such conditions. Disclosed herein are embodiments of WDD that can be used to minimize the load on the spinal column of a person, whether standing, walking, sitting or lying down, based on the principles already described herein. The disclosed systems may also be integrated into the existing products and used in combination with other devices.

It should be noted that decompression of the spinal cord is a risky procedure that needs to be done with utmost care under the supervision of highly trained personnel. It is hoped that by using the WDD described in this application, the need for spinal decompression may be obviated. Various embodiments of the apparatus to support the spine are described below.

Accordingly, it is an objective of the present invention to disclose a method and an embodiment of WDD useful for supporting the spine and various parts of the vertebral column and torso muscles. As shown in FIG. 10A, the device 1010 may comprise at least one brace, an upper brace 1012 and a lower brace 1014, which may cover the torso partially or completely. There is no limitation on the width and height of the braces, and therefore, in some embodiments, the braces may cover substantially larger portions of the torso or other parts of the body. Without limitation, the braces may be supported by a supporting rod or a plate 1013 and fixed in place using the screw 1017. The inner surface of the brace supports the WBEs, which contact the user's body either directly or indirectly. The lower brace 1014 may be supported by the waist region of the user. The user may use the braces alone, or in combination with other casts or any other stabilizing devices used over the injured portion. The braces may be positioned on the injured portion in some embodiments, or above and below the injured portion of the torso/spine in additional embodiments. The braces shown in FIG. 10A or 10B may be integrated with a chair or other similar devices, as appropriate.

Shown in FIG. 10B is an additional embodiment of a brace 1020 to support the torso of a person, comprises at least one frame, which may include a neck and a head piece 1015, and a torso piece 1009. Front neck flaps 1018 and abdomen and chest flaps 1019 may cover front side of a person either partially or completely. A plate or rod 1016 made up of several articulated pieces that may be flexible support the back part of the WDD, and similar kind of plates may be included in the flaps and the sides. The WBEs 1016 are supported on the inner surface of the head and neck and torso pieces of the frame and come into contact with the body of the person either directly or indirectly. The body weight of the user is supported by the lower edge of the torso piece of the frame, which in turn rests on the waist region of the body.

To operate an embodiment of the device, shown in FIG. 10A, the user positions the upper brace 1012 at a level higher than the injured muscle, joint, inter-vertebral disc or vertebrae, and secures the brace to the torso, using various securing means. Another brace may be positioned at about the waist region of the person, and secured to the torso. To relieve the load on the injured part, the user then exerts pressure on the WBEs, with a net upward pressure on the upper brace and fixes it in place using the rods/plates 1013 and screw 1017, such that the weight of the body located in and above the upper brace 1012 is now transferred to the WBEs and the supporting frame (not shown) and rod 1013. The supporting rod 1013 transfers the weight of the upper portion of the body (e.g., above the damaged or the inflamed area of the spinal cord) to the lower brace 1014, located at the waist region, thereby, relieving the weight on the injured portions of the spine. As the WBEs exert pressure on larger surface, and the pressure is exerted from all directions (with a net upward force), minimal shear forces are expected at the location where the upper brace comes into contact with the skin, thereby increasing the comfort of the user wearing the brace. The supporting rod 1013 may be flexible to allow free movement of the torso. An embodiment of the WDD shown in FIG. 10B may also be operated in a similar manner. The neck and head piece may be useful in relieving the load of the head on the neck region and will minimize neck pain in injuries involving structures in the cervical portion of the user, and may be useful in cases of cervical injuries.

An embodiment of the WDD described in FIG. 10A, may also be used to provide relief to sufferers of low back pain or sciatica, or to decompress the inter-vertebral discs, or to relieve the lower parts of the spine from the weight of the upper segments of the body. To operate the device for these purposes, the user secures the WDD shown in FIG. 10A to the torso, or will be seated, for e.g., in a chair integrated with the embodiment of WDD shown in FIG. 10A or 10B. The person then secures the upper brace 1012 to torso, corresponding to an area of the intervertebral disc where decompression is needed or below the vertebrae where a spinal nerve is being pinched. The lower brace 1014 is secured to the waist/pelvic region. The user then activates the WBE and transfers the weight of the upper portion of the body on to the supporting frame (not shown), and to rod 1013, and finally transferring the load of the upper body on to the lower brace. This process itself is expected to relieve the pressure on the intervertebral discs, causing decompression or the pressure on the pinched nerves. For additional decompression, the user then slowly increases distance between the lower and upper braces, such that the weight of the upper portion of the body is completely transferred on to the supporting rod 1013, and therefore, the weight of the upper no longer presses on the lower regions, and the upward force may slightly lift/stretch the upper portion, thereby providing relief similar to the one experiences when decompressed using some of the commercially available devices. To provide such a relief, some of the other embodiments depicted in FIGS. 2A, 4A, 4H, and the like, may be used as well. Because the device relieves the offending pressure on the injured portion of the spinal structures, the WDD provides relief from the pain and allows time for the lesions to heal.

In addition, to providing relief, the WDD may be used to support the spine after various surgical procedures on the spine to strengthen it. Likewise, the WDD system may be used in conjunction with traditional back braces to relieve back pain. For example, while the brace stabilizes the spinal column, the upper body weight of the person, above the injured portion, may be transferred to the frame of the WDD, thereby relieving the pressure on the injured region. The phrase "spinal column" is used herein to include vertebrae and the associated nerves, inter-vertebral discs, the joints, ligaments, muscles, and the like, that are part of the supporting structures of the back.

The WDD may also be integrated into the design of traditional back braces in order to increase the comfort level of patients while using the traditional braces. This is because, the traditional braces, often exert pressure at locations where they contact the body of the person and exert both pressure and friction (and shear forces). As the pressure and the shear forces are concentrated at such locations, especially when the brace moves against the body surface, the braces often cause significant stress leading to discomfort. It is desirable therefore, to have braces that do not exert undue pressure at the site of contact. Therefore, when the lumbar, thoracic, cervical or whole torso braces (e.g., Boston brace) fitted with the disclosed WDD system, they will be better tolerated. In such a brace, while the spinal column is stabilized by the brace, the weight of the body above the injured regions will be transferred to the frame of the brace (supported by frame of the chair, mattress, or other structures of the frame).

Several types of orthosis (e.g. knee-ankle-foot orthosis, lumbar support) are often used to support and rehabilitate people with various disease conditions bones, joints or muscles, including for e.g., arthritis, injuries, or following surgeries. To keep the weight of the body off of injured portion of a body such as spine or a leg, various devices, such as crutches and orthosis are used. Crutches that are held by one or both hands placed under the armpit are often used to off-load a person's body weight from an injured leg or the leg cast. However, these types of supports are difficult to use and restrict the mobility of a person and can sometimes lead to soreness or injury to the muscles around the arm pit area. The support devices currently available on the market, although protect the injured portion of the region from bearing the body weight, cause that weight to the shifted onto a contra lateral side of the limb or cause the weight to be concentrated on a limited regions of the body, leading to additional damage to other parts of the body or slowing down recovery. Some of the devices like Ottobock Sensor Walk® or other gait control devices help with walking of a patient while using an orthosis, however, they do not completely take weight off of the injured leg, as needed, or do not allow a person to have good control on how much weight they can place on an injured portion (e.g., foot), due to their inherent design limitations.

A detailed description of the various applications of WDD for use in humans is provided below, but, no figures are included for these embodiments, herein. The devices work in a similar manner as described earlier for other embodiments of WDD. An example of a knee orthosis is used herein to describe the operation of the embodiment, to support a person with knee joint arthritis or a surgery of the knee.

To operate the embodiment of the WDD, the device may be designed in the shape of a leg or similar other shapes, and will be secured to a person's injured leg, with the WBEs covering the portion of the leg at least above and below the knee joint, with the upper end supported by pelvis or thigh and the lower end of the frame of the device supported by the floor (or shoe). The frame may be a single piece or multiple pieces with joints at pelvic, knee and ankle joints for flexibility. The WDD are thereby used alone or combined with various orthosis currently used to support the injured portions of the body. To use the device, the user activates the WBEs and off-loads at least some of the body weight, onto the WBEs and to the frame by various means as described earlier (e.g., inflating a bladder, using torsion type spring or exerting or using a combination of mechanisms described in earlier embodiments), thereby relieving any load on the injured leg. The amount of load to be off-loaded onto the frame may be controlled by modifying the pressure exerted by the WBEs and by the adjusting the tension of the frame, or other means. As the WBEs spread the weight on a wider surface area of the leg, the device is better tolerated than the traditional orthosis, since the amount of pressure experienced at the skin is lesser when WDD mechanism is integrated into the orthosis.

Weight-distribution methods and devices as disclosed herein may also be used to support patients with open wounds soon after surgery. Often it is advantageous for the patients to get up on their feet and walk soon after several types of surgeries, to minimize potential complications, provided the patient is allowed to bear weight on the weight-bearing regions. Due to pain related to surgery, and because the patient has to carry their own body weight, the patient, needs to be supported manually on such walks. Therefore, a WDD, such as the WDD suit embodiment mentioned hereinabove will advantageously provide such a support for the patient during this period.

Various types of braces are prescribed to be used for a long period of time such as the Boston brace (for correcting curvature of spine in adolescent patients with scoliosis), or for lifelong use, such as a leg prostheses used by amputees including veterans and some victims of automobile accidents. Often these devices cause pain at the location where the device meets the body either due to excessive pressure, shear forces or friction, because those places are subjected to repeated rubbing, impact, and often are exposed to the amputated bone stump from within. The methods and WDD devices disclosed herein may be integrated with such devices to distribute the weight over a larger surface area of the body and thereby minimize injury to the local tissue.

Prolonged standing or even moderate walking causes foot pain to some people. Pain may be result of several factors, including repeated mechanical injury, bad shoes, injuries to ligaments, muscles, bone fractures, over stretching of bursa and fascia due over use, etc. In some people anatomical structure of the foot, e.g., either low or high arch feet may cause foot pain. Similarly, injury to the plantar fascia may cause inflammation and pain of the foot. Cushioned soles, gel pads, soft insoles, inflatable bladders, springs, and the like, that dampen and conserve energy while walking or jogging, have improved the user comfort significantly over the years. Spring-loaded shoes are particularly useful while walking as they minimize the energy required for walking. While such products have increased the comfort level of the user, users still suffer from significant foot pain, due the stresses on the foot caused by the body weight and the repeated injury due to stretching (while walking), people continue to experience foot pain even after the use of the above devices. Therefore, it will be advantageous to have a system that will help reduce the overall pressure on the soles of a person's feet. Disclosed herein are methods and some embodiments of WDD that can be used to decrease the pressure and overall load on the feet of a person to prevent injury to the foot or mitigate pain.

Depicted in FIG. 10C are some embodiments of a shoe incorporating the method and WDD mechanism, as disclosed herein, to minimize the load on the sole of a foot. The device 1021 comprises a frame 1023 and a WBEs 1026, supporting leg 1025. An additional plate that may run through the length of the boot comes into contact with several spokes 1027 at the ankle level that connects the supporting rod with the sole 1029 of the shoe 1030. The device increases the comfort of a user (of shoes), by re-distributing the load from the feet to the surface of the rest of the leg, so that the wearer feels less stress on the muscles, tendons, joints and bursa of the feet. In some embodiments, shoes of knee height (e.g., boots) will have WBEs located on the inner surface touching surrounding the lower portion of the leg (below knee). WBEs may also be located on the inner surface of the shoes touching all sides of the foot. The boots are made up of an outer frame that can support the weight of the body. The frame may be reinforced by plates or rods that extend from the base of toes all the way to knee, but contain flexible joints to allow for easy movement. The WBEs located on the inner surface of the boots exert pressure on the legs and feet by various means, for e.g., mechanical means or by using inflatable bladders located within the frame. When a user wears the shoes and tightens them securely, followed by inflating the bladder (not shown in the figure), or activating the WBEs that push against the leg, due to the pressure exerted by the WBEs, the body weight is re-distributed from the soles of the feet to extensive surface areas covering the leg, such as up to the knee regions. As a result of such off-loading of weight on a larger surface, the pressure exerted on the soles of the feet decreases. In some embodiments, the boots may be extended up to the thigh or higher to further reduce the strain on the feet or the legs.

FIG. 10C-1 illustrates some embodiments of a WDD integrated with shoes containing springs. Several designs of the shoes with springs are available in the market. Disclosed in FIG. 10C-1 is an embodiment of WDD that combines the advantage of spring shoe, which conserves energy, with WDD mechanism, which reduces the pressure on the plantar surface. Although springs are shown only under the heel, there is no limitation on the size number of location of the springs. As illustrated, a method and a WDD is provided herein, wherein the shoe-like device has springs 1024 mounted at the bottom of the sole as shown in FIG. 10C-1. The WDD may cover the legs up to knees or higher with the frame, which extends from the top edge of the WDD (near knee) to heel, so that when a person walks, the pressure from the sole (due to compression of the springs) is transmitted directly to the WBEs supporting the legs. As the WBEs that surround the lower portion of the legs are designed to directly transfer the pressure from the legs to the springs in the soles, less pressure is exerted on the soles. The springs operate by absorbing the impact from walking and jogging and as such the compression energy stored in the springs is transmitted directly to the WBEs through the frame supporting the shoes. Therefore, the wearer of the WDD device integrated with shoes will feel less pressure in the feet, which translates to increased comfort. Further, as the pressure on the feet is reduced, it allows any painful or injured parts of the foot to relax and recover.

Spring shoes are known to be energy efficient as they store and return the compressed energy back to person using them, and therefore a person uses less energy while walking. Likewise, when WBEs of the push-spring type are used in a WDD that is integrated with or without spring-loaded shoes will conserve energy further, as the user does not loose energy when walking. In some embodiments, the sole plate shown in the FIG. 10C-1, may be in the form of a curved shape (e.g., semicircular), or similar other shape so as to allow the frame to maintain contact with the plate when an individual walks, and thereby allowing the body weight of the patient continuously off-loaded onto the frame and soleplate. Therefore, a soldier using a spring-loaded shoes, and WDD with WBEs that comprise push-spring type springs, and a exoskeleton, will have a significantly improved performance, as the soldier can carry heavy weights, over a long distance, using very little energy. A separate figure was not included for these embodiments.

Similarly, people using the above set up (spring-loaded shoes, together with WDD with push-type WBEs and an exoskeleton) will be able to walk longer distances with minimum energy. The individual user may be able to off-load a certain fraction of the body weight, e.g., ranging from 0.001 to 100%, onto the frame, to relieve pain, e.g., foot pain and as well as for decreasing the amount of work required to maintain balance while standing or walking, etc.

Patients with diabetes often develop foot ulcers, because the integrity of the skin and the underlying tissue including the blood vessels is compromised. Often they lose sensitivity in the affected regions due to peripheral neuropathy, which increases the risk for development of foot ulcers. Peak pressures of up to 899 kPA (.about.6750 mm Hg) were reported on the soles of foot for healthy people while walking on plantar pressure (Kwon and Mueller, 2001, Phys Ther 81: 828-835). Based on walking patterns, body weight, and anatomy of the foot and walking and jogging speed, pressures on the foot are likely to exceed the above value on some locations on the foot. In diabetes patients, because the vasculature, and the integrity of the skin is compromised, they are more prone to both the pressure as well as the shear forces exerted on both plantar surfaces and on other parts of foot they often develop foot ulcers.

Several soft soled shoes are available to provide support to this population. However, there are currently no effective devices available that reduce the amount of pressure and shear forces exerted on the feet of a diabetic person, which contribute to the pressure ulcer development.

Disclosed herein are WDD devices and methods to decrease the pressure and the shear forces on the diabetic foot. No separate figure is included to describe the WDD for diabetic foot ulcers. The disclosure is similar to what has been described hereinabove for the various embodiments of shoes depicted in FIGS. 10C and 10C.1. The device for preventing or treating diabetic foot ulcers comprises a shoe shaped structure that fits a person's foot and ankle, as well as a part or whole of the leg (e.g., up to the knees or above).

In some embodiments, the device looks like a boot that is knee-high or more. Supported on the inner surface of the device are WBEs, which contact the bottom, sides and top of the foot, as well as the leg. The WBEs may be comprised of either inflatable structures, mechanical structures (e.g., springs) and supported by an external layer and a frame.

To the use device, the user, after wearing the shoe-shaped device transfers their body weight from the soles to the WBEs by either inflating them, via the torsion spring-type mechanism or using a mechanism described earlier (e.g., see FIG. 4J) which are customized for the shoes. Because the WBEs are supported by the outer frame of the shoes, which is in contact with the ground, the weight of the person is now distributed on to both sole of the person as well as outer surface of the legs. As a result, there is less pressure on the soles of the person with diabetes. Therefore, a diabetic patient using said embodiments of the WDD integrated with shoes will experience significantly less pressure and shear forces (due to WBEs) compared to other shoes currently available. Some embodiments of the WDD device may provide support to the torso or thighs, instead of supporting the leg (below knee) or foot (not shown in the figure) of diabetic patients who are prone to development of foot ulcers, so as to reduce the pressure on the plantar surface of the foot when the patient stands upright or moving. In such cases, the patient may be able to use regular shoes, however, as the weight of the person is supported by the WDD, the pressure on the soles will be reduced. Based on the amount of weight off-loaded onto the frame, the device may reduce the pressure and shear forces on the plantar surface or other locations of the body that are prone to pressure ulcer development to less than 32 mm Hg. In some cases, pressure and shear forces on human body at locations prone to pressure ulcer development may be reduced to, e.g., 0 to 32 mm Hg, 32 to 100 mm Hg, 100 to 600 mm Hg with the use of the device.

Although, only some embodiments of shoes are shown in the figure, diabetic patients are susceptible to pressure ulcers on the back of the heel, due to pressure applied when lying down or at the buttocks or thigh region when sitting. In those patients, some of the WDD embodiments disclosed hereinabove for a bed (e.g., FIGS. 8 A-C, and FIG. 9) or chair (e.g., FIG. 4A, 4I, 4H), may be used.

Alternatively, the device may just cover the leg of a patient up to knees or thighs, with a frame that fits the sole of the shoe, to support the weight of the patient (figure not shown). This allows the device to be retrofitted to any type of footwear, and therefore a diabetes patient, for example, who is prone to develop foot ulcers will be able to continue to use any type of shoe, without concern about developing foot ulcers. In such an embodiment, only the leg portion of the device will have WBEs on the inner surface.

Because humans are bipedal they use chairs, seats, stools, tables, benches, sofas, etc. to sit conveniently and remove strain on the feet, by sitting on the buttocks, but still maintaining an erect position during much of the day, which is the most comfortable anatomic position to conduct various activities without expending much energy.

Various types of furniture are used (e.g., chairs, or seats) to comfortably accommodate a person's weight while seated, when working or traveling. However, the body of a seated person occupies a larger footprint compared to a person that is standing. Therefore, for example in an airplane, or in a bus or a train, more space is used by person when seated, as opposed to standing up. Similarly, for people traveling in a first class or business class seat, still more foot print space (or area) is provided per traveler, to allow the traveler to stretch their bodies, horizontally, to relieve the pressure on the spine and other weight-bearing structures. As a result, higher fuel is burnt to transport a passenger between destinations.

Therefore, disclosed herein are methods and embodiments of WDD to provide support to the body of a person who is standing upright, in such a way that the person feels a comfort level that is similar or higher than if he/she were to sit down on a chair/seat. The disclosed method and embodiments may also be used to decrease the amount of area required to accommodate a person in a transportation system or in any accommodation.

No separate figures are included to depict the embodiments described below to support the person in an upright position. The method of weight distribution and various embodiments of the WDD for example, as depicted in FIG. 6A herein, that supports a person while standing may be used to support people while traveling in vehicles or while working or doing various other activities. Several other methods and embodiments described herein (e.g., FIGS. 2A, 4A, 4H, 4I, 4J, 8B) with appropriate modifications may be used to support a person in a standing position. When a person is supported by the WDD when standing up, the person does not need to exert any additional effort to stay up on the feet, as the weight of the person is borne by the WDD. The system comprises a portable WDD (as shown in FIG. 6A) or a WDD integrated, e.g., into existing furniture, a wall, a frame, a chassis of a vehicle that supports a person while standing. To operate the device, the person secures oneself to the device, and transfers body weight by means of a lever or electrical control, which relieves the pressure off the person's legs and feet. The person may transfer the whole body weight, or only the upper or lower or partial body weight, onto the frame, by changing the amount and location of the pressure exerted by the WBEs.

Such a device may be able to replace the need for chairs, seats and similar other equipment from day to day use. For example, there may not be any need to use chairs in the office, that are traditionally used for sitting while working, if the WDDs are used as described. Similarly, in airplanes, trains or buses, the traditional seats may be replaced with seats integrated with the WDDs, so that passengers may be able to relax while in a standing upright position, while at the same time using less space. Currently, passengers in the first and business classes in the flights enjoy more space to stretch and lie down while flying, while the passengers in the economy/coach class are sit in a rather uncomfortable position during the long flights. When seats integrated with WDD are used, the passengers in the coach/economy class will receive the same relaxation that the first/business class passengers receive now, as they can spread their body weight from the spine to other parts of body effectively. This can be done either manually or using electrical controls, and in a manner that does not comprise the safety of the passengers. Either the push type or pull type of forces may be used by the WDDs for spreading the weight of the user on a wider surface area. Either inflatable or non-inflatable type of WDDs or a combination thereof may be used. The use of the device is similar to how a WDD integrated into chair is used, as explained earlier.

Patients often are not able to bear full body weight on legs or back due to an injury, surgery, or a disease condition or due to old age. But, patients often are required to undergo physical therapy or exercises, soon after surgery during rehabilitation to prevent complications and hasten recovery. However, patients are often not allowed to bear any weight on the injured limb or the vertebrae during this recovery period. Various devices are available in the market for patients to exercise, while helping them to keep the body weight off the injured part of the body. These include harnesses or railings fitted over tread mills, exercise machines with counter weights, tread mills that use air pressure to keep a person afloat (e.g., Alter-G® tread mill), etc. However, all these methods are not effective in consistently preventing from body weight from being accidentally placed on the injured part or require expensive equipment (Alter-G® treadmill).

Accordingly, disclosed herein are methods and embodiments of WDDs useful for restricting the amount of weight that can be borne on an injured portion of a body part (e.g., leg or spine). FIG. 6A, shows an exemplary device used to keep weight off of the limbs and/or spine while standing. FIGS. 2A, and 4A show additional embodiments of WDDs that can be used by a patient to relieve an injured spine from weight-bearing functions. For the purposes of reducing the amount of weight, for example, on an injured limb, the user wears a WDD, as described herein, and off-loads the body weight to the WBEs, which in turn transfer the weight on to the frame, which rests for example on the chair or ground.

Figure 10D:
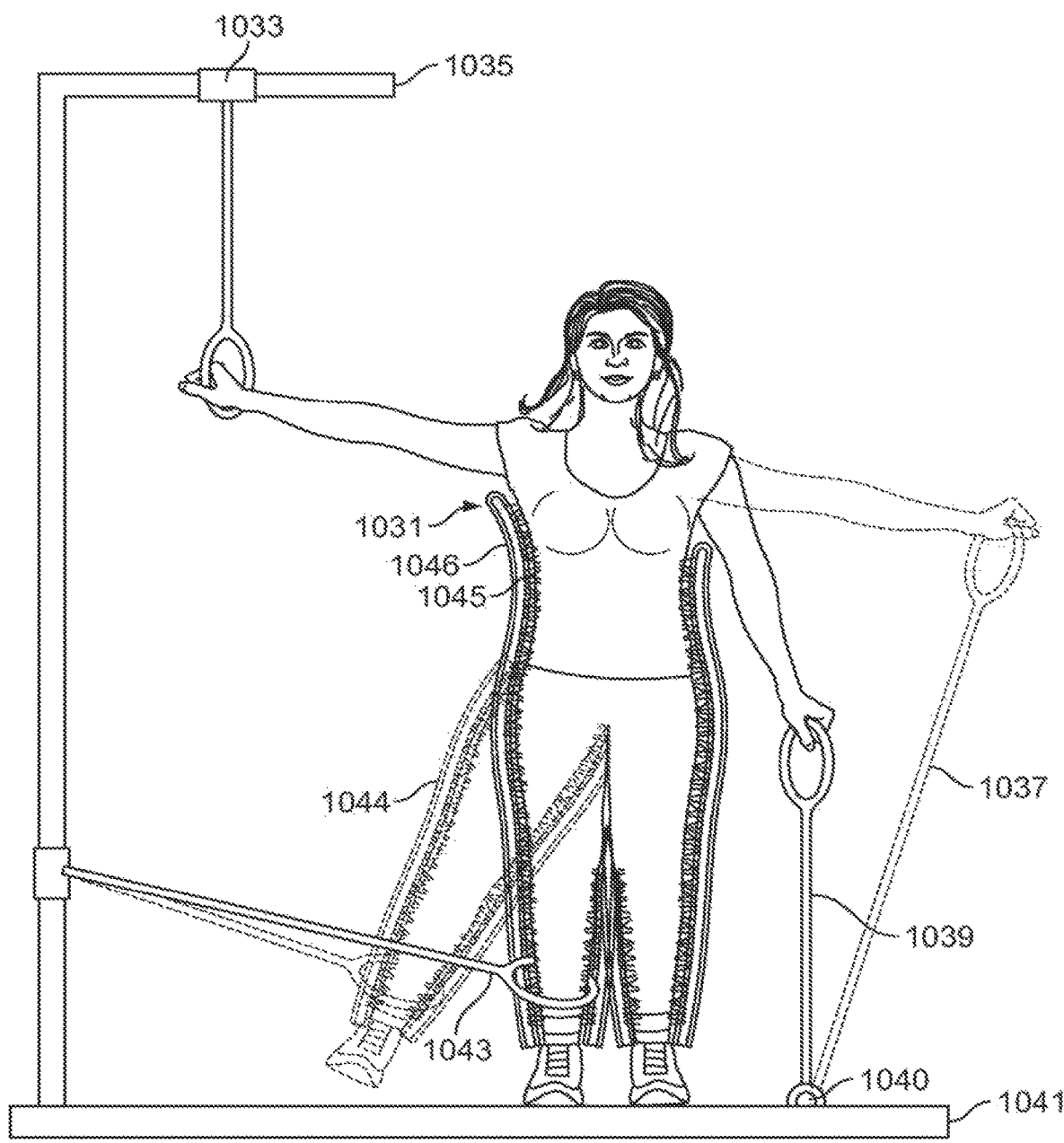
FIG. 10D illustrates an embodiment of WDD useful for providing exercise to persons who cannot bear significant amount of loads on their joints, as a possible replacement of aquatic therapy.
Figure 10E:
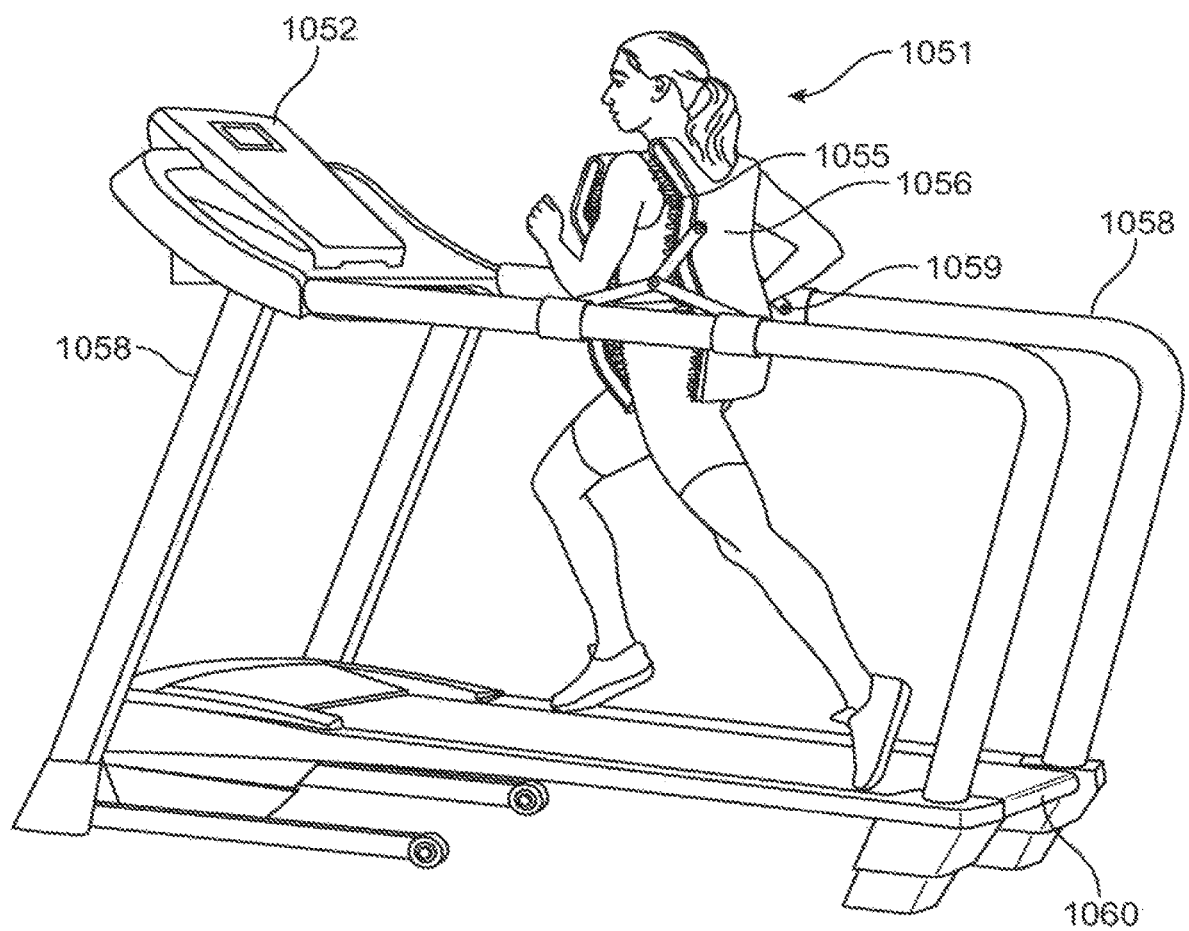
FIG. 10E illustrates an embodiment of WDD integrated into a treadmill for limiting the amount of weight a person can place on the feet, during rehabilitation.

Embodiments of WDDs that may be used for rehabilitation of people, who are unable to bear weight on the spine or lower limbs are shown in FIG. 10E. The WDD device 1051 comprises an outer frame 1056, which supports WBEs 1055, which support the body as described earlier. The frame is attached using anchoring means 1059 to the horizontal bars of the treadmill 1052, on which the person is able to walk or run. The height of the frame from the treadmill belt 1060 may be adjusted by tightening or loosening the anchoring means 1059 or by increasing or decreasing the height of vertical bars 1058. The anchoring means may comprise strong push or extension type springs or similar devices, which allow unlimited upward displacement of a user within the WDD, but which however limit the extent to which the user can be lowered, so as to limit the amount of contact the user's feet make with the treadmill belt 1060. The anchoring means may also be provided with powered pistons or other means that may continuously change the tension in response to the load on them, to maintain a predetermined height. The WDD, the anchoring means, the treadmill and the belt may be provided with pressure sensors, such that when the user starts walking or jogging, the pressure and the load on various parts of the body and the treadmill may be used to adjust the amount of load the user may be allowed to exert on the belt. The frame and the WBEs may cover part or a significant portion of the body of the user.

It should be noted that the embodiment of WDD on a treadmill is provided here as an example, and hence several alternate designs using the mechanism of WDD are possible, to limit the amount of weight on an injured portion while exercising. For example, in some embodiments, as exemplified in FIGS. 10D and 10E, a user may be able to use WDDs that are ambulatory, which may be used to limit the amount of weight that can be place on an injured portion.

Additional embodiments of the WDD include a frame and WBEs on a harness or a hoop that support the outer frame, and which are suspended over the treadmill and wherein the height is adjustable such that the user may be able to touch the feet on the treadmill and able to place only a desired amount of weight on the feet. The harness and the hoop may contain a vertical displacement suspension system (e.g., using a spring mechanism and a motor), to support the vertical displacement of the person over a desired range (to accommodate walking or running). The amount of vertical displacement may be adjusted either manually or using electrical controls to accommodate people of different sizes and needs. The treadmill and/or the hoop (or harness) may be fitted with sensors to display, e.g., the weight of the user, the weight placed on the hoop and the weight placed on the treadmill, which can be controlled either manually or using controls. The system may contain additional controls to enter body weight, height, and display various parameters, including time, distance covered, calories burned and the like. The user can start exercising by selecting the amount of weight to be borne on the feet and by adjusting the height of the hoop supporting the frame of the WDD. As needed, the user may be able to increase the load on the feet slowly during a recovery period as appropriate.

In addition to controlling the amount of weight that can be placed on the feet, the user, by adjusting the force with which the hoop (harness) and the WBEs push/exert force on the body, the amount of weight that can be placed on an injured limb can be controlled. For example, for a person who is injured below the knee, and who can only bear 20% of the body weight during recovery from surgery, the WBEs can be adjusted such that all weight will be borne by the thighs and torso, so that when the person starts walking the force from the ground is transmitted to thigh and torso, while allowing only a small portion of the force to be experienced by the region below the knee. The device can be used for various applications including preconditioning, prosthetic usage or neuromuscular training, to maintain cardiovascular function and muscle and bone strength during recovery from surgery, and the like. Another application of the device and the method is to provide support to overweight persons, or people with for example arthritis of the knees, etc., who may not be able to bear their whole weight on their feet, either in day-to-day activities and/or are limited by their body when they choose to engage in physical activities or exercise.

Aquatic therapy is a method of exercise (which is also called hydrotherapy, pool therapy or water therapy), is a form of physical therapy used for patient rehabilitation after an injury, in elderly people, in people with para- or quadriplegia, and the like. The advantage of aquatic therapy is that a patient can perform the exercises without placing undue effort/stress on joints or bones, because the buoyancy force of the water is used to support the body during rehabilitation. The viscosity and resistance force of the water may also be used to provide exercise to the user.

Aquatic therapy, however, is not suitable or affordable to everyone due to the expenses involved in building and maintaining a pool and the requirement for an instructor to be present at all times. Further, for patients with open wounds, aquatic therapy is not indicated due to potential risk of water contamination/wound infection.

Therefore, various embodiments of a WDD described below may be used, e.g., by people with open wounds using a "dry-therapy" that involves no water during rehabilitation. Either selected lower extremities of the body or the whole body may be supported using the WDD.

Accordingly, disclosed herein are methods and embodiments of WDDs for providing exercise to a patient without using a water pool, but getting the same benefit of aquatic therapy. FIG. 10D depicts an embodiment of a WDD that comprises a frame 1046 and WBEs 1045 that covers the body either partially or a significant portion thereof. Arms were shown to be free, however, WDDs may be used to support the arms as well. The person may use elastic bands of predetermined strength 1043 (for legs), 1039 (for arms), to provide resistance. The bands may be anchored to a top frame 1035 using an anchoring means 1033, and/or to the floor 1041 using anchoring means 1040. When the arm is raised, the elastic band may be displaced to a new position 1037 thus increasing the resistance, and similarly, when the leg is moved to a new position 1044 the resistance of the band may decrease. Although elastic bands are used as an example here, they may be replaced by weights, springs, ropes with pulleys and weights, and the like. Instead of bands, a uniform resistance may be applied throughout the length of arms and legs, to mimic the forces exerted by water, by either resistance devices built into the WDD or using external force. The WDD shown in the figure may be a portable device, or may be integrated into a wall support and/or other exercise devices at home or in the gymnasium.

To exercise using an embodiment of the WDD apparatus shown in FIG. 10D, the user secures the device to the body, and exerts pressures against the body using WBEs and the frame, and using a manual lever or powered controls (not shown) off-loads the desired amount of weight on to the WBEs and frame. As a result, load is taken off of the spine and lower limbs of the user and the user will be is able to exercise easily without exerting significant loads on the joints or parts of the body. The advantage of the system is that these devices are cheaper and may be used for providing exercise to patients with open wounds and without the use of pools.

The device shown in FIG. 10D may also be used to either support patients with various heart disease conditions, e.g., myocardial infarction, congestive heart failure (CHF), or to allow them to exercise without significant stress. In some of the CHF patients, for example, who may not be able to tolerate any significant stress on their heart, the said WDD may be used to provide exercise in such patients. As the device allows the user to off-loads desired amount of body weight onto the frame, the device decreases the oxygen and nutritional needs of the body, decreases the total peripheral resistance against which the weakened heart has to pump, and therefore, relieves the heart from excessive load, thereby allowing the heart to recover.

Venous thrombosis is a risk that travelers face on long-haul flights. Deep vein thrombosis (DVT) is a disease of the deeper veins, resulting from a combination of venous stasis and hypercoagulability, and to a lesser extent additional changes in the blood vessel. Travelers are advised to keep moving often by exercising their feet, hydrating themselves frequently and to use compression stockings to prevent venous thrombosis. DVT develops primarily due to compression of leg veins, that bear the weight of the upper body, and due to the shear forces applied on the veins in the thighs due to the sliding of the thigh bones and muscles while the skin of the thighs is held back by the friction of the seat cover. Lack of ability to fully stretch the legs to relieve the pressure on the veins, coupled with less frequent movement of the limbs, further complicates the risk to develop DVT.

High DVT-risk passengers are advised to use knee-high graduated compression stockings, 15-30 mmHg at the ankle. While these measures decrease the incidence of DVT, there is no effective solution to prevent the development of the DVT.

Therefore, disclosed herein are methods and embodiments of WDD to prevent development of DVT in patients, e.g., during long haul flights, or in those that are required to sit at one place for long hours compromising the local blood circulation. A separate figure is not included to depict these embodiments, however, some of the embodiment are similar to the WDDs integrated into seat or a chair as depicted in FIGS. 2A, 4A, 4H and 4I, which is integrated into the seat, or may be a portable WDD worn by the user, for example, as shown in FIG. 6A. The WDD in the embodiment may be used to off-load the body weight of the torso and the thighs onto the frame of the WDD, which may be supported by the seat/chair, thereby relieving the pressure as well as shear forces on the buttocks, coccyx and underside of the thighs, as well as on the veins returning blood from the legs. While the traditional treatments mainly focus on providing compressive forces to maintain the pressure in the veins, the embodiment of WDD disclosed herein, are very unique in that they act by relieving the root cause of the DVT, i.e., the forces that compress the leg veins. Such embodiments, in addition to relieving the pressure off of the spine, minimize the DVT incidence related to travel.

Throughout this application, it should be noted that humans were mentioned, however, the embodiments and the methods of weight distribution may also be used in all animals.

The weight distribution method and the device disclosed hereinabove may be used for either transportation or rehabilitation of various animals including but not limited to cattle, horses, dogs and cats, pigs, sheep and goat and the like for providing support while recovering from musculoskeletal injuries, while rescuing, and to support the weight of the animals for use in transportation or for recreation activities.

Injured legs of animals are often supported by various casts and frames during recovery, to stabilize the bones and limbs as well as to take off some weight from the injured legs. Often animals are also placed in slings to allow for further support. However, the slings exert pressure at limited locations of the body and are not comfortable. Therefore, methods and embodiments of WDDs disclosed herein may be modified to fit an individual animal's anatomy, such that once the animal's legs, for example, are put in a cast, the body weight of the animal is supported by the frame of the WDD. Additionally, wheels attached to the frame of WDDs may allow animals to ambulate while walking. Joints may be provided in the frame to allow animals to flex the legs, as appropriate. For example, a horse or dog with a broken radius of the right leg, may therefore have the bone fixed using pins and casts, but will have WDD supporting the front portion of the body, and thereby transfer the weight born by the right leg onto the frame of the WDD that supports the front leg. To accomplish this, the animal's neck and shoulder region as well as some portion of the thoracic and abdominal regions may be covered with WDD, and the WBEs exert pressure on this area. The weight of the body is therefore transferred onto the WDD frame that supports the right leg (or both front legs). Such a system not only protects the injured leg, it also protects the contra-lateral leg, because it bears an extra-load as a result of the injury to the other leg. A separate figure is not shown to depict the embodiment, however, it is understood, that the methods and principles described for the WDD hereinabove, with appropriate modifications may be used.

Farm animals, such as cattle, horses, sheep, pigs, birds, etc are often transported by trucks over long distances. During such transportation, animals often are subjected to significant stress, because they have to use their legs to support themselves over the bumps and curves of the roads, leading to injuries, poor performance or poor quality of the meat. The animals usually do not lie down during such transportation, because the subcutaneous tissue including muscles and bones slide over the skin and cause shear to the underlying tissue, and as such lying down while traveling becomes very stressful and injurious to the animals. Therefore, methods and some embodiments of WDD systems described herein may be used to support animals during such transit periods, to minimize stress and injury. The WDDs may be integrated into the chassis of the carrying or shipping container, to the cages, and/or fitted to individual animals. (A figure of an exemplary embodiment is not included for these embodiments).

Embodiments of the WDDs to support animal body weight comprises various types of WBEs discussed hereinabove, which are supported by a frame comprising an inflatable bladder or non-inflatable mechanical structures (e.g., springs) as previously disclosed. The WBEs may partially or completely cover ventral and lateral aspects of the animal, and may include the dorsal aspect. Animals may also be fitted with a suit of WDD that will allow them to off-load some of the weight onto the frame, so that less strain is exerted by them while traveling. During the use, the WBEs of the WDDs come into contact with the body surface of the animal and pressure is applied as described earlier, such that the weight is off-loaded from their feet onto the WBEs. When the WDD is integrated into the chassis of the transportation vehicle/container, either the sides, floor or roof of the vehicle that supports the WBEs may be moved to come into contact with the animal, and appropriate amount of pressure exerted on the WBEs to allow the partial or the complete weight of the animal to be transferred onto the supporting structure, thereby relieving the pressure on the feet of the animal. In some embodiments, only part of the weight of the animal is transferred on the WDD and the rest is borne by the animal's feet when they are being transported. Because the pressure is distributed over an extensive areas of the body surface, and because the WBEs are flexible enough to move with the contact point on the skin to a certain extent, the shear forces on the skin and subcutaneous tissue of the animal resulting from the sliding forces on the body during transit are expected to be minimal compared to a situation where the animal would be, if the animal were to resting against the hard chassis or floor of the transportation vehicle.

Some embodiments of the WDD may be used to rescue and transport aquatic animals such as whales, dolphins, etc that end up beaching themselves, or that are injured, when they are required to be transported live to various locations. These animals, as their weight is usually borne by the entire surface of their body when they are in water, when they beach themselves on land, their lungs or other organs tend to collapse under their own weight. Traditional transportation systems like a sling made of tough fabric works well, however, the fabric exerts pressure mainly on the bottom ⅓rd of the animal, which may stresses an animal when supported in this fashion for long time.

Therefore, some embodiments of WDD systems and methods are disclosed herein to rescue and transport large marine animals. The principle of rescue is based on the observation, that entire body of the animal is used when the animal is in the sea to bear its weight, but when the animal beaches, the entire weight is borne by one side of the animal which causes significant discomfort and injury to the animal. Therefore, the disclosed WDD mechanism consists of exerting pressure against the animal body using WBEs to exert hydrostatic like forces that are approximately equivalent to the weight of the animal. In some embodiments, the rescue device comprises of a U-shaped device, which is larger than the size of the animal, with inner lining comprising a large number of WBEs, which may be inflated using either a pneumatic or hydraulic means. In some embodiments push type or roller type WBEs may be used as well. Once the U-shape device is passer under and around the animal, the inner lining is secured to a strong frame capable of withstanding the weight of the animal. Then the WBEs are inflated with a total pressure that is approximately equivalent to the size of the animal. As the WBEs push against the animal, while supported by the outer frame, the weight of the animal is shifter from bottom portion touching the ground to all over the surface of the body. The animal now may be transported to a desired location or moved back to the sea.

Although, the invention is mostly directed at the body weight distribution of living things, the WDD technology may also be applied to additional fields. Transportation of ships and large boats over land are difficult as these are heavy and the supporting frame work of these large vessels is not usually built to be carried over land. Further, dedicated equipment is required to avoid damage to the hull due to accidental excessive pressure at individual locations. The hulls of the vessels are designed to withstand pressure from water, which tends to spread out over the entire surface of the ship that is underwater, unlike land based vehicles, which are usually supported by various structures including wheels/axels that come into contact with the chassis on limited locations. Note that ships are periodically brought into dry docks or floating dry docks are used to keep the ship dry for maintenance while at sea. The ships on these dry docks are often supported on pillars that come into contact with the ship at certain predetermined locations, which are strong enough with stand the weight of the ship. As the ship's hulls are usually made of steel plates of about 1.0" to 1.5"" thick, they are not designed to handle significant loads, which is the reason why a ship is not supported using hull. The invention disclosed herein, distributes the weight of the ship onto hull in a uniform way, in a manner similar to how water exerts forces on the hull, but without using the water.

Therefore, disclosed herein are methods and WDD devices to safely transport ships or large boats on land. The embodiments of WDDs may comprise a support structure capable of carrying the size and weight of the vessel. Such a vehicle may be a large truck or a flat-bed like vehicle that is fitted with a frame, made of, e.g., metal or a combination of several materials, and is capable of supporting the entire load of the vessel. The flat-bed like vehicle may have wheels and may be able to use either custom rails or roads. There is no limitation on the width, length or height of the vehicle. The frame may be in the shape of a U or V, customized to fit the shape of individual vessels.

Figure 11:
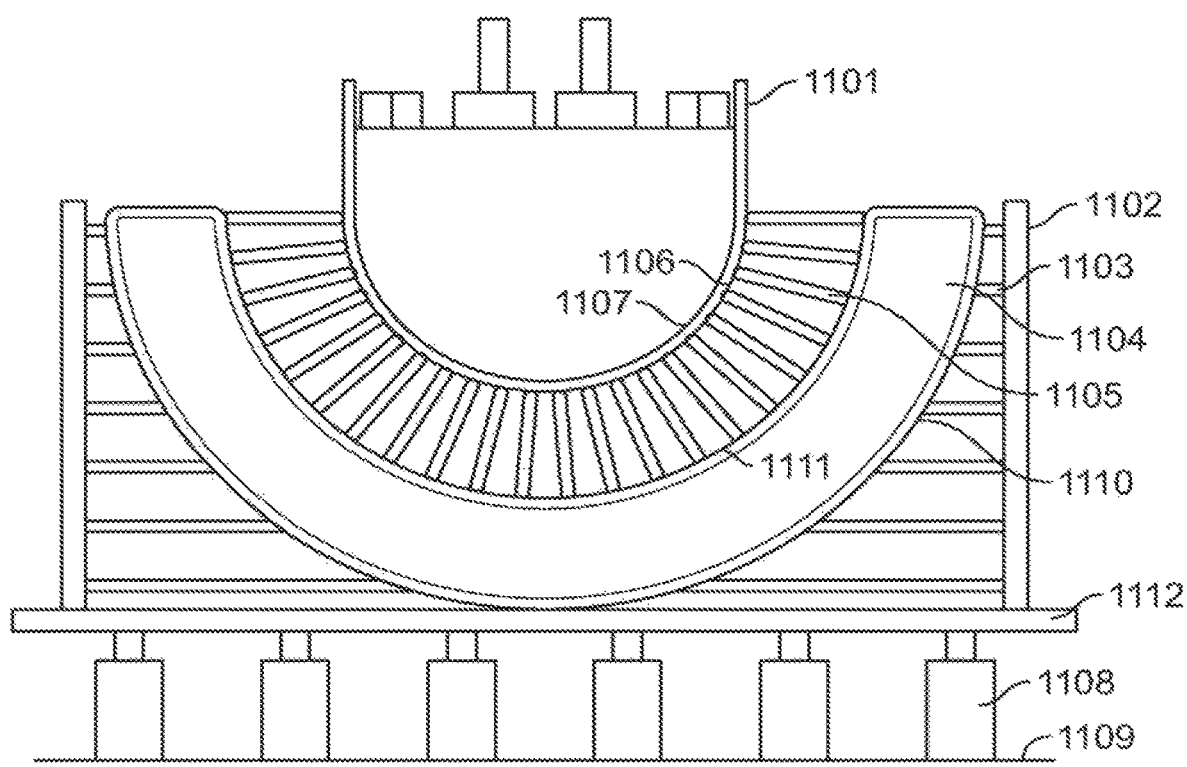
FIG. 11 shows an embodiment of a WDD mechanism integrated into a flat bed type vehicle, suitable for carrying large water borne vessels on land.

FIG. 11 shows an illustrative example of some embodiments of WDD device useful for over the land transportation of large water borne vessels, including ships. The weight of the ship 1101 is borne by the WBEs' 1105. The WBEs are covered by a sheet 1106 that protects the hull 1107 of the ship. The WBEs may be supported by a bladder 1104, which is located within a frame with an inner wall of the frame 1111 and an outer wall of the frame 1110. The outer wall of the frame 1110, in turn is supported by side panels 1102 of the flatbed vehicle that the. The floor 1112 of the flat bed vehicle supports the bottom part of the outer frame 1110. The flat bed vehicle rides on wheels 1108, which either can use land or special railings built to bear the weight of the ship.

The WBEs supported on the inner surface of the frame may comprise of several types, e.g. e.g., push spring type WBEs, inflatable structures, or telescoping hydraulic structures, and the like, whose strength may be adjusted using controls that are operated by hydraulic, electrical or other type mechanisms. There is no limitation on the number of WBEs for a given area. In some embodiments, the number of the WBEs per given area is large enough such that the pressure exerted on the hull does not exceed the amount of pressure the hull would have been subjected when in water.

When activated, the WBEs may come into contact with the hull and be able to exert force against the hull of the vessels that is mounted on the vehicle, using the frame to support the WBEs. The WBEs may be designed as push springs that get compressed when the load of the ship is placed them, thereby exerting uniform pressure all around the ship. In some embodiments, the WBEs may use active force to exert pressure against the hull of the vessel.

All WBEs may communicate with a central inflatable element (bladder) or a reservoir containing a fluid under certain pressure, such that the pressure exerted on the WBEs may be controlled. WBEs that use different mechanical means to distribute the pressure may also be used. WBEs can quickly reduce any significant pressure applied on a single location by distributing or re-distributing the pressure onto other WBEs, so that the potential damage to the hull is avoided. The tips of WBEs may have a softer surface to prevent any damage to the hull, or may have a soft cover between the hull and the tips of WBEs. WBEs may comprise various elements that allow easy gripping or sliding of the ship against WBEs, and/or sensors to measure pressure, direction of force, etc. Additional inflatable, protective or adjustable structures may be present between the WBEs and hull to facilitate easy mounting, sliding, or for securing of the vessel to the frame mounted on the transportation vehicle.

To secure the vessel, the transport vehicle may be placed (for example, by sliding the vehicle into water using rails), under the vessel, when the vessel to be transported is still in water. The vessel may be secured in the holding area of the transportation vehicle, such that the free ends of the WBEs come into contact with the hull. At this stage, the WBEs may be pushed up against the hull, such that the total force against the hull of the ship is adequate to support the ship weight, once it is pulled out of water. Pressure on hull at any place is designed not to exceed the maximum pressure experienced when in water. When the transportation vehicle, carrying the vessel is pulled out of the water, at that stage, all the weight of the vessel which till then was borne by the surrounding water, is then transferred onto the WBEs, and in turn, onto the frame once it is out of water. When the weight is distributed on all WBEs, the vessel appears as if suspended by the WBEs, and the pressure on the hull at the bottom of the vessel may be similar to other locations on the hull, or a gradient of forces may be applied. Because in some embodiments, all of WBEs communicate with each other, any changes in the position of the vessel that causes any shift in weight of the vessel onto one side or the other, or onto a single area can quickly be redistributed onto a larger surface area of the hull, by facilitating or engaging other WBEs, that are farther away from that area to apply extra force against the vessel, and thereby prevent any significant pressure on a single location. This is exactly what happens when the vessel is in the water, where the swaying of the ship which causes the ship's weight to shift, is borne by hydrostatic forces exerted by water, which are distributed on a larger area of the hull. The more surface area of the hull is covered by the WBEs, the less will be the pressure in a given area on the hull. In these embodiments, water is replaced by the WBEs, such that the total force exerted by the WBEs is adequate to support the weight of the ship, while not exceeding the hydrostatic pressure exerted by the water on the ship's hull at any particular location. There are several advantages to such type of transportation. For example, the vessels can be brought onto the land far away from the water, on to an in-land port to load and unload goods, thereby, any coastal city with or without natural harbor may be able bring-in ships on land. Vessels may be transported across stretches of land that separate two large water bodies, without the need to go through various canals like Suez or Panama canals. Vessels may also be brought on to land for repairs or safe storage.

The effect of microgravity on human physiology has been well documented over the past several decades. These effects include loss of bone and muscle loss, fluid shift, nausea and vomiting, pains in the body, increased length of the body and the like. Research conducted over the past several decades by NASA, European, Russian, Japanese and other space agencies, resulted in some of the exercise regimens that were shown to be effective in minimize some of the adverse effects, but nevertheless these regimens do not prevent all the adverse effects. Russian, European, Japanese and other space agencies have come up with several solutions to counteract the effect of microgravity on humans. These efforts have reached critical urgency recently, due to the planned exploration of Mars, which requires a very prolonged stay in the space as well as in hypo or hyper gravitational (<1 g- or >1 g-force) conditions in space or on other planets.

Disclosed herein are some and embodiments to address some of the adverse effects astronauts or any other person that enters space beyond the earth's atmosphere may experience during space journey. Also disclosed in this application is the usefulness of some of these embodiments to various applications on earth, including to prevent bone loss during bed rest and to prevent orthostatic hypotension.

It is to be noted that the word "microgravity" is mentioned here to capture conditions on planets other than earth, as well as those in the space above earth's atmosphere, where for e.g., the astronauts living in the international space station or similar accommodations/vehicles, although are within the earth's gravitational field, the astronauts do not experience the gravitational effects as they fall toward (travel around) the earth's gravitational field.

In microgravity conditions in the space, astronauts experience a different set of physiological challenges on the musculo-skeletal and cardiovascular systems, as compared to living on earth. Because the human body's biochemical, cellular, physiological process and anatomical structures are designed to function in earth's gravitation field, exposure to weightlessness in the space for prolonged periods causes several adverse effects, including loss of bone density and muscle strength, leading to a weakened musculoskeletal system in astronauts, increased intraocular pressure, and blurred vision. As the stress on the muscles and bones in the space are very less, they tend to lose their strength in microgravity. This is somewhat analogous to loss of muscle strength and bone density observed in people with restricted mobility, e.g., during prolonged bed rest.

To counter microgravity effects, astronauts exercise in space using various devices that use springs, elastic bands, vacuum, intermittent and advance resistance devices (iRED and aRED), harnesses to provide resistance to the muscles and to exert loads that are similar to body weight. Additionally, vibration plates are used to increase the bone density. One system that uses bungee-cord like bands used by astronauts, which applies resistance force on astronauts during exercise, did not prevent the loss of muscle strength and bone density, was found to be not effective, most likely due to inadequate load applied (probably .about.60 to 70 percent of load on the astronaut's body weight). Further, the astronauts did not tolerate the local pressure exerted by the bungee cords on the skin and local tissue, due to the excessive pressure and shear forces experienced at the contact surface. Other devices, that astronauts used in the past to combat bone and muscle loss is a system that applies negative pressure on the lower body using Lower Body Negative Pressure (LBNP) device. The LBNP comprises a chamber that contains a treadmill, which relies on negative pressure on the body to provide weight-like load on the body. The LBNP system was shown to prevent loss of cardiovascular function, cardiac muscle, restore blood pressure, and slowed down some bone loss. The latest device, the aRED system, in particular allows astronauts to exert up to 600 lb force, has been shown to be effective in preventing bone and muscle loss. Astronauts, typically spend about 2 hours or more a day in an exercise regimen with aRED. Although, the overall density of the bone remained the same, it appears that there is an increase in the turnover of the bone, the exact mechanism of which is not clear.

Exerting loads/forces on astronaut's body which mimic body weight of a person (similar to what was experienced on earth) for longer hours will likely help in reducing such bone and muscle loss. Although it may not be possible to exert a 1 g-force on astronauts living on the space station, some proposed designs of the spacecrafts with attached centrifuge type accommodations may exert centrifugal force, which may exert effects that are similar to the gravitational force experienced by the body will hopefully help the astronauts. However, such systems are costly and difficult to construct and maintain. Therefore, there is a need for novel methods and devices to exert body weight like forces on an astronaut's body to prevent adverse effects on muscles and bones and other systems of the body.

In some embodiments, a Load Concentration Device (LCD) is designed to exert forces on the body of humans that are perceived as body weight-like force, in some aspects. Both LCDs and the WDDs act in a similar manner in terms of exerting forces on the body, i.e., they exert forces using WBEs such that the required force can be applied on the body without significant increase in the pressure or shear forces where the WBEs come into contact with the skin surface. The major difference between WDD and LCD is that, in general, the WDDs on earth distribute forces away from weight-bearing structures, while the LCD in the microgravity environment concentrates the load on the weight-bearing structures of the body. The device disclosed herein is termed LCD, because some embodiments, the LCD is able to concentrate disparate forces exerted on the body by the WBEs (or other structures) onto the weight-bearing structures of the body. Although, the Weight-Bearing Elements (WBEs) used in the LCDs may be more aptly called load exerting elements, LEEs (as there is no weight in the microgravity), for the sake of simplicity, the term WBEs is used in this disclosure. The disclosed methods and devices are useful in microgravity conditions, such as observed in International Space Station, various spacecrafts that operate beyond earth's atmosphere, as well as for use on other planets such as Mars, where the gravity is approximately 38% of earth's gravitational force.

Further, it should be noted that the term "weight-bearing structures" does not refer to any discrete structures, but rather, it is a general term meant to capture the various structures of the body that experience the load, based on the direction of force and posture of the body. It should be clarified that the weight-bearing structures do not have to be just a foot or seat of a person. These could be internal structures such as various bones, for example vertebrae located at any part of the spinal column, they could be ribs or shoulder blades that take load when a person is lying down, some of the joints that connect various parts of the body when weights are lifted, the tendons and the muscles and the bone to which they are anchored when they work against the gravity, e.g., either to lift weights or to maintain body posture. For example, while the spine, legs, joints in the legs and the soles of the feet may be the weight-bearing structures, when a person stands, the buttocks and the spine and underside of the thighs become the weight-bearing structures, when a person is seated. In a standing or sitting person, the joints of various vertebrae and the legs may also be considered as weight-bearing structures. When a person is lying down, depending on the position, the back or sides of the head, shoulders, ribs etc may be considered as weight-bearing structures. The terms "space craft" or "space station" are used to refer to any vehicle, living accommodation or similar contraption that is located outside of the earth's atmosphere. The term "space" when used with reference astronauts, microgravity conditions, space station, etc is used to mean "outer space outside of earth's atmosphere." Although, the term "astronaut" is used in the operation of LCD, it is understood, that LCD is also useful for people on earth for various applications.

Methods and some embodiments of LCDs are disclosed herein that are useful for creating body weight-like effect on the body of an astronaut in the space or other locations away from earth's atmosphere. The invention as disclosed herein may be configured to employ WBEs to apply forces on the body, such that the net force is directed towards the usual weight-bearing regions, e.g., the vertebral column, the buttocks, legs, joints and feet, depending on the position of the person. The LCD system may be provided with a frame that may be inherently unstable and requires counteractive forces by the body to maintain the upright position of the astronaut. The LCD system, through WBEs and the frame also exerts forces on the body, which need to be counteracted by the continuous action of the muscles to maintain the posture or even to perform an activity, and therefore, requires the astronaut to use muscles, and exerts forces on the bones, thus facilitating maintenance of muscle mass/strength and the bone density/architecture.

Unlike other exercise devices that used by astronauts currently, e.g., bungee cords or straps to apply loads on the body (e.g., Russian penguin suit worn by astronauts, for use while exercising on the RED machine), an LCD exerts a body weight-like load on the weight-bearing regions of the body, without causing significant shear forces, at the contact areas with the skin, and therefore, the device is expected to be tolerated well. The WBEs of the LCD exert pressure in all directions, however, because the forces acting on the opposite directions of the body cancel out, only the net force acting towards the feet, buttocks or other weight-bearing structures of the astronaut will be felt, depending on the position of the astronaut. The physiological responses to such externally applied loads using LCDs are expected to be somewhat similar to the how the body responds to true gravitational forces, and therefore, leads to increased muscle tone and bone density. Usage of the device LCD also decreases the previously reported bone turnover in astronauts, because the direction of orientation of the external loads exerted by the LCD on the body are designed to be somewhat similar to the magnitude, direction and duration of the loads experienced on earth.

In some embodiments, the magnitude of the force exerted by WBEs located on the LCD may be the same at all locations, or in some embodiments may have a gradient with higher force on the head, shoulders, and decreasing towards the feet, when a person is standing. In some embodiments, similar decreasing magnitude of gradient of forces from top to bottom may be applied on the body in other postures. For example, in a person lying down horizontally on a bed, a gradient of higher to lower force may be exerted on the body, starting from the top side to the bottom side (e.g., in a person lying in supine position, higher forces will be on the abdomen, chest, face, front side of legs, while lower forces will be on the back, back of head, buttocks and backside of legs). The total force exerted on a person or individual body parts may be proportional to the mass of a person or individual body parts, and the magnitude of the forces may be less than, equal to or more than the 1-g force. The forces exerted on the body may be a push-type of force (for example "push springs" or inflatable structures) or pull-type of force (e.g., straps, elastic bands, fabric or "extension-type springs" to maintain tension) as described in various embodiments herein.

An earthly application of the LCD described herein is that they may also be used for exerting increased loads on people on earth, who have restricted mobility (e.g., those undergoing bed rest). LCDs may also be used, for example, in healthy people who wish to increase their muscle/bone strength/mass during exercise. A detailed description of some of the embodiments is provided below.

Figure 10F:
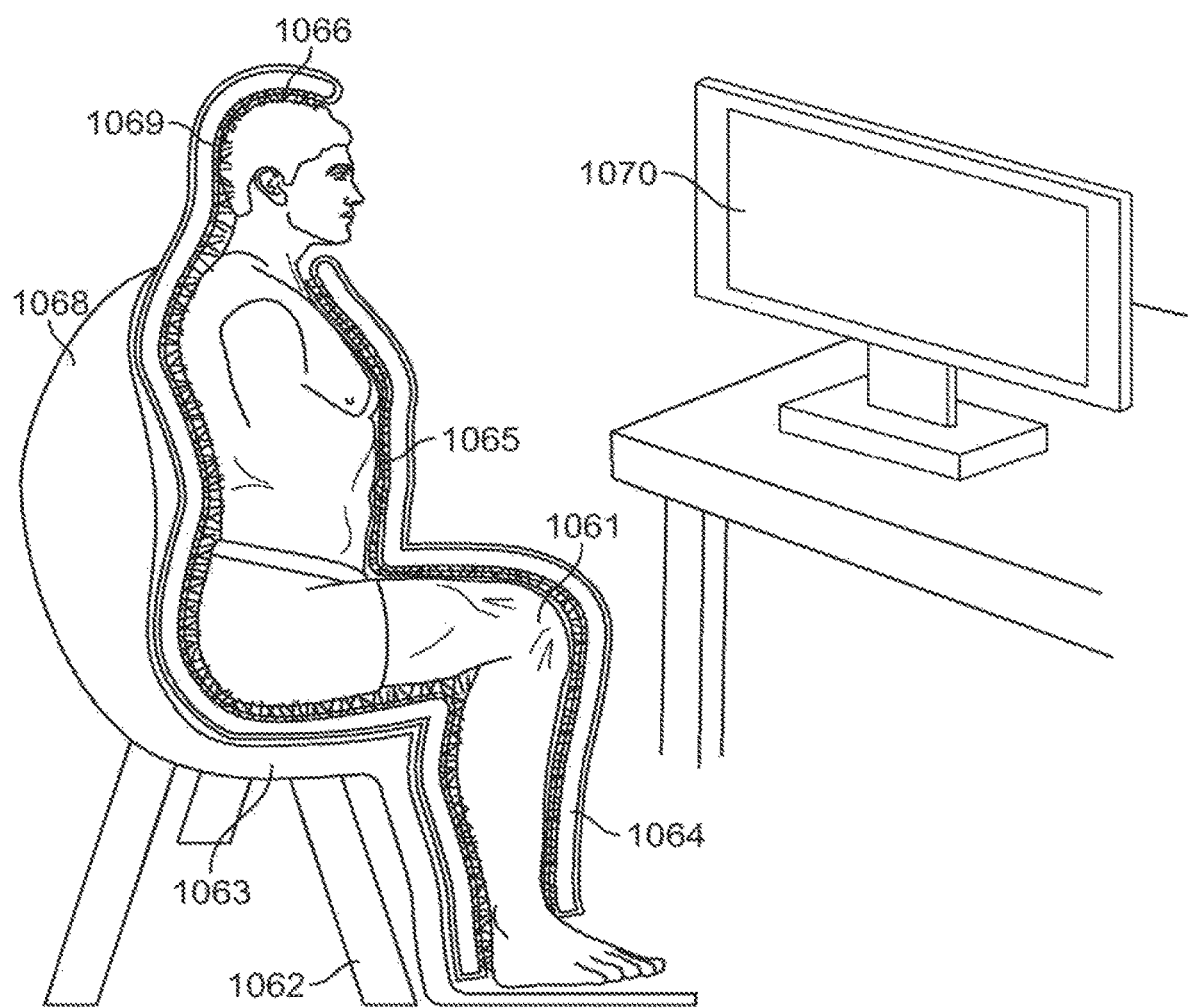
FIG. 10F illustrates an embodiment of WDD and LCD integrated into a motion simulator.
Figure 10G:
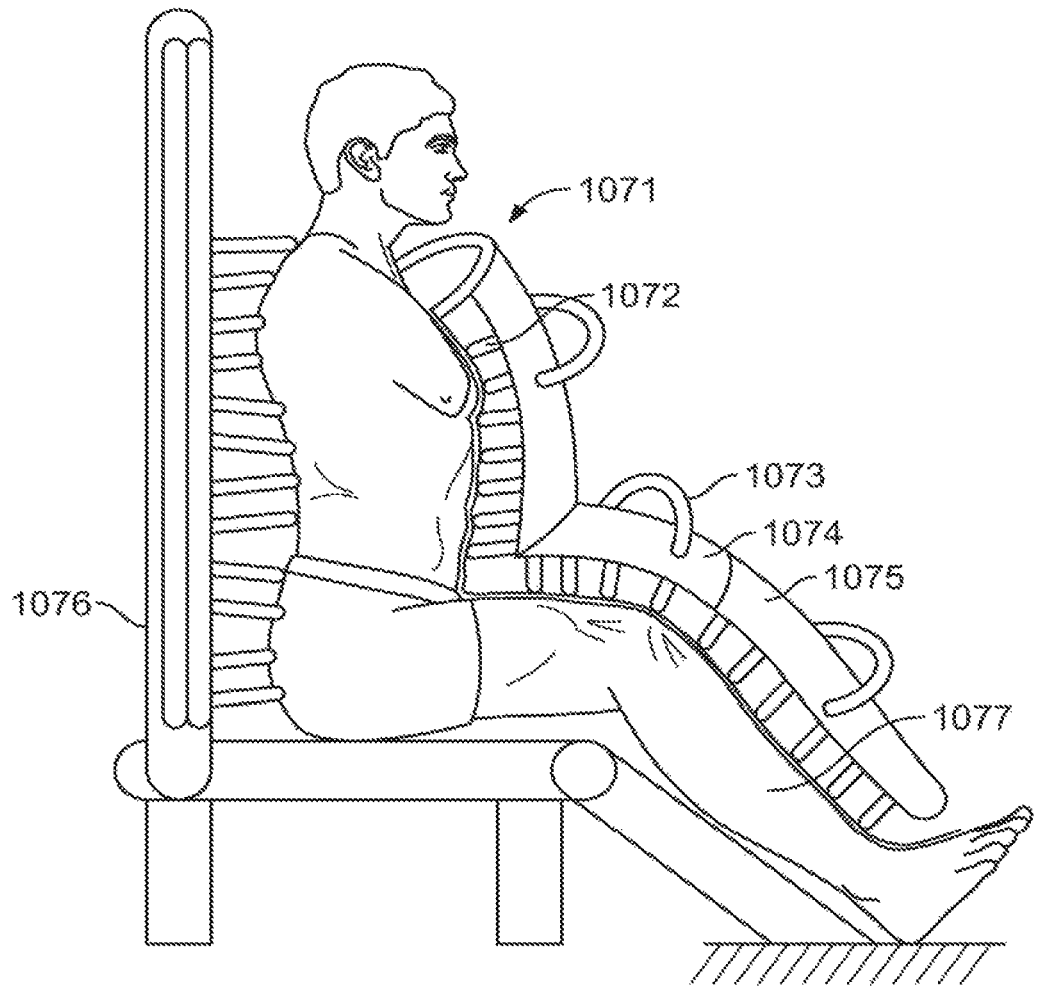
FIG. 10G illustrates an embodiment of LCD integrated into a chair for use by astronauts to exert force on a body while seated in microgravity conditions
Figure 10H:
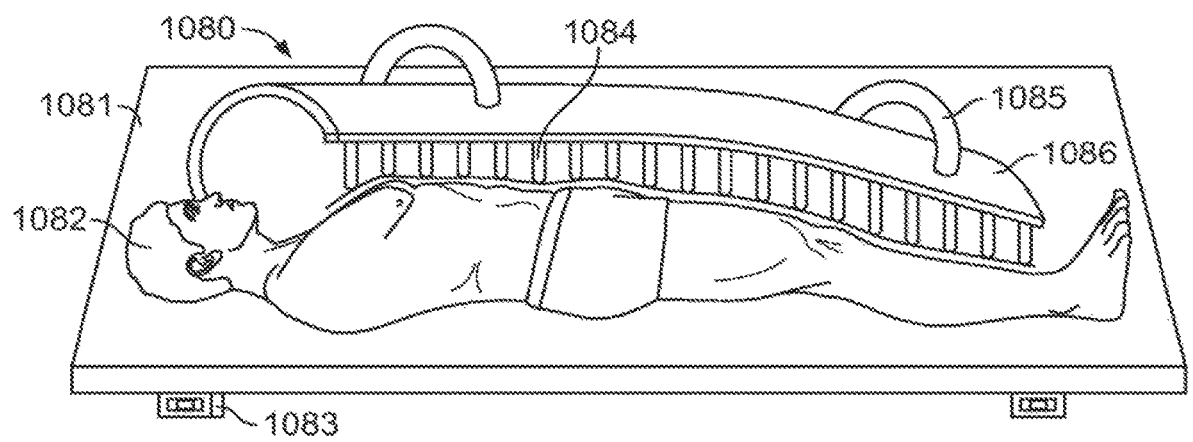
FIG. 10H illustrates an embodiment of LCD integrated into a bed/sleeping quarter for use by astronaut to exert force while sleeping/resting in microgravity conditions.
Figure 10I:
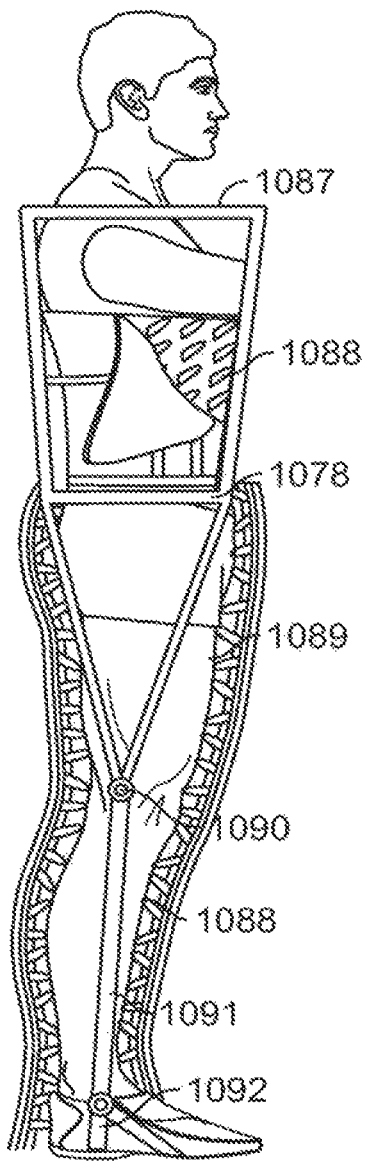
FIG. 10I illustrates an embodiment of an LCD with a frame and WBE to exert forces on an astronaut in space to counter effects of microgravity or on people on earth to prevent osteoporosis or for rehabilitation.

FIG. 10I, shows some embodiments of LCDs and WDDs which use the principles and methods described earlier for various embodiments of WDDs, except that the LCDs exert pressure downwards towards the feet or any other weight-bearing structure of the person, without significant increase in the pressure or shear forces at the contact points on the skin and underlying tissue. The embodiment of the device shown in FIG. 10I may also be used as a WDD as described herein above to distribute the weight from weight-bearing structures of the a person, however, details of the operation are not repeated herein again.

The embodiment of the device comprises an outer frame 1087, part of which may be above the shoulders, and which supports the WBEs 1088. Additional embodiments of inflatable structures or springs or other devices that are required to exert force on the WBEs (not shown) are disclosed hereinabove. Pressure sensors may be located at various places throughout the LCD (not shown). The body of a person, from the waist downwards, may be supported by another frame 1089, which may be joined to the upper frame 1087 at the waist level through a joint 1078. The leg frame may have a knee joint 1090 which adds flexibility to the frame. The leg frame 1089 may have additional supporting structures 1091 that connect to the waist joint 1078 on the upper end and is supported by the ankle plates 1092, which in turn connect the rest of the frame to the soles of the shoes. In some embodiments, the entire outer frame that covers the head, neck, torso and both legs may be attached to a foot plate (or shoes) worn by the astronaut (portions of frame covering head and neck are not shown in the figure). Not shown in the figure are the parts of the frame that comprise springs or similar devices that exert forces on the body in various directions, as well as similar structures that make it inherently unstable, when the alignment varies from vertical position (e.g., make a person bend towards one side or the other, making them prone to fall), which therefore, requires a continuous effort by the astronaut, to maintain upright posture. Also not shown in the figure are, structures in some embodiments that loosely attach/connect/anchor the astronaut's feet, head, shoulders or other parts of the body to the floor, roof or other structures of the space craft/station that may be used to exert forces against the body of the astronaut, to create body weight-like effect. In some embodiments, forces exerted through using magnets, vacuum/suction cups, Velcro-like or nanostructures that are similar to those located on a gecko feet, or other structures exert pneumatic, electrical or hydraulic forces may be used to hold feet of astronaut on the floor of space station. The feet are free to be detached when the astronaut uses adequate force, so as to walk or move from one part of the station the next. Alternatively, similar forces may be used to press down an astronaut to the floor. The frame of the LCD together with various means that secure the feet of the astronaut to the floor, give the true feeling of body weight on in space.

The WBEs 1088 exert force on the body of the user in all directions (e.g., upward, downward, horizontal, at an angle to the surface of the skin or inward or outward), by pushing against the frame such that the net force is directed downwards (towards the feet of the person) when standing. Without limitation, several mechanisms may be used to exert forces on the astronaut's body. Inflatable bladders, electrical means, mechanical means, and the like may be used to exert pressure on the WBEs. The frame may also be used to exert a force in all directions on the astronaut's body, using either external force or using inbuilt springs or similar other devices. External forces, e.g., pushing forces from the roof of the space station, or pulling forces from the floor of the space station, may also be used. The force exerted by the WBEs on individual parts of the body may be proportional to the mass of the said individual body part. The total force exerted on the body of a person may be equivalent, higher or lower than the weight of the same person on earth (i.e., gravitational force experienced by the same person when on earth). As a result, the astronaut feels the pressure that pushes down from head/shoulders down towards the feet/floor, and therefore, to maintain the posture or move, the astronaut will used muscles against these external forces, thereby strengthening the muscles and the bones.

In some embodiments, the LCD frame around the body of the person, may be equipped to be pushed down towards the floor using external supports, for example, a supporting structure from the roof (not shown in the figure). Exertion of such an external force requires a person to exert counter force against that force to maintain, for e.g., an upright posture. The objective here is to allow the person to experience a force that is somewhat similar to the gravitational force all the time. Instead of applying force from roof of the spacecraft, the sole plate of the shoes of a person, to which the LCD frame connects, may be anchored loosely to the floor of the spacecraft by various means (e.g., magnetic force, or an elastic or spring mechanism that slides along the floor on rails), so as to allow the astronaut to move freely, but requires additional energy to lift the feet (not shown in the figure). Because, the WBE and the frame exert a downward force on the user, the muscles of the user must work continuously to maintain an erect posture. Such an activity promotes muscle strength as well as preserves bone mass. The suit described in FIG. 10I may have tension built into it (e.g., by inserting extension-type springs, which when stretched exert pressure, or using push-spring type WBEs, which exert a load when compressed), and the astronaut may have to stretch the suit to wear it. Therefore, once worn, the suit may be able exert pressure on the body without the need for additional external force.

Figure 10J:
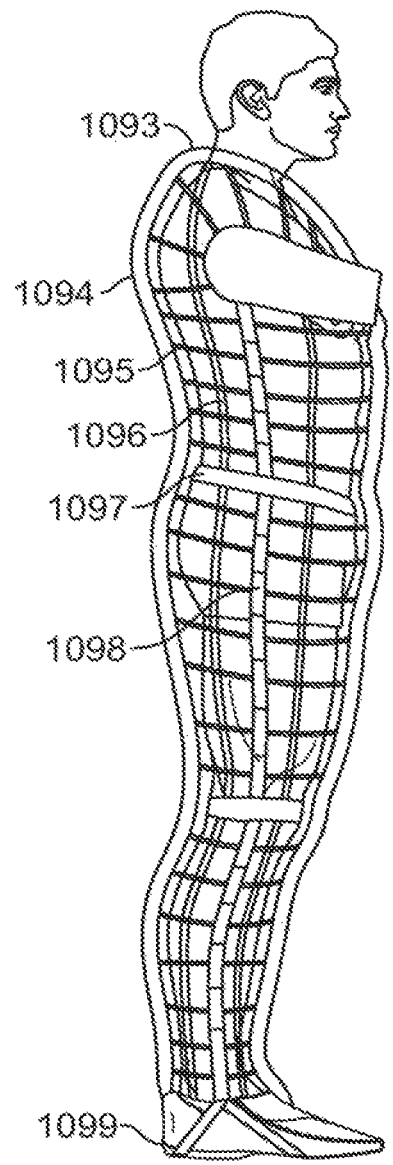
FIG. 10J illustrates an embodiment of an LCD with bands and a frame to exert forces on an astronaut in space to counter effects of microgravity or people on earth.

FIG. 10J shows some embodiments of LCDs and WDDs, which looks more like a regular article of clothing worn by the people. The mechanism of LCDs and WDDs of the FIG. 10J is best explained by also referring to the embodiments of WDDs and LCDs presented in the FIGS. 1C, 4L and 4M, and the descriptions provided in the respective sections of the disclosure.

The operation of LCD part of the device is disclosed hereinbelow. The device may be used as WDD with appropriate modifications, to cause WBEs to exert a net upward force on the body so as to reduce the load on the weight-bearing structures of the body. The details of the operation for WDD are similar to the LCD as described below and hence are not described here separately.

The embodiments of LCDs and WDDs depicted in FIG. 10J comprises several bands that go around the body in horizontal 1095 and/or vertical 1096 directions. Bands may also surround the body vertically and at an angle to the vertical bands (not shown). The bands may comprise straps, ropes, threads, belts, elastic material, inflatable tubes, and the like, without any limitation. In some embodiments the bands may be woven together or present in multiple layers. Bands may be composed of external tubes, through which ropes or threads are inserted to allow for free movement of the ropes to exert pressure on body of the person, without directly contacting the body of the person. The bands are connected to a frame 1094 that may made be rigid or flexible, and are used for anchoring the bands that run in various directions around the body. Additional belts or rings at the waist region 1097 or at the knee region may be provided to connect various bands that run vertically, horizontally or at an angle, such that pressure may be applied on the torso when the person is seated or standing in a staged manner, for e.g., straps from the shoulder may connect to the waist ring, waist rings may connect to leg ring at knee region, and then to the sole plate. The frame may contain a shoulder plate 1093 and a sole plate 1099 which may be used as an anchor for various bands. Additional stronger vertical bands 1098 may run through the length of the torso, or the leg pieces of the suit to add vertical force to the suit. Different bands may have different tensile strength as appropriate, for e.g., the tensile strength of the bonds in LCD may be adjusted so that a net downward force is applied on the body. As shown in FIGS. 4L and 4M, the bands may be used to exert force against the body without the use of WBEs. Because each band is tethered to the frame and the tension of each band may be controlled using various manual or electrical controls (not shown in the figure), the bands may be used exert a pulling force against the body. The pulling forces may be directed in the upward, downward, horizontal, inward directions or at an angle to the surface of the skin. Because the forces that act on the opposite directions cancel out, a net downward force towards the feet of the person may be exerted using the suit described in FIG. 10J. Because, the forces are exerted in all directions on the body, the shear forces on the skin and the subcutaneous tissue are minimized and therefore, an astronaut (or a user wearing the device on earth) may feel more comfortable and tolerate the forces for longer periods. The frame may be incorporated into the suit. In addition to the bands, the frame may be endowed with characteristics to exert upward or downward force on the body. In some embodiments, the suit may require stretching for the astronaut to put it on, and therefore, may exert a load on the body even without the use of external forces.

To operate the embodiments of LCDs presented in FIGS. 10I and 10J, the user, e.g., an astronaut, wears the LCD and secures it to the body, and causes the suit to exert pressure either by the action of in-built springs/elastic bands, or by activating the WBEs to exert pressure by either manually using a lever (not shown in the figure), or using electrical controls (not shown) to exert a net push or pull force towards the feet of the person. The LCD may be stretched by force, before the astronaut wears the LCD, such that when secured to the body, a continuous load (less than, equivalent to 1 g-force or higher) is applied on the body or body parts. The sole plate of the shoes, may remain free from the floor, or may be attached to the floor using external force (e.g., elastic, magnetic forces, by applying force from the roof, etc.), and can be provided with detachable means for use when the astronaut walks. When the astronaut is in an upright position, the pulling forces exerted on the body are borne by the vertebral column, and the long bones. Various muscles contract and relax appropriately to keep a person balance on the feet, when standing, such that there is a net load is on the vertebral column and the legs in a top down direction. Although a significant load is exerted on a person's body using LCD, as the load is distributed all over the surface of an astronaut, the force exerted by the LCDs is expected to be tolerated well by the astronauts.

Loads on the body of the user may be exerted in a staged manner. For example, FIG. 10J, the bands that surround the torso may exert pressure on the torso by exerting a net pulling force using the waist ring 1097 as an anchor. The bands that surround the thigh region, may further pull the waist ring downwards using the knee ring part of the frame (not numbered in the figure) as an anchor. As a result the knees now bear the load of both torso and the thighs. The leg bands that surround the legs (from knee to foot), then may pull the knee ring downwards towards the feet using the sole plate 1099 as an anchor. As a result the load of the whole body is exerted on the feet, supported by the sole plate. Therefore, an astronaut wearing the above LCD has to use muscles constantly, against such pulling force to maintain the balance. The spring type mechanisms located in the frame supporting the bands, and holding the feet to the floor of the space station may further help in increasing the effectiveness of the LCD shown in FIG. 10J, while exerting minimal shear or frictional forces on the body.

The embodiment of LCD shown in FIG. 10I, which contains WBEs that exert pushing forces against the body surface, likewise, may increase the load on the body in a staged manner. The individual sections of the frame that support the torso, thighs, and legs, transfer load onto the sections below in a sequential manner, and finally on to the feet of the person supported by the ankle plate 1092.

In addition to the loading force, because the skeletal structures on the earth are subjected to impact forces when a person walks or jogs, to mimic such a force, the LCD may be combined with additional devices, that apply an additional impact force to a user's skeleton (for example, by making appropriately timed impacts on the soles of the feet with a force approximately equal to the force exerted on a person's feet while on earth) to stimulate/maintain the osteoblastic activity. Such a force using the LCD may be more appropriate than the vibration plates currently used to maintain bone density, because such forces may maintain the alignment of the microstructures in the original direction. Note that that while use of vibration plates may increase bone density, bone turnover may continue as reported, suggesting that bone density may increase in response to the vibration forces, in various directions, but it is not clear if such an increase is beneficial to the astronaut, in terms of increasing the bone strength.

Although not shown in the figures, similar forces may be exerted on a user to provide weight-like feeling to the arms and to preserve arm strength. For example, in addition to the force towards the wrists, material that is covering arms may exert additional downward pressure on the arms when the arms are raised, such that the force exerted on the arms simulates weight of the arm on earth.

The LCD may be worn by the astronaut for a significant part of the day and night, such that for every movement of the body the astronaut has to push against the load exerted by the WBEs and the frame. For example, the load on the torso can be distributed such that the astronaut has to continuously push against the frame covering the torso, and in this process continuously exercises the tarsal muscles. In a similar manner, the direction of the load on the arms of the astronaut may always be directed downward, when the person is in the upright position, such that there is stress on the shoulder bones and the joints. This ensures that the person feels the weight of the hands when they are used to perform various tasks.

The WBEs and the frames may be fitted with additional sensors and electrical controls that keep the WBEs force always directed towards the feet when standing.

Various push-type or pull type springs, or torsion-type springs or others may be used to exert force on the body of the astronaut and offer resistance for movement in any direction. Since the gravitational forces continuously exert loads on a person's body, various cellular and physiological systems (including bones, muscles, etc), maintain a dynamic equilibrium with the body of a person while on earth. Therefore, substituting the exercise using aRED system or other means for a limited number of hours in a day probably may not be adequate to maintain the physiological integrity of the astronauts, based on the some of the available data astronauts that lived in the international space station for extended periods of time. Therefore, disclosed herein are methods and some embodiments to exert continuous loads on various parts of an astronaut's body, similar to those loads experienced by a person on the earth. The WBD proposed in this application, when worn continuously therefore is expected to prevent deterioration of the muscle, bone and prevent any CV effects, when the astronauts spend prolonged period in space or on other planets. The portable embodiments of LCDs described hereinabove may be used to exert forces on the astronaut's body for a significant portion of the day (and night), even when the astronaut is sleeping. While sleeping, the loads may be exerted from front to back, side to side or vice versa. Additional embodiments of the LCD are proposed in the following sections that will allow the loads to be applied to the astronaut's body when they are seated or sleeping.

It should be noted that in certain situations, it may be appropriate to apply loads from bottom up towards the head of a person. In such cases, the LCD may be modified appropriately to apply the forces in the desired direction. Forces may also be applied in more than one direction, for e.g., from bottom and the top, to increase the overall load, to target particular parts of the skeleton or muscular system to increase the bone density or strength. Although, the LCDs are designed to minimize shear force, in some embodiments, the WBEs may apply force such that shear forces are exerted on the skin and muscles of the body. In some locations of the body (e.g., underside of thighs and on buttocks), it may be appropriate to direct the force of the WBEs such that shear forces are exerted on these locations, as these parts of the body often are subjected to shear forces on earth, and such type of forces may be appropriate to maintain their integrity.

Some embodiments of LCDs, whether they are standalone portable devices to support astronaut's when they are standing in upright position, or integrated into a chair-like or bed-like devices, may be enabled to exert either full loads equivalent to what they experience on the earth, may exert significantly more weight than what they experience at 1 g gravitation force on earth, or may exert only a fraction of the load experienced on the earth to the whole body or a part thereof, using the WBEs (also referred to as "surface contact elements") and frame. Therefore, in some instance the amount of load exerted on the body may be 0 to 100% of the load experienced at 1-g force on earth, or forces that are higher than forces observed at 1-g force (e.g., 1.5-g or 2-g), or in some embodiments the forces exerted may be 5, 10, 20, 30, 50, 70 or 90% of the forces noted at 1-g force on earth.

The devices depicted in FIGS. 10I and 10J may be used distribute the weight away from the weight-bearing regions of the body, by exerting a net upward force on the body, as described for various WDDs hereinabove and hence were not repeated.

At present, astronauts are not required to sit down on a chair or lie down on a bed, while in space, as they do not experience weight due to microgravity conditions. Therefore, they can stand up (floating) all day and sleep while in upright posture. The traditional chairs and beds as used on earth, to support the body weight, therefore, are not required in the space station at this time. Such lack of loads on the astronaut's body for a significant amount of time in a day is likely responsible for some of the adverse effects observed on their bodies.

Therefore, disclosed herein are methods and some embodiments of LCDs in which loads on an astronaut's body are maintained while in a seated or lying down posture which simulate the conditions or earth's gravity. In some embodiments, the devices may looks like chairs or beds, and benefit astronauts by exerting loads when they are seated or lying down.

The device may exert a net downward pressure on a seated astronaut, from head/shoulders down towards buttocks. The astronaut, in an effort to maintain an erect posture and body balance, works against such these forces, using the various muscles of the body, e.g., neck and torso muscles, exerts counter force. Such a counter force exerted by the muscles is essential to maintain muscle strength, bone density, and preserve the normal functioning of other systems.

Similarly, exerting force using the disclosed LCD while the astronaut is sleeping, results in the forces being exerted from one side of the body the other (e.g., front to back, side to side or vice versa), and therefore, the astronaut's respiratory muscles will be required to work against such forces (chest weight), thereby preventing the loss of mass and strength of muscles that aid in respiration, and muscles and bones that support the body while sleeping.

Methods and embodiments of devices to apply loads on the body while the astronaut is seated or while lying down are described hereinbelow.

Embodiments of LCD integrated into chairs and a method to exert loads, for e.g., on the head, neck and torso of the person directed downwards on the vertebral column, towards the buttocks, thighs, legs and feet when the astronaut is in the seated position are disclosed herein.

People on earth spend a significant amount of their time in a seated position, as it is more comfortable than standing. While seated, they support the weight of their head, arms, shoulders and the torso, on the spine, buttocks and thighs (sacrum, coccyx and thighs), and therefore, microstructures in their bones in these weight-bearing regions, are aligned during bone formation to withstand the stresses in this direction. Therefore, the embodiments of LCD described below exert loads on astronauts, while seated in chair on the weight-bearing regions, in a manner very similar to how their bodies are subjected to gravitation-induced loads while on earth. Therefore, applying such forces using the LCDs minimizes the bone remodeling and loss of muscle mass during their stay in the outer space, while preventing loss of muscle strength and bone density.

FIG. 10G illustrates embodiments of LCDs integrated into a chair-type device 1071 that may be used by astronauts to exert pressure on the weight-bearing structures of the body while seated. In some embodiments, the chair may comprise a bottom portion that looks like a regular office chair, with backrest and a seat (and contain a frame and WBEs—not shown in the figure), and a top portion, that comprise a frame and WBEs. The backrest of the chair may be movable in some embodiments, to allow for free movement of the user. The device comprises a chair 1076 and a front cover 1074 which comprise a frame that supports various WBEs 1072 which contact the body of a seated astronaut 1077 either directly or indirectly. In some embodiments, the LCD may comprise a torso-section, thigh-section, and a leg-section 1075. The frame 1074 of the device may be supported by hinged rods 1073 that may be anchored to the chair or external support.

To operate the embodiment of LCD integrated into chair-like device shown in FIG. 10G, the astronaut sits on the seat of the bottom portion of the chair 1076 and closes the top cover 1074, which may be pressed against the body of the astronaut either manually or using electrical controls. The top cover of the chair when secured may cover part of or all of head, back part of neck, and the front part of the torso, thighs, legs and the top bottom of the feet. WBE may be located on several parts of the chair, including top and bottom sections and backrest. The WBEs located on the top section and on the backrest of the chair, are activated to exert pressure on the shoulders and torso of a person, such that the net force is directed downwards to the buttocks and other weight-bearing regions. Similar forces may be exerted on the head, arms and legs of the astronaut. Loads that are equal to, higher or lower than 1 g-force may be applied on torso and various parts of the body, and the load exerted may be proportional to the mass of individual body parts. The direction of load may be adjusted such that the net force on the torso is directed towards the buttocks and underside of thighs of the astronaut, when seated in upright position. The thighs in a similar manner may see more pressure applied on the top and sides such that a net load is felt by the underside of the thighs that contact the seat of the chair. The legs and the feet, like wise will have pressure applied from towards the feet. Pressure may also be exerted by the frame or individual sections of the frame (not shown), by means of springs or similar means, on the body from all sides of the torso such that the forces are balanced when the astronaut is in vertical position, but if the astronaut leans in direction, the springs in the frame exert forces on the body in the direction of leaning. Efforts by the astronaut to maintain the balance will result in the body experiencing the sensation similar to the body weight, when seated in the above chair integrated with LCD.

As a result of the pressure exerted by the device, while limited amount of pressure and shear forces are experienced by the parts of body that come into contact with the WBEs (e.g., located on all sides of the torso), while both pressure and shear forces will be experienced by weight-bearing regions of the body that come into contact with the seat of the chair, which is advantageous as it adds additional natural stresses to the portions of the body of the astronaut.

The pressure exerted on the individual portions of the body may be proportional to the mass of the body, such that the part of the body experiences loads that equivalent to what they are subjected to on earth (in 1 g-force condition).

It is to be understood that the terms, up and down, bottom and top may not be exactly applicable to Space environment, but for the purpose of this present application, these are used to in the same sense as they are used on the earth.

Astronauts spend approximately ⅓rd of the time in the space resting/sleeping, and therefore, it is advantageous to exert forces on their body while resting in such a manner that resembles those loads they would experience while sleeping on earth. Therefore, a method and an embodiment of a LCD are disclosed that may be used to exert forces on astronauts while they are sleeping.

FIG. 10H shows an embodiment of LCD that 1080 that is integrated into a bed 1081, which may be anchored to a fixed structure using anchors 1083. Similar to the chair, the astronaut's bed will have at least two parts, a bottom part that may be made up of a soft or a hard top mattress. The top portion comprises WBEs 1084, which contact the body of the astronaut, and are supported by top cover containing frame 1086. The top cover may either be lowered or raised, using the hinged rods 1085, which also may also be used to press the frame 1086 against the body of the astronaut. In some embodiments the cover will be a hard or semi-hard surface, or soft surface to allow force to be exerted against weight-bearing portions of the body. WBEs may be located on all parts of the top portion of the bed that come into contact with the body surface.

To operate the device, the astronaut lies down horizontally on the bed, and secures the top cover 1086 to the body. WBEs from the top cover exert pressure on top of the body on the front (if the person is lying supine), and on the sides of the body. The forces exerted by the WBEs on the body may be in various directions including downward, horizontal, upward, and at an angle to the surface, but with a net downward force with an objective to exert force on the weight-bearing regions (e.g., back of head, shoulder blades, buttocks, back of the calf region and the ankle). As a result, it is possible to exert pressure on the body without causing shear forces on the skin and underlying tissue. The total pressure exerted on each portion of the body-part may be applied proportionally to the mass of that particular part of the body; forces less than, equal to or higher than 1 g-force may be applied. When WBEs exert force for e.g., on the front and lateral sides of the astronaut when resting in supine position on the bed, the weigh-bearing structures on the back including back of the head, back side of the torso, buttocks and the legs will experience the load. While the pressure and shear forces on the front and sides where the WBEs contact the surface of the skin are minimal, skin and underlying tissue on the back of the astronaut (sleeping in the supine position) will experience increased pressure as well as shear forces, which is desirable in microgravity conditions. The load on various weight-bearing regions of the body may be changed with change in the position of the astronaut on the bed. The continuous load experienced by the astronauts while in horizontal position helps to maintain the density of the bone and strength of various muscles that support the body when in horizontal position.

Loss of muscle strength of mass of respiratory muscles in astronauts following prolonged stay in the space has been reported earlier. The embodiments of LCDs described hereinabove, in addition to maintaining the strength of the muscles and bones that support the body while in sleeping position (the bed), or while seated (chair) will prevent loss of strength and mass of respiratory muscles. When the WBEs exert forces on the chest and abdomen of the astronaut who is for example sleeping, the force causes the chest and abdominal cavities of the astronaut to slightly collapse, which forces the respiratory muscles (e.g., diaphragm) to push against such the walls of the chest and abdomen. Such additional effort required by the muscles to provide adequate oxygen to the body, leading maintaining the strength and mass of these muscles.

An additional effect of the pressure exerted by the LCD on the chest and abdominal walls is that, the increased pressure causes some of the fluid that shifted into the thoracic and the abdominal cavities will be forced to be redistributed to rest of the body, similar to how it is on the earth. Fluid shift from legs into the abdominal, thoracic and cranial regions occur due to lack of gravitational force on the blood, such a shift causes several adverse effects on the CV system as described herein below, which includes loss of blood volume and even loss of cardiac muscle strength and the mass. Exertion of pressure on the abdominal and chest cavities, while sleeping (using bed), sitting (using chair) or walking (using portable suit) will result in normal fluid distribution to various parts of the body, thereby decreasing adverse effects on CV system.

It is to be noted that if the beds are positioned vertically, and if astronauts prefers to sleep in the vertical position, in such cases the whole body suits or a modified bed that exerts force from front to the back, or side to side and vice versa may be used to exert forces on the astronauts while sleeping/resting.

In addition to the adverse effect on the bone and muscle, astronauts also experience headward fluid shift within the body, due to microgravity, resulting in the increased intracerebral pressure and increased intraocular pressure. The cephaloid is shifted to the upper body leading to various symptoms including puffing of the face, increased intracerebral and intraocular pressure and the like. Prolonged stays in microgravity conditions also result in diminished autonomic nervous system mediated contraction of the blood vessels (decreased baroreceptor reflex and increased vascular compliance) in the lower parts of the body. Upon returning to earth, the blood pools in the lower parts of the body due to gravity, resulting in low cerebral blood flow in the brain, leading to orthostatic intolerance that leads to dizziness or syncope. The orthostatic intolerance continues for some time, until the astronauts acclimate to the earth's gravity.

Disclosed herein are some methods and embodiments of the LCD that are useful while the astronaut is standing (portable suit), or while sitting or lying down (chair- and bed-like LCD) that exert pressure on a body, and may be used to counteract the microgravity-induced fluid shift to the upper body, head and brain, and the resulting adverse physiological effects (e.g., edema, puffing of the face, abnormal vision related increased intraocular/intracerebral blood pressure, etc.) while the astronauts are in the space.

Disclosed herein are some methods and embodiments of WDDs that are useful to counteract the adverse effects related to pooling of blood in the lower regions of the body due to increased vascular compliance, resulting in lower blood pressure and dizziness (orthostatic intolerance) in astronauts upon returning to earth. Such embodiments may be portable suits type, chairs or beds type of weight distribution devices that have been described hereinabove in the application, to distribute the weight of a person.

Disclosed herein are also some methods and embodiments of WDDs that are useful to decrease the load on heart in people on earth. Various embodiments of the LCD system disclosed hereinabove, depicted in FIGS. 10I, 10J, 10G and 10H, and the respective methods may be used to counteract the effects of microgravity on the cardiovascular system of an astronaut. In some embodiments, the disclosed LCD systems and methods exert resistance (exerted by the WBEs) to the venous flow from the legs and arms of the astronaut. The resistance may be applied uniformly all over the body and/or in various patterns such as in a gradient fashion. Because the pressure applied on the astronaut's body while using the devices, when the astronaut is in upright position, may be higher on the head, neck and torso compared to legs, the cephaloid fluid shift is minimized to some extent with this device. Lower or higher resistance on the peripheral veins may be applied by either elastic bands, or inflatable devices that are position around the circumference of the legs or arms, or by positioning, for example, an inflatable, elastic or similar structure along the length of the peripheral vein(s) above the skin. As significant portion of the blood from the legs is returned through deeper leg veins, it some embodiments, the pattern of arrangement of WBEs placed around the circumference of the legs may be configured to maximize pressure on the deeper veins. The gradient of downward compressive pressure creates resistance for the venous return from the legs back to the heart, thereby reducing potential cephaloid shift of the fluid that is currently experienced by astronauts.

In some embodiments, when the astronaut is standing in an upright position, the amount of pressure exerted on the body may be equal at all locations or in a gradient fashion, with higher pressure on the head, neck and torso region decreasing towards feet. A wide variety of range of pressures may be applied on the body using LCD. The objective is to mimic the loads experienced in the terrestrial environment. For example, in some embodiments, the following pressure may be used on an astronaut who is about 6 feet tall, starting from head, neck and shoulders towards feet, 136, 113, 90, 67, 45 and 22 mm Hg at 6, 5, 4, 3, 2 feet and 1 foot height, respectively, from the sole of the feet using the WBEs. The actual pressures used and the area of the body surface covered by the WBEs and the frame may be adjusted based on the application and position of the astronaut, with reference to floor. Note that the pressures mentioned are in addition to the 760 mm Hg of pressure maintained within the space accommodation (e.g., international space station) or the vehicle.

In some astronauts, the autonomic reflex diminishes, following prolonged stay in the microgravity in microgravity conditions, leading to development of orthostatic hypotension on return to earth. Embodiments of the LCD system may be useful in maintaining the baroreceptor reflex and venous compliance in astronauts during space travel as follows. The pressure exerted on the venous system, at any location of the body or overall body may be dialed down or up based on the position of the person to prevent excessive pooling of the blood in the lower extremities. When the astronaut, who is wearing the LCD device stands up from a seated or lying position, the direction of the forces exerted on the body change. Such a change in direction of the pressure (directed towards the feet), results in increased blood pressure in lower extremities, and a transient drop in the upper regions of the body and a decreased cerebral blood flow. These changes in blood pressure due to the forces exerted by the LCD on the vascular system cause a baroreceptor mediated constriction of capillaries in the lower extremities, restoring the blood pressure to the normal level. This is how the LCD helps the astronaut to maintain ability to exert a peripheral arterial-venous reflex mechanism, and normal blood pressure while in space, and help the astronauts to recover fast from potential orthostatic intolerance after landing.

It is to be noted that the pressure exerted by WBEs of the LCD is analogous to the hydrostatic forces on the body. Therefore, adding this additional load onto the body using the LCD forces heart to work against such external pressure to pump approximately 7000 liters of the blood each day. Therefore, an additional added benefit of the peripheral resistance exerted by the LCD to the venous circulation and the pressure on overall body is that the heart now has to pump against this load, which leads to increased cardiac heart muscle strength and prevent any decrease in its size during the stay in the space. The pressure exerted on the body may be optimized to prevent any accidental excessive restriction of the circulation, poor oxygenation to certain parts of the body, or chronic overload on the heart, that may result in hypertrophy of the heart and other associated adverse effects.

Orthostatic hypotension of postural hypotension is a disorder characterized by sudden loss of blood pressure when the patient stands up from lying or sitting position, due to pooling of the blood in the lower extremities. Orthostatic hypotension is associated with various disease conditions including tumors of the adrenal glands, dysautonomic disorders (e.g. resulting from Parkinson's disease), diabetes, and with usage of some drugs including vasodilators, diuretics, etc., cause hypotension in several people. A similar condition may also be experienced by the returning astronauts, who spent significant amount of time in the space, due to failure of the autonomic system to respond to the pooling of the blood in the lower extremities due to gravity.

Therefore, an embodiment of a WDD is disclosed, which in some embodiments exerts a gradient of pressure on the venous system with slightly higher pressure at the feet may help maintain the blood pressure in the orthostatic hypotensive patients as well as for astronauts. The WBEs located on the WDD device in some embodiments exert pressure in a gradient manner, with higher pressure at the bottom, and lower pressure towards the chest. As a result, pooling of the blood in the legs and other lower portions of the body is minimized, which allows the user to maintain the blood pressure when standing or changing position from lying to sitting or standing.

In some embodiments, the WDD device used for preventing the orthostatic may not have to support or weight of the person and therefore, just exerting adequate pressure to prevent pooling of the blood may be adequate. The additional weight-distribution function of the WDD may be helpful in early stages of acclimatization to the earth's gravitational force.

In some embodiments, a combination of WDD and LCD mechanisms may the used. In some embodiments of WDD and LCD, just the pressure may be exerted on the body, without causing the weight to be shifted onto frame. For example, the lower part of the body may use WDD type of device, while pressure may be exerted on the upper part of the body to prevent significant fluid shift.

It is to be noted that although, resistance to venous circulation by the LCD was mentioned hereinabove as the one of the mechanism for the improved cardiovascular benefits, additional factors such as the gradient of increased pressure on upper regions of the body including on the head, neck, arms, chest, abdomen, pelvic region and the thighs also plays a role in preventing the fluid shift towards the upper body, as they will now have to work against such pressure. Therefore, the fluid (the blood and the tissue fluid) is forced to find an equilibrium, which results in shifting back to the states experienced on the earth.

On earth, motion sickness (seasickness, air sickness, travel sickness, simulation sickness, etc.) are conditions caused in people, when they are subjected to conflicting visual, and other sensory inputs such on the vestibular system. Various embodiments of WDD and LCD are disclosed useful for mitigating the motion sickness in people on earth.

Astronauts experience space motion sickness and vomiting in microgravity conditions. Lack of gravitation-related stimulation of priopioceptors in the legs, coupled with visual and other sensory inputs (due to lack of orientation), particularly on the vestibular system, likely contribute to the motion sickness in astronauts. Methods and some embodiments of LCD are disclosed here to mitigate the motion sickness by stimulating the proprioceptors in the weight-bearing regions of the body (e.g., feet, leg joints, spine and the like) of the astronauts.

An example of a person sailing on a ship is used here to explain the mechanism of action of WDD useful for mitigating motion sickness. A person standing on a deck of ship experiences sway of the ship as it moves in the water. The person tries to maintain the upright posture by tightening the appropriate muscles of the legs as well as the torso. As a result of swaying, the pressure on the receptors that sense the mechanical forces and the pressure on various structures of the body are stimulated. With the higher magnitude and frequency of swaying motion of the ship, the more intense will be the feedback from various body parts to the CNS. The body weight of a person plays a significant role in this stimulation. Due to swaying, the body weight of the person shifts from one leg to the other, or from one part of the sole to the other constantly, as well as the load experienced by different parts of the body. The same thing happens to the body weight of a person, when sitting or sleeping; the weight shifts from one region to the other depending on, sway of the ship, or movement of the vehicle, while the visual and vestibular inputs may not completely be synchronized with the changes in the position of the pressure that the body experiences.

Disclosed herein are systems that can be worn when a person is sitting, standing or lying down; and a second system that may be integrated into any supporting structure such as chair, auto-seat, airplane-seat, bed, mattress, etc.

A person experiencing or susceptible to motion sickness may wear the WDD suit (see FIG. 6A), and transfers the body weight to the WBEs and the frame. As very minimal load is placed on the feet, when the ship sways, the WDD minimizes the stimulation of baroreceptors located in the joints, and a as a result less nauseating feeling is felt by the wearer of the WDD.

A user who is seated or lying down still experiences motion sickness on as the rolling motion of the ship (or movement of a vehicle) may still exert pressure at different parts of the body with each role, in the absence of synchronous visual/vestibular cues, which results in conflicting messages transmitted to the central nervous system (CNS). To minimize such effects on the CNS, the application discloses a system and a method to minimize motion sickness when a person is seated or lying down. The said system is integrated into the chair, bed, mattress or the like. The system and the device are similar to the embodiments of the WDD and LCDs described earlier (e.g., FIGS. 2A, 4A, 8B). To use the device to minimize motion sickness, the user secures himself/herself to the WDD integrated into a chair, and allows the body weight to be transferred to the frame (through WBEs). As the weight of the frame (and the body) is borne by the chair, when the ship rolls back and forth, the person feels pressure on the surface of the body that keeps shifting from the one side to the other with each roll. However, the magnitude of the pressure on the surface of the body (per unit area) is significantly less compared to that exerted on the weight-bearing regions, and therefore, there is less amount of stimulation, thereby decreasing the intensity and/or frequency of motion sickness.

Motion sickness is a major concern in astronauts in the space, which is triggered by the lack of proper visual cues for orientation, lack of vestibular neuronal stimulation and prioprioceptors feedback to due to microgravity conditions. The motion sickness is often temporary and several pharmacological therapies are available to minimize it. Nevertheless, there are no effective means to prevent or alleviate these effects on the astronauts.

Therefore, methods and devices are disclosed to prevent or treat motion sickness in astronauts. The system and the LCD described earlier, either as a suit to be used while standing, or integrated into chairs of beds, may be used by the astronauts to minimize motion sickness. The system acts by exerting pressure on various parts of the body, such that the astronaut feels pressure on the prioprioceptors located in the muscles and bones of various parts of the body. Because the lack of pressure/load on weight-bearing regions of the body in space (together with other factors including the vestibular activation and visual cues) contributes to the motion sickness in space, the device mitigates motion sickness by exerting pressure on the body resulting in loads on the various weight-bearing structures of the body using LCD as described hereinabove. The resulting pressure on the proprioceptors minimizes their contributions towards the motion sickness.

To use the device, the astronaut wears the LCD or sits or lies down on a chair or a bed integrated with LCD mechanism. Application of a force by the WBEs on the body in various directions, resulting in a net downward loading of various weight-bearing regions of the body, which may reduce the motion sickness by appropriately stimulation of the proprioceptors.

Methods and some embodiments of the LCDs and WDDs disclosed herein may be used in training of astronauts on earth, to simulate weightless conditions and for research on volunteers or animals on earth to investigate the effects of weightlessness and for development of counter measures.

Astronauts train in reduced weight conditions on earth, such as underwater (e.g., using Neutral Buoyancy Facility), in preparation for the space flights. The disclosed inventions may be used alone or in combination with other devices for providing a more realistic sensation of weightlessness, as well as exert some of the weightlessness related effects on the astronauts, when training for the missions. Further, WBD may also be used as a research tool in the laboratory on volunteers or astronauts, to investigate the physiological effects of exposure to prolonged weightlessness on various systems of the body and may be particularly useful in addressing the problem of observed bone and muscle loss in astronauts. The device, for example may be able to replace the standalone zero gravity treadmill or other similar devices that NASA uses for simulating exercise in zero gravity.

An additional potential application of the device is an anti-gravity suit to be worn by astronauts or pilots that are subjected high g-forces during take-off or while maneuvering aircraft. Anti-gravity suits (inflatable suits or suits with self contained liquid) are used to prevent blood pooling in various locations of the body when pilots or astronauts are subjected to excessive g-force, which result in hypoxia to the brain leading to dizziness or even fainting that could be fatal.

Methods and some embodiments of devices to prevent adverse effects of high g-force effects using various embodiments of WDDs or LCDs previously described (e.g., FIGS. 10G, 10I and 10J) are disclosed herein. The user wears the devices described in FIGS. 10I and 10J, or sits in seats integrated with LCD (e.g., 10G), and exerts force on the body, when the body is subjected to high g-forces. The amount of force exerted by the LCD may be equal to the magnitude and opposite to the direction of g-force exerted on the body. Such a counteractive force exerted by the LCD prevents the blood pooling in vessels under high g-forces. The invention offers advantage over the traditional anti-g devices, in that, in addition to preventing pooling of the blood, the device also minimizes high shear forces exerted on the body under high g-force, which further minimizes the potential damage to the user.

Patients or elderly who are wheel chair-bound or bed-ridden loose muscle and bone strength, due to lack of stressful activity and load on the weight-bearing regions of the body. It is not practical to lift them up and provide them appropriate exercise needed to maintain muscle strength or maintain bone density. Therefore, methods and some embodiments of devices are disclosed hereinbelow to exert loads on the muscles and bones of people that are prone to lose muscle strength or bone density (e.g., advanced age), without raising them out of bed or the wheel chair. Some embodiments of the devices exert loads from the head/shoulders or from the waist down towards direction of feet, so as to maintain muscle strength and the bone density. Some of the embodiments of the devices may also be used to exert loads on healthy people, who wish to exercise against resistance or additional loads to increase muscle strength or bone density.

Loads on the body of a person are exerted using embodiments of LCDs described hereinabove. The LCDs may be in the form a suit to be worn by a person. Or, it may be integrated into the chair or bed of a person, such that either whole body or individual parts of the body may be subjected to similar stresses that a person experiences while standing or sitting. When the LCD is integrated into a bed, loads may be exerted on the user from head/shoulders/waist down towards the feet, such that the person has to push against the applied force to maintain the position on the bed. The amount of force applied may be adjusted based on the individual situations. The LCD is be similar to the embodiment shown in FIGS. 10G, 10I and 10J, where the direction of load is from the head towards the buttocks or towards the feet of the person. A person undergoing bed rest may use LCD device integrated into a bed, similar to what is shown in FIG. 10G.

Gravity plays a central role in organisms. Changes in expression profiles of several genes were observed in vitro and in vivo systems in response to gravity and microgravity conditions. Organisms on the land, respond to gravitational forces through various signaling pathways, including mechanosensors that induce deformation of gap junctions containing calcium-sensitive stretch receptors, which trigger secondary messenger activation through pathways similar to those involved in integrin-dependent activation and allow cell-to-cell communications, as well as by activation of ion channels.

In microgravity conditions, quiescent osteoblasts are slow to enter the cell cycle, and it is likely that lack of gravity itself may be a significant factor in bone loss in spaceflight. Preliminary data from STS 76 flight studies results indicated that osteoblasts cells held in G-0 (microgravity) conditions, show significant diminished mRNA induction in immediate early growth genes/growth factors including cox-2, c-myc, bcl2, TGF beta1, bFGF and PCNA, when compared to ground and 1-G (normal gravity conditions on earth) flight controls (Hughes-Fulford, 2001, J Gravit Physiol., 8(1):P1-4)

To understand changes associated with cephaloid fluid re-distribution in astronauts, mouse brain mRNA expressions profiles following hind-limb unloading were assessed (Frigeri, et al 2008; Experimental Brain Research 191(3): 289-300). Hind limb-unloading resulted in up-regulation of genes including those that affect transport of small molecules and ions into the cells (TIC class) and down-regulation of genes that affect cell junction, adhesion, extracellular matrix (JAE genes). Hind limb-unloading causes an alteration in homeostasis which results in a shift toward a more hyper-coagulative state with an increased risk of venous thrombosis. Hypergravity (2 G to 3 G) conditions also result in increased induction of cyclooxygenase-2 (COX-2) in mouse heart and bone marrow, a rate-limiting enzyme for prostaglandin biosynthesis, that plays a critical role in several inflammatory pathways (Oshima, et al., 2005 Biochem Biophys Res Commun, 330(3):928-33). These increases in COX-2 levels were also associated with increased levels of hypoxia-inducible factor (HIF)-1alpha, and its downstream genes such as inducible nitric oxide synthase, vascular endothelial growth factor, and heme oxygenase-1. Therefore, disclosed hereinbelow are methods and systems to decrease the levels of cycloxygenase-1 and -2, up-regulation of early growth genes/growth factors including cox-2, c-myc, bcl2, TGF beta1, bFGF and PCNA in astronauts and in patients with various metabolic and cardiovascular disease conditions.

Hypertension (increased blood pressure) is a chronic disease that affects millions of people worldwide, and is considered to be a disease of multi-factorial origin. Normal blood pressure in the body is 120/80 mm Hg (systolic/diastolic pressure), and blood pressure higher than 140/90 mm Hg is considered to be hypertension by the physicians.

Increased total peripheral vascular resistance is attributed as one of the major causes for hypertension, although increased cardiac output and sympathetic activity may play a critical role in early stages of development of hypertension.

Various causes including endothelial inflammation, diabetes, narrowing of arteries and small arterioles due to permanent structural changes, perturbations of the renin-angiotensin system, and sympathetic nervous system that control the constriction of capillaries may cause increased peripheral resistance. Susceptibility to hypertension varies based on genetic susceptibility, race, life style, obesity, etc. Several drugs and devices in the market are available to treat hypertension. These intervene with various molecular pathways (receptors) or other mechanisms.

Despite significant progress in research and in the management of hypertension, the exact causes for hypertension are still unknown. Based on the observations of blood pressure in astronauts in the international space station (ISS) and other research publications, it is clear that the gravitational forces acting on the human body play a key role in maintenance of the normal blood pressure in humans and other living organisms. The weight of the tissue that surrounds the various capillaries tends to collapse these vessels, and therefore, the heart has to work against these forces to pump the blood through the vascular system. These forces exerted by the surrounding tissue, together with other forces that hinder the flow of the blood in the vascular system together are termed as the 'total peripheral resistance'. The observed blood pressure in a person at any time is an equilibrium point between the gravitational forces acting on the body (total peripheral resistance) plus additional factors and the cardiac output.

Interestingly, the peripheral resistance is decreased when healthy volunteers or patients with hypertension, enter water, resulting in reduced peripheral resistance, while the cardiac output increased. Head-out water immersion exercises in patients with coronary artery disease (CAD), resulted in a decrease in peripheral vascular resistance, and an increase in stroke volume and cardiac output. These results suggest that exertion of hydrostatic forces on humans in a manner similar to how water in a swimming pool acts on a human body will be effective in reducing the peripheral resistance, either alone or in combination with other interventions including life style changes, drugs or devices. It is however, not practical to use pools to decrease blood pressure on a regular basis.

Water immersion to the neck increases central blood volume and evokes a marked diuresis and natriuresis. Results from the study of water immersion in 10 normal volunteers for 3 hrs resulted in down regulation of sympathetic nervous system (decreased plasma levels and urinary excretion of norepinephrine and epinephrine), increased urine volume, increased plasma concentrations of atrial natriuretic peptide, and increased renal dopa-dopamine system, which resulted in decreased blood pressure (Grossman et al., 1992, Am J Physiol., 262 (6 Pt2):R993. A "dry" therapeutic immersion, was used to treat hypertonic crisis in 26 patients suffering from stage II essential hypertension, which resulted diuretic effects (Ivanov and Markova, 1990, Ter Arkh., 62(12):44-7).

The renin-angiotensin-aldosterone system (RAS) is a well-established therapeutic target in the treatment of heart failure. Substantial advances have been made with existing agents-angiotensin-converting enzyme inhibitors, angiotensin II-receptor blockers, and mineralocorticoid-receptor antagonists (Lang and Struthers, 2013, Nat Rev Cardiol. 2013; 10(3):125-34). However, because several of the pharmacological interventions are associated with adverse effects, substantial need exists for a non-pharmaceutical means to reduce the activation of RAS.

Therefore, disclosed herein are methods and some embodiments of WDDs that are useful for decreasing the peripheral vascular resistance in humans and thereby help in prevention or treatment of hypertension. The underlying mechanism and how the said WDD devices prevent/treat the said hypertension are described hereinbelow.

Various portable embodiments of the WDDs depicted in FIGS. 6A, 10I and 10J, or the stationary WDDs integrated into other furniture, such as chairs as shown in FIGS. 2A, 4A and 8B may be used to prevent and treat hypertension in humans. It may not be required to cover the whole body of a user with the device. Covering either legs alone, or legs plus up to the waist, chest region or above of the person may be adequate to minimize the peripheral vascular resistance in a person. The device may be used continuously or for a short time only. The forces exerted by the WBEs located on the WDDs may be in a gradient fashion, with higher forces at the bottom, and decreasing slowly as one moves in an upward direction towards the head.

In some embodiments, the WDDs for reducing the peripheral vascular resistance may not be required to exert amounts of forces to relieve the load from the weight-bearing structures of the body. Instead, it may be adequate to exert adequate force against the individual parts of the body just to counteract the effect of the gravitational forces on that region. In some embodiments, a pressure-exerting tubular sock-like device (not shown in the figure) with reinforced bands that wraps around the legs and torso, or individual body parts of a person, exerting a gradient of high to low forces starting from feet towards the head are useful to decrease the peripheral resistance. Such embodiments that help in reducing the total peripheral vascular resistance, without decreasing the load on skeletal system may be useful for long term use.

To operate the device the user wears the device and activates the WBEs, such that a net upward force is exerted on the body, in a direction opposite to the gravitational forces. Because the WBEs exert pressure on a large surface area and in all directions, the forces acting in opposite directions cancel out, and therefore, only minimal shear forces and pressure exerted on the skin or the underlying tissue at the contact location. As pressure is exerted on the tissue in opposite direction to the gravitational forces, the capillaries that are located in the tissue experience less pressure from the tissue. Because of lack of external pressure, the total resistance in the capillaries decreases, reducing the overall blood pressure in the vascular system of the user. It is to be noted, that due to overall increase in the pressure on the extremities, fluid moves to the central vascular space, resulting in increased cardiac output, but without an associate increase in peripheral resistance due to decreased peripheral resistance.

Use of some embodiments of the WDD, decreases the total energy demands of the body (e.g., by decreasing amount of effort required by the muscles to maintain upright posture, due to off-loading the body weight onto the frame), decreases total peripheral resistance, increases the central volume, also results in down regulate the RAS in the system in heart failure patients and those with hypertension.

Because use of WDD may result in natriuresis, increased urinary output, and decreases plasma volume, to avoid potential hyper coagulative changes, the amount of body weight off-loaded onto the frame may modified, according to individual patient needs. Therefore, while in some cases a 100% of the individual's body weight may be transferred to the frame, in other instances, any amount weight from 0 to 99.999% of the body weight may be transferred onto the frame. In some embodiments, exerting pressure all over the body that may range from 0 to 50 mm Hg, 51 to 300 mm Hg or 300 to 1000 mm Hg at certain regions of the body, or whole body using the WBEs, but without transferring the weight onto the frame of the WDD may done to increase the cardiovascular function.

The WDD device may be useful either for regular use in people with hypertension, or management of hypertension due to increased peripheral resistance in certain emergency care situations, or to reduce load on the cardiovascular system. Even when the total peripheral vascular resistance is within the normal range, the WDD device may be useful in people with compromised cardiovascular system, e.g., as in the case of congestive heart failure, myocardial infarction, etc., where it is important decrease over all load on the heart. In patients with pre-hypertension (e.g., blood pressure between 120/80 and 140/90 mm Hg), they may be benefited with the use of the device, as it may prevent their progression to full blown hypertension. The device may also be particularly useful in patients with higher body mass index (BMI), as they are at higher risk of developing hypertension due to increased peripheral resistance due increased body weight.

An additional application of the WDD devices and the methods is in patients with ascites or edema, which may be related to various conditions (e.g., cirrhosis of liver, kidney diseases, etc). Head-out water immersion is often used in the patients who are resistant to dialysis and ultrafiltration. Embodiments of WDDs as described hereinabove may be used in these patients, which results in expansion of the central fluid volume due to fluid shift from peripheral compartments, natriuresis (increased sodium excretion) leading to decreased edema.

The methods and WDDs disclosed above may also be used to in athletes for fast recovery from muscle soreness, and in patients for the physical therapy. To operate the device, the user will secure the device to the whole body and activate the WBEs to decrease the peripheral vascular resistance. Increased blood circulation to the muscles lead to increased intracellular and intravascular nutrient and waste exchange, and reduced muscle edema leading to rapid recovery.

The incidence of type II diabetes mellitus has been increasing all over the world. The disease is caused by multiple factors including genetic, environmental, obesity, pregnancy, life style related including factors such as diet and exercise. A number of life-style and diet-modification based interventions, pharmaceutical and biotechnology therapies, medical-devices, surgical options are available to the patients to control or treat diabetes. However, these did not reduce the number of new people developing diabetes. Therefore, identification and prevention of causes of diabetes are very important to control this epidemic.

It has been reported that sitting for long periods increases once risk of diabetes, heart disease and death. This risk is independent of any amount of physical exercise the individual may be doing, suggesting sitting for longer hours may be one reason for the noted increase in the incidence of diabetes. Adults on average spend about 50 to 70% of their time sitting down. Therefore, research has shown that by limiting the amount of time spent sitting down can reduce the risk of diabetes and heart disease. An additional interesting observation is that diabetes, hypertension and increased insulin resistance are closely linked to obesity. It is likely that when a person is seated, the collapse of blood circulation to the muscles of the buttocks, and thighs and increased pressure on the veins in legs returning blood from leg muscles, may be contributing to the increased risk in diabetes. Since it may be difficult to decrease the amount of time a person sits, therefore, by decreasing the peripheral vascular resistance and improving the blood circulation to the muscle tissue while a person sitting using one of the embodiments WDD may result in improvement in increased glucose uptake by muscles and prevent or treat diabetes and improve overall metabolic profile in people.

Renin-Angiotensin-Aldosterone system (RAS) appears to have a direct role in the pathogenesis of diabetes. Increased activation of the renin-angiotensin system (RAS) has been related to cardiovascular disease and type 2 diabetes mellitus. RAS blockade reduces the incidence of type 2 diabetes, which has been explained by improved insulin secretion and insulin sensitivity (Goossens, 2012, Obes Facts. 5(4):611-24. Additionally, patients with essential hypertension are at increased risk of type 2 (non-insulin-dependent) diabetes RAS mediated increases in oxidative stress, inflammation, and free fatty acids concentrations potentially contribute to beta-cell dysfunction in diabetes. Blockade of the RAS may protect against the development of de-novo diabetes in "at risk" patients and protect pancreatic islets (Cooper et al 2006, J Hypertens Suppl., 24(1):557-63). Dulawa, et al., 1987, Z Gesamte Inn Med., 42(11):298-302, reported effects of water immersion, on the RAS system in 83 diabetic and 34 healthy patients. In both groups, the plasma renin activity, plasma aldosterone and vasopressin levels, were suppressed by water immersion. Quantitative but not qualitative differences between diabetics and normals were observed in this study.

Therefore, disclosed herein are methods and some embodiments of WDDs useful for prevention and/or treatment of type II diabetes mellitus, metabolic disorders and heart diseases in people. In addition to decreasing the total peripheral resistance, some of the WDD systems may reduce the activation of RAS system, without use of pharmacological interventions. Some devices may be enabled to maintain the blood glucose values in diabetic patients to within normal range (70 to 100 mg/dL), or decrease the values to below 300, 200, 140 or 120 mg/dl, based on the severity of the disease.

Various portable embodiments of the WDDs depicted in FIGS. 6A, 10I and 10J, or the stationary WDDs integrated into other furniture, such as chairs as shown in FIGS. 2A, 4A and 8B may be used to prevent and treat diabetes mellitus and metabolic disorders in humans. Covering either legs alone, or legs plus up to the waist, chest region or above of the person may be adequate to minimize the peripheral vascular resistance and improving blood circulation in a person. The device may be used continuously or for a short time only at multiple times. It may be not necessary for the entire weight of the person to be off-loaded onto a frame when using this device. The mere act of off-loading of the weight of a person for short duration may help decrease the peripheral resistance. As an example, chairs integrated with the WDD may have automated mechanisms that periodically work to off load a person's body weight.

Preeclampsia, also referred to as pregnancy-induced hypertension is an elevation of blood pressure, and abnormal kidney function, and increased protein in urine that develops after 5th month of pregnancy. Preeclampsia when nutrient and oxygen supply to the fetus is restricted, due to various factors. Hypertension>140/90 mm Hg is a characteristic feature of preeclampsia. If left untreated, the disease might proceed to more severe form called ecclampsia that lead to maternal and fetal death. The condition affects a significant number of pregnancies in the U.S., is responsible for premature deliveries, and up to 80% of maternal deaths. Various factors including genetics, history of preeclampsia in the family, exercise, presence of hypertension or diabetes before the onset of pregnancy, maternal endothelial dysfunction, increased expression of factors like soluble fms-like tyrosine kinase (sFltl), decreased levels of placental growth factor (PGF) and vascular endothelial growth factor (VEGF), play a key role in the development of preeclampsia. Uterine arterial pressure in normal women averages 84.3 mm Hg (79.3 to 89.3 mm Hg), while in the early pre-eclampsia, late-preeclampsia, or gestational hypertension patients, it is approximately 93.5 mm Hg (86 to 101 mm Hg) (Larochelle, et al., Am J Hypertens. 1994 February; 7(2):120-8).

However, the pathophysiology of hypertension and proteinuria in pregnancy are still not clear. Uroplacental ischemia appears to be a major reason for the preeclampsia, largely due to the increased demands of the fetus outgrowing the blood supply capacity of the placenta. However, observations of post-partum preeclampsia, especially in women of higher body mass index suggests, that preeclampsia is multi-factorial disease.

Several reports in the literature suggest that either static water immersion or water immersion exercises may help women with preeclampsia. Some of the available reports are summarized below.

Based on a series of studies conducted by Katz, V L (Katz, 1996, Semin Perinatol., 20(4):285-91), several benefits of water immersion exercises were noted in pregnant women, including reduction of extravascular edema, expansion of central blood volume, which may lead to increased uterine blood flow. This force is proportional to the depth of immersion. The increase in blood volume is proportional to the woman's edema. A marked diuresis and natriuresis accompanies the fluid shifts. The buoyancy of water supports the pregnant women. Studies of pregnant women exercising in the water have shown less fetal heart rate changes in the water than on land in response to exertion. Pregnant women's heart rates and blood pressures during water exercise are lower than on land exercise, reflecting the immersion-induced increase in circulating blood volume.

In 39 healthy pregnant women and 45 women with mild or moderate late pregnancy toxaemia water immersion induced a prompt and marked fall in systolic and diastolic blood pressure, significant decrease of plasma renin activity, aldosterone and vasopressin (Kokot et al., 1983, Proc Eur Dial Transplant Assoc., 20:557-61).

Water immersion in 18 healthy women between 20 and 33 weeks gestation who underwent static water immersion for 30 minutes over several days, resulted in marked dieresis suggesting potential use of this technique relieves edema during pregnancy relieving effects similar to static immersion (Kent, et al., 1999, Obstet Gynecol., 94(5 Pt 1):726-9).

Effects of water immersion for 3 hrs in 7 preeclamptic patients and 7 normal pregnant control patients, and 7 nonpregnant women, showed increased cardiac output, decreased diastolic blood pressure and heart rate, decreased peripheral resistance, although, the effects appear to be transient (Elvan-Taspinar, et al., 2006, Am J Obstet Gynecol., 195(6): 1590-5).

A few clinical trials are in progress using water immersion to treat preeclampsia (http://www.clinicaltrials.gov/ct2/show/NCT01799343).

Bed rest and various pharmaceutical treatments, are currently used to manage the condition and the symptoms to prolong the pregnancy, without jeopardizing the maternal health, however, all treatments are always not effective. Bed rest has been reported to increase blood flow to the fetus, as the maternal needs for the blood supply decreases when a person lies down. Bed rest, while it decreases the blood pressure compared to when a person is standing, the long term benefits of it in treating preeclampsia are still controversial, most likely due to some of the adverse effects associated with lack of adequate exercise. Additionally, adverse effects associate with prolonged bed rest including loss of bone density and muscle strength, and blood clots is a major concern.

Edema during pregnancy is normal and often resolves itself after delivery. Sitting or lying down with feet up, or bed rest are often used. Management of edema using pharmacological interventions is often based on the underlying cause; diuretics are often used to relieve edema. Water immersion has been reported to be a effective means to resolve edema, due to hydrostatic forces on the body causing a central shift in the fluid and increased dieresis.

Anecdotal evidence points to benefits of water-immersion in preeclampsia. Controlled clinical trials in small number of patients using short periods of immersion have reported central redistribution of blood volume, decreased total peripheral resistance, systolic and diastolic blood pressure and increased cardiac output. Most of the changes that occurred during water immersion reverted to baseline values within two hours after the procedure. Long term data with the use of water immersion on preeclampsia is not available.

Preterm birth affects approximately 12.5% of pregnancies in the US and about 5-7% worldwide. The premature delivery appears to be multi-factorial and inflammation of the uterus, placental membranes, infection, etc appear to play a role, although the exact mechanism is still not known. Bed rest is prescribed in 70% percent of the cases to delay preterm delivery, although the efficacy of bed rest in delaying delivery has been questioned recently. Several adverse effects including lack of exercise, lack of social interactions, circulatory and musculo-skeletal loss, are some of the disadvantages of bed rest. Therefore, embodiments of WDD and the methods disclosed herein may be used to delay preterm birth. The WDD is superior to bed rest as it allows the person to be mobile, provides adequate exercise, and may help in decreasing blood pressure as well as inflammation associated with some of pregnancies.

So far there is no permanent cure for the disease, other than the termination of the pregnancy.

Therefore, disclosed herein are methods and some embodiments of WDDs useful for prevention and/or treatment of preeclampsia, ecclampsia, hypertension and edema, and preterm birth associated with pregnancy.

Some portable embodiments of the WDDs depicted in FIGS. 6-A, 10I and 10J, or the stationary WDDs integrated into other furniture, such as chairs and beds as shown in FIGS. 2A, 4A and 8B may be used to prevent and treat hypertension and preeclampsia in humans. No additional figures of the embodiments of WDDs intended use in pregnancy are included herein. It is to be noted that in some embodiments, the WDD can just surround the abdomen and pelvic cavities, and supported by frame that surrounds just the torso, without any leg frame.

In some embodiments, the device may cover whole body or part of the body of the user, for example, just the legs, or up to waist of the user. The user may use the device, continuously or intermittently during the pregnancy. Both portable (e.g., suit like WDDs) and fixed type (e.g., WDDs integrated into chair) may be used as appropriate. To operate the device, the user secures the device to the body, and exerts pressure on the body using WBEs, thereby transferring at least a portion of body weight onto the frame. In some embodiments, the device may exert same force at all locations of the body. In some embodiments, the forces exerted by the WBEs located on the WDDs may be in a gradient fashion, with higher forces at the bottom, and decreasing slowly as one moves in an upward direction towards the head. It is to be noted that in some embodiments, the user WDD may comprise a suit with bands that exert gradient of pressure on the body, or bladders (without WBEs) that exert a gradient of the pressure on the body, without a need for transferring weight on to the frame. Because the forces from the WBEs that act in opposite directions cancel out, leaving a net upward force acting against the gravitational forces on the body that exerts minimal shear force on the skin and underlying tissue. The WBEs exert pressure on the capillaries supplying the soft tissues of the body, however the pressure is much smaller compared to the pressure due to the body weight on these tissues. As a result, the tissue pressure on the capillaries decreases with the use of WDD, resulting in a drop in the total peripheral resistance, which in turn leads to drop in the blood pressure, central fluid shift, increased cardiac output, decreased peripheral edema, increase urine output, natriuresis and improved blood circulation to the placenta, and thereby either preventing or mitigating some of the effects of preeclampsia or ecclampsia.

The effectiveness of the WDDs in improving the preeclampsia may be measured by monitoring the blood pressure, various biomarkers in the blood, blood supply to the placenta and fetus using uterine artery pressure using Doppler flow meters. Uterine arterial pressure preeclampsia women has been reported to increase on average to 93.5 mm Hg (range 86 to 101 mm Hg), depending on the stage of pre-ecclampsia in, compared to health control value of average 84.3 mm Hg (79.3 to 89.3 mm Hg) (Larochelle, et al., Am J Hypertens. 1994 February; 7(2):120-8). Some embodiments of WDD therefore are enabled to decrease the uterine artery pressure in women to normal range or pre-eclamptic value, which may range from 30 to 140 mm Hg or 50 to 100 mm Hg, or 79 to 89 mm Hg, and the like. Some embodiments of WDD may also be enabled to decrease the blood pressure to normal range and increase cardiac out pregnant women.

Gestational diabetes is a major concern in pregnancy and the exact mechanism is not known. The gestational diabetes increases the risk of development of hypertension and vice versa, and interaction of these two conditions during pregnancy has been reported in the literature. The WDD usage on a regular basis by patients who are at high risk of developing diabetes, decreases plasma glucose levels, increases insulin sensitivity and either prevents, mitigates or delays development of diabetes. The WDD accomplishes this by decreasing the total peripheral resistance, which in turn improves the blood circulation to muscles which use glucose, as well as by improving blood circulation to liver and kidney due to increased central redistribution of blood. Such changes lead to increased glucose uptake by muscle tissue, improved gluconeogenesis by liver, and promote active exchange of nutrients, metabolites among various organs of the body.

The device offers advantage over water immersion, in that it exerts forces that are similar to hydrostatic forces on the body of the user, without the need for use of swimming pools or bathtubs, which can be expensive, and are difficult to use on a regular basis.

Some embodiments of WDDs may also be used to decrease edema in various parts of the body, as the forces exerted by the WBEs help redistribute the fluid to the central compartment of the body thereby encouraging natriuresis, and increased glomerular filtration. Indirect benefits of the device due to decreased peripheral vascular resistance may include, increased blood supply to the placenta/fetus and thereby minimizing any potential risk to the fetus.

Some embodiments of the WDD may be used to treat or prevent various conditions of pregnancy where the blood supply to the fetus and the placenta does not keep up with the growing demands of the fetus. The device may accomplish this by reducing the pressure on the arteries and veins that supply blood to the uterus/placenta, as well as by decreasing maternal demands.

Some embodiments of WDDs may be used to prevent bleeding due to placenta previa. In placenta previa, wherein the placenta comes close to the cervix, bleeding may occur due to weight of the fetus pushing down on placenta towards the cervix. By using WDD to support the abdomen (both the abdomen, uterus and the fetus), the device minimizes the load of the fetus on the placenta, and hence is useful in prevention of complications related to this condition. In some embodiments A WDD that just supports the abdomen and pelvic regions of the body may be instead of covering the whole body.

Premature contractions occur in several pregnancies, due to various factors, which can lead to premature births. Bed rest is often helpful in minimizing such contractions. The WDD system disclosed herein may be used for minimizing premature contractions.

Hemorrhoids are defined as the symptomatic enlargement and al displacement of the normal anal cushions. The condition affects millions of people worldwide. The exact cause of hemorrhoids is not known, but a large number of factors might contribute to the development of hemorrhoids, including increased pressure on the veins in abdomen, constipation and prolonged straining, pregnancy and child birth, increased pressure in the portal vessels, etc. Additional mechanisms that affect the anal cushions were proposed as causative factors for hemorrhoids. Usually there are three major and several minor anal cushions surround the anal canal. When these cushions weaken and deteriorate the anal canal slides posteriorly causing hemorrhoids.

Of the two types of hemorrhoids, the internal and external, the internal ones tend to cause more bleeding, but often without pain, while the external ones are ones that cause most discomfort to a large number of people. Several therapeutic, medical device and surgical options are available to prevent or treat hemorrhoids, including ice packs, sitz bath, hemorrhoidal creams (e.g., Preparation-H®), rubber band ligation, injection sclerotherapy, photocoagulation using lasers or infrared light, hemorrhoidectomy, and the like. Lying down compared to sitting or standing relieves hemorrhoidal pain, as the pressure of abdominal contents on the veins is less when a person is lying down. It is suggested that hanging oneself upside down or at angle using inversion table provides temporary relief, as the swelling is reduced, likely due to gravitational forces of facilitating the drainage of the varicose veins. However, these options most often do not cause complete resolution of the problem or are associated with various risks.

Varicose veins is another condition that affects humans due to their ability to walk upright on their hind limbs, which results increased pressure on the veins of the legs and feet. Varicose veins are characterized by engorgement of veins in the legs. The condition may be benign, but more of cosmetic issue for some, while for others the condition may cause significant discomfort and complications. Several treatment options including compression stockings, surgical stripping of the intima of the veins, laser surgery, and the like are used. However, none of these solutions are satisfactory, and do not address the root cause, which is the increased pressure in the veins as a result of gravitational forces.

Therefore, disclosed herein are methods and some embodiments of WDDs useful for prevention and/or treatment of hemorrhoids and varicose veins in humans.

Some portable embodiments of the WDDs depicted in FIGS. 6-A, 10I and 10J, or the stationary WDDs integrated into other furniture, such as chairs and beds as shown in FIGS. 2A, 4A and 8B may be used to provide relief from, to prevent and/or treat the hemorrhoids and varicose veins in humans. No additional figures of the embodiments of WDDs intended use in pregnancy are included herein.

Some embodiments of the WDD device that treat the hemorrhoids may cover the whole body, or just the torso, and the weight of the frame supported by either waist or a leg-frame a described hereinabove. In such embodiments, the WBEs exert a net upward pressure on the torso, especially on the abdomen and the pelvis, so as to reduce the pressure on the veins located in the hemorrhoids (in anal canal cushions). Similarly, for the treatment of varicose veins, the WDDs supported by the leg frame may just cover legs, or both legs and torso.

To operate the device, the user secures the device to the body, and exerts pressure on the body using WBEs. By doing so, in some embodiments the user may transfer at least a portion of body weight onto the frame, while in other embodiments the device just increases the pressure without transferring body weight onto the frame. As disclosed hereinabove, the advantage of using WDD to exert pressure on the body is that shear forces and frictional forces are minimized when using WDD.

When used to treat the hemorrhoids, as a result of the net upward pressure applied on the abdomen and pelvis, the weight of the internal structures bearing on the anal cushions decreases, which leads to disengorgement of the veins in the hemorrhoids. As a result both the swelling of the both the external and the internal hemorrhoids decreases providing relief to the user. The same process can be used in pregnant women, who tend to develop hemorrhoids during pregnancy.

When used to treat the varicose veins, WDDs place around the legs (and torso) exerts increased pressure on the leg veins, and causes central shift of the blood from leg veins. As a result, the engorgement of the veins is decreased. Unlike compression socks, which can mainly exerts pressure on the surface veins of the legs, the WDD exerts pressure both on the surface veins as well as the deep veins located in the legs, while causing the central shift of the fluid.

Prolonged use of WDD or complete unloading of body weight onto WBEs and the frame may cause significant unloading of the spine and other skeletal structures in the body, remodeling of bone due to change weight bearing structures, reduced muscle strength, obesity and metabolic disorders due to decreased energy demands, motion sickness, decreased ability to maintain balance due to decreased tone of pressure sensors, tone down sympathetic nervous system that control blood pressure making a person susceptible to orthostatic hypotension, causes shift of peripheral fluid leading to increased central volume, reduced strength of heart and diaphragm, pulmonary edema, reduced compliance, decreased rennin-angiotensin-aldosterone system, change in gene expression profiles of several genes e.g., certain genes that related to cellular matrix proteins such as gap junctions, or ion transport channels, and the like. Likewise, prolonged use of LCD may result in the opposite effects to currently noted adverse effects in the space, for e.g., increased abnormal bone remodeling, cardiovascular issues, abnormal fluid shift to other locations of body, etc.

Therefore, some embodiments of both WDD and LCDs may cover only fraction of a body, and may off-load only a fraction of a body weight that is safe, or exert only partial loads on the body, WBEs programmed to change the location where pressure is applied after a certain period of time, exert alternating pressure, programmed to either increase or decrease pressure in the opposite direction to compensate, use a combination of LCD and WDD, and the like. Automated software controls to warn the user or sensors equipped to detect the changes in various parameters in musculo-skeletal or markers in the blood, detailed user instructions may be incorporated in the design of some embodiments of WDDs and LCDs.

Motion simulators are widely used for the purposes of entertainment in amusement parks, in virtual reality games, for simulating various environments and for training (e.g., flight simulators). Some of the simulators simulate motion by moving the simulation chair in various directions, including leaning backward, forward, sideways, and providing jolts or vibrations employing several various mechanical, hydraulic or other systems (e.g., Hex-axis horizontal simulator).

The status of a human body in relation to the surroundings is perceived by various signals that the brain gets from pressure and touch receptors, prioprioceptors (e.g., receptors located in joints, muscles and tendons, inner ear), vestibular system, and visual and auditory cues or based on various instruments. For example, receptors like Merkel's receptors when stimulated provide the sense of light touch, texture and shape of an object. Similarly, proprioceptors provide information on the position and orientation of the body to the brain. Brain integrates the inputs from these systems to understand the current status of the body, and takes appropriate action, for example, activates or relaxes certain group of motor muscles to maintain balance of the person while standing.

However, the inputs to the somatosensory, vestibular and other sensory systems and the integration of various signals by the brain can be exploited to simulate motion. Input from motion simulation systems is often synchronized with visual and/or auditory signals to create or enhance the experience of virtual reality. For example, leaning backwards in a simulator chair, when coupled with audio/video feedback gives the sensation of speeding forward, because leaning back causes the back of the seated person to be pressed against the backrest, since this is what happens when a vehicle suddenly accelerates. Similarly, tilting the simulator chair forward, results in pressure on the seat belt, which when coupled with audio/visual cues gives the feeling of falling forward or downward. Increased pressure on the sides of the body coupled with visual cues may be perceived as a rotational motion of the chair by the seated person.

While the current systems that simulate motion are very sophisticated, there still exists a need for advanced motion simulation methods and systems.

Disclosed herein are methods and some embodiments of a WDDs and LCDs for simulating the feeling of motion in a user. The embodiments of the system create feeling of various types of motions including, pitch, roll, vertical (heave), yaw, lateral (sway) and surge type of motions, provide tactile feedback sensations, various sensations of acceleration, deceleration, traveling at constant velocity, and feelings of weightlessness, floating or suspended in a liquid, flying, and the like, in a simulated environments or virtual reality (VR). The said method and the devices may be applied for several applications, for example, for entertainment purposes (to simulate rides in amusement parks), playing video games, enhance experience in VR environment, to train for the operation of various equipment, and practicing various activities.

In the traditional motion simulation systems, the entire base (or even the whole compartment for a better immersive experience) is physically moved through various degrees of freedom (e.g., 3 or 6 degrees of freedom) to create sensations of position change or change in the artificial g-force on the body to simulate reality. In these simulators, the gravity vector, which is represented as weight, is used here as a surrogate for the acceleration or deceleration or angular rotation. As a result of these motions, the body is pressed against the seat or the restraining belt or the bar, either on the back, sides or the front resulting in the person to assume that body is moving in a direction opposite to that of where the pressure points are experienced providing an experience to the user that closely simulates the real situation.

FIG. 10F illustrates embodiments of WDDs/LCDs integrated into a simulation chair 1069, comprising a seat 1063 and supporting legs 1062. The WDD/LCD surrounds the user 1061 viewing a screen 1070 that provides audio and video sensory input. The WDD/LCD comprises of a head piece 1066 that covers all sides of the head and neck, and a torso piece 1065 that covers the torso, and a leg piece 1064 that covers the legs. Note that only LCD/WDD integrated into an embodiment of chair-like simulator is shown, however, the LCD/WDD may be integrated with additional devices such as bed, a portable suit, etc. Not shown in the figure are sensors that measure the pressure exerted by the body, are electrical controls, and motors or pumps that are required to exert force on the body through WBEs, and foot pedals or hand controls required to interact with the audio and video inputs for gamin purposes. The chair may completely or partially surround a person. For example, when simulating motions of complete immersion in water or a fluid, to simulate weightless conditions, it may be advantageous to cover the whole body. The WBE are capable of both distributing pressure away from the weight-bearing regions (e.g., buttocks and thighs) an/or exerting additional loads (for example to simulate g-force) using the principles and mechanism of WDD and LCD described hereinabove.

The embodiments of WDD/LCD systems disclosed herein, to simulate motion may be used together with or instead of various simulators that physically move a person through various degrees of freedom. The disclosed system exerts either an increased or decreased pressure on the body to create the sensation of various movements. The WDD/LCD systems together with the WBEs act to simulate various experiences like accelerating, decelerating, floating, diving, flying, etc, by using pressure on various parts of the body as a surrogate for g-force. For example, when a person is seated in a chair fitted with a combination of WDD/LCD, which surrounds the person on all four sides plus, top and bottom, pressure exerted on the front of the torso may cause the back of the seated person to be pressed against the backrest of the simulation chair, and may be used to create the feeling of a forward movement to the body (when synchronized with audio/video signals). This is possible, since when pressure is exerted using WDD/LCD, the user may not feel significant increase in the pressure on the front side of the body, but if one limits the amount of area on which the pressure can be applied on the back of the seat, then the user may feel higher pressure on the back, as opposed to the front portion. In a similar way, pressure exerted from front, and both sides of the torso may also be focused on the back of a person, adding extra pressure to the back, giving the feeling that a person is accelerating forward. If the WBEs located on the backrest of the seat are configured to change into various firmness and shapes, ridges or bumps created on the backrest by the WBEs, instead of a soft cushiony feeling, it may be possible for the user to experience increased pressure at the contact point between the back of the torso and the backrest of the seat, when the WBEs are used to exert pressure from front and sides. Such a increased pressure may perceived as an increased speed or going up by the user depending on the other inputs. For example, a moving video input may be provided to give the user a feeling that he/she is going up, pushing from the front using all front surface of the body, but focusing the force on the back on a few points, to make the person feel he/she is going up.

Although, only a torso is illustrated in the figure, it is to be understood that individual parts or the whole body of person may be used to exert pressure for simulation of reality. Although, a chair is used as an example, the system may comprise a suit that covers a part of or the full body and be independent of any supporting structures. The system may be incorporated into various supporting structures (e.g., bed, mattress, a table, a seat, suspended by springs or ropes, or magnetic forces, suspended in fluid media), or integrated into various environments such as flight simulator, driving simulator, thrill rides, various training missions for the military, for training physicians or engineers for various tasks, or with various gaming consoles/equipment, etc.

When pushed from back towards the front direction, because the person may be pushed against front flap of the WDD/LCD that supports anterior portion of the torso, pressure is felt at the contact points between the front supporting surface and on abdomen and chest. When such a pressure is integrated with audio/video feed, it may simulate the feeling of deceleration, as this is similar to what happens to a person traveling in car, when sudden brakes are applied. Again bumps or ridges on the front flap, and applying force on the sides plus back may help to increase the sensation of pressure against the front portion of the person. In a similar fashion, it is possible to simulate movement to the left or right, by exerting force in the opposite direction.

Rotational movement may also be simulated, by exerting a force on one or more sides of a person, and then moving the force around the person, in such a manner that it synchronizes with the audio/video signals. The pressure on the body that changes in its location, in synchrony with the audio/video input may be perceived as angular movement. For example, pressure exerted by the force on the opposite sides of WDD/LCD, for example, can change from backrest to the sides, and then again to the backrest, giving the feeling that a person who is accelerating forward, took a slight curve at high speed and then, after negotiating the curve continued to accelerate in the forward direction. Similarly, movement in additional directions or a combination of directions may be simulated using pressure from at least one or more sides of the body. For example, bumps on a road may be simulated by increasing pressure on the buttocks, by pushing down using the head and torso. Such an effect may be created by connecting the WBEs/frames of the WDD/LCD to either manual, electrical, mechanical, pneumatic or hydraulic means.

The WBEs that surround a user and help simulate the motion by at least two different methods: One, when they exert pressure on one side, they may do so by exerting low pressure on a wider surface of the body, such that the force is not clearly perceived by that side of the body. A second method is that they may exert higher pressure on a small location on the body, to make the user feels the force. In both instances although same amount of total force is applied on the body, only in the later case, the pressure is perceived by the user. Combination or variation of these techniques, together with changing the location of the pressure in sync with the audio/video inputs, will be used simulate various motions. The surface characteristics of the WBEs, including the firmness, shape, direction of force may also be changed to simulate various motions or sensations. For example, the backrest of the seat which is comprised of the WBEs, on some occasion may be changed to give the sensation of smooth hard surface, or made to look like a series of ridges or bumps, or a soft cushion, thereby either minimizing or enhancing the effect of pressure felt by the body.

Simulating a condition of floating or immersion in a fluid (with or without any support), however, is more challenging for the existing conventional technology. Therefore, described in this disclosure are methods and some embodiments of devices to simulate motions that provide the feeling of floating over, or immersed in a fluid with or without any supporting structures (e.g., staying suspended or staying at the bottom of a pool), without the requirement to physically place the user in actual fluid. One of the objectives is to provide the user a feeling of floating freely for example, in the water, or submerged underwater, and suspended freely or standing on a supporting structure in the water. The simulation may be used for simulating swimming, various water sports and activities, defense or space research training, virtual reality games in water, etc. In some embodiments, the device may look like a chair or other equipment, and covers only a part of a body or a whole body.

To experience the sensation of floating or immersion in a fluid, the user secures oneself to the simulator (which may be in the form of a chair, bed or a portable suit), and applies pressure using WBEs from all sides. When the net force on the user is directed against the gravitational force on the body, and the net force in the upward or downward direction is approximately zero, the user gets the feeling of weightlessness and feels immersed completely in water (in synch with the appropriate audio/video feed). When the net upward force exerted by the WBEs is higher than the gravitational force, the person may get the feeling of floating (when combined with audio/video inputs). Likewise, to simulate the various movements (forward, backward, above or below) of the user in the water, e.g., swimming, the WBEs exert force against the body surface or arms or legs of the user, in such manner that the force is spread over a large surface that would come into contact with the water in real life. For example, for a user who is simulating a swimmer, and using arms as paddles to swim forward, force may be exerted on the palms and entire length of the bottom and the sides of the arm as it comes in the contact with the water (in the simulated environment). Higher force on the front and sides of a person may provide the feeling of floating, while high force on the head and shoulders but less force on the other parts of the body may give the feeling of diving into the depth. Similarly, the undulating force of the water on the body may be simulated by applying force on large surfaces of the body on the sides that are facing the water, while less weight on the surfaces away from the water. A moving force exerted by the WDEs on the surface of a body may mimic wave action. Synchronizing these movements and the forces on the body exercised by the WBEs with audio/video signals enhance the quality of the simulation, providing the user an improved experience of virtual reality.

The same process that is described for simulation of floatation or immersion in water may be used to create a sensation of weightlessness or may be used to simulate flying. Astronauts and pilots may be, for example, trained using the virtual reality systems described herein.

Further, the same process may also be used to simulate driving, or play other sports. Various motions such as acceleration, breaking, negotiating curves, etc may be simulated by applying pressure or removing pressure from appropriate locations of the body in synchrony with the audio/video inputs. In the standard simulators, as the whole chassis of the simulator base moves, effects of movement can also be experienced by the vestibular organ. To simulate the effects on the head, in some embodiments the system may be configured to provide input to the head, neck and vestibular organs. Such effects may be accomplished using a frame and WBEs that surrounds the head, and neck head of a person (e.g., like a helmet), which may be connected to the rest of the system or stay separate, and used exert either sustained or discontinuous forces to the head neck, to create the feeling of various forces (acceleration, deceleration, rotational, or impact forces, etc), without causing any injury.

The advantage of the disclosed methods of simulation using WDD/LCD is that, in some embodiments, they do not require hydraulic, pneumatic, electrical mechanisms, etc., that are required for the conventional simulators to move the chassis of the occupant's compartment. Instead, it is possible to provide motion simulation in a chair or a suit that is stationary, can be manufactured at relatively low cost and which occupies less space. The disclosed system may be combined with existing simulators to enhance the simulation experience.

The system may comprise inflatable or non-inflatable structures to support the WBEs. The WBEs may exert force against the body of the user using external power or by manual means. The simulator may include various sensors that measure the pressure, direction of force, posture, etc. Electrical or similar other motors may be used that can quickly increase or decrease the pressure, and change the location and intensity of the force in synchronization with the audio/video input may be used. Electrical or electronic controls that are driven by software may be used to make changes to the pressure and other parameters.

It should be noted that although WBEs and the WDD or LCDs are mentioned as required for simulation, it is possible that inflatable structures that exert pressure against the body or elastic or non-elastic structures that exert a pulling force against the body may be used to simulate motion effect.

Although, the WDD/LCD are designed to minimize shear forces, in some conditions, it may be more appropriate for these devices to exert shear forces on selected parts of the body (e.g., underside of thighs, buttocks, etc), in some conditions. Such an effect may be achieved by exerting parallel forces on skin, in a single direction, instead of multiple directions.

Several sensors may be located together with WBEs or integrated with WBEs, such that they may be used to provide tactile sensation. The WDD and LCD may be used to simulate the feeling of weight, weightlessness, various types of forces against the body, or various types of sensations including touch, temperature etc or touch using the WDD and LCDs disclosed herein. Some embodiments of LCD/WDD may also be used to simulate the tactile sensations exerted on the body. For example, in some embodiments, WBEs may be located within gloves worn by a user such that by exerting pressure at selected locations of the palm and the fingers, one may experience the feeling of weight, touch or other sensations. Similarly, by applying different forces, direction of forces and the location of force against the front and back portions of the torso, the device may be able to simulate, for example, sensations, including weight on the body. In some embodiments, additional equipment may be used to exert either hot or cold sensation, smells etc together with the WDD and LCD to enhance the experience in the simulated environment. In some embodiments, the WBEs may become rigid structures so as to exert shear forces on the skin, so as to simulate the feeling of stretching, or being held another person.

In some embodiments, a sheet made up of material capable of change texture or a soft silicone type material may be placed in between the WBEs and the skin of the user. Changing the surface of the sheet material, from smooth to rough texture may increase the ability of the palm to simulate various structures.

In additional embodiments, the WBEs and sensors may be located on additional body locations or parts, for example hands, feet, fingers and may be used for the purposes of creating or simulating various sensations including tactile, increased or decreased pressure, etc, for possible applications in telemedicine, shopping, interactive games and to simulate other activities. For example, a physician using the WDD/LCD may be able to examine an injured portion of a patient that may also be using WDD/LCD or other similar data collecting devices. A nurse or a healthcare provider may be able to collect a patient's data using WDD/LCD and upload the data for physician's assessment. Similarly, a shopper may be able to feel the weight of an item to be purchased if the data about that particular item is stored in a database, previously using the WDD/LCD or other devices. Similarly, it is possible to add interactive motion effects to various games using the WDD/LCD. If the data is included in the game, the person wearing the WDD/LCD simulator may be able to feel various weight, force, or motion related effects while playing the games. Similarly, various users wearing WDD/LCD simulators may be able to interact or simulate various forces, tactile or motions to interact with one another.

Various methods and the embodiments of the WDD and LCD, that may be used either as stand-alone devices or integrated into other equipment/furniture/suits (e.g., hospital bed, chairs, airplane or automobile seats, simulators), may have additional electronic hardware equipment (e.g., processors, computers, displays, input/output devices, sensors, transmitters, energy source, motors) and various software programs for effective operation of the devices. Some of user data, e.g., name, age, height may be entered into the system manually, while additional data, such as pressure, shear forces, temperature, humidity, load, direction of force, and other parameters such as EKG, tissue oxygenation, may be obtained using sensors incorporated into the WDD or LCD.

The sensors may be connected by suitable electrical leads to a microprocessor unit containing programmable means, and memory means, for automated operation of the means used to move the WBEs (which may include, e.g., valves, manifold assembly, pumps, pistons, or other controller means, such a mechanical controller elements). The data are used by the processor to allow for appropriate changes e.g., change the amount and direction and location of the force exerted by WBEs. Manual control means (not shown) may be operatively connected to the microprocessor for operation in a manual mode. Manually operated electrically connected buttons (not shown) may be provided for use by an operator to provide instructions such as the pressure or pressure profile that will be applied by the tactile force elements on the body. The microprocessor may be operatively connected to various conventional interfaces and networks, including the internet.

Figure 12:
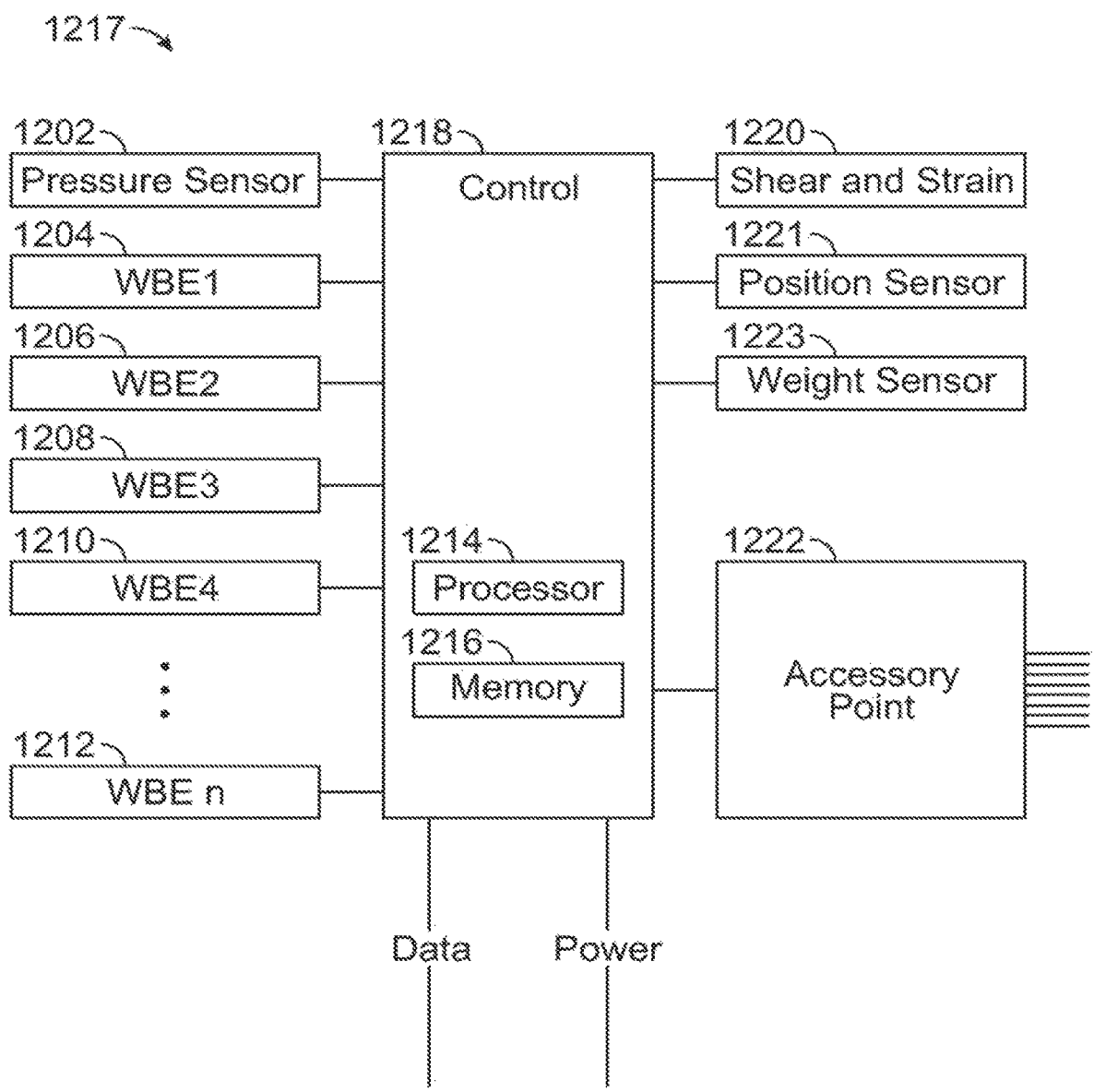
FIG. 12 illustrates an embodiment of a sensors and controls for exerting pressure using WDD/LCD on a human body.

In some embodiments, as shown in the block diagram of FIG. 12, a control unit provides power and communication functionality to the multiple monitoring and treatment devices in addition to monitoring and adjusting the forces by the WBEs on the interior surface of the present apparatus. The control unit 1218 in FIG. 12 includes a processor 1214 and a computer-readable memory 1216. The control unit 1218 can be in the form of a unit designed specifically for use in the apparatus or can be in the form of a computer or hand held device running a software application. The control unit 1218 receives data from one or more pressure distribution sensors 1202 and provides power and operating instructions to multiple WBEs 1204, 1206, 1208, 1210, 1212. The control unit 1218 may also connected to treatment and monitoring equipment such as temperature monitor, an EKG, respiratory monitor, EEG, strain/shear sensors 1220, weight sensors 1223, accelerometers to monitor the movement in any directions, position monitors 1220, user interface for the user to input information, and other devices that monitor a condition of a user of the apparatus. The control unit 1218 may also be connected to a multiple-port accessory input 1222. Additional devices such as cameras, pulse-oximeters, bacterial detectors and ultrasound probes, can be connected to an available accessory port when modularly attached to the inner surface of the apparatus. In addition to providing power to these devices, the control unit facilitates one or two-way communication between the devices and external devices or networks (e.g., monitor screens, Hospital).

When used for reducing blood pressure, the device may be able to monitor the heart rate, EKG and blood pressure of the user and change the pressure on an individual accordingly.

In certain specific embodiments, additional software features may be added for complete functionality of device. For example, when motion is simulated using WDD and LCD, the data collected from the sensors may be integrated or synchronized with various inputs, such as video, audio, tactile, etc., and used to exert increased or decreased pressure on specific locations of the body.

Figure 13:
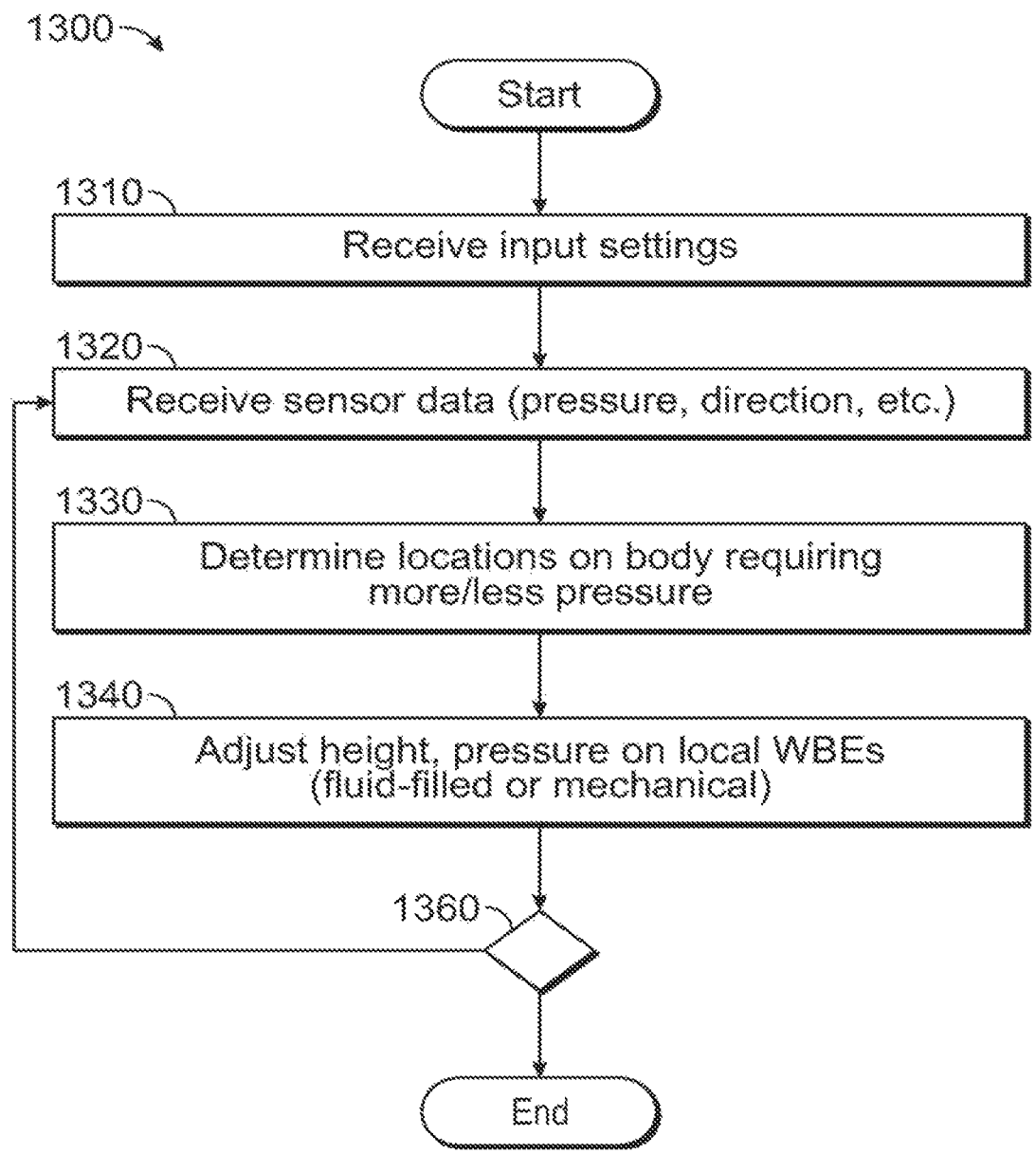
FIG. 13 illustrates an embodiment of a flowchart diagram for a software system for operation of WDD/LCD.

Some embodiments of WDD and LCDs may be operated using the process 1300 as depicted in FIG. 13. To use the device, the user secures the device to be body, and enters the user details and required settings using user-interface. The inputs settings 1310 are entered into the system are stored. The system then acquires data 1320 related to various parameters including local pressure, direction of force against the body surface at local area, etc. The system then determines the appropriate changes required at relevant locations on the body 1330, and executes the changes for example, either increase or decrease the pressure, inflates or deflates the structures by turning the motors on or off as shown in 1340. The system monitors these input settings and the acquired data continuously 1360, and either stops taking any further action, or repeats the steps from 1320 to 1360 in continuous fashion. For example, if the user after inputting personal data on weight and height, and chooses to off-load about 50% of body weight onto the frame, the system collects the data on position of the user and which parts of the user's body are in contact with the WBEs, and the pressure on various sensors located on different parts of the body, and then calculates how much pressure is required to be removed, e.g., from the underside of thighs and buttocks, and then using motors or pumps exerts pressure on the WBEs located on different location of the body, till a predetermined amount of pressure from thighs and buttocks is removed.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A system for exerting forces on a body of a mammal, the system comprising:

a) a support structure comprising a cover anchored to a chair, the support structure defining a space at least partially surrounded by the cover and the chair when the cover is placed into a closed configuration relative to the chair, wherein the cover is configured to be pressed against the body in the closed configuration; and b) a plurality of surface contacting units associated with the space, wherein the plurality of surface contacting units are configured to exert a gradient of forces in a direction upon a surface of the body located in the space, such that a shear force between a skin of the body and an underlying structure below the skin is similar to shear exerted on the body by water in a swimming pool;

wherein the system is configured to distribute loads away from primary weight bearing structures of the body, by exerting forces on non-weight bearing regions of the body; and wherein the gradient forces are configured to simulate gravitational forces on the body.

2. The system of claim 1, wherein the system is configured to apply a net force to the body in a direction of gravity so as to increase the net force or weight on the body or various parts of the body.

3. The system of claim 1, wherein a support unit together with the plurality of surface contacting units are configured to exert force on an astronaut living in a microgravity environment or on a planet other than earth to simulate a body weight.

4. The system of claim 1, wherein the gradient of forces are exerted on an astronaut to provide pressure or loads to simulate gravitational force on the body.

5. A system of claim 1, wherein the system further comprises: a plurality of fluid-filled inflatable structures associated with the space, wherein the plurality of fluid-filled inflatable structures are configured to exert a net force upon the body or a body part retained in the space, and a plurality of either manual or electrical power sources are enabled to increase or decrease a pressure in the plurality of fluid-filled inflatable structures.

6. The system of claim 1, wherein the system comprises sensors configured to sense at least one of position, acceleration, deceleration, humidity, a blood pressure, respirations, various electrical signals related to vital signs, EKG, or EEG of the body, wherein the sensors are electrically interconnected, and wherein the system comprises a computerized structure configured for detecting a presence of the body or a body part in the space, measuring a force or a pressure at a location on the body or the body part and adjusting the force or the pressure exerted on the body or the body part at the location.

7. The system of claim 1, wherein the system is adapted to prevent or treat various disease conditions of a patient with metabolic and/or cardiovascular disorders, wherein the system is configured to exert either equal pressure at all locations or a variable pressure on the body in a gradient fashion with the forces decreasing from bottom towards head, resulting in a net upward force on the body, but with minimal shear forces on the skin and underlying tissues, and the system is configured to off-load a fraction or whole of a weight of the patient in a range from 0 to 100%, 0.00001% to 1%, 1% to 10%, 10% to 50%, 50% to 90%, or 90% to 99.9999%, onto the plurality of surface contacting units, which in turn is enabled to transfer the weight to a floor or other supporting structures, wherein the system is configured to decrease total peripheral resistance in the patient and decrease blood pressure.

8. The system of claim 7, wherein the system is configured to shift blood and fluid from a periphery to a central pool, and increase cardiac output.

9. The system of claim 7, wherein the system is configured to increase natriuresis, urinary output and decrease edema.

10. The system of claim 7, wherein the system is configured to reduce a rennin-angiotensin-aldosterone system.

11. The system of claim 7, wherein the system is configured to decrease sympathetic tone of a nervous system.

* * * * *